US008889878B2

(12) United States Patent
Heil et al.

(10) Patent No.: US 8,889,878 B2
(45) Date of Patent: Nov. 18, 2014

(54) HALOALKY-SUBSTITUTED AMIDES AS INSECTICIDES AND ACARICIDES

(75) Inventors: Markus Heil, Leichlingen (DE); Eike Kevin Heilmann, Düsseldorf (DE); Alexander Sudau, Leichlingen (DE); Tobias Kapferer, Düsseldorf (DE); Friedrich August Mühlthau, Bad Soden am Taunus (DE); Peter Jeschke, Bergisch Gladbach (DE); Arnd Voerste, Köln (DE); Ulrich Görgens, Ratingen (DE); Klaus Raming, Leverkusen (DE); Ulrich Ebbinghaus-Kintscher, Dortmund (DE); Mark Drewes, Langenfeld (DE); Martin Adamczewski, Köln (DE); Angela Becker, Düsseldorf (DE)

(73) Assignee: Bayer CropScience AG, Monheim (DE)

(*) Notice: Subject to any disclaimer, the term of this patent is extended or adjusted under 35 U.S.C. 154(b) by 0 days.

(21) Appl. No.: 12/913,251

(22) Filed: Oct. 27, 2010

(65) Prior Publication Data
US 2011/0105532 A1 May 5, 2011

Related U.S. Application Data

(60) Provisional application No. 61/255,227, filed on Oct. 27, 2009.

(30) Foreign Application Priority Data

Oct. 27, 2009 (EP) .................................. 09174176

(51) Int. Cl.
| | | |
|---|---|---|
| A01N 43/40 | (2006.01) |
| C07D 211/70 | (2006.01) |
| A01N 43/653 | (2006.01) |
| C07D 331/04 | (2006.01) |
| C07C 281/02 | (2006.01) |
| C07C 233/83 | (2006.01) |
| C07C 237/20 | (2006.01) |
| A01N 37/18 | (2006.01) |
| A01N 37/30 | (2006.01) |
| C07C 317/32 | (2006.01) |
| A01N 43/38 | (2006.01) |
| C07C 311/14 | (2006.01) |
| C07C 237/22 | (2006.01) |
| C07D 213/82 | (2006.01) |
| A01N 43/16 | (2006.01) |
| C07C 323/41 | (2006.01) |
| A01N 43/58 | (2006.01) |
| C07D 209/42 | (2006.01) |
| A01N 43/56 | (2006.01) |
| C07C 233/66 | (2006.01) |
| A01N 43/12 | (2006.01) |
| C07D 401/12 | (2006.01) |
| A01N 43/08 | (2006.01) |
| C07C 255/57 | (2006.01) |
| C07D 405/12 | (2006.01) |
| C07C 255/24 | (2006.01) |
| A01N 43/10 | (2006.01) |
| A01N 43/60 | (2006.01) |
| C07D 249/08 | (2006.01) |
| A01N 41/06 | (2006.01) |
| C07D 409/12 | (2006.01) |
| C07D 213/40 | (2006.01) |
| A01N 43/02 | (2006.01) |
| C07C 233/13 | (2006.01) |
| A01N 43/54 | (2006.01) |
| A01N 43/82 | (2006.01) |
| A01N 43/50 | (2006.01) |
| C07D 307/85 | (2006.01) |
| C07D 213/56 | (2006.01) |
| C07C 233/65 | (2006.01) |
| C07C 233/74 | (2006.01) |
| C07D 271/06 | (2006.01) |
| A01N 37/34 | (2006.01) |

(52) U.S. Cl.
CPC ............ *C07D 307/85* (2013.01); *A01N 43/653* (2013.01); *C07D 331/04* (2013.01); *C07C 281/02* (2013.01); *C07C 233/83* (2013.01); *C07C 237/20* (2013.01); *A01N 37/18* (2013.01); *A01N 37/30* (2013.01); *C07C 317/32* (2013.01); *A01N 43/38* (2013.01);

(Continued)

(58) Field of Classification Search
None
See application file for complete search history.

(56) References Cited

U.S. PATENT DOCUMENTS 4,267,345 A 5/1981 Malen et al.
5,298,527 A 3/1994 Grammenos et al.

(Continued)

FOREIGN PATENT DOCUMENTS

EP 0 539 588 A1 1/1992
EP 0 513 580 A2 4/1992

(Continued)

OTHER PUBLICATIONS

Alberico, D. & Lautens, M., "Palladium-Catalyzed Alkylation-Alkenylation Reactions: Rapid Access to Tricyclic Mescaline Analogues," *Synlett* 18:2969-2972, George Thieme Verlag Stuttgart, Germany (2006).

(Continued)

*Primary Examiner* — Heidi Reese
(74) *Attorney, Agent, or Firm* — Sterne, Kessler, Goldstein & Fox P.L.L.C.

(57) ABSTRACT

The present invention relates to halogen-substituted amide derivatives of the general formula (I)

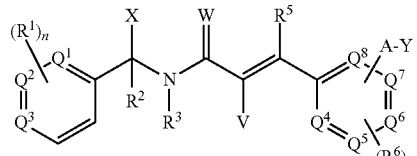

in which $R^1$ to $R^6$, $Q^1$ to $Q^8$, A, V, W, X, Y, n and m are each defined as described in the description—and to a process for preparation thereof and to the use thereof as insecticides and acaricides.

13 Claims, No Drawings

(52) U.S. Cl.
CPC ............. *C07C 311/14* (2013.01); *C07C 237/22* (2013.01); *C07D 213/82* (2013.01); *A01N 43/16* (2013.01); *C07C 323/41* (2013.01); *A01N 43/58* (2013.01); *C07C 2101/04* (2013.01); *C07D 209/42* (2013.01); *A01N 43/56* (2013.01); *C07C 233/66* (2013.01); *A01N 43/12* (2013.01); *C07D 401/12* (2013.01); *A01N 43/08* (2013.01); *C07C 255/57* (2013.01); *C07D 405/12* (2013.01); *C07C 255/24* (2013.01); *A01N 43/10* (2013.01); *A01N 43/60* (2013.01); *C07D 249/08* (2013.01); *A01N 41/06* (2013.01); *C07D 409/12* (2013.01); *C07D 213/40* (2013.01); *A01N 43/02* (2013.01); *C07C 233/13* (2013.01); *A01N 43/54* (2013.01); *A01N 43/82* (2013.01); *A01N 43/50* (2013.01); *C07D 213/56* (2013.01); *C07C 233/65* (2013.01); *C07C 233/74* (2013.01); *C07C 2101/02* (2013.01); *C07D 271/06* (2013.01); *A01N 37/34* (2013.01); *C07C 2102/08* (2013.01); *A01N 43/40* (2013.01)
USPC .......................................... 546/339; 514/345

(56) References Cited

U.S. PATENT DOCUMENTS

| | | |
|---|---|---|
| 5,716,624 A | 2/1998 | Bernardon |
| 5,955,495 A | 9/1999 | Bös et al. |
| 6,252,090 B1 | 6/2001 | Vasudevan et al. |
| 2004/0220415 A1 | 11/2004 | Schmeck et al. |
| 2006/0281780 A1 | 12/2006 | Goto et al. |
| 2007/0112011 A1 | 5/2007 | Kuhnert et al. |
| 2008/0305955 A1 | 12/2008 | Bretschneider et al. |
| 2009/0076282 A1 | 3/2009 | Toriyabe et al. |
| 2009/0247551 A1 | 10/2009 | Jeschke et al. |
| 2009/0253749 A1 | 10/2009 | Jeschke et al. |
| 2011/0306499 A1 | 12/2011 | Bretschneider et al. |

FOREIGN PATENT DOCUMENTS

| | | |
|---|---|---|
| EP | 1 445 253 A1 | 8/2004 |
| JP | 2002/201193 A | 7/2002 |
| WO | WO 01/77101 A1 | 10/2001 |
| WO | WO 02/096858 A1 | 12/2002 |
| WO | WO 03/064411 A1 | 8/2003 |
| WO | WO 2004/104001 A2 | 12/2004 |
| WO | WO 2005/035486 A1 | 4/2005 |
| WO | WO 2005/080336 A1 | 9/2005 |
| WO | WO 2006/056433 A2 | 6/2006 |
| WO | WO 2006/082400 A1 | 8/2006 |
| WO | WO 2006/100288 A2 | 9/2006 |
| WO | WO 2007/043677 A1 | 4/2007 |
| WO | WO 2007/057407 A2 | 5/2007 |
| WO | WO 2007/095229 A2 | 8/2007 |
| WO | WO 2007/149134 A1 | 12/2007 |
| WO | WO 2008/005954 A2 | 1/2008 |
| WO | WO 2008/019760 A1 | 2/2008 |
| WO | WO 2008/104503 A1 | 9/2008 |
| WO | WO 2009/055077 A1 | 4/2009 |

OTHER PUBLICATIONS

Rosauer, K.G., et al., "Novel 3,4-Dihydroquinolin-2(1*H*)-one Inhibitors of Human Glycogen Phosphorylase α," *Bioorganic & Medicinal Chemistry Letters* 13(24):4385-4388, Elsevier Ltd., England (2003).
Sall, D.J., et al., "Use of Conformationally Restricted Benzamidines as Arginine Surrogates in the Design of Platelet GPIIb-IIIa Receptor Antagonists," *Journal of the American Chemical Society* 40:2843-2857, The American Chemical Society, United Staes (1997).
Sampath Kumar, H.M., et al., "Non Solvent Reaction: Ammonium Acetate Catalyzed Highly Convenient Preparation of Trans-Cinnamic Acids," *Synthetic Communications* 28:3811-3815, Marcel Dekker Inc., New York, United States (1998).
Schaudt, M. & Blechert, S., "Total Synthesis of (+)-Astrophylline," *Journal of Organic Chemistry* 68:2913-2920, American Chemical Society, United States (2003). Anderson, G.W., et al., "A Reinvestigation of the Mixed Carbonic Anhydride Method of Peptide Synthesis", *Journal of the American Chemical Society* 89(19):5012-5017, American Chemical Society, Washington DC, United States (1967).
Baur, P., et al., "Polydisperse Ethoxylated Fatty Alcohol Surfactants as Accelerators of Cuticular Penetation. 1. Effects of Ethoxy Chain Length and the Size of the Penetrants," *Pesticide Science* 51(2):131-152, Wiley, Chichester, Royaume-Uni, Great Britain (1997).
Brown, W.G., "Reductions by Lithium Aluminum Hydride," *Organic Reactions* 6: 470-508, John Wiley & Sons, United States (1951).
Bumagin, N.A., et al., "Palladium-Catalyzed Reactions of Acrylic Acid and Styrene with Aryl Halides in Water," *Russian Journal of Organic Chemistry* 31(4):439-444, Springer, Heidelberg, Germany (1995).
Cai, M.-Z., et al., "Silica-Supported Poly-γ-Mercaptopropylsiloxane Palladium(0) Complex: A Highly Active and Stereoselective Catalyst for Arylation of Styrene and Acrylic Acid," *Synthesis*: 521-523, Thieme, Germany (Oct. 1996).
Colas, C. & Goeldner, M., "An Efficient Procedure for the Synthesis of Crystalline Aryldiazonium Trifluoroacetates—Synthetic Applications," *European Jounal of Organic Chemistry* :1356-1366, Wiley-VCH Verlag GmbH & Co. KGaA, Weinheim Germany (1999).
Dann, O., et al., "Synthesen biskationischer, trypanocider 1-Benzofuran-Verbindungen," *Liebigs Annalen der Chemie* 10:1836-1869, Wiley-VCH Verlag GmbH & Co. KGaA, Weinheim, Germany (1982).
Hartung, W.H., "Catalytic Reduction of Nitriles and Oximes," *Journal of the American Chemical Society* 50:3370-3374, Easton, PA, Washington DC, United States (1928).
Henecka, H., "Umwandlung von Carbonsäuren," *Methoden der Organischen Chemie* 8:463, Houben-Weyl, Thieme, Germany (1952).
Kang, T.-S., et al., "Synthesis and antioxidant activities of 3,5-dialkyoxy-4-hydroxycinnamamides," *Bioogranic & Medicinal Chemistry Letters* 18:1663-1667, Elsevier Ltd., United Kingdom (2008).
Kato, K., et al., "Enzymatic resolution of 2,2,2-trifluoro-1-arylethylamine derivatives by *Pseudomonas fluorescens* lipase in organic solvents," *Journal of Molecular Catalysis* 30:61-68, Elsevier, The Netherlands (2004).
Khosropour, A.R., et al., "Synthesis of *trans*-cinnamic acids from aryl aldehydes and aryl aldehyde bisulfite adducts with malonic acid using piperazine," *Journal of Chemical Research* 45(36):364-365, Wiley-VCH Verlag GmbH & Co. KGaA, Weinheim, Germany (2005).
König, W. & Geiger, R., "Eine neue Methode zur Synthese von Peptiden: Aktivierung der Carboxylgruppe mit Dicyclohexylcarbodiirnid unter Zusatz von 1-Hydroxybenzotriazolen," *Chemische Berichte* 103(3):788-798, Wiley-VCH Verlag GmbH & Co. KGaA Weinheim, Germany (1970).
Lindwall, H.G. & Mantell, G.J., "Synthesis and Reactions of Indole Carboxylic Acids; Pyridindolones from Indole-2-Carboxyacetalylbenzylamides," *Journal of organic Chemistry* 18(4):345-357, American Chemical Society, United States (1953).
Liu, P., et al., "Study on the Heck Arylation Reaction Catalyzed by Chitosan-Immobilized Palladium(0) Complex," *Chinese Journal of Organic Chemistry* 24:59-62, British Library—"The World's Knowledge", Shanghai Institute of Organic Chemistry and Chinese Chemical Society, China (2004).
Magdolen, P., et al., "Ultrasound effect on the synthesis of 4-alkyl-(aryl)aminobenzaldehydes," *Tetrahedron* 57:4781-4785, Elsevier Science Ltd., The Netherlands (2001).
Ohomom, Y., et al., "Radioiodinated *N*-(2-Aminoethyl)-2-chloro-4-iodobenzamide: A New Ligand for Monoamine Oxidase B Studies with Single Photon Emission Computer Tomography," *Chemical Prarmaceutical Bulletin* 42(4):913-916, Pharmaceutical Society of Japan, Japan (Apr. 1994).
Ohomom, Y., et al., "Synthesis and Evaluation of Iodinated Benzamide Derivatives as Selective and Reversible Monoamine

(56) References Cited

OTHER PUBLICATIONS

Oxidase B Inhibitors," *Chemical Prarmaceutical Bulletin* 40(7):1789-1792, Pharmaceutical Society of Japan, Japan (1992).

Patel, D.V., et al. "Synthesis of the Proposed Penultimate Biosynthetic Triene Intermediate of Monensin A," *Journal of the American Chemical Society* 108:4603-4614, The American Chemical Society, United States (1986).

Peltier, M.D. & Delepine, M.M., "Chimie Organique—Sur les acides ortho-toluiques halogénés et leurs esters méthyliques," *Comptes Rendus Chimie*:357, Séance du Jan. 18, 1954, the French Academy of Sciences (1954).

Sharma, M.L. & Kaur, S., "Synthesis of quaternary salts of ammonia from cinnamic acids and their plant growth retardant activity," *Journal of the Indian Chemical Society* 84(6):612-614, Indian Chemical Society, India (2007).

Solabannavar, S.B., et al., "Application of Arnberlite IRA-400 (Basic) as a Base in Heck Reaction," *Synthetic Communications* 33(3):361-365, Marcel Dekker Inc., New York, United Staes (Feb. 2003).

Wiedemann, J., et al., "Direkte Synthese von Trifluormethylketonen aus Carbonsäureestern: Trifluormethylierung mit Trimethyl(trifluormethyl)silan," *Angew Chem* 110(6):880-881, Wiley-VCH Verlag, GmbH, Germany (1998).

Wiley, R.H. & Smith, N.R., "*m*-Nitrostyrene," *Organic Syntheses Collective* vol. 4:731, Organic Synthesis, Inc., American Chemical Society (1963).

Woodward, R.B., "*m*-Hydroxybenzaldehyde," *Organic Syntheses Collective* vol. 3:453, Organic Synthesis, Inc., American Chemical Society (1955).

Yue, X., et al., "Metal-mediated *gem*-Difluoroallylation of *N*-Acylhydrazones: Highly Efficient Synthesis of α,α-Difluorohomoallylic Amines," *Chinese Journal of Chemistry* 27:141-150, Wiley-VCH Verlag GmbH & Co. KGaA, Weinheim, Germany (2009).

English language Abstract of Japanese Patent Publication No. 2002-201193 A, Japanese Patent Office, Patent & Utility Model Gazette DB, Patent Abstract of Japan, (2002).

European Search Report for European Application No. 09174176.9-2103, European Patent Office, Germany, dated May 27, 2010.

HALOALKY-SUBSTITUTED AMIDES AS INSECTICIDES AND ACARICIDES

This application claims benefit under 35 U.S.C. §119(e) to U.S. Provisional Application No. 61/255,227, filed Oct. 27, 2009, the entirety of which is incorporated by reference herein.

The present invention relates to novel pesticides, to a process for preparation thereof and to the use thereof as active ingredients, especially to the use thereof as insecticides and acaricides.

The literature describes particular cinnamides and use thereof as medicaments; see, for example, WO-A-2002/096858. It has now been found that, surprisingly, particular amides, especially haloalkyl-substituted amides, possess strong insecticidal and acaricidal properties coupled with simultaneously good plant tolerance, favourable homeotherm toxicity and good environmental compatibility. The inventive novel compounds are, however, not disclosed in WO-A-2002/096858.

The present invention therefore provides compounds of the general formula (I)

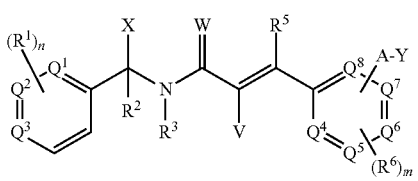

(I)

where
$R^1$ is hydrogen, halogen, nitro, cyano, optionally monosubstituted or identically or differently polysubstituted $C_1$-$C_6$-alkyl, $C_2$-$C_6$-alkenyl, $C_2$-$C_6$-alkynyl, $C_1$-$C_6$-alkoxy, $C_1$-$C_6$-alkylthio, $C_1$-$C_6$-alkylsulphinyl, $C_1$-$C_6$-alkylsulphonyl, $C_3$-$C_6$-cycloalkyl, $C_1$-$C_6$-alkylcarbonyl, $C_1$-$C_6$-alkoxyimino-$C_1$-$C_6$-alkyl, $C_1$-$C_6$-alkoxycarbonyl, $C_1$-$C_6$-alkylaminocarbonyl, $C_1$-$C_6$-dialkylaminocarbonyl, $C_1$-$C_6$-alkylaminosulphonyl, $C_1$-$C_6$-alkylsulphonylamino, tri($C_1$-$C_6$-alkyl)silyl, aryl, hetaryl, aryl-$C_1$-$C_4$-alkyl, or hetaryl-$C_1$-$C_4$-alkyl,
  where the substituents are each independently selected from halogen, cyano, nitro, hydroxyl, $C_1$-$C_6$-alkyl, $C_1$-$C_6$-alkoxy, $C_3$-$C_6$-cycloalkyl, $C_1$-$C_6$-haloalkoxy, $C_1$-$C_6$-alkylthio, $C_1$-$C_6$-alkylsulphenyl, $C_1$-$C_6$-alkylsulphonyl, aryl, hetaryl, arylalkyl or hetarylalkyl,
  where the aryl, hetaryl, arylalkyl, hetarylalkyl substituents are optionally monosubstituted or identically or differently polysubstituted by halogen, cyano, nitro, hydroxyl, $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy, $C_1$-$C_6$-haloalkyl, $C_1$-$C_6$-haloalkoxy or $C_1$-$C_6$-alkylthio,
or
$R^1$ is a $C_1$-$C_4$ carbon chain which optionally contains 1-2 heteroatoms from the group of N, S, O, which is bonded to two adjacent ring positions and which forms an aliphatic, aromatic, heteroaromatic or heterocyclic ring which is optionally mono- or polysubstituted by $C_1$-$C_6$-alkyl or halogen, in which case n is 2,
n is 1, 2 or 3,
$R^2$ is hydrogen, cyano, hydroxyl, amino, optionally monosubstituted or identically or differently polysubstituted $C_1$-$C_6$-alkyl, $C_2$-$C_6$-alkenyl, $C_2$-$C_6$-alkynyl, $C_1$-$C_6$-alkoxy, $C_3$-$C_6$-cycloalkyl, optionally monosubstituted or identically or differently polysubstituted aryl, hetaryl or optionally monosubstituted or identically or differently polysubstituted aryl-$C_1$-$C_6$-alkyl or hetaryl-$C_1$-$C_4$-alkyl,
  where the substituents are each independently selected from halogen, cyano, nitro, hydroxyl, amino, $C_1$-$C_6$-alkyl, $C_1$-$C_6$-alkoxy, $C_3$-$C_6$-cycloalkyl, $C_1$-$C_6$-haloalkoxy, $C_1$-$C_6$-alkylthio, amino, $C_1$-$C_6$-alkylamino, $C_1$-$C_6$-dialkylamino, $C_1$-$C_4$-alkylcarbonylamino or $C_1$-$C_4$-dialkylcarbonylamino,
or
$R^2$ is an optionally mono- or polysubstituted $C_2$-$C_4$-alkyl chain which may be interrupted by O, S or N, forming, with $Q^1$, a 5-7-membered ring optionally interrupted by O, S or N, and the substituents are each independently selected from halogen and $C_1$-$C_6$-alkyl,
$R^3$ is hydrogen, optionally monosubstituted or identically or differently polysubstituted $C_1$-$C_6$-alkyl, $C_2$-$C_6$-alkenyl, $C_2$-$C_6$-alkynyl, $C_3$-$C_6$-cycloalkyl, aryl-$C_1$-$C_6$-alkyl, $C_1$-$C_6$-alkylcarbonyl, $C_1$-$C_6$-alkylsulphonyl, arylcarbonyl, hetarylcarbonyl, $C_1$-$C_6$-alkoxycarbonyl or aryloxycarbonyl,
  where the substituents are each independently selected from halogen, cyano, nitro, hydroxyl, $C_1$-$C_6$-alkyl, $C_1$-$C_6$-alkoxy, $C_3$-$C_6$-cycloalkyl, $C_1$-$C_6$-haloalkoxy, $C_1$-$C_6$-alkylthio, aryl, hetaryl, arylalkyl, hetarylalkyl, $C_1$-$C_4$-alkoxycarbonyl, aminocarbonyl, $C_1$-$C_4$-alkylaminocarbonyl or $C_1$-$C_4$-dialkylaminocarbonyl,
  where the aryl, hetaryl, arylalkyl, hetarylalkyl substituents are optionally monosubstituted or identically or differently polysubstituted by halogen, cyano, nitro, hydroxyl, $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy, $C_1$-$C_6$-haloalkyl, $C_1$-$C_6$-haloalkoxy or $C_1$-$C_6$-alkylthio,
V is $R^4$, or
  is a bivalent chemical moiety which is selected from —O—, —CH$_2$O—, —S—, —N($R^8$)—, —N=C($R^9$)—, —C($R^9$)=N— and —C($R^9$)=C($R^{10}$)— and which is bonded to $Q^4$ via a single bond, where the second (right-hand) connection site in each case is connected to $Q^4$, where
$R^4$ is hydrogen, halogen or optionally monosubstituted or identically or differently polysubstituted $C_1$-$C_6$-alkyl, where the substituents are each independently selected from halogen, $C_1$-$C_6$-alkyl or $C_1$-$C_6$-alkoxy,
$R^8$ is hydrogen, cyano, hydroxyl, optionally monosubstituted or identically or differently polysubstituted $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy, $C_1$-$C_6$-alkylcarbonyl, arylcarbonyl, hetarylcarbonyl, $C_1$-$C_6$-alkoxycarbonyl, arylalkyl or $C_1$-$C_4$-alkylsulphonyl,
  where the substituents are each independently selected from halogen, cyano, nitro, hydroxyl, $C_1$-$C_6$-alkyl or $C_1$-$C_6$-alkoxy, $C_1$-$C_4$-alkoxycarbonyl, amino, $C_1$-$C_6$-alkylamino, $C_1$-$C_6$-dialkylamino, aminocarbonyl, $C_1$-$C_6$-alkylaminocarbonyl, $C_1$-$C_6$-dialkylaminocarbonyl and aryl-$C_1$-$C_6$-alkoxy,
$R^9$ and $R^{10}$ are each independently hydrogen, halogen, optionally monosubstituted or identically or differently polysubstituted $C_1$-$C_6$-alkyl or $C_3$-$C_6$-cycloalkyl,
  where the substituents are each independently selected from halogen and $C_1$-$C_6$-alkyl,
$R^5$ is hydrogen, halogen or optionally monosubstituted or identically or differently polysubstituted $C_1$-$C_6$-alkyl or $C_1$-$C_6$-alkoxy,
  where the substituents are each independently selected from halogen and $C_1$-$C_6$-alkyl, $R^6$ is hydrogen, halogen, nitro, cyano, amino, hydroxyl, optionally monosubstituted or identically or differently polysubstituted $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy, ($C_1$-$C_6$-alkoxy)carbonyl, $C_1$-$C_6$-alkylamino, formyl, ($C_1$-$C_6$-alkyl)carbonyl, $C_1$-$C_6$-alkoxyimino-$C_1$-$C_6$-alkyl, $C_1$-$C_6$-dialkylamino, ($C_1$-$C_6$-alkylamino)carbonyl, ($C_1$-$C_6$-dialkylamino)carbonyl, $C_1$-$C_6$-alkylthio, $C_1$-$C_6$-alkylsulphinyl, $C_1$-$C_6$-alkylsulphonyl, $C_1$-$C_6$-alkylaminosulphonyl, $C_1$-$C_6$-alkylsulphonylamino, aryl, hetaryl, aryl-$C_1$-$C_4$-alkyl or hetaryl-$C_1$-$C_4$-alkyl,
  where the substituents are each independently selected from halogen, cyano, nitro, hydroxyl, amino, $C_1$-$C_6$-alkyl, $C_1$-$C_6$-alkoxy, $C_3$-$C_6$-cycloalkyl, $C_1$-$C_6$-haloalkoxy, $C_1$-$C_6$-alkylthio, aryl, hetaryl, arylalkyl or hetarylalkyl,
  where the aryl, hetaryl, arylalkyl, hetarylalkyl substituents are optionally monosubstituted or identically or differently polysubstituted by halogen, cyano, nitro, hydroxyl, $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy, $C_1$-$C_6$-haloalkyl, $C_1$-$C_6$-haloalkoxy or $C_1$-$C_6$-alkylthio, or $R^6$ is a $C_1$-$C_4$ carbon chain which optionally contains 1-2 heteroatoms from the group of N, S, O, which is bonded to two adjacent ring positions $Q^4$ to $Q^8$ and forms an aliphatic, aromatic or heteroaromatic ring which is optionally mono- or polysubstituted by $C_1$-$C_6$-alkyl or halogen, in which case m is 2, m is 0, 1, 2, 3, X is $C_1$-$C_6$-haloalkyl or $C_3$-$C_6$-halocycloalkyl which is optionally additionally mono- to trisubstituted, where the substituents are each independently selected from hydroxyl, cyano, $C_1$-$C_4$-alkoxy, $C_1$-$C_4$-haloalkoxy, $C_1$-$C_4$-alkoxycarbonyl, $C_1$-$C_4$-alkylaminocarbonyl and $C_1$-$C_4$-dialkylaminocarbonyl, W is O or S, A-Y together are cyano, or are optionally mono- or polysubstituted hetaryl, heterocyclyl or oxoheterocyclyl,
  where the substituents are selected from halogen, nitro, cyano, amino, hydroxyl, from optionally monosubstituted or identically or differently polysubstituted amino, $C_1$-$C_6$-alkyl, $C_1$-$C_6$-alkoxy, $C_1$-$C_6$-alkoxy-$C_1$-$C_6$-alkyl, $C_1$-$C_6$-alkylcarbonyl, $C_2$-$C_6$-alkenyl, $C_2$-$C_6$-alkynyl, $C_3$-$C_6$-cycloalkyl, aryl, hetaryl, $C_1$-$C_6$-arylalkyl, $C_1$-$C_6$-hetarylalkyl, aryloxy, hetaryloxy, sulphonyl, $C_1$-$C_6$-alkylthio, $C_1$-$C_6$-alkylsulphinyl, $C_1$-$C_6$-alkylsulphonyl, $C_1$-$C_6$-alkoxycarbonyl or $C_1$-$C_6$-alkylaminocarbonyl,
  where the substituents are each independently selected from halogen, nitro, cyano, $C_1$-$C_6$-alkyl, $C_1$-$C_6$-haloalkyl, $C_1$-$C_6$-alkoxy, $C_1$-$C_6$-haloalkoxy, $C_3$-$C_6$-cycloalkyl, $C_3$-$C_6$-cycloalkylcarbonyl, $C_1$-$C_6$-alkylthio, $C_1$-$C_6$-alkylsulphinyl, $C_1$-$C_6$-alkylsulphonyl, ($C_1$-$C_6$-alkoxy)carbonyl, $C_2$-$C_6$-alkenyl, $C_2$-$C_6$-alkynyl, $C_1$-$C_6$-alkylamino, $C_3$-$C_6$-cycloalkylamino, ($C_1$-$C_6$-alkyl)$C_3$-$C_6$-cycloalkylamino or di($C_1$-$C_4$)alkylamino, or A is a bivalent chemical moiety which is selected from the moieties —$NR^{13}C(=O)$—, —$NR^{13}C(=S)$—, —$C(R^{11})(R^{12})NR^{13}C(=O)$—, —$C(R^{11})(U)NR^{13}C(=O)$—, —$C(R^{11})(R^{12})N(U)C(=O)$—, —$C(R^{11})(R^{12})NR^{13}C(=S)$—, —$C(=O)NR^{13}$—, —$C(=O)NR^{13}CH_2$—, —$C(=S)NR^{13}$—, —$C(=S)NR^{13}CH_2$—, —$C(=O)NR^{13}C(R^{11})$—, —$C(R^{11})=N$—O—, —$C(NH_2)=N$—O—, —$C(R^{11})=N$—$OCH_2C(=O)NR^{13}$—, —$C(R^{11})(R^{12})NR^{13}C(=O)NR^{14}$—, —$C(R^{11})(R^{12})NR^{13}C(=O)CH_2S$—, —$NR^{13}(C=O)NR^{14}$—, —$C(=O)$—, —$C(=N$—O—$R^{13})$—, —$C(=O)O$—, —$C(=O)OCH_2C(=O)$—, —$C(=O)OCH2C(=O)NR^{13}$—, —$C(=O)NR^{13}CH_2C(=O)NR^{14}$—, —$C(=O)NR^{13}CH_2C(=O)$—, —$C(=O)NR^{13}CH_2C(=O)O$—, —$C(=O)NR^{13}NR^{14}C(=O)$—, —$C(=O)NR^{13}NR^{14}$—, —$N(R^{13})$—, —$C(R^{11})(R^{12})NR^{13}$—, —$S(=O)p$—, —$S(=O)_2NR^{13}$—, —$NR^{13}S(=O)_2$—, —$C(R^{11})(R^{12})NR^{13}S(=O)_2$—, —$SO(=N$—CN)—, —$S(=N$—CN)—, —$C(=O)NHS(=O)_2$—, —$C(=O)N(R^{13})$—O—, —$C(=O)CH(CN)$— or —$CH(CN)NR^{13}$—, where the first (left-hand) connection site in the bivalent chemical moieties is connected to the ring at one of positions $Q^4$ to $Q^8$ and the second (right-hand) connection site to Y, where U is an optionally substituted $C_2$-$C_4$-alkyl which, together with a carbon atom adjacent to the connection site of A to the ring at positions $Q^4$ to $Q^8$, forms a 5-7-membered ring,
  where the substituents are each independently selected from $C_1$-$C_3$-alkyl, $C_1$-$C_3$-alkoxy and halogen, and where p may assume the values of 0, 1 or 2, and where $R^{11}$ and $R^{12}$ are each independently hydrogen, cyano or optionally monosubstituted or identically or differently polysubstituted $C_1$-$C_4$-alkyl, or $C_3$-$C_6$-cycloalkyl,
  where the substituents are each independently selected from halogen, cyano, nitro, hydroxyl, $C_1$-$C_6$-alkyl and $C_1$-$C_6$-alkoxy, or $R^{11}$ and $R^{12}$ together are $C_2$-$C_5$-alkyl or $C_3$-$C_5$-alkenyl, which forms a 3-6-membered ring which may optionally contain 1 to two double bonds, or $R^{11}$ and $R^{13}$ together are $C_2$-$C_5$-alkyl or $C_3$-$C_5$-alkenyl, which forms a 3-7-membered ring which may optionally contain 1 to two double bonds, and where $R^{13}$ and $R^{14}$ are each independently hydrogen, optionally monosubstituted or identically or differently polysubstituted $C_1$-$C_6$-alkyl or $C_3$-$C_6$-cycloalkyl, $C_1$-$C_6$-alkylcarbonyl, $C_1$-$C_6$-alkoxycarbonyl or aryloxycarbonyl,
  where the substituents are each independently selected from halogen, cyano, nitro, hydroxyl, $C_1$-$C_6$-alkyl or $C_1$-$C_6$-alkoxy, or $R^{13}$ and $R^{14}$ together are $C_2$-$C_5$-alkyl or $C_3$-$C_5$-alkenyl, which forms a 3-7-membered ring which may optionally contain 1 to two double bonds, Y is hydrogen, optionally monosubstituted or identically or differently polysubstituted $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkenyl, aryl, hetaryl, heterocyclyl or oxoheterocyclyl,
  where the substituents are selected from halogen, nitro, cyano, hydroxyl, from optionally monosubstituted or identically or differently polysubstituted amino, $C_1$-$C_6$-alkyl, $C_2$-$C_6$-alkenyl, $C_2$-$C_6$-alkynyl, $C_3$-$C_6$-cycloalkyl, $C_1$-$C_6$-alkylcarbonyl, $C_1$-$C_6$-alkoxy, $C_1$-$C_6$-alkoxycarbonyl, $C_1$-$C_6$-alkylthio, $C_1$-$C_6$-alkylsulphinyl, $C_1$-$C_6$-alkylsulphonyl, $C_1$-$C_6$-alkoxycarbonyl, $C_1$-$C_6$-alkylaminocarbonyl, $C_1$-$C_6$-dialkylaminocarbonyl, $C_1$-$C_6$-alkylaminosulphonyl, $C_1$-$C_6$-alkylsulphonylamino, aryl, hetaryl, $C_1$-$C_6$-arylalkyl, $C_1$-$C_6$-hetarylalkyl, aryloxy, hetaryloxy or heterocyclyl, $C_1$-$C_6$-alkoxy, $C_1$-$C_6$-alkyl, $C_1$-$C_6$-alkylcarbonyl, sulphonyl, sulphinyl, $C_1$-$C_6$-alkylthio, or $C_1$-$C_6$-alkoxycarbonyl,
  where the substituents are each independently selected from halogen, $C_1$-$C_6$-alkyl, hydroxyl, amino, $C_1$-$C_6$-alkylcarbonyl, $C_1$-$C_6$-haloalkyl, $C_1$-$C_6$-alkoxy, $C_1$-$C_6$-haloalkoxy, $C_3$-$C_6$-cycloalkyl, $C_3$-$C_6$-cycloalkylcarbonyl, cyano, nitro, $C_1$-$C_6$-alkylthio, $C_1$-$C_6$-alkylsulphinyl, $C_1$-$C_6$-alkylsulphonyl, ($C_1$-$C_6$-alkoxy)carbonyl, $C_2$-$C_6$-alkenyl, $C_2$-$C_6$-alkynyl, $C_1$-$C_6$-alkylamino, $C_3$-$C_6$-cycloalkylamino, ($C_1$-$C_6$-alkyl)$C_3$-$C_6$-cycloalkylamino, di($C_1$-$C_4$)alkylamino or $C_1$-$C_6$-alkylaminocarbonyl, $Q^1$ to $Q^3$ are each independently a carbon atom which is substituted by hydrogen or by $R^1$, or is N, where the number of nitrogen atoms in $Q^1$ to $Q^3$ is not more than 2, $Q^4$ is a carbon atom which is substituted by hydrogen or $R^6$ or which is bonded to V, in which case V is not $R^4$, or is N, $Q^5$ to $Q^8$ are each independently a carbon atom which is substituted by hydrogen, $R^6$ or A-Y, or is N, where the number of nitrogen atoms in $Q^4$ to $Q^8$ is not more than 2, where exactly one of $Q^5$, $Q^6$, $Q^7$, $Q^8$ is substituted by A-Y, and also salts and N-oxides of compounds of the formula (I), and the use thereof for controlling animal pests.

The compounds of the formula (I) may, if appropriate, be present in different polymorphic forms or as a mixture of different polymorphic forms. Both the pure polymorphs and the polymorph mixtures form part of the subject-matter of the invention, and can be used in accordance with the invention.

The compounds of the formula (I) include any diastereomers or enantiomers present, and also E/Z isomers.

The substituted acrylamides are defined in general terms by the formula (I). Preferred radical definitions of the formulae above and specified below are given hereinafter. These definitions apply equally to the end products of the formula (I) and to all intermediates.

Preferred, more preferred and most preferred compounds of the formula (I), and preferred, more preferred and most preferred methods for controlling pests using compounds of the formula (I), are considered to be those where $R^1$ is preferably hydrogen, halogen, nitro, cyano, optionally monosubstituted or identically or differently polysubstituted $C_1$-$C_4$-alkyl, $C_2$-$C_6$-alkenyl, $C_2$-$C_4$-alkynyl, $C_1$-$C_4$-alkoxy, $C_1$-$C_4$-alkylthio, $C_1$-$C_4$-alkylsulphinyl, $C_1$-$C_4$-alkylsulphonyl, $C_3$-$C_4$-cycloalkyl, $C_1$-$C_4$-alkylcarbonyl, $C_1$-$C_4$-alkoxycarbonyl, $C_1$-$C_4$-alkylaminocarbonyl, $C_1$-$C_4$-dialkylaminocarbonyl or $C_1$-$C_4$-alkylaminosulphonyl, where the substituents are each independently selected from halogen, cyano, nitro, hydroxyl, $C_1$-$C_4$-alkyl, $C_1$-$C_4$-alkoxy, $C_3$-$C_4$-cycloalkyl, $C_1$-$C_4$-haloalkoxy and $C_1$-$C_4$-alkylthio, n is preferably 1, 2 or 3, $R^2$ is preferably hydrogen, cyano, hydroxyl, amino, optionally monosubstituted to identically or differently trisubstituted $C_1$-$C_4$-alkyl, $C_2$-$C_4$-alkenyl, $C_2$-$C_4$-alkynyl, $C_1$-$C_4$-alkoxy or $C_3$-$C_6$-cycloalkyl, where the substituents are each independently selected from halogen, cyano, nitro, hydroxyl, amino, $C_1$-$C_4$-alkyl and $C_1$-$C_4$-alkoxy, $R^3$ is preferably hydrogen, optionally monosubstituted or identically or differently polysubstituted $C_1$-$C_4$-alkyl, $C_2$-$C_4$-alkenyl, $C_2$-$C_4$-alkynyl, $C_3$-$C_4$-cycloalkyl, aryl-$C_1$-$C_4$-alkyl, $C_1$-$C_4$-alkylcarbonyl, $C_1$-$C_4$-alkylsulphonyl, arylcarbonyl, hetarylcarbonyl, $C_1$-$C_4$-alkoxycarbonyl or aryloxycarbonyl, where the substituents are each independently selected from halogen, cyano, nitro, hydroxyl, $C_1$-$C_6$-alkyl, $C_1$-$C_6$-alkoxy, $C_3$-$C_6$-cycloalkyl, $C_1$-$C_6$-haloalkoxy, $C_1$-$C_6$-alkylthio, $C_1$-$C_4$-alkoxycarbonyl, aminocarbonyl, $C_1$-$C_4$-alkylaminocarbonyl and $C_1$-$C_4$-dialkylaminocarbonyl, V is preferably $R^4$, or is a bivalent chemical moiety which is selected from —O—, —S—, —N($R^8$)—, —C($R^9$)=N—, —N=C($R^9$)— and)—C($R^9$)=C($R^{10}$)— and which is bonded to $Q^4$ via a single bond, where the second (right-hand) connection site in each case is connected to $Q^4$, where $R^4$ is preferably hydrogen, halogen or optionally monosubstituted or identically or differently polysubstituted $C_1$-$C_4$-alkyl, where the substituents are each independently selected from halogen, $C_1$-$C_4$-alkyl and $C_1$-$C_4$-alkoxy, $R^8$ is preferably hydrogen, cyano, hydroxyl, optionally monosubstituted or identically or differently polysubstituted $C_1$-$C_4$-alkyl, $C_2$-$C_6$-alkenyl, $C_2$-$C_6$-alkynyl, $C_3$-$C_6$-cycloalkyl, $C_1$-$C_4$-alkoxy, $C_1$-$C_6$-alkoxycarbonyl, arylalkyl, or $C_1$-$C_4$-alkylcarbonyl, where the substituents are each independently selected from halogen, cyano, nitro, hydroxyl, $C_1$-$C_6$-alkyl, $C_1$-$C_6$-alkoxy, $C_1$-$C_4$-alkoxycarbonyl, aminocarbonyl, $C_1$-$C_4$-alkylaminocarbonyl or $C_1$-$C_4$-dialkylaminocarbonyl and aryl-$C_1$-$C_4$-alkoxy, $R^9$ and $R^{10}$ are preferably each independently hydrogen, halogen or optionally monosubstituted or identically or differently polysubstituted $C_1$-$C_4$-alkyl, where the substituents are each independently selected from halogen, cyano and $C_1$-$C_6$-alkyl, $R^5$ is preferably hydrogen, halogen or optionally monosubstituted or identically or differently polysubstituted $C_1$-$C_4$-alkyl, where the substituents are each independently selected from halogen, $C_1$-$C_4$-alkyl or $C_1$-$C_4$-alkoxy, $R^6$ is preferably hydrogen, halogen, nitro, cyano, amino, hydroxyl, optionally monosubstituted or identically or differently polysubstituted $C_1$-$C_4$-alkyl, $C_2$-$C_4$-alkenyl, $C_2$-$C_4$-alkynyl, $C_3$-$C_5$-cycloalkyl, $C_1$-$C_4$-alkoxy, ($C_1$-$C_4$-alkoxy)carbonyl, $C_1$-$C_4$-alkylamino, formyl, ($C_1$-$C_4$-alkyl)carbonyl, $C_1$-$C_4$-alkoxyimino-$C_1$-$C_4$-alkyl, $C_1$-$C_4$-dialkylamino, ($C_1$-$C_4$-alkylamino)carbonyl, ($C_1$-$C_4$-dialkylamino)carbonyl, $C_1$-$C_4$-alkylthio, $C_1$-$C_4$-alkylsulphinyl, $C_1$-$C_4$-alkylsulphonyl, $C_1$-$C_4$-alkylaminosulphonyl or $C_1$-$C_4$-alkylsulphonylamino, where the substituents are each independently selected from halogen, cyano, nitro, hydroxyl, amino, $C_1$-$C_6$-alkyl, $C_1$-$C_6$-alkoxy, $C_3$-$C_6$-cycloalkyl, $C_1$-$C_6$-haloalkoxy and $C_1$-$C_6$-alkylthio, or $R^6$ is preferably a $C_1$-$C_4$ carbon chain which optionally contains 1-2 heteroatoms from the group of N, S, O, which is bonded to two adjacent ring positions $Q^4$ to $Q^8$ and which forms an aliphatic, aromatic or heteroaromatic ring which is optionally mono- or polysubstituted by $C_1$-$C_6$-alkyl or halogen, in which case m is 2, m is preferably 0, 1, 2, 3, X is preferably $C_1$-$C_4$-haloalkyl or $C_3$-$C_5$-halocycloalkyl, which is optionally additionally mono- to trisubstituted by hydroxyl, cyano or $C_1$-$C_4$-alkoxy, W is preferably O or S, A-Y together are preferably cyano or are optionally mono- or polysubstituted heterocyclyl or oxoheterocyclyl from the group of pyrrolyl, oxazolyl, isoxazolyl, thiazolyl, isothiazolyl, pyrazolyl, imidazolyl, 1,2,3-triazolyl, 1,2,4-triazolyl, 1,2,3-oxadiazolyl, 1,2,4-oxadiazolyl, 1,3,4-oxadiazolyl, 1,2,3-thiadiazolyl, 1,2,4-thiadiazolyl, 1,3,4-thiadiazolyl, tetrazolyl, pyridyl, pyrimidinyl, pyridazinyl, pyrazinyl, 1,2,4-triazinyl, 1,3,5-triazinyl, pyrrolidinyl, isoxazolidinyl, pyrazolidinyl, oxazolidinyl, thiazolidinyl, imidazolidinyl, imidazolidinyl, 1,2,4-oxadiazolidinyl, 1,2,4-thiadiazolidinyl, 1,2,4-triazolidinyl, 1,3,4-oxadiazolidinyl, 1,3,4-thiadiazolidinyl, 1,3,4-triazolidinyl, pyrrolinyl, isoxazolinyl, 2,3-dihydropyrazolyl, 3,4-dihydropyrazolyl, 4,5-dihydropyrazolyl, 2,3-dihydrooxazolyl, 3,4-dihydrooxazolyl, piperidinyl, oxopyrrolidinyl, 3-oxo-1,2,4-triazolidinyl, 5-oxo-1,2,4-triazolidinyl, dioxopyrrolidinyl, oxomorpholinyl, oxopiperidinyl and oxopiperazinyl, where the substituents are selected from halogen, nitro, cyano, amino, hydroxyl, from optionally monosubstituted or identically or differently polysubstituted amino, $C_1$-$C_6$-alkyl, $C_1$-$C_6$-alkoxy, $C_1$-$C_6$-alkoxy-$C_1$-$C_6$-alkyl, $C_1$-$C_6$-alkylcarbonyl, $C_2$-$C_6$-alkenyl, $C_2$-$C_6$-alkynyl, $C_3$-$C_6$-cycloalkyl, aryl, hetaryl, $C_1$-$C_6$-arylalkyl, $C_1$-$C_6$-hetarylalkyl, aryloxy, hetaryloxy, $C_1$-$C_6$-alkylthio, $C_1$-$C_6$-alkylsulphinyl, $C_1$-$C_6$-alkylsulphonyl, $C_1$-$C_6$-alkoxycarbonyl and, $C_1$-$C_6$-alkylaminocarbonyl, where the substituents are each independently selected from halogen, nitro, cyano, $C_1$-$C_6$-alkyl, $C_1$-$C_6$-haloalkyl, $C_1$-$C_6$-alkoxy, $C_1$-$C_6$-haloalkoxy, $C_3$-$C_6$-cycloalkyl, $C_3$-$C_6$-cycloalkylcarbonyl, $C_1$-$C_6$-alkylthio, $C_1$-$C_6$-alkylsulphinyl, $C_1$-$C_6$-alkylsulphonyl, ($C_1$-$C_6$-alkoxy)carbonyl, $C_2$-$C_6$-alkenyl, $C_2$-$C_6$-alkynyl, $C_1$-$C_6$-alkylamino, $C_3$-$C_6$-cycloalkylamino, ($C_1$-$C_6$-alkyl)$C_3$-$C_6$-cycloalkylamino or di($C_1$-$C_4$)alkylamino, or A is preferably a bivalent chemical moiety which is selected from the moieties —$NR^{13}C(=O)$—, —$NR^{13}C(=S)$—, —$C(R^{11})(R^{12})NR^{13}C(=O)$—, —$C(R^{11})(U)NR^{13}C(=O)$—, —$C(R^{11})(R^{12})NR^{13}C(=S)$—, —$C(=O)NR^{13}$—, —$C(=O)N(R^{13})$—O—, —$C(=O)NR^{13}CH_2$—, —$C(=S)NR^{13}$—, —$C(=S)NR^{13}CH_2$—, —$C(=O)NR^{13}CH=N$—O—, —$C(R^{11})=N$—O—, —$C(NH2)=N$—O—, —$C(R^{11})=N$—$OCH_2C(=O)NR^{13}$—, —$C(R^{11})(R^{12})NR^{13}C(=O)NR^{14}$—, —$C(R^{11})(R^{12})NR^{13}C(=O)CH_2S$—, —$NR^{13}(C=O)NR^{14}$—, —$C(=O)$—, —$C(=N$—O—$R^{13})$—, —$C(=O)O$—, —$C(=O)OCH2C(=O)NR^{13}$—, —$C(=O)OCH_2C(=O)NH$—, —$C(=O)NR^{13}CH_2C(=O)NR^{14}$—, —$C(=O)NR^{13}CH_2C(=O)$—, —$C(=O)NR^{13}CH_2C(=O)O$—, —$C(=O)NR^{13}NR^{14}C(=O)$—, —$C(=O)NR^{13}NR^{14}$—, —$N(R^{13})$—, —$C(R^{11})(R^{12})NR^{13}$—, —$S(=O)_p$—, —$S(=O)_2NR^{13}$—, —$NR^{13}S(=O)_2$—, —$C(R^{11})(R^{12})NR^{13}S(=O)_2$—, —$C(=O)CH(CN)$— or —$CH(CN)NR^{13}$—, where the first (left-hand) connection site in the bivalent chemical moieties is connected to the ring at one of positions $Q^4$ to $Q^8$ and the second (right-hand) connection site to Y, where p may preferably assume the values of 0, 1 or 2, and where U is preferably an optionally substituted $C_2$-$C_4$-alkyl which, together with a carbon atom adjacent to the connection site of A on the ring at positions $Q^4$ to $Q^8$, forms a 5-6-membered ring, where the substituents are each independently selected from halogen, $C_1$-$C_3$-alkyl and $C_1$-$C_3$-alkoxy, and where $R^{11}$ and $R^{12}$ are preferably each independently hydrogen, cyano or optionally monosubstituted to identically or differently trisubstituted $C_1$-$C_4$-alkyl or $C_3$-$C_6$-cycloalkyl, where the substituents are each independently selected from halogen, cyano, nitro, hydroxyl, $C_1$-$C_6$-alkyl or $C_1$-$C_6$-alkoxy, or $R^{11}$ and $R^{12}$ together are $C_2$-$C_5$-alkyl or $C_3$-$C_5$-alkenyl, which forms a 3-6-membered ring which may optionally contain 1 to two double bonds, or $R^{11}$ and $R^{13}$ together are $C_2$-$C_5$-alkyl or $C_3$-$C_5$-alkenyl, which forms a 3-7-membered ring which may optionally contain 1 to two double bonds, and where $R^{13}$ and $R^{14}$ are each preferably independently hydrogen, optionally monosubstituted or identically or differently polysubstituted $C_1$-$C_4$-alkyl or $C_3$-$C_6$-cycloalkyl, $C_1$-$C_4$-alkylcarbonyl, $C_1$-$C_4$-alkoxycarbonyl or aryloxycarbonyl, where the substituents are each independently selected from halogen, cyano, nitro, hydroxyl, $C_1$-$C_4$-alkyl and $C_1$-$C_4$-alkoxy, or $R^{13}$ and $R^{14}$ together are $C_2$-$C_5$-alkyl or $C_3$-$C_5$-alkenyl, which forms a 3-7-membered ring which may optionally contain 1 to two double bonds, Y is preferably hydrogen or optionally monosubstituted or identically or differently polysubstituted $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkenyl, is an optionally monosubstituted or identically or differently polysubstituted phenyl or is an optionally monosubstituted or polysubstituted heterocycle from the group of thienyl, furanyl, pyrrolyl, oxazolyl, isoxazolyl, thiazolyl, isothiazolyl, pyrazolyl, imidazolyl, 1,2,3-triazolyl, 1,2,4-triazolyl, 1,2,3-oxadiazolyl, 1,2,4-oxadiazolyl, 1,3,4-oxadiazolyl, 1,2,3-thiadiazolyl, 1,2,4-thiadiazolyl, 1,3,4-thiadiazolyl, tetrazolyl, pyridinyl, pyrimidinyl, pyridazinyl, pyrazinyl, 1,2,4-triazinyl, 1,3,5-triazinyl, pyrrolidinyl, isoxazolidinyl, pyrazolidinyl, oxazolidinyl, thiazolidinyl, imidazolidinyl, 1,2,4-oxadiazolidinyl, 1,2,4-thiadiazolidinyl, 1,2,4-triazolidinyl, 1,3,4-oxadiazolidinyl, 1,3,4-thiadiazolidinyl, 1,3,4-triazolidinyl, pyrrolinyl, isoxazolinyl, 2,3-dihydropyrazolyl, 3,4-dihydropyrazolyl, 4,5-dihydropyrazolyl, 2,3-dihydrooxazolyl, 3,4-dihydrooxazolyl, piperidinyl, tetrahydrothienyl, piperazinyl, morpholinyl, thiomorpholinyl, dihydropyranyl, tetrahydropyranyl, tetrahydrothienyl, 1,4-dioxanyl, 1,3-dioxanyl, dioxolanyl, dioxolyl, tetrahydrofuranyl, dihydrofuranyl, oxetanyl, thietanyl, oxidothietanyl, dioxidothietanyl, oxiranyl, azetidinyl, oxazetidinyl, oxaziridinyl, oxazepanyl, oxazinanyl, azepanyl, oxopyrrolidinyl, dioxopyrrolidinyl, oxomorpholinyl, oxopiperidinyl, oxopiperazinyl or oxotetrahydrofuranyl, where the substituents are selected from halogen, nitro, cyano, hydroxyl, from optionally monosubstituted or identically or differently polysubstituted amino, $C_1$-$C_6$-alkyl, $C_1$-$C_6$-alkoxy, $C_1$-$C_6$-alkoxy-$C_1$-$C_6$-alkyl, $C_1$-$C_6$-alkylcarbonyl, $C_2$-$C_6$-alkenyl, $C_2$-$C_6$-alkynyl, $C_3$-$C_6$-cycloalkyl, aryl, hetaryl, $C_1$-$C_6$-arylalkyl, $C_1$-$C_6$-hetarylalkyl, aryloxy, hetaryloxy, $C_1$-$C_6$-alkylthio, $C_1$-$C_6$-alkylsulphinyl, $C_1$-$C_6$-alkylsulphonyl, $C_1$-$C_6$-alkoxycarbonyl or heterocyclyl, where the substituents may each independently be selected from halogen, nitro, hydroxyl, amino, cyano, $C_1$-$C_6$-alkyl, $C_1$-$C_6$-alkylcarbonyl, $C_1$-$C_6$-haloalkyl, $C_1$-$C_6$-alkoxy, $C_1$-$C_6$-haloalkoxy, $C_3$-$C_6$-cycloalkyl, $C_3$-$C_6$-cycloalkylcarbonyl, $C_1$-$C_6$-alkylthio, $C_1$-$C_6$-alkylsulphinyl, $C_1$-$C_6$-alkylsulphonyl, ($C_1$-$C_6$-alkoxy)carbonyl, $C_2$-$C_6$-alkenyl, $C_2$-$C_6$-alkynyl, $C_1$-$C_6$-alkylamino, $C_3$-$C_6$-cycloalkylamino, ($C_1$-$C_6$-alkyl)$C_3$-$C_6$-cycloalkylamino, di($C_1$-$C_4$)alkylamino or $C_1$-$C_6$-alkylaminocarbonyl, $Q^1$ to $Q^3$ are preferably each independently a carbon atom which is substituted by hydrogen or by $R^1$, or is N, where the number of nitrogen atoms in $Q^1$ to $Q^3$ is not more than 2, $Q^4$ is preferably a carbon atom which is substituted by hydrogen or $R^6$ or which is bonded to V, in which case V is not $R^4$, or is N, $Q^5$ to $Q^8$ are preferably each independently a carbon atom which is substituted by hydrogen, $R^6$ or A-Y, or is N, where the number of nitrogen atoms in $Q^4$ to $Q^8$ is not more than 2, where exactly one of $Q^5$, $Q^6$, $Q^7$, $Q^8$ is substituted by A-Y, $R^1$ is more preferably hydrogen, halogen, nitro, cyano, optionally monosubstituted or identically or differently polysubstituted $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_1$-$C_4$-alkylcarbonyl, $C_1$-$C_4$-alkoxycarbonyl, $C_1$-$C_4$-alkylaminocarbonyl, $C_1$-$C_4$-dialkylaminocarbonyl or $C_1$-$C_4$-alkylaminosulphonyl, where the substituents are each independently selected from halogen, cyano, nitro, hydroxyl, $C_1$-$C_4$-alkyl, $C_1$-$C_4$-alkoxy, $C_3$-$C_4$-cycloalkyl, $C_1$-$C_4$-haloalkoxy or $C_1$-$C_4$-alkylthio, n is more preferably 1, 2 or 3, $R^2$ is more preferably hydrogen, cyano, hydroxyl, optionally monosubstituted to identically or differently trisubstituted $C_1$-$C_4$-alkyl or $C_1$-$C_4$-alkoxy, where the substituents are each independently selected from halogen, cyano, nitro, hydroxyl, amino, $C_1$-$C_4$-alkyl and $C_1$-$C_4$-alkoxy, $R^3$ is more preferably hydrogen, optionally monosubstituted or identically or differently polysubstituted $C_1$-$C_4$-alkyl, $C_2$-$C_4$-alkenyl, $C_2$-$C_4$-alkynyl, $C_1$-$C_4$-alkylcarbonyl, $C_1$-$C_4$-alkylsulphonyl, $C_1$-$C_4$-alkoxycarbonyl or aryloxycarbonyl, where the substituents are each independently selected from halogen, cyano, nitro, hydroxyl, $C_1$-$C_6$-alkyl, $C_1$-$C_6$-alkoxy or $C_1$-$C_4$-alkoxycarbonyl, V is more preferably $R^4$, or is a bivalent chemical moiety which is selected from —O—, S and —N($R^8$)— and which is bonded to $Q^4$ via a single bond, where $R^4$ is more preferably hydrogen or optionally monosubstituted to identically or differently trisubstituted $C_1$-$C_4$-alkyl, where the substituents are each independently selected from halogen, $C_1$-$C_4$-alkyl and $C_1$-$C_4$-alkoxy, $R^8$ is more preferably hydrogen, cyano, hydroxyl, optionally monosubstituted or identically or differently polysubstituted $C_1$-$C_4$-alkyl, $C_2$-$C_4$-alkenyl, $C_3$-$C_4$-alkynyl, aryl-$C_1$-$C_4$-alkyl, $C_1$-$C_4$-alkoxy, $C_1$-$C_6$-alkoxycarbonyl or $C_1$-$C_4$-alkylcarbonyl, where the substituents are each independently selected from halogen, cyano, nitro, hydroxyl, $C_1$-$C_6$-alkyl, $C_1$-$C_6$-alkoxy, $C_1$-$C_4$-alkoxycarbonyl, aminocarbonyl, $C_1$-$C_4$-alkylaminocarbonyl, $C_1$-$C_4$-dialkylaminocarbonyl or aryl-$C_1$-$C_4$-alkoxy, $R^5$ is more preferably hydrogen, or optionally monosubstituted to identically or differently trisubstituted $C_1$-$C_4$-alkyl, where the substituents are each independently selected from halogen, $C_1$-$C_4$-alkyl or $C_1$-$C_4$-alkoxy, $R^6$ is more preferably hydrogen, halogen, nitro, cyano, optionally monosubstituted or identically or differently polysubstituted $C_1$-$C_4$-alkyl, $C_2$-$C_4$-alkynyl, $C_1$-$C_4$-alkoxy, ($C_1$-$C_4$-alkyl)carbonyl, ($C_1$-$C_4$-alkylamino)carbonyl, ($C_1$-$C_4$-dialkylamino)carbonyl, $C_1$-$C_4$-alkylthio, $C_1$-$C_4$-alkylsulphinyl, $C_1$-$C_4$-alkylsulphonyl, $C_1$-$C_4$-alkylaminosulphonyl or $C_1$-$C_4$-alkylsulphonylamino, where the substituents are each independently selected from halogen, cyano, nitro, $C_1$-$C_6$-alkyl, $C_1$-$C_6$-alkoxy, $C_1$-$C_6$-haloalkoxy and $C_1$-$C_6$-alkylthio, or $R^6$ is more preferably —OCH$_2$O—, —OCF$_2$O—, —OCH$_2$CH$_2$O—, —OCF$_2$CF$_2$O— or —CH=CH—CH=CH—, where the substituents form a ring, in each case via two adjacent radicals selected from $Q^4$ to $Q^8$, m is more preferably 0, 1, 2, 3, X is more preferably $C_1$-$C_4$-haloalkyl or $C_3$-$C_5$-halocycloalkyl, which is optionally additionally mono- to trisubstituted by hydroxyl, cyano or $C_1$-$C_4$-alkoxy, W is more preferably O, A-Y together are more preferably cyano or are optionally mono- or polysubstituted heterocyclyl from the group of pyrrolyl, oxazolyl, isoxazolyl, thiazolyl, isothiazolyl, pyrazolyl, imidazolyl, 2-imidazolinyl, 1,2,3-triazolyl, 1,2,4-triazolyl, 1,2,3-oxadiazolyl, 1,2,4-oxadiazolyl, 1,3,4-oxadiazolyl, 1,2,3-thiadiazolyl, 1,2,4-thiadiazolyl, 1,3,4-thiadiazolyl, tetrazolyl, pyridyl, pyrimidinyl, pyridazinyl, pyrazinyl, 1,2,4-triazinyl and 1,3,5-triazinyl, where the substituents are selected from halogen, nitro, cyano, hydroxyl, from optionally monosubstituted or identically or differently polysubstituted amino, $C_1$-$C_4$-alkyl, $C_1$-$C_4$-alkoxy, $C_1$-$C_4$-alkoxy-$C_1$-$C_4$-alkyl, $C_2$-$C_4$-alkynyl, $C_1$-$C_6$-alkylthio, $C_1$-$C_6$-alkylsulphinyl, $C_1$-$C_6$-alkylsulphonyl, $C_3$-$C_6$-cycloalkyl, aryl and hetaryl, where the substituents are each independently selected from halogen, hydroxyl, amino, nitro, cyano, $C_1$-$C_6$-alkyl, $C_1$-$C_6$-haloalkyl, $C_1$-$C_6$-alkoxy, $C_1$-$C_6$-haloalkoxy, $C_3$-$C_6$-cycloalkyl, $C_3$-$C_6$-cycloalkylcarbonyl, $C_1$-$C_6$-alkylthio, $C_1$-$C_6$-alkylsulphinyl, $C_1$-$C_6$-alkylsulphonyl, ($C_1$-$C_6$-alkoxy)carbonyl, $C_2$-$C_6$-alkenyl, $C_2$-$C_6$-alkynyl, $C_1$-$C_6$-alkylamino, $C_3$-$C_6$-cycloalkylamino, ($C_1$-$C_6$-alkyl)$C_3$-$C_6$-cycloalkylamino, di($C_1$-$C_4$)alkylamino or $C_1$-$C_6$-alkylaminocarbonyl, A is more preferably a bivalent chemical moiety which is selected from the moieties —NR$^{13}$C(=O)—, —C(R$^{11}$)(R$^{12}$)NR$^{13}$C(=O)—, —C(=O)O—, —C(R$^{11}$)(U)NR$^{13}$C(=O)—, —C(R$^{11}$)(R$^{12}$)N(U)C(=O)—, —C(=O)NR$^{13}$—, —C(=O)N(R$^{13}$)—O—, —C(=O)NR$^{13}$CH$_2$—, —C(=O)NR$^{13}$CH=N—O—, —C(R$^{11}$)=N—O—, —C(R$^{11}$)=N—OCH$_2$C(=O)NR$^{13}$—, —C(R$^{11}$)(R$^{12}$)NR$^{13}$C(=O)NR$^{14}$—, —C(R$^{11}$)(R$^{12}$)NR$^{13}$C(=O)CH$_2$S—, —NR$^{13}$(C=O)NR$^{14}$—, —C(=O)—, —C(=N—O—R$^{13}$)—, —C(=O)NR$^{13}$CH$_2$C(=O)NR$^{14}$—, —C(=O)NR$^{13}$CH$_2$C(=O)—, —C(=O)NR$^{13}$CH$_2$C(=O)O—, —C(=O)NR$^{13}$NR$^{14}$C(=O)—, —C(=O)NR$^{13}$NR$^{14}$—, —N(R$^{13}$)—, —C(R$^{11}$)(R$^{12}$)NR$^{13}$—, —S(=O)$_p$—, —S(=O)$_2$NR$^{13}$—, —NR$^{13}$S(=O)$_2$—, —C(R$^{11}$)(R$^{12}$)NR$^{13}$S(=O)$_2$—, C(=O)CH(CN)— or —CH(CN)NR$^{13}$—, where the first (left-hand) connection site in the bivalent chemical moieties is connected to the ring at one of positions $Q^4$ to $Q^8$ and the second (right-hand) connection site to Y, where p may more preferably assume the values of 0, 1 or 2; and where U is more preferably an optionally substituted $C_2$-$C_4$-alkyl which, together with a carbon atom adjacent to the connection site of A on the ring at positions $Q^4$ to $Q^8$, forms a 5-6-membered ring, where the substituents are each independently selected from $C_1$-$C_3$-alkyl and halogen, and where $R^{11}$ and $R^{12}$ are more preferably each independently hydrogen, $C_1$-$C_4$-alkyl or $C_1$-$C_4$-haloalkyl, or $R^{11}$ and $R^{12}$ together are $C_2$-$C_5$-alkyl or $C_3$-$C_5$-alkenyl, which forms a 3-6-membered ring which may optionally contain 1 to two double bonds, or $R^{11}$ and $R^{12}$ together are $C_2$-$C_5$-alkyl or $C_3$-$C_5$-alkenyl, which forms a 3-7-membered ring which may optionally contain 1 to two double bonds, and where $R^{13}$ and $R^{14}$ are more preferably each independently hydrogen, optionally monosubstituted or identically or differently polysubstituted $C_1$-$C_4$-alkyl or $C_3$-$C_6$-cycloalkyl, $C_1$-$C_4$-alkylcarbonyl, aryloxycarbonyl or $C_1$-$C_4$-alkoxycarbonyl,
   where the substituents are each independently selected from halogen, cyano, $C_1$-$C_4$-alkyl and $C_1$-$C_4$-alkoxy,
or
$R^{13}$ and $R^{14}$ together are $C_2$-$C_5$-alkyl or $C_3$-$C_5$-alkenyl, which forms a 3-7-membered ring which may optionally contain 1 to two double bonds,
Y is more preferably hydrogen or optionally monosubstituted or identically or differently polysubstituted $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkenyl, is an optionally monosubstituted or identically or differently polysubstituted phenyl or is an optionally mono- or polysubstituted heterocycle from the group of thienyl, furanyl, pyrrolyl, oxazolyl, isoxazolyl, thiazolyl, isothiazolyl, pyrazolyl, imidazolyl, 1,2,3-triazolyl, 1,2,4-triazolyl, 1,2,3-oxadiazolyl, 1,2,4-oxadiazolyl, 1,3,4-oxadiazolyl, 1,2,3-thiadiazolyl, 1,2,4-thiadiazolyl, 1,3,4-thiadiazolyl, tetrazolyl, pyridinyl, pyrimidinyl, pyridazinyl, pyrazinyl, 1,2,4-triazinyl, 1,3,5-triazinyl, piperazinyl, morpholinyl, tetrahydropyranyl, 1,4-dioxanyl, 1,3-dioxanyl, dioxolanyl, dioxolyl, tetrahydrofuranyl, dihydrofuranyl, oxetanyl, thietanyl, oxidothietanyl, dioxidothietanyl, oxiranyl, azetidinyl, oxazetidinyl, oxazepanyl, oxazinanyl, azepanyl, oxopyrrolidinyl, dioxopyrrolidinyl, oxomorpholinyl, oxopiperidinyl, oxopiperazinyl and oxotetrahydrofuranyl,
   where the substituents are selected from halogen, nitro, cyano, hydroxyl, from optionally monosubstituted or identically or differently polysubstituted amino, $C_1$-$C_6$-alkyl, $C_1$-$C_6$-alkoxy, $C_1$-$C_6$-alkoxy-$C_1$-$C_6$-alkyl, $C_1$-$C_6$-alkylcarbonyl, $C_2$-$C_6$-alkenyl, $C_2$-$C_6$-alkynyl, $C_3$-$C_6$-cycloalkyl, aryl, hetaryl, $C_1$-$C_6$-arylalkyl, $C_1$-$C_6$-hetarylalkyl, aryloxy, hetaryloxy, $C_1$-$C_6$-alkylsulphinyl, $C_1$-$C_6$-alkylsulphonyl, $C_1$-$C_6$-alkylthio, $C_1$-$C_6$-alkoxycarbonyl and heterocyclyl,
   where the substituents may each independently be selected from halogen, nitro, hydroxyl, amino, cyano, $C_1$-$C_6$-alkyl, $C_1$-$C_6$-alkylcarbonyl, $C_1$-$C_6$-haloalkyl, $C_1$-$C_6$-alkoxy, $C_1$-$C_6$-haloalkoxy, $C_3$-$C_6$-cycloalkyl, $C_3$-$C_6$-cycloalkylcarbonyl, $C_1$-$C_6$-alkylthio, $C_1$-$C_6$-alkylsulphinyl, $C_1$-$C_6$-alkylsulphonyl, ($C_1$-$C_6$-alkoxy)carbonyl, $C_2$-$C_6$-alkenyl, $C_2$-$C_6$-alkynyl, $C_1$-$C_6$-alkylamino, $C_3$-$C_6$-cycloalkylamino, ($C_1$-$C_6$-alkyl)$C_3$-$C_6$-cycloalkylamino, di($C_1$-$C_4$)alkylamino and $C_1$-$C_6$-alkylaminocarbonyl,
$Q^1$ to $Q^3$ are more preferably each independently a carbon atom which is substituted by hydrogen or by $R^1$, or is N, where the number of nitrogen atoms in $Q^1$ to $Q^3$ is not more than 1,
$Q^4$ is more preferably a carbon atom which is substituted by hydrogen or $R^6$ or which is bonded to V, in which case V is not $R^4$, or is N,
$Q^5$ to $Q^8$ are more preferably each independently a carbon atom which is substituted by hydrogen, $R^6$ or A-Y, or is N, where the number of nitrogen atoms in $Q^4$ to $Q^8$ is not more than 1, where exactly one of $Q^5$, $Q^6$, $Q^7$, $Q^8$ is substituted by A-Y,
$R^1$ is most preferably hydrogen, nitro, cyano, fluorine, chlorine, bromine, iodine, methyl, ethyl, n- or i-propyl, fluoromethyl, chloromethyl, trichloromethyl, difluoromethyl, dichlorofluoromethyl, chlorodifluoromethyl, trifluoromethyl, fluoroethyl, chloroethyl, difluoroethyl, dichloroethyl, trifluoroethyl, chlorofluoroethyl, chlorodifluoroethyl, fluorodichloroethyl, tetrafluoroethyl, pentafluoroethyl, chlorotetrafluoroethyl, trichloroethyl, heptafluoro-n-propyl, heptafluoroisopropyl, methoxy, ethoxy, n- or i-propoxy, fluoromethoxy, difluoromethoxy, trifluoromethoxy, methylthio, ethylthio, difluoromethylthio, trifluoromethylthio, chlorodifluoromethylthio, methylsulphinyl, trifluoromethylsulphinyl, trifluoromethylsulphonyl, methylsulphonyl, ethylsulphonyl, acetyl, propionyl, methoxycarbonyl, ethoxycarbonyl, methylaminocarbonyl, dimethylaminocarbonyl or ethylaminocarbonyl,
n is most preferably 1, 2 or 3,
$R^2$ is most preferably hydrogen, methyl or ethyl,
$R^3$ is most preferably hydrogen, methyl, ethyl, 2-ethynyl, 2-propenyl, methoxymethyl, ethoxymethyl, methylcarbonyl, ethylcarbonyl, methoxycarbonyl, ethoxycarbonyl, n-propoxycarbonyl, i-propoxycarbonyl, n-butoxycarbonyl, t-butoxycarbonyl or phenoxycarbonyl,
V is most preferably $R^4$, or is —O— or —N($R^8$)—, and is bonded to $Q^4$ via a single bond, where
$R^4$ is most preferably hydrogen or methyl, and
$R^8$ is most preferably hydrogen, methyl, ethyl, methylcarbonyl, ethylcarbonyl, methoxymethyl, ethoxymethyl, cyanomethyl, cyanoeth-2-yl, propyl, phenylmethyl, prop-2-en-1-yl, prop-2-yn-1-yl, benzyloxy, methoxycarbonyl, ethoxycarbonyl, methoxycarbonylmethyl, ethoxycarbonylmethyl, methoxycarbonyleth-2-yl, ethoxycarbonyleth-2-yl, amidomethyl, amidoethyl or amidoprop-3-yl,
$R^5$ is most preferably hydrogen,
$R^6$ is most preferably hydrogen, nitro, cyano, fluorine, chlorine, bromine, iodine, methyl, ethyl, n- or i-propyl, n-, i-, s- or t-butyl, ethynyl, propynyl, fluoromethyl, chloromethyl, trichloromethyl, difluoromethyl, dichlorofluoromethyl, chlorodifluoromethyl, trifluoromethyl, fluoroethyl, chloroethyl, difluoroethyl, dichloroethyl, trifluoroethyl, chlorofluoroethyl, chlorodifluoroethyl, fluorodichloroethyl, tetrafluoroethyl, pentafluoroethyl, chlorotetrafluoroethyl, trichloroethyl, heptafluoro-n-propyl, heptafluoroisopropyl, methoxy, ethoxy, n- or i-propoxy, fluoromethoxy, difluoromethoxy, trifluoromethoxy, methylthio, ethylthio, difluoromethylthio, trifluoromethylthio, chlorodifluoromethylthio, methylsulphinyl, trifluoromethylsulphinyl, trifluoromethylsulphonyl, methylsulphonyl, ethylsulphonyl, acetyl, propionyl, methoxycarbonyl, ethoxycarbonyl, methylaminocarbonyl, ethylaminocarbonyl or dimethylaminocarbonyl,
m is most preferably 0, 1 or 2,
X is most preferably trifluoromethyl, difluoromethyl, fluoromethyl, chlorodifluoromethyl, dichlorofluoromethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2-chloro-2,2-difluoroethyl, 1,1-difluoroethyl, pentafluoroethyl, heptafluoro-n-propyl or nonafluoro-n-butyl,
W is most preferably O,
A-Y together are most preferably cyano or are optionally mono- or polysubstituted heterocyclyl from the group of 1,2,4-oxadiazol-3-yl, 1H-imidazol-1-yl, 1H-pyrazol-1-yl, 1H-1,2,4-triazol-1-yl, 1H-1,2,3-triazol-1-yl, 1H-1,3,4-triazol-1-yl, 1H-1,2,3,4-tetrazol-1-yl or 2H-1,2,3,4-tetrazol-1-yl,
   where the substituents are selected from fluorine, chlorine, cyano, hydroxyl, amino, methyl, ethyl, difluoromethyl, trifluoromethyl, pentafluoroethyl, n- or i-propyl, cyclopropyl, methoxy, ethoxy, n- or i-propoxy, fluoromethoxy, difluoromethoxy, trifluoromethoxy, fluoroethoxy, difluoroethoxy, trifluoroethoxy, methylthio, methylsulphinyl, methylsulphonyl, ethylthio, ethylsulphinyl, ethylsulphonyl, methoxycarbonyl, ethoxycarbonyl, methylaminocarbonyl or dimethylaminocarbonyl,
or A is most preferably a bivalent chemical moiety which is selected from the moieties —NR$^{13}$C(=O)—, —C(R$^{11}$)(R$^{12}$)NR$^{13}$C(=O)—, —C(R$^{11}$)(R$^{12}$)NR$^{13}$S(=O)$_2$—, —C(=O)NR$^{13}$—, —C(=O)N(R$^{13}$)—O—, —C(=O)NR$^{13}$CH$_2$—, —S(=O)$_p$—, —S(=O)$_2$NR$^{13}$—, —C(=O)O—, —C(=O)NR$^{13}$CH$_2$C(=O)NR$^{14}$—, —C(R$^{11}$)(R$^{12}$)NR$^{13}$—, C(R$^{11}$)(U)NR$^{13}$C(=O)—, and —C(=O)NR$^{13}$NR$^{14}$—, where the first (left-hand) connection site in the bivalent chemical moieties is connected to the ring at one of positions Q$^4$ to Q$^8$ and the second (right-hand) connection site to Y, where U is most preferably ethyl or n-propyl which, together with a carbon atom adjacent to the connection site of A to the ring in positions Q$^4$ to Q$^8$, forms a 5- or 6-membered ring, p is most preferably 0, 1, 2, and where R$^{11}$ and R$^{12}$ are most preferably each hydrogen or methyl, R$^{13}$ and R$^{14}$ are most preferably each hydrogen, methyl, ethyl, cyclopropyl, cyanoethyl, 2-ethynyl, 2-propenyl, methoxymethyl, ethoxymethyl, methylcarbonyl, ethylcarbonyl, n-propylcarbonyl, i-propylcarbonyl, n-butylcarbonyl, t-butylcarbonyl, methoxycarbonyl, ethoxycarbonyl, n-propoxycarbonyl, i-propoxycarbonyl, n-butoxycarbonyl, t-butoxycarbonyl or phenoxycarbonyl, Y is most preferably hydrogen or optionally monosubstituted or identically or differently polysubstituted methyl, ethyl, n- or i-propyl, n-, i-, s- or t-butyl, n-, i-, s-, t- or neo-pentyl, cyclopropyl, cyclobutyl, cyclopentyl, cyclohexyl, ethenyl, propenyl, butenyl, pentenyl, ethynyl, propynyl, butynyl or pentynyl, where up to 5 substituents may be selected from fluorine and chlorine, and up to 2 substituents may be selected from bromine, cyano, nitro, hydroxyl, amino, methylamino, dimethylamino, cyclopropyl, trifluoromethyl, methoxy, ethoxy, n- or i-propoxy, fluoromethoxy, difluoromethoxy, trifluoromethoxy, fluoroethoxy, difluoroethoxy, trifluoroethoxy methylthio, methylsulphinyl, methylsulphonyl, ethylthio, ethylsulphinyl, ethylsulphonyl, methoxycarbonyl and ethoxycarbonyl, and one substituent may be selected from optionally mono- to trisubstituted phenyl, pyridin-2-yl, pyridin-3-yl pyridin-4-yl, thiazol-2-yl, thiazol-4-yl, furan-2-yl, pyrazol-1-yl, pyrazol-5-yl and pyrazol-3-yl, where the substituents may be selected from fluorine, chlorine, bromine, cyano, nitro, hydroxyl, methyl, ethyl, n- or i-propyl, amino, methylamino, dimethylamino, cyclopropyl, methoxy, ethoxy, n- or i-propoxy, fluoromethoxy, difluoromethoxy, trifluoromethoxy, fluoroethoxy, difluoroethoxy, trifluoroethoxy, methylthio, methylsulphinyl, methylsulphonyl, ethylthio, ethylsulphinyl or ethylsulphonyl, or is an optionally mono- to trisubstituted oxetan-3-yl, thietan-3-yl, 1-oxidothietan-3-yl, 1,1-dioxidothietan-3-yl, tetrahydrofuran-2-yl, tetrahydrofuran-3-yl, tetrahydropyran-2-yl, tetrahydropyran-3-yl, tetrahydropyran-4-yl, 1,3-dioxan-2-yl, 1,3-dioxan-3-yl, 1,3-dioxan-4-yl, 1,4-dioxan-2-yl, morpholin-1-yl, phenyl, pyridin-2-yl, pyridin-3-yl, pyridin-4-yl, pyrimidin-2-yl, pyrimidin-4-yl, pyrimidin-5-yl, pyridazin-3-yl, pyrazin-2-yl, furan-2-yl, furan-3-yl, thiophen-2-yl, thiophen-3-yl, pyrrol-2-yl, thiazol-2-yl, thiazol-4-yl, thiazol-5-yl, 1,2,4-thiadiazol-5-yl, oxazol-2-yl, oxazol-4-yl, oxazol-5-yl, isoxazol-3-yl, isoxazol-4-yl, isoxazol-5-yl, 1,2,3-oxdiazol-4-yl, 1,3,4-oxdiazol-2-yl, 1H-imidazol-2-yl, 1H-imidazol-4-yl, 1H-imidazol-5-yl, 1H-pyrazol-3-yl, 1H-pyrazol-4-yl, 1H-pyrazol-5-yl, 1H-1,2,4-triazol-3-yl, 1H-1,2,4-triazol-5-yl, 1H-1,2,3-triazol-4-yl, 1H-1,2,3-triazol-5-yl, 2H-1,2,3-triazol-2-yl, 2H-1,2,3-triazol-4-yl, 1H-1,3,4-triazol-2-yl, 1H-1,2,3,4-tetrazol-5-yl, 2-oxopiperidin-3-yl, 2-oxotetrahydrofuran-3-yl or 5-oxotetrahydrofuran-2-yl, where the substituents may be selected from fluorine, chlorine, bromine, cyano, nitro, hydroxyl, amino, methyl, ethyl, difluoromethyl, trifluoromethyl, pentafluoroethyl, n- or i-propyl, cyclopropyl, methoxy, ethoxy, n- or i-propoxy, fluoromethoxy, difluoromethoxy, trifluoromethoxy, fluoroethoxy, difluoroethoxy, trifluoroethoxy, methylthio, methylsulphinyl, methylsulphonyl, ethylthio, ethylsulphinyl, ethylsulphonyl, methoxycarbonyl, ethoxycarbonyl, methylaminocarbonyl and dimethylaminocarbonyl, Q$^1$ to Q$^3$ are most preferably each independently a carbon atom which is substituted by hydrogen or by R$^1$ or is N, where the number of nitrogen atoms in Q$^1$ to Q$^3$ is not more than 1, Q$^4$ is most preferably a carbon atom which is substituted by hydrogen or R$^6$ or which is bonded to V, in which case V is not R$^4$, Q$^5$ to Q$^8$ are most preferably each independently a carbon atom which is substituted by hydrogen, R$^6$ or A-Y, or is N, where the number of nitrogen atoms in Q$^5$ to Q$^8$ is not more than 1 and where exactly one of Q$^5$, Q$^6$, Q$^7$, Q$^8$ is substituted by A-Y.

The above-specified individual general, preferred, more preferred and most preferred definitions for the substituents R$^1$ to R$^6$, X, W, A, Y, and Q$^1$ to Q$^8$ can be combined with one another as desired in accordance with the invention.

Preferred inventive compounds are novel compounds of the formulae (IA) to (ID)

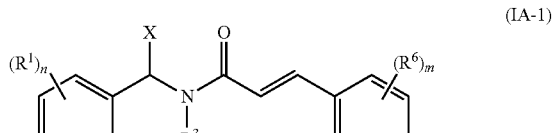
(IA-1)

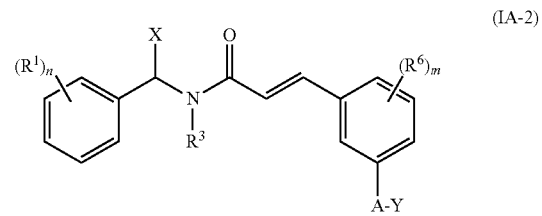
(IA-2)

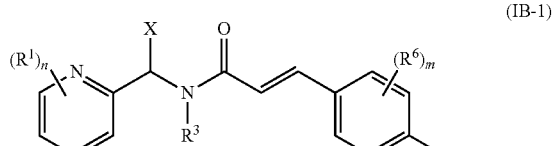
(IB-1)

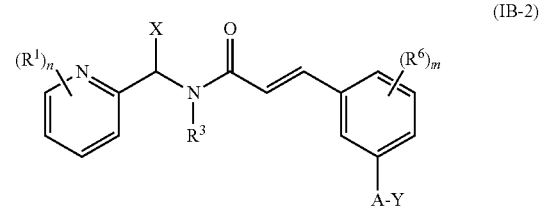
(IB-2)

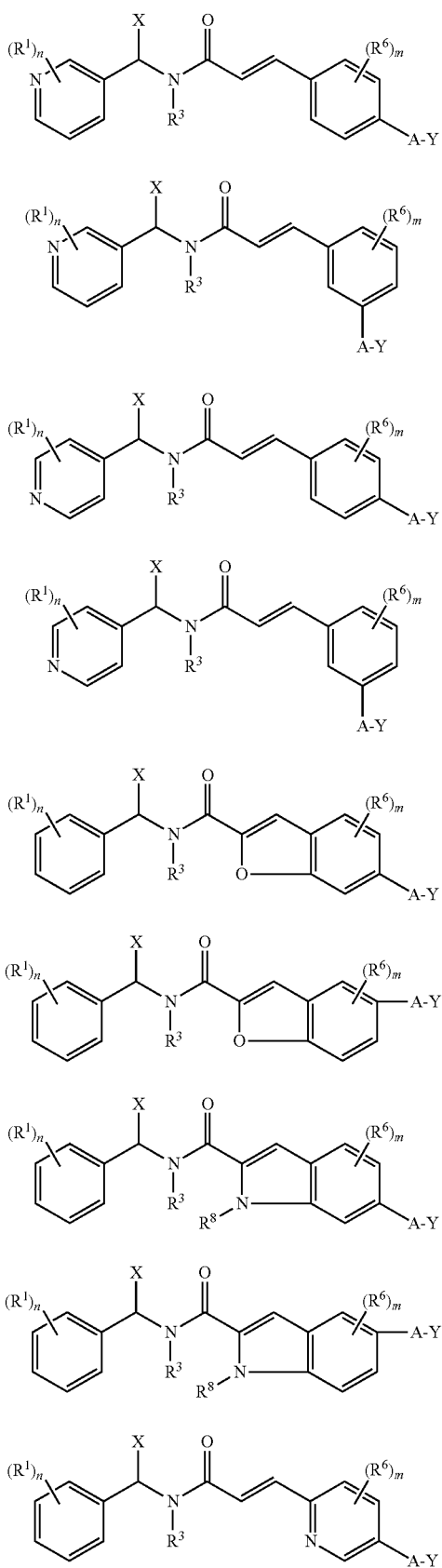

in which (R¹)ₙ, R³, R⁸, (R⁶)ₘ, X, A and Y (i.e. A, Y and A-Y) represent the abovementioned general, preferred, more preferred and most preferred definitions.

Likewise preferred inventive compounds are the compounds of the general formulae (Ia), (Ib), (Ic), (Id), (Ie), (If) and (Ig) shown in tables 1 to 7, and especially the specific compounds listed in tables 1 to 7.

The present compounds of the general formula (I) may optionally have a chiral carbon atom.

According to the rules by Cahn, Ingold and Prelog (CIP rules), these substituents may have either an (R) or an (S) configuration.

The present invention encompasses compounds of the general formula (I) both with (S) and with (R) configuration at the particular chiral carbon atoms, which means that the present invention covers the compounds of the general formula (I) in which the carbon atoms in question each independently have (1) an (R) configuration; or
(2) an (S) configuration.

If a plurality of chiral centres are present in the compounds of the general formula (I) or the formulae (IA) to (ID), any desired combinations of the configurations of the chiral centres are possible, which means that (1) one chiral centre may have (R) configuration and the other chiral centre (S) configuration;
(2) one chiral centre may have (R) configuration and the other chiral centre (R) configuration; and
(3) one chiral centre may have (S) configuration and the other chiral centre (S) configuration.

The compounds of the formula (I) likewise encompass any diastereomers or enantiomers present, and also E/Z isomers and salts and N-oxides of compounds of the formula (I), and the use thereof for controlling animal pests.

The invention also relates to the use of the inventive compounds of the general formula (I) for producing pesticides.

The invention also relates to pesticides comprising inventive compounds of the general formula (I) and/or salts thereof in biologically active contents of >0.00000001% by weight, preferably >0.001% by weight to 95% by weight, based on the weight of the pesticide.

The invention also relates to methods for controlling animal pests, in which inventive compounds of the general formula (I) are allowed to act on animal pests and/or the habitat thereof.

The inventive active ingredients, given good plant tolerance, favourable homeotherm toxicity and good environmental compatibility, are suitable for protecting plants and plant organs, for increasing harvest yields, for improving the quality of the harvested material and for controlling animal pests, especially insects, arachnids, helminths, nematodes and molluscs, which are encountered in agriculture, in horticulture, in animal husbandry, in forests, in gardens and leisure facilities, in the protection of stored products and of materials, and in the hygiene sector. They can preferably be used as crop protection agents. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus* spp., *Aceria sheldoni, Aculops* spp., *Aculus* spp., *Amblyomma* spp., *Amphitetranychus viennensis, Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Halotydeus destructor, Hemitarsonemus* spp., *Hyalomma* spp., *Ixodes* spp., *Latrodectus mactans, Metatetranychus* spp., *Nuphersa* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici.*

From the class of the Bivalva, for example, *Dreissena* spp.

From the order of the Chilopoda, for example, *Geophilus* spp., *Scutigera* spp.

From the order of the Coleoptera, for example, *Acalymma vittatum, Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apion* spp., *Apogonia* spp., *Atomaria* spp., *Attagenus* spp., *Bruchidius obtectus, Bruchus* spp., *Cassida* spp., *Cerotoma trifurcata, Ceutorrhynchus* spp., *Chaetocnema* spp., *Cleonus mendicus, Conoderus* spp., *Cosmopolites* spp., *Costelytra zealandica, Ctenicera* spp., *Curculio* spp., *Cryptorhynchus lapathi, Cylindrocopturus* spp., *Dermestes* spp., *Diabrotica* spp., *Dichocrocis* spp., *Diloboderus* spp., *Epilachna* spp., *Epitrix* spp., *Faustinus* spp., *Gibbium psylloides, Hellula undalis, Heteronychus arator, Heteronyx* spp., *Hylamorpha elegans, Hylotrupes bajulus, Hypera postica, Hypothenemus* spp., *Lachnosterna consanguinea, Lema* spp., *Leptinotarsa decemlineata, Leucoptera* spp., *Lissorhoptrus oryzophilus, Lixus* spp., *Luperodes* spp., *Lyctus* spp., *Megascelis* spp., *Melanotus* spp., *Meligethes aeneus, Melolontha* spp., *Migdolus* spp., *Monochamus* spp., *Naupactus xanthographus, Niptus hololeucus, Oryctes rhinoceros, Oryzaephilus surinamensis, Oryzaphagus oryzae, Otiorrhynchus* spp., *Oxycetonia jucunda, Phaedon cochleariae, Phyllophaga* spp., *Phyllotreta* spp., *Popillia japonica, Premnotrypes* spp., *Psylliodes* spp., *Ptinus* spp., *Rhizobius ventralis, Rhizopertha dominica, Sitophilus* spp., *Sphenophorus* spp., *Sternechus* spp., *Symphyletes* spp., *Tanymecus* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus.*

From the order of the Diplopoda, for example, *Blaniulus guttulatus.*

From the order of the Diptera, for example, *Aedes* spp., *Agromyza* spp., *Anastrepha* spp., *Anopheles* spp., *Asphondylia* spp., *Bactrocera* spp., *Bibio hortulanus, Calliphora erythrocephala, Ceratitis capitata, Chironomus* spp., *Chrysomyia* spp., *Cochliomyia* spp., *Contarinia* spp., *Cordylobia anthropophaga, Culex* spp., *Cuterebra* spp., *Dacus oleae, Dasyneura* spp., *Delia* spp., *Dermatobia hominis, Drosophila* spp., *Echinocnemus* spp., *Fannia* spp., *Gastrophilus* spp., *Hydrellia* spp., *Hylemyia* spp., *Hyppobosca* spp., *Hypoderma* spp., *Liriomyza* spp. *Lucilia* spp., *Musca* spp., *Nezara* spp., *Oestrus* spp., *Oscinella frit, Pegomyia* spp., *Phorbia* spp., *Prodiplosis* spp., *Psila rosae, Rhagoletis* spp., *Stomoxys* spp., *Tabanus* spp., *Tannia* spp., *Tetanops* spp., *Tipula* spp.

From the class of the Gastropoda, for example, *Anion* spp., *Biomphalaria* spp., *Bulinus* spp., *Deroceras* spp., *Galba* spp., *Lymnaea* spp., *Oncomelania* spp., *Pomacea* spp., *Succinea* spp.

From the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp, *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti.*

It is additionally possible to control protozoa, such as *Eimeria.*

From the order of the Heteroptera, for example, *Anasa tristis, Antestiopsis* spp., *Blissus* spp., *Calocoris* spp., *Campylomma livida, Cavelerius* spp., *Cimex* spp., *Collaria* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Monalonion atratum, Nezara* spp., *Oebalus* spp., *Pentomidae, Piesma quadrata, Piezodorus* spp., *Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.

From the order of the Homoptera, for example, *Acyrthosipon* spp., *Acrogonia* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chloroita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Drosicha* spp., *Dysaphis* spp., *Dysmicoccus* spp., *Empoasca* spp., *Eriosoma* spp., *Erythroneura* spp., *Euscelis bilobatus, Ferrisia* spp., *Geococcus coffeae, Hieroglyphus* spp., *Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva* spp., *Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus,*

Sogata spp., Sogatella furcifera, Sogatodes spp., Stictocephala festina, Tenalaphara malayensis, Tinocallis caryaefoliae, Tomaspis spp., Toxoptera spp., Trialeurodes spp., Trioza spp., Typhlocyba spp., Unaspis spp., Viteus vitifolii, Zygina spp.

From the order of the Hymenoptera, for example, Athalia spp., Diprion spp., Hoplocampa spp., Lasius spp., Monomorium pharaonis, Vespa spp.

From the order of the Isopoda, for example, Armadillidium vulgare, Oniscus asellus, Porcellio scaber.

From the order of the Isoptera, for example, Acromyrmex spp., Atta spp., Cornitermes cumulans, Microtermes obesi, Odontotermes spp., Reticulitermes spp, From the order of the Lepidoptera, for example, Acronicta major, Adoxophyes spp., Aedia leucomelas, Agrotis spp., Alabama spp., Amyelois transitella, Anarsia spp., Anticarsia spp., Argyroploce spp., Barathra brassicae, Borbo cinnara, Bucculatrix thurberiella, Bupalus piniarius, Busseola spp., Cacoecia spp., Caloptilia theivora, Capua reticulana, Carpocapsa pomonella, Carposina niponensis, Chematobia brumata, Chilo spp., Choristoneura spp., Clysia ambiguella, Cnaphalocerus spp., Cnephasia spp., Conopomorpha spp., Conotrachelus spp., Copitarsia spp., Cydia spp., Dalaca noctuides, Diaphania spp., Diatraea saccharalis, Earias spp., Ecdytolopha aurantium, Elasmopalpus lignosellus, Eldana saccharina, Ephestia kuehniella, Epinotia spp., Epiphyas postvittana, Etiella spp., Eulia spp., Eupoecilia ambiguella, Euproctis spp., Euxoa spp., Feltia spp., Galleria mellonella, Gracillaria spp., Grapholitha spp., Hedylepta spp., Helicoverpa spp., Heliothis spp., Hofmannophila pseudospretella, Homoeosoma spp., Homona spp., Hyponomeuta padella, Kakivoria flavofasciata, Laphygma spp., Laspeyresia molesta, Leucinodes orbonalis, Leucoptera spp., Lithocolletis spp., Lithophane antennata, Lobesia spp., Loxagrotis albicosta, Lymantria spp., Lyonetia spp., Malacosoma neustria, Maruca testulalis, Mamestra brassicae, Mocis spp., Mythimna separata, Nymphula spp., Oiketicus spp., Oria spp., Orthaga spp., Ostrinia spp., Oulema oryzae, Panolis flammea, Parnara spp., Pectinophora spp., Perileucoptera spp., Phthorimaea spp., Phyllocnistis citrella, Phyllonorycter spp., Pieris spp., Platynota stultana, Plusia spp., Plutella xylostella, Prays spp., Prodenia spp., Protoparce spp., Pseudaletia spp., Pseudoplusia includens, Pyrausta nubilalis, Rachiplusia nu, Schoenobius spp., Scirpophaga spp., Scotia segetum, Sesamia spp., Sparganothis spp., Spodoptera spp., Stathmopoda spp., Stomopteryx subsecivella, Synanthedon spp., Tecia solanivora, Thermesia gemmatalis, Tinea pellionella, Tineola bisselliella, Tortrix spp., Trichoplusia spp., Tuta absoluta, Virachola spp.

From the order of the Orthoptera, for example, Acheta domesticus, Blatta orientalis, Blattella germanica, Dichroplus spp., Gryllotalpa spp., Leucophaea maderae, Locusta spp., Melanoplus spp., Periplaneta americana, Schistocerca gregaria.

From the order of the Siphonaptera, for example, Ceratophyllus spp., Xenopsylla cheopis.

From the order of the Symphyla, for example, Scutigerella spp.

From the order of the Thysanoptera, for example, Anaphothrips obscurus, Baliothrips biformis, Drepanothris reuteri, Enneothrips flavens, Frankliniella spp., Heliothrips spp., Hercinothrips femoralis, Rhipiphorothrips cruentatus, Scirtothrips spp., Taeniothrips cardamoni, Thrips spp.

From the order of the Thysanura, for example, Lepisma saccharina.

The phytoparasitic nematodes include, for example, Aphelenchoides spp., Bursaphelenchus spp., Ditylenchus spp., Globodera spp., Heterodera spp., Longidorus spp., Meloidogyne spp., Pratylenchus spp., Radopholus similis, Trichodorus spp., Tylenchulus semipenetrans, Xiphinema spp.

If appropriate, the compounds of the formula (I) can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (mycoplasma-like organisms) and RLO (rickettsia-like organisms). If appropriate, they can also be employed as intermediates or precursors for the synthesis of other active ingredients.

The present invention further relates to formulations, and application forms prepared from them, such as crop protection compositions and/or pesticides, such as drench, drip and spray liquors, comprising at least one of the active ingredients of the invention. The application forms may comprise further crop protection agents and/or pesticides, and/or activity-enhancing adjuvants such as penetrants, examples being vegetable oils such as, for example, rapeseed oil, sunflower oil, mineral oils such as, for example, liquid paraffins, alkyl esters of vegetable fatty acids, such as rapeseed oil or soybean oil methyl esters, or alkanol alkoxylates, and/or spreaders such as, for example, alkylsiloxanes and/or salts, examples being organic or inorganic ammonium or phosphonium salts, examples being ammonium sulphate or diammonium hydrogenphosphate, and/or retention promoters such as dioctyl sulphosuccinate or hydroxypropylguar polymers and/or humectants such as glycerol and/or fertilizers such as ammonium, potassium or phosphorus fertilizers, for example.

Examples of typical formulations include water-soluble liquids (SL), emulsifiable concentrates (EC), emulsions in water (EW), suspension concentrates (SC, SE, FS, OD), water-dispersible granules (WG), granules (GR) and capsule concentrates (CS); these and other possible types of formulation are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations may comprise active agrochemical compounds other than one or more active ingredients of the invention.

The formulations or application forms in question preferably comprise auxiliaries, such as extenders, solvents, spontaneity promoters, carriers, emulsifiers, dispersants, frost protectants, biocides, thickeners and/or other auxiliaries, such as adjuvants, for example. An adjuvant in this context is a component which enhances the biological effect of the formulation, without the component itself having a biological effect. Examples of adjuvants are agents which promote the retention, spreading, attachment to the leaf surface, or penetration.

The active ingredients can be converted to the customary formulations, such as solutions, emulsions, wettable powders, water- and oil-based suspensions, powders, dusts, pastes, soluble powders, soluble granules, granules for broadcasting, suspension-emulsion concentrates, natural materials impregnated with active ingredient, synthetic materials impregnated with active ingredient, fertilizers and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers. The formulations are prepared either in suitable plants or else before or during the application.

The auxiliaries used may be those substances which are suitable for imparting particular properties, such as certain technical properties and/or also particular biological properties, to the formulation of the active ingredient and/or to the application forms prepared from these formulations (for example pesticides or crop protection compositions, such as spray liquors or seed dressings). Typical useful auxiliaries include: extenders, solvents and carriers.

Suitable extenders are, for example, water, polar and non-polar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

In principle, it is possible to use all suitable solvents. If the extender used is water, it is also possible to employ, for example, organic solvents as auxiliary solvents. Essentially, suitable liquid solvents are:
aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

All suitable carriers may in principle be used. Suitable solid carriers are especially:
for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks.

It is also possible to use liquefied gaseous extenders or solvents. Especially suitable are those extenders or carriers which are gaseous at standard temperature and under standard pressure, for example aerosol propellant gases, such as halohydrocarbons, and also butane, propane, nitrogen and carbon dioxide.

Examples of emulsifiers and/or foam generators, dispersants or wetting agents with ionic or nonionic properties or mixtures of these surface-active substances are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyl taurates), phosphoric esters of polyethoxylated alcohols or phenols, fatty acid esters of polyols, and derivatives of the compounds containing sulphates, sulphonates and phosphates, for example alkylaryl polyglycol ethers, alkylsulphonates, alkylsulphates, arylsulphonates, protein hydrolysates, lignosulphite waste liquors and methylcellulose. The presence of a surface-active substance is advantageous if one of the active ingredients and/or one of the inert carriers is water-insoluble and if the application is effected in water.

Useful emulsifiers and/or foam-formers are especially: for example, nonionic and anionic emulsifiers, such as polyoxyethylene fatty acid esters, polyoxyethylene fatty alcohol ethers, for example alkylaryl polyglycol ethers, alkylsulphonates, alkylsulphates, arylsulphonates and also protein hydrolysates; suitable dispersants are nonionic and/or ionic substances, for example from the classes of the alcohol-POE and/or POP ethers, acid and/or POP—POE esters, alkylaryl and/or POP—POE ethers, fat- and/or POP—POE adducts, POE- and/or POP-polyol derivatives, POE- and/or POP-sorbitan or -sugar adducts, alkyl or aryl sulphates, alkyl- or arylsulphonates and alkyl or aryl phosphates or the corresponding PO-ether adducts. In this context, POP means polyoxypropylene oxide, POE polyoxyethylene oxide, PO propylene oxide, and EO ethylene oxide. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulphonic acid derivatives, unmodified and modified celluloses, aromatic and/or aliphatic sulphonic acids and their adducts with formaldehyde.

Tackifiers such as carboxymethylcellulose, natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations.

It is possible to use dyes such as inorganic pigments, for example iron oxide, titanium oxide and Prussian Blue, and organic dyes, such as alizarin dyes, azo dyes and metal phthalocyanine dyes, and trace nutrients such as salts of iron, manganese, boron, copper, cobalt, molybdenum and zinc.

It is possible if appropriate for still further additives to be present in the formulations and the application forms derived therefrom. Further possible additives are perfumes, mineral or vegetable, optionally modified oils, waxes and nutrients (including trace nutrients), such as salts of iron, manganese, boron, copper, cobalt, molybdenum and zinc. Further additives are, for example, fragrances, protective colloids, binders, adhesives, thickeners, thixotropic substances, penetrants, retention promoters, stabilizers, sequestrants, complexing agents, humectants, spreaders. In general, the active ingredients can be combined with any solid or liquid additive commonly used for formulation purposes.

Stabilizers, such as low-temperature stabilizers, preservatives, antioxidants, light stabilizers or other agents which improve chemical and/or physical stability may also be present.

Suitable retention promoters include all those substances which reduce the dynamic surface tension, such as dioctyl sulphosuccinate, or increase the viscoelasticity, such as hydroxypropylguar polymers, for example.

Suitable penetrants in the present context include all those substances which are typically used in order to enhance the penetration of active agrochemical compounds into plants. Penetrants in this context are defined in that, from the (generally aqueous) application liquor and/or from the spray coating, they are able to penetrate the cuticle of the plant and thereby increase the mobility of the active compounds in the cuticle. This property can be determined using the method described in the literature (Baur et al., 1997, Pesticide Science 51, 131-152). Examples include alcohol alkoxylates such as coconut fatty ethoxylate (10) or isotridecyl ethoxylate (12), fatty acid esters such as rapeseed or soybean oil methyl esters, fatty amine alkoxylates such as tallowamine ethoxylate (15), or ammonium and/or phosphonium salts such as ammonium sulphate or diammonium hydrogen-phosphate, for example.

The formulations contain preferably between 0.00000001 and 98% by weight of active ingredient, more preferably between 0.01 and 95% by weight of active ingredient, most preferably between 0.5 and 90% by weight of active ingredient, based on the weight of the formulation.

The active ingredient may be present in its commercial standard formulations, and in the application forms prepared from these formulations, in a mixture with other active agrochemical ingredients such as insecticides, attractants, sterilants, bactericides, acaricides, nematicides, fungicides, growth regulators, herbicides, safeners, fertilizers, semiochemicals, or else with agents for improving the plant properties.

When used as insecticides, the inventive active ingredients may also be present, in their commercial standard formulations, and in the application forms prepared from these formulations, in a mixture with synergists. Synergists are compounds by which the action of the active ingredients is enhanced, without any need for the synergist itself to be active.

When used as insecticides, the inventive active ingredients may also be present, in their commercial standard formulations, and in the application forms prepared from these formulations, in a mixture with inhibitors, which prevent degradation of the active ingredient after application in the environment of the plant, on the surface of plant parts or in plant tissues.

The active ingredient content of the application forms (pesticides) prepared from the commercial standard formulations may vary within wide ranges. The active ingredient concentration of the application forms may be from 0.00000001 up to 95% by weight of active ingredient, preferably between 0.00001 and 1% by weight, based on the weight of the application form.

Application is effected in a customary manner appropriate to the application forms.

The treatment of the plants and plant parts with the inventive active ingredients is effected directly or by action on their environment, habitat or storage space by the customary treatment methods, for example by dipping, spraying, atomizing, irrigating, evaporating, dusting, fogging, broadcasting, foaming, painting, spreading, injecting, watering (drenching), drip irrigating and, in the case of propagation material, especially in the case of seeds, additionally by dry seed dressing, wet seed dressing, slurry seed dressing, by incrusting, by coating with one or more coats, etc. It is also possible to deploy the active ingredients by the ultra-low volume method, or to inject the active ingredient preparation or the active ingredient itself into the soil.

A preferred direct treatment of the plants is foliar application, i.e. inventive active ingredients are applied to the foliage, in which case it is possible to adjust the treatment frequency and the application rate to the infestation pressure of the particular pest.

In the case of systemically active compounds, the inventive active ingredients get into the plants via the root structure. In that case, the plants are treated by the action of the inventive active ingredients on the habitat of the plants. This can be done, for example, by drenching, or mixing into the soil or the nutrient solution, i.e. the site of the plant (e.g. soil or hydroponic systems) is impregnated with a liquid form of the inventive active ingredients, or by soil application, i.e. the inventive active ingredients are introduced into the site of the plants in solid form (for example in the form of granules). In the case of paddy rice crops, this may also be accomplished by metered addition of the inventive compounds in a solid application form (for example as granules) into a flooded paddy field.

The inventive active ingredients can be used, as they are or in formulations thereof, also in mixtures with known fungicides, bactericides, acaricides, nematicides or insecticides, in order thus, for example, to broaden the spectrum of action or to preclude development of resistance. In many cases, synergistic effects are obtained, i.e. the efficacy of the mixtures is greater than the sum of the efficacy of the individual compounds.

Useful mixing partners include, for example, the following compounds:

Insecticides/Acaricides/Nematicides:

The active ingredients identified here by their common name are known and are described in the pesticide handbook ("The Pesticide Manual" 14th Ed., British Crop Protection Council 2006) or can be found on the Internet (e.g. http://www.alanwood.net/pesticides).

(1) Acetylcholinesterase (AChE) inhibitors, such as, for example, carbamates, for example alanycarb, aldicarb, bendiocarb, benfuracarb, butocarboxim, butoxy-carboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, for example acephate, azamethiphos, azinphos (-methyl, -ethyl), cadusafos, chlorethoxyfos, chlorfenvinphos, chlormephos, chlorpyrifos (-methyl), coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion (-methyl), phenthoate, phorate, phosalone, phosmet, phosphamidon, phoxim, pirimiphos (-methyl), profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel antagonists, for example organochlorines, for example chlordane and endosulfan (alpha-); or fiproles (phenylpyrazoles), for example ethiprole, fipronil, pyrafluprole and pyriprole.

(3) Sodium channel modulators/voltage-dependent sodium channel blockers, such as, for example, pyrethroids, for example acrinathrin, allethrin (d-cis-trans, d-trans), bifenthrin, bioallethrin, bioallethrin-S-cyclopentenyl, bioresmethrin, cycloprothrin, cyfluthrin (beta-), cyhalothrin (gamma-, lambda-), cypermethrin (alpha-, beta-, theta-, zeta-), cyphenothrin [(1R)-trans-isomers], deltamethrin, dimefluthrin, empenthrin [(EZ)-(1R)-isomers], esfenvalerate, etofenprox, fenpropathrin, fenvalerate, flucythrinate, flumethrin, fluvalinate (tau-), halfenprox, imiprothrin, metofluthrin, permethrin, phenothrin [(1R)-trans-isomer], prallethrin, profluthrin, pyrethrins (pyrethrum), resmethrin, RU 15525, silafluofen, tefluthrin, tetramethrin [(1R)-isomers], tralomethrin, transfluthrin and ZXI 8901; or DDT; or methoxychlor.

(4) Nicotinergic acetylcholine receptor agonists, such as, for example, neonicotinoids, for example acetamiprid, clothianidin, dinotefuran, imidacloprid, nitenpyram, thiacloprid, thiamethoxam; or nicotine.

(5) Allosteric acetylcholine receptor modulators (agonists), for example spinosyns, for example spinetoram and spinosad.

(6) Chloride channel activators, such as, for example, avermectins/milbemycins, for example abamectin, emamectin benzoate, lepimectin and milbemectin.

(7) Juvenile hormone analogues, for example hydroprene, kinoprene, methoprene; or fenoxycarb; pyriproxyfen.

(8) Active ingredients with unknown or non-specific mechanisms of action, such as, for example, fumigants, for example methyl bromide and other alkyl halides; or chloropicrin; sulphuryl fluoride; borax; tartar emetic.

(9) Selective antifeedants, for example pymetrozine; or flonicamid.

(10) Mite growth inhibitors, for example clofentezine, diflovidazin, hexythiazox, etoxazole.

(11) Microbial disruptors of the insect gut membrane, for example Bacillus thuringiensis subspecies israelensis, Bacillus sphaericus, Bacillus thuringiensis subspecies aizawai, Bacillus thuringiensis subspecies kurstaki, Bacillus thuringiensis subspecies tenebrionis, and BT plant proteins, for example Cry1Ab, Cry1Ac, Cry1Fa, Cry2Ab, mCry3A, Cry3Ab, Cry3Bb, Cry34/35Ab1.

(12) Oxidative phosphorylation inhibitors, ATP disruptors, for example diafenthiuron; or organotin compounds, for example azocyclotin, cyhexatin, fenbutatin oxide; or propargite; tetradifon.

(13) Oxidative phoshorylation decouplers acting by interrupting the H proton gradient, for example chlorfenapyr and DNOC.

(14) Nicotinergic acetylcholine receptor antagonists, for example bensultap, cartap (hydrochloride), thiocylam, and thiosultap (sodium).

(15) Chitin biosynthesis inhibitors, type 0, for example benzoylureas, for example bistrifluoron, chlorfluazuron, diflubenzuron, flucycloxuron, flufenoxuron, hexaflumuron, lufenuron, novaluron, noviflumuron, teflubenzuron and triflumuron.

(16) Chitin biosynthesis inhibitors, type 1, for example buprofezin.

(17) Moulting disruptors, for example cyromazine.

(18) Ecdysone agonists/disruptors, such as, for example, diacylhydrazines, for example chromafenozide, halofenozide, methoxyfenozide and tebufenozide.

(19) Octopaminergic agonists, for example amitraz.

(20) Complex-III electron transport inhibitors, for example hydramethylnone; acequinocyl; fluacrypyrim.

(21) Complex-I electron transport inhibitors, for example from the group of the METI acaricides, for example fenazaquin, fenpyroximate, pyrimidifen, pyridaben, tebufenpyrad, tolfenpyrad; or rotenone (Denis).

(22) Voltage-dependent sodium channel blockers, for example indoxacarb; metaflumizone.

(23) Inhibitors of acetyl-CoA carboxylase, for example tetronic acid derivatives, for example spirodiclofen and spiromesifen; or tetramic acid derivatives, for example spirotetramat.

(24) Complex-IV electron transport inhibitors, for example phosphines, for example aluminium phosphide, calcium phosphide, phosphine, zinc phosphide; or cyanide.

(25) Complex-II electron transport inhibitors, for example cyenopyrafen.

(28) Ryanodine receptor effectors, for example diamides, for example flubendiamide, chlorantraniliprole (Rynaxypyr), cyantraniliprole (Cyazypyr) and also 3-bromo-N-{2-bromo-4-chloro-6-[(1-cyclopropylethyl)carbamoyl]phenyl}-1-(3-chloropyridin-2-yl)-1H-pyrazole-5-carboxamide (known from WO2005/077934) or methyl 2-[3,5-dibromo-2-({[3-bromo-1-(3-chloropyridin-2-yl)-1H-pyrazol-5-yl]carbonyl}amino)benzoyl]-1,2-dimethylhydrazinecarboxylate (known from WO2007/043677).

Further active ingredients with unknown mechanism of action, for example azadirachtin, amidoflumet, benzoximate, bifenazate, chinomethionat, cryolite, cyflumetofen, dicofol, fluensulfone (5-chloro-2-[(3,4,4-trifluorobut-3-en-1-yl) sulphonyl]-1,3-thiazole), flufenerim, pyridalyl and pyrifluquinazon; and also products based on Bacillus firmus (I-1582, BioNeem, Votivo) and also the known active ingredients below 4-{[(6-bromopyrid-3-yl)methyl] (2-fluoroethyl) amino}furan-2(5H)-one (known from WO 2007/115644),
4-{[(6-fluoropyrid-3-yl)methyl](2,2-difluoroethyl) amino}furan-2(5H)-one (known from WO 2007/115644),
4-{[(2-chloro-1,3-thiazol-5-yl)methyl](2-fluoroethyl) amino}furan-2(5H)-one (known from WO 2007/115644),
4-{[(6-chloropyrid-3-yl)methyl](2-fluoroethyl) amino}furan-2(5H)-one (known from WO 2007/115644),
4-{[(6-chloropyrid-3-yl)methyl](2,2-difluoroethyl) amino}furan-2(5H)-one (known from WO 2007/115644),
4-{[(6-chloro-5-fluoropyrid-3-yl)methyl](methyl) amino}furan-2(5H)-one (known from WO 2007/115643),
4-{[(5,6-dichloropyrid-3-yl)methyl](2-fluoroethyl) amino}furan-2(5H)-one (known from WO 2007/115646),
4-{[(6-chloro-5-fluoropyrid-3-yl)methyl](cyclopropyl) amino}furan-2(5H)-one (known from WO 2007/115643),
4-{[(6-chloropyrid-3-yl)methyl](cyclopropyl)amino}furan-2(5H)-one (known from EP-A-0 539 588), 4-{[(6-chloropyrid-3-yl)methyl](methyl)amino}furan-2(5H)-one (known from EP-A-0 539 588), [(6-chloropyridin-3-yl)methyl](methyl)oxido-λ⁴-sulphanylidenecyanamide (known from WO 2007/149134), [1-(6-chloropyridin-3-yl)ethyl](methyl) oxido-λ⁴-sulphanylidenecyanamide (known from WO 2007/149134) and its diastereomers (A) and (B)

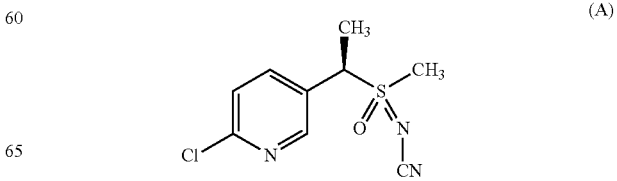

(A)

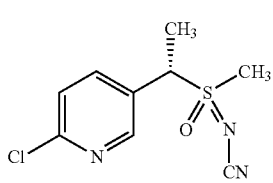

(B)

(also known from WO 2007/149134), [(6-trifluoromethylpyridin-3-yl)methyl](methyl)oxido-λ⁴-sulphanylidenecyanamide (known from WO 2007/095229), sulfoxaflor (also known from WO 2007/149134), 11-(4-chloro-2,6-dimethylphenyl)-12-hydroxy-1,4-dioxa-9-azadispiro[4.2.4.2]tetradec-11-en-10-one (known from WO 2006/089633), 3-(4'-fluoro-2,4-dimethylbiphenyl-3-yl)-4-hydroxy-8-oxa-1-azaspiro[4.5]dec-3-en-2-one (known from WO 2008/067911), 1-[2-fluoro-4-methyl-5-[(2,2,2-trifluoroethyl)sulphinyl]phenyl]-3-(trifluoromethyl)-1H-1,2,4-triazole-5-amine (known from WO 2006/043635), [(3S,4aR,12R,12aS,12bS)-3-[(cyclopropylcarbonyl)oxy]-6,12-dihydroxy-4,12b-dimethyl-11-oxo-9-(pyridin-3-yl)-1,3,4,4a,5,6,6a,12,12a,12b-decahydro-2H,11H-benzo[f]pyrano[4,3-b]chromen-4-yl]methyl cyclopropanecarboxylate (known from WO 2006/129714), 2-cyano-3-(difluoromethoxy)-N,N-dimethylbenzenesulphonamide (known from WO2006/056433), 2-cyano-3-(difluoromethoxy)-N-methylbenzenesulphonamide (known from WO2006/100288), 2-cyano-3-(difluoromethoxy)-N-ethylbenzenesulphonamide (known from WO2005/035486), 4-(difluoromethoxy)-N-ethyl-N-methyl-1,2-benzothiazole-3-amine 1,1-dioxide (known from WO2007/057407) and N-[1-(2,3-dimethylphenyl)-2-(3,5-dimethylphenyl)ethyl]-4,5-dihydro-1,3-thiazole-2-amine (known from WO2008/104503).

Fungicides (1) Ergosterol biosynthesis inhibitors, for example aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulphate, imibenconazole, ipconazole, metconazole, myclobutanil, naftifine, nuarimol, oxpoconazole, paclobutrazol, pefurazoate, penconazole, piperalin, prochloraz, propiconazole, prothioconazole, pyributicarb, pyrifenox, quinconazole, simeconazole, spiroxamine, tebuconazole, terbinafine, tetraconazole, triadimefon, triadimenol, tridemorph, triflumizole, triforine, triticonazole, uniconazole, uniconazole-p, viniconazole, voriconazole, 1-(4-chlorophenyl)-2-(1H-1,2,4-triazol-1-yl)cycloheptanol, methyl 1-(2,2-dimethyl-2,3-dihydro-1H-inden-1-yl)-1H-imidazole-5-carboxylate, N'-{5-(difluoromethyl)-2-methyl-4-[3-(trimethylsilyl)propoxy]phenyl}-N-ethyl-N-methylimidoformamide, N-ethyl-N-methyl-N'-{2-methyl-5-(trifluoromethyl)-4-[3-(trimethylsilyl)propoxy]phenyl}imidoformamide and O-[1-(4-methoxyphenoxy)-3,3-dimethylbutan-2-yl]-1H-imidazole-1-carbothioate.

(2) Respiration inhibitors (respiratory-chain inhibitors), for example bixafen, boscalid, carboxin, diflumetorim, fenfuram, fluopyram, flutolanil, fluxapyroxad, furametpyr, furmecyclox, isopyrazam mixture of the syn-epimeric racemate 1RS,4SR,9RS and of the anti-epimeric racemate 1RS,4SR,9SR, isopyrazam (anti-epimeric racemate), isopyrazam (anti-epimeric enantiomer 1R,4S,9S), isopyrazam (anti-epimeric enantiomer 1S,4R,9R), isopyrazam (syn-epimeric racemate 1RS,4SR,9RS), isopyrazam (syn-epimeric enantiomer 1R,4S,9R), isopyrazam (syn-epimeric enantiomer 1S,4R,9S), mepronil, oxycarboxin, penflufen, penthiopyrad, sedaxane, thifluzamid, 1-methyl-N-[2-(1,1,2,2-tetrafluoroethoxy)phenyl]-3-(trifluoromethyl)-1H-pyrazole-4-carboxamide, 3-(difluoromethyl)-1-methyl-N-[2-(1,1,2,2-tetrafluoroethoxy)phenyl]-1H-pyrazole-4-carboxamide, 3-(difluoromethyl)-N-[4-fluoro-2-(1,1,2,3,3,3-hexafluoropropoxy)phenyl]-1-methyl-1H-pyrazole-4-carboxamide and N-[1-(2,4-dichlorophenyl)-1-methoxypropan-2-yl]-3-(difluoromethyl)-1-methyl-1H-pyrazole-4-carboxamide.

(3) Respiration inhibitors (respiratory-chain inhibitors) on the complex III of the respiratory chain, for example ametoctradin, amisulbrom, azoxystrobin, cyazofamid, dimoxystrobin, enestroburin, famoxadon, fenamidon, fluoxastrobin, kresoxim-methyl, metominostrobin, orysastrobin, picoxystrobin, pyraclostrobin, pyrametostrobin, pyraoxystrobin, pyribencarb, trifloxystrobin, (2E)-2-(2-{[6-(3-chloro-2-methylphenoxy)-5-fluoropyrimidin-4-yl]oxy}phenyl)-2-(methoxyimino)-N-methylethanamide, (2E)-2-(methoxyimino)-N-methyl-2-(2-{[({(1E)-1-[3-(trifluoromethyl)phenyl]-ethylidene}amino)oxy]methyl}phenyl)ethanamide, (2E)-2-(methoxyimino)-N-methyl-2-{2-[(E)-({1-[3-(trifluoromethyl)phenyl]ethoxy}imino)methyl]phenyl}ethanamide, (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide, (2E)-2-{2-[({[(2E,3E)-4-(2,6-dichlorophenyl)but-3-en-2-ylidene]amino}oxy)methyl]phenyl}-2-(methoxyimino)-N-methylethanamide, 2-chloro-N-(1,1,3-trimethyl-2,3-dihydro-1H-inden-4-yl)pyridine-3-carboxamide, 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, methyl (2E)-2-{2-[({cyclopropyl[(4-methoxyphenyl)imino]methyl}sulphanyl)methyl]phenyl}-3-methoxyprop-2-enoate, N-(3-ethyl-3,5,5-trimethylcyclohexyl)-3-(formylamino)-2-hydroxybenzamide, 2-{2-[(2,5-dimethylphenoxy)methyl]phenyl}-2-methoxy-N-methylacetamide and (2R)-2-{2-[(2,5-dimethylphenoxy)methyl]phenyl}-2-methoxy-N-methylacetamide.

(4) Mitosis and cell division inhibitors, for example benomyl, carbendazim, chlorfenazole, diethofencarb, ethaboxam, fluopicolid, fuberidazole, pencycuron, thiabendazole, thiophanate-methyl, thiophanate, zoxamide, 5-chloro-7-(4-methylpiperidin-1-yl)-6-(2,4,6-trifluorophenyl)-[1,2,4]triazolo[1,5-a]pyrimidine and 3-chloro-5-(6-chloropyridin-3-yl)-6-methyl-4-(2,4,6-trifluorophenyl)pyridazine.

(5) Compounds with multi-site activity, for example Bordeaux mixture, captafol, captan, chlorothalonil, copper preparations such as copper hydroxide, copper naphthenate, copper oxide, copper oxychloride, copper sulphate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram-zinc, oxine-copper, propamidine, propineb, sulphur and sulphur preparations such as, for example, calcium polysulphide, thiram, tolylfluanid, zineb and ziram.

(6) Resistance inductors, for example acibenzolar-S-methyl, isotianil, probenazole and tiadinil.
(7) Amino acid and protein biosynthesis inhibitors, for example andoprim, blasticidin-S, cyprodinil, kasugamycin, kasugamycin hydrochloride hydrate, mepanipyrim and pyrimethanil.
(8) ATP production inhibitors, for example fentin acetate, fentin chloride, fentin hydroxide and silthiofan.
(9) Cell wall synthesis inhibitors, for example benthiavalicarb, dimethomorph, flumorph, iprovalicarb, mandipropamid, polyoxins, polyoxorim, validamycin A and valifenalate.
(10) Lipid and membrane synthesis inhibitors, for example biphenyl, chloroneb, dicloran, edifenphos, etridiazole, iodocarb, iprobenfos, isoprothiolane, propamocarb, propamocarb hydrochloride, prothiocarb, pyrazophos, quintozene, tecnazene and tolclofos-methyl.
(11) Melanin biosynthesis inhibitors, for example carpropamid, diclocymet, fenoxanil, fthalide, pyroquilon and tricyclazole.
(12) Nucleic acid synthesis inhibitors, for example benalaxyl, benalaxyl M (kiralaxyl), bupirimate, clozylacon, dimethirimol, ethirimol, furalaxyl, hymexazol, metalaxyl, metalaxyl-M (mefenoxam), ofurace, oxadixyl and oxolinic acid.
(13) Signal transduction inhibitors, for example chlozolinate, fenpiclonil, fludioxonil, iprodione, procymidon, quinoxyfen and vinclozoline.
(14) Decouplers, for example binapacryl, dinocap, ferimzone, fluazinam and meptyldinocap.
(15) Further compounds, for example benthiazole, bethoxazin, capsimycin, carvone, chinomethionat, chlazafenon, cufraneb, cyflufenamid, cymoxanil, cyprosulfamide, dazomet, debacarb, dichlorophen, diclomezine, difenzoquat, difenzoquat methylsulphate, diphenylamine, ecomat, fenpyrazamine, flumetover, fluoromid, flusulfamide, flutianil, fosetyl-aluminium, fosetyl-calcium, fosetyl-sodium, hexachlorobenzene, irumamycin, methasulphocarb, methyl isothiocyanate, metrafenone, mildiomycin, natamycin, nickel dimethyldithiocarbamate, nitrothal-isopropyl, octhilinone, oxamocarb, oxyfenthiin, pentachlorophenol and its salts, phenothrin, phosphoric acid and its salts, propamocarb-fosetylate, propanosine-sodium, proquinazid, pyrrolnitrin, tebufloquin, tecloftalam, tolnifanid, triazoxide, trichlamide, zarilamide, 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-methoxyphenoxy)-3,3-dimethylbutan-2-yl 1H-imidazole-1-carboxylate, 2,3,5,6-tetrachloro-4-(methylsulphonyl)pyridine, 2,3-dibutyl-6-chlorothieno[2,3-d]pyrimidin-4(3H)-one, 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, 2-butoxy-6-iodo-3-propyl-4H-chromen-4-one, 2-chloro-5-[2-chloro-1-(2,6-difluoro-4-methoxyphenyl)-4-methyl-1H-imidazol-5-yl]pyridine, 2-phenylphenol and its salts, 3,4,5-trichloropyridine-2,6-dicarbonitrile, 3-[5-(4-chlorophenyl)-2,3-dimethyl-1,2-oxazolidin-3-yl]pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, 5-amino-1,3,4-thiadiazole-2-thiol, 5-chloro-N'-phenyl-N'-(prop-2-yn-1-yl)thiophene-2-sulphonohydrazide, 5-methyl-6-octyl[1,2,4]triazolo[1,5-a]pyrimidin-7-amine, ethyl (2Z)-3-amino-2-cyano-3-phenylprop-2-enoate, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)methyl]-2,4-dichloropyridine-3-carboxamide, N-[1-(5-bromo-3-chloropyridin-2-yl)ethyl]-2,4-dichloropyridine-3-carboxamide, N-[1-(5-bromo-3-chloropyridin-2-yl)ethyl]-2-fluoro-4-iodopyridine-3-carboxamide, N-{(E)-[(cyclopropylmethoxy)imino][6-(difluoromethoxy)-2,3-difluorophenyl]methyl}-2-phenylacetamide, N-{(Z)-[(cyclopropylmethoxy)imino][6-(difluoromethoxy)-2,3-difluorophenyl]methyl}-2-phenylacetamide, N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, pentyl {6-[({[(1-methyl-1H-tetrazol-5-yl)(phenyl)methylidene]amino}oxy)methyl]pyridin-2-yl}carbamate, phenazine-1-carboxylic acid, quinolin-8-ol and quinolin-8-ol sulphate (2:1).
(16) Further compounds, for example 1-methyl-3-(trifluoromethyl)-N-[2'-(trifluoromethyl)biphenyl-2-yl]-1H-pyrazole-4-carboxamide, N-(4'-chlorobiphenyl-2-yl)-3-(difluoromethyl)-1-methyl-1H-pyrazole-4-carboxamide, N-(2',4'-dichlorobiphenyl-2-yl)-3-(difluoromethyl)-1-methyl-1H-pyrazole-4-carboxamide, 3-(difluoromethyl)-1-methyl-N-[4'-(trifluoromethyl)biphenyl-2-yl]-1H-pyrazole-4-carboxamide, N-(2',5'-difluorobiphenyl-2-yl)-1-methyl-3-(trifluoromethyl)-1H-pyrazole-4-carboxamide, 3-(difluoromethyl)-1-methyl-N-[4'-(prop-1-yn-1-yl)biphenyl-2-yl]-1H-pyrazole-4-carboxamide, 5-fluoro-1,3-dimethyl-N-[4'-(prop-1-yn-1-yl)biphenyl-2-yl]-1H-pyrazole-4-carboxamide, 2-chloro-N-[4'-(prop-1-yn-1-yl)biphenyl-2-yl]pyridine-3-carboxamide, 3-(difluoromethyl)-N-[4'-(3,3-dimethylbut-1-yn-1-yl)biphenyl-2-yl]-1-methyl-1H-pyrazole-4-carboxamide, N-[4'-(3,3-dimethylbut-1-yn-1-yl)biphenyl-2-yl]-5-fluoro-1,3-dimethyl-1H-pyrazole-4-carboxamide, 3-(difluoromethyl)-N-(4'-ethynylbiphenyl-2-yl)-1-methyl-1H-pyrazole-4-carboxamide, N-(4'-ethynylbiphenyl-2-yl)-5-fluoro-1,3-dimethyl-1H-pyrazole-4-carboxamide, 2-chloro-N-(4'-ethynylbiphenyl-2-yl)pyridine-3-carboxamide, 2-chloro-N-[4'-(3,3-dimethylbut-1-yn-1-yl)biphenyl-2-yl]pyridine-3-carboxamide, 4-(difluoromethyl)-2-methyl-N-[4-(trifluoromethyl)biphenyl-2-yl]-1,3-thiazole-5-carboxamide, 5-fluoro-N-[4'-(3-hydroxy-3-methylbut-1-yn-1-yl)biphenyl-2-yl]-1,3-dimethyl-1H-pyrazole-4-carboxamide, 2-chloro-N-[4'-(3-hydroxy-3-methylbut-1-yn-1-yl)biphenyl-2-yl]pyridine-3-carboxamide, 3-(difluoromethyl)-N-[4'-(3-methoxy-3-methylbut-1-yn-1-yl)biphenyl-2-yl]-1-methyl-1H-pyrazole-4-carboxamide, 5-fluoro-N-[4'-(3-methoxy-3-methylbut-1-yn-1-yl)biphenyl-2-yl]-1,3-dimethyl-1H-pyrazole-4-carboxamide, 2-chloro-N-[4'-(3-methoxy-3-methylbut-1-yn-1-yl)biphenyl-2-yl]pyridine-3-carboxamide, (5-bromo-2-methoxy-4-methylpyridin-3- yl)(2,3,4-trimethoxy-6-methylphenyl)methanone and N-[2-(4-{[3-(4-chlorophenyl)prop-2-yn-1-yl]oxy}-3-methoxyphenyl)ethyl]-N2-(methylsulphonyl)valinamide.

All of the stated mixing partners of classes (1) to (16) can form salts, where appropriate with suitable bases or acids, provided they are capable of so doing on the basis of their functional groups.

All plants and plant parts can be treated in accordance with the invention. Plants should be understood to mean in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts should be understood to mean all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

The inventive treatment of the plants and plant parts with the active ingredients is effected directly or by allowing the compounds to act on the environment, habitat or storage space by the customary treatment methods, for example by immersion, spraying, evaporation, fogging, scattering, painting on, injection, pouring on, and, in the case of propagation material, especially in the case of seeds, also by applying one or more coats.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts", "parts of plants" and "plant parts" have been explained above.

More preferably, plants of the plant cultivars which are in each case commercially available or in use are treated according to the invention. Plant cultivars should be understood to mean plants having novel properties ("traits") which have been obtained by conventional breeding, by mutagenesis or by recombinant DNA techniques. These can be cultivars, bio- or genotypes.

Preferred plants are those from the group of the useful plants, ornamentals, turfs, commonly used trees which are employed as ornamentals in public and private areas, and forestry trees. Forestry trees include trees for the production of timber, pulp, paper and products made from parts of the trees.

The term useful plants as used in the present context refers to crop plants which are employed as plants for obtaining foodstuffs, feedstuffs, fuels or for industrial purposes.

The useful plants which can be treated with the inventive active ingredients include, for example, the following types of plants: turf, vines, cereals, for example wheat, barley, rye, oats, rice, maize and millet/sorghum; beet, for example sugar beet and fodder beet; fruits, for example pome fruit, stone fruit and soft fruit, for example apples, pears, plums, peaches, almonds, cherries and berries, for example strawberries, raspberries, blackberries; legumes, for example beans, lentils, peas and soya beans; oil crops, for example oilseed rape, mustard, poppies, olives, sunflowers, coconuts, castor oil plants, cacao beans and peanuts; cucurbits, for example pumpkin/squash, cucumbers and melons; fibre plants, for example cotton, flax, hemp and jute; citrus fruit, for example, oranges, lemons, grapefruit and tangerines; vegetables, for example spinach, lettuce, asparagus, cabbage species, carrots, onions, tomatoes, potatoes and bell peppers; Lauraceae, for example avocado, *Cinnamomum*, camphor, or also plants such as tobacco, nuts, coffee, aubergine, sugarcane, tea, pepper, grapevines, hops, bananas, latex plants and ornamentals, for example flowers, shrubs, deciduous trees and coniferous trees. This enumeration does not represent any limitation.

The following plants are considered to be particularly suitable target crops for the treatment with the inventive active ingredients: cotton, aubergine, turf, pome fruit, stone fruit, soft fruit, maize, wheat, barley, cucumber, tobacco, vines, rice, cereals, pear, beans, soya beans, oilseed rape, tomato, bell pepper, melons, cabbage, potatoes and apples.

Examples of trees which can be improved in accordance with the method according to the invention are: *Abies* sp., *Eucalyptus* sp., *Picea* sp., *Pinus* sp., *Aesculus* sp., *Platanus* sp., *Tilia* sp., *Acer* sp., *Tsuga* sp., *Fraxinus* sp., *Sorbus* sp., *Betula* sp., *Crataegus* sp., *Ulmus* sp., *Quercus* sp., *Fagus* sp., *Salix* sp., *Populus* sp.

Preferred trees which can be improved in accordance with the method according to the invention are: from the tree species *Aesculus: A. hippocastanum, A. pariflora, A. carnea*; from the tree species *Platanus: P. aceriflora, P. occidentalis, P. racemosa*; from the tree species *Picea: P. abies*; from the tree species *Pinus: P. radiate, P. ponderosa, P. contorta, P. sylvestre, P. elliottii, P. montecola, P. albicaulis, P. resinosa, P. palustris, P. taeda, P. flexilis, P. jeffregi, P. baksiana, P. strobes*; from the tree species *Eucalyptus: E. grandis, E. globulus, E. camadentis, E. nitens, E. obliqua, E. regnans, E. pilularus*.

Particularly preferred trees which can be improved in accordance with the method according to the invention are: from the tree species *Pinus: P. radiate, P. ponderosa, P. contorta, P. sylvestre, P. strobes*; from the tree species *Eucalyptus: E. grandis, E. globulus* and *E. camadentis*.

Very particularly preferred trees which can be improved in accordance with the method according to the invention are: horse chestnut, Platanaceae, linden tree, maple tree.

The present invention can also be applied to any turfgrasses, including cool-season turfgrasses and warm-season turfgrasses.

Depending on the plant species or plant cultivars, their location and growth conditions (soils, climate, vegetation period, diet), the inventive treatment may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The transgenic plants or plant cultivars (obtained by genetic engineering) which are preferably to be treated according to the invention include all plants which, by virtue of the genetic modification, received genetic material which imparts particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products. Further and particularly emphasized examples of such traits are a better defense of the plants against animal and microbial pests, such as against insects, mites, phytopathogenic fungi, bacteria and/or viruses, and also increased tolerance of the plants to certain herbicidally active ingredients. Examples of transgenic plants which may be mentioned are the important crop plants, such as cereals (wheat, rice), maize, soya beans, potatoes, sugar beet, tomatoes, peas and other vegetable varieties, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized in particular are increased defense of the plants against insects, arachnids, nematodes and slugs and snails by virtue of toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (referred to hereinbelow as "Bt plants"). Traits that are also particularly emphasized are the increased defense of the plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active ingredients, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya beans), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plant cultivars will be developed and/or marketed in the future.

The plants listed can be treated according to the invention in a particularly advantageous manner with the compounds of the general formula I and/or the active ingredient mixtures according to the invention. The preferred ranges stated above for the active ingredients or mixtures also apply to the treatment of these plants. Particular emphasis is given to the treatment of plants with the compounds or mixtures specifically mentioned in the present text.

In addition, the inventive compounds can be used to control a multitude of different pests, including, for example, harmful sucking insects, biting insects and other pests which are plant parasites, stored material pests, pests which destroy industrial material, and hygiene pests including parasites in the animal health sector, and for the control thereof, for example the elimination and eradication thereof. The present invention thus also includes a method for controlling pests.

In the animal health sector, i.e. in the field of veterinary medicine, the active ingredients according to the present invention act against animal parasites, especially ectoparasites or endoparasites. The term "endoparasites" includes especially helminths such as cestodes, nematodes or trematodes, and protozoa such as coccidia. Ectoparasites are typically and preferably arthropods, especially insects such as flies (biting and licking), parasitic fly larvae, lice, hair lice, bird lice, fleas and the like, or acaricides such as ticks, for example hard ticks or soft ticks, or mites such as scab mites, harvest mites, bird mites and the like.

These parasites include:

From the order of the Anoplurida, for example, *Haematopinus* spp., *Linognathus* spp., *Pediculus* spp., *Phtirus* spp. and *Solenopotes* spp.; specific examples are: *Linognathus setosus, Linognathus vituli, Linognathus ovillus, Linognathus oviformis, Linognathus pedalis, Linognathus stenopsis, Haematopinus asini macrocephalus, Haematopinus eurysternus, Haematopinus suis, Pediculus humanus capitis, Pediculus humanus corporis, Phylloera vastatrix, Phthirus pubis, Solenopotes capillatus;*

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.; specific examples are: *Bovicola bovis, Bovicola ovis, Bovicola limbata, Damalina bovis, Trichodectes canis, Felicola subrostratus, Bovicola caprae, Lepikentron ovis, Werneckiella equi;*

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; specific examples are: *Aedes aegypti, Aedes albopictus, Aedes taeniorhynchus, Anopheles gambiae, Anopheles maculipennis, Calliphora erythrocephala, Chrysozona pluvialis, Culex quinquefasciatus, Culex pipiens, Culex tarsalis, Fannia canicularis, Sarcophaga carnaria, Stomoxys calcitrans, Tipula paludosa, Lucilia cuprina, Lucilia sericata, Simulium reptans, Phlebotomus papatasi, Phlebotomus longipalpis, Odagmia ornata, Wilhelmia equina, Boophthora erythrocephala, Tabanus bromius, Tabanus spodopterus, Tabanus atratus, Tabanus sudeticus, Hybomitra ciurea, Chrysops caecutiens, Chrysops relictus, Haematopota pluvialis, Haematopota italica, Musca autumnalis, Musca domestica, Haematobia irritans irritans, Haematobia irritans exigua, Haematobia stimulans, Hydrotaea irritans, Hydrotaea albipuncta, Chrysomya chloropyga, Chrysomya bezziana, Oestrus ovis, Hypoderma bovis, Hypoderma lineatum, Przhevalskiana silenus, Dermatobia hominis, Melophagus ovinus, Lipoptena capreoli, Lipoptena cervi, Hippobosca variegata, Hippo-*

*bosca equina, Gasterophilus intestinalis, Gasterophilus haemorroidalis, Gasterophilus inermis, Gasterophilus nasalis, Gasterophilus nigricornis, Gasterophilus pecorum, Braula coeca;*

From the order of the Siphonapterida, for example *Pulex* spp., *Ctenocephalides* spp., *Tunga* spp., *Xenopsylla* spp., *Ceratophyllus* spp.; specific examples are: *Ctenocephalides canis, Ctenocephalides felis, Pulex irritans, Tunga penetrans, Xenopsylla cheopis;*

From the order of the heteropterida, for example, *Cimex* spp., *Triatoma* spp., *Rhodnius* spp. and *Panstrongylus* spp.

From the order of the Blattarida, for example *Blatta orientalis, Periplaneta americana, Blattela germanica* and *Supella* spp. (e.g. *Supella longipalpa*);

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Rhipicephalus* (*Boophilus*) spp., *Dermacentor* spp., *Haemophysalis* spp., *Hyalomma* spp., *Dermanyssus* spp., *Rhipicephalus* spp. (the original genus of multihost ticks), *Ornithonyssus* spp., *Pneumonyssus* spp., *Raillietia* spp., *Pneumonyssus* spp., *Sternostoma* spp., *Varroa* spp., *Acarapis* spp.; specific examples are: *Argas persicus, Argas reflexus, Ornithodorus moubata, Otobius megnini, Rhipicephalus* (*Boophilus*) *microplus, Rhipicephalus* (*Boophilus*) *decoloratus, Rhipicephalus* (*Boophilus*) *annulatus, Rhipicephalus* (*Boophilus*) *calceratus, Hyalomma anatolicum, Hyalomma aegypticum, Hyalomma marginatum, Hyalomma transiens, Rhipicephalus evertsi, Ixodes ricinus, Ixodes hexagonus, Ixodes canisuga, Ixodes pilosus, Ixodes rubicundus, Ixodes scapularis, Ixodes holocyclus, Haemaphysalis concinna, Haemaphysalis punctata, Haemaphysalis cinnabarina, Haemaphysalis otophila, Haemaphysalis leachi, Haemaphysalis longicorni, Dermacentor marginatus, Dermacentor reticulatus, Dermacentor pictus, Dermacentor albipictus, Dermacentor andersoni, Dermacentor variabilis, Hyalomma mauritanicum, Rhipicephalus sanguineus, Rhipicephalus bursa, Rhipicephalus appendiculatus, Rhipicephalus capensis, Rhipicephalus turanicus, Rhipicephalus zambeziensis, Amblyomma americanum, Amblyomma variegatum, Amblyomma maculatum, Amblyomma hebraeum, Amblyomma cajennense, Dermanyssus gallinae, Ornithonyssus bursa, Ornithonyssus sylviarum, Varroa jacobsoni;*

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.; specific examples are: *Cheyletiella yasguri, Cheyletiella blakei, Demodex canis, Demodex bovis, Demodex ovis, Demodex caprae, Demodex equi, Demodex caballi, Demodex suis, Neotrombicula autumnalis, Neotrombicula desaleri, Neoschongastia xerothermobia, Trombicula akamushi, Otodectes cynotis, Notoedres cati, Sarcoptis canis, Sarcoptes bovis, Sarcoptes ovis, Sarcoptes rupicaprae* (=*S. caprae*), *Sarcoptes equi, Sarcoptes suis, Psoroptes ovis, Psoroptes cuniculi, Psoroptes equi, Chorioptes bovis, Psoergates ovis, Pneumonyssoidic mange, Pneumonyssoides caninum, Acarapis woodi.*

The inventive active ingredients are also suitable for controlling arthropods, helminths and protozoa which attack animals. The animals include agricultural livestock, for example cattle, sheep, goats, horses, pigs, donkeys, camels, buffalo, rabbits, chickens, turkeys, ducks, geese, cultured fish, honeybees. The animals also include domestic animals—also referred to as companion animals—for example dogs, cats, caged birds, aquarium fish, and test animals, for example hamsters, guinea pigs, rats and mice.

The control of these arthropods, helminths and/or protozoa should reduce cases of death and improve the performance (for meat, milk, wool, hides, eggs, honey etc.) and the health of the host animal, and so the use of the inventive active ingredients enables more economically viable and easier animal husbandry.

For example, it is desirable to prevent or to interrupt the uptake of blood from the host by the parasites (if relevant). Control of the parasites can also contribute to preventing the transmission of infectious substances.

The term "control" as used herein with regard to the field of animal health means that the active ingredients act by reducing the occurrence of the parasite in question in an animal infested with such parasites to a harmless level. More specifically, "control" as used herein means that the active ingredient kills the parasite in question, retards its growth or inhibits its proliferation.

In general, the inventive active ingredients can be employed directly when they are used for the treatment of animals. They are preferably employed in the form of pharmaceutical compositions which may comprise the pharmaceutically acceptable excipients and/or auxiliaries known in the prior art.

In the sector of animal health and in animal husbandry, the active ingredients are employed (=administered) in a known manner, by enteral administration in the form of, for example, tablets, capsules, potions, drenches, granules, pastes, boluses, the feed-through process and suppositories, by parenteral administration, for example by injection (intramuscular, subcutaneous, intravenous, intraperitoneal inter alia), implants, by nasal administration, by dermal administration in the form, for example, of dipping or bathing, spraying, pouring on and spotting on, washing and powdering, and also with the aid of moulded articles containing the active ingredient, such as collars, earmarks, tailmarks, limb bands, halters, marking devices, etc. The active ingredients can be formulated as a shampoo or as suitable formulations applicable in aerosols or unpressurized sprays, for example pump sprays and atomizer sprays.

In the case of employment for livestock, poultry, domestic pets, etc., the inventive active ingredients can be employed as formulations (for example powders, wettable powders ["WP"], emulsions, emulsifiable concentrates ["EC"], free-flowing compositions, homogeneous solutions and suspension concentrates ["SC"]), which contain the active ingredients in an amount of 1 to 80% by weight, directly or after dilution (e.g. 100- to 10 000-fold dilution), or they can be used as a chemical bath.

In the case of use in the animal health sector, the inventive active ingredients can be used in combination with suitable synergists or other active ingredients, for example acaricides, insecticides, anthelmintics, anti-protozoal agents.

It has also been found that the inventive compounds have a strong insecticidal action against insects which destroy industrial materials. Accordingly, the present invention also relates to the use of the inventive compounds for protecting industrial materials against infestation or destruction by insects.

The following insects may be mentioned as examples and as preferred—but without any limitation:

Beetles, such as *Hylotrupes bajulus, Chlorophorus pilosis, Anobium punctatum, Xestobium rufovillosum, Ptilinus pectinicornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Mint-* hes rugicollis, Xyleborus spec. Tryptodendron spec. Apate monachus, Bostrychus capucins, Heterobostrychus brunneus, Sinoxylon spec. Dinoderus minutus;

Hymenopterons, such as Sirex juvencus, Urocerus gigas, Urocerus gigas taignus, Urocerus augur;

Termites, such as Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;

Bristletails, such as Lepisma saccharina.

Industrial materials in the present connection should be understood to mean non-living materials, such as, preferably, plastics, adhesives, sizes, papers and cardboards, leather, wood and processed wood products and coating compositions.

The ready-to-use compositions may, if appropriate, comprise further insecticides and, if appropriate, one or more fungicides.

The inventive compounds can likewise be employed for protecting objects which come into contact with seawater or brackish water, especially hulls, screens, nets, buildings, moorings and signalling systems, against fouling.

Furthermore, the inventive compounds, alone or in combinations with other active ingredients, may be employed as antifouling agents.

In domestic, hygiene and stored-product protection, the active ingredients are also suitable for controlling animal pests, in particular insects, arachnids and mites, which are found in enclosed spaces such as, for example, dwellings, factory halls, offices, vehicle cabins and the like. They can be used to control these pests alone or in combination with other active ingredients and auxiliaries in domestic insecticide products. They are active against sensitive and resistant species and against all developmental stages. These pests include:

From the order of the Scorpionidea, for example, Buthus occitanus.

From the order of the Acarina, for example, Argas persicus, Argas reflexus, Bryobia ssp., Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.

From the order of the Araneae, for example, Aviculariidae, Araneidae.

From the order of the Opiliones, for example, Pseudoscorpiones chelifer, Pseudoscorpiones cheiridium, Opiliones phalangium.

From the order of the Isopoda, for example, Oniscus asellus, Porcellio scaber.

From the order of the Diplopoda, for example, Blaniulus guttulatus, Polydesmus spp.

From the order of the Chilopoda, for example, Geophilus spp.

From the order of the Zygentoma, for example, Ctenolepisma spp., Lepisma saccharina, Lepismodes inquilinus.

From the order of the Blattaria, for example, Blatta orientalies, Blattella germanica, Blattella asahinai, Leucophaea maderae, Panchlora spp., Parcoblatta spp., Periplaneta australasiae, Periplaneta americana, Periplaneta brunnea, Periplaneta fuliginosa, Supella longipalpa.

From the order of the Saltatoria, for example, Acheta domesticus.

From the order of the Dermaptera, for example, Forficula auricularia.

From the order of the Isoptera, for example, Kalotermes spp., Reticulitermes spp.

From the order of the Psocoptera, for example, Lepinatus spp., Liposcelis spp.

From the order of the Coleoptera, for example, Anthrenus spp., Attagenus spp., Dermestes spp., Latheticus oryzae, Necrobia spp., Ptinus spp., Rhizopertha dominica, Sitophilus granarius, Sitophilus oryzae, Sitophilus zeamais, Stegobium paniceum.

From the order of the Diptera, for example, Aedes aegypti, Aedes albopictus, Aedes taeniorhynchus, Anopheles spp., Calliphora erythrocephala, Chrysozona pluvialis, Culex quinquefasciatus, Culex pipiens, Culex tarsalis, Drosophila spp., Fannia canicularis, Musca domestica, Phlebotomus spp., Sarcophaga carnaria, Simulium spp., Stomoxys calcitrans, Tipula paludosa.

From the order of the Lepidoptera, for example, Achroia grisella, Galleria mellonella, Plodia interpunctella, Tinea cloacella, Tinea pellionella, Tineola bisselliella.

From the order of the Siphonaptera, for example, Ctenocephalides canis, Ctenocephalides felis, Pulex irritans, Tunga penetrans, Xenopsylla cheopis.

From the order of the Hymenoptera, for example, Camponotus herculeanus, Lasius fuliginosus, Lasius niger, Lasius umbratus, Monomorium pharaonis, Paravespula spp., Tetramorium caespitum.

From the order of the Anoplura, for example, Pediculus humanus capitis, Pediculus humanus corporis, Pemphigus spp., Phylloera vastatrix, Phthirus pubis.

From the order of the Heteroptera, for example, Cimex hemipterus, Cimex lectularius, Rhodinus prolixus, Triatoma infestans.

In the field of household insecticides, they are used alone or in combination with other suitable active ingredients, such as phosphoric esters, carbamates, pyrethroids, neonicotinoids, growth regulators or active ingredients from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

Illustration of the Processes and Intermediates

The invention also relates to a process for preparing compounds of the general formula (I)

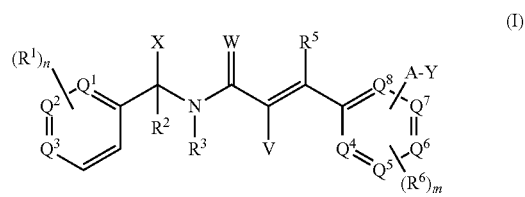

where $Q^1$ to $Q^8$, $R^1$ to $R^6$, A, X, Y, V, m and n are each defined as described above, in which a) amines of the general formula (III)

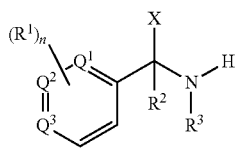
(III)

are reacted with carboxylic acids or carbonyl halides of the general formula (II)

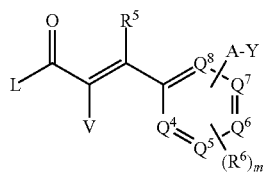
(II)

where L is halogen or hydroxyl to obtain compounds of the general formula (I) in which W is O (oxygen atom), and b) optionally, the compounds of the general formula (I) in which W is O (oxygen atom) are subsequently reacted with a thionating reagent to obtain compounds of the general formula (I) in which W is S (sulphur atom).

The invention also relates to compounds of the general formula (I) in which V is $R^4$ and $R^4$ is hydrogen, and in which additionally $R^5$ is hydrogen, and in which additionally W is O. These compounds correspond to the compounds of the general formula (I-3) in Formula Scheme 3 shown below.

The invention also relates to a preferred alternative process for preparing the inventive compounds of the general formula (I-3), which is shown in Formula Scheme 3, in which a) amines of the general formula (III)

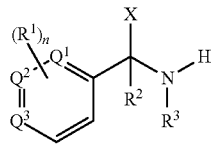
(III)

are reacted with acrylic acid derivatives of the general formula (V)

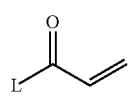
(V)

to obtain acrylamides of the general formula (VI)

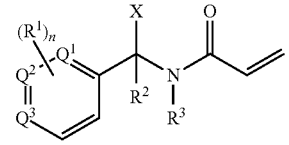
(VI)

and b) the acrylamides of the general formula (VI) are subsequently reacted with halogen compounds of the general formula (VII)

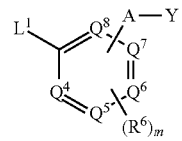
(VII)

in the presence of a palladium catalyst
to obtain compounds of the general formula (I-3), and where L is halogen or hydroxyl, and where $L^1$ is chlorine, bromine, iodine or triflate.

The invention further also relates to the compounds of the general formula (VI) which are obtained as intermediates in the process for preparing compounds of the general formula (I-3). A preferred compound of the general formula (VI) is N-{2,2,2-trifluoro-1-[3-(trifluoromethyl)phenyl]ethyl}-acrylamide, the preparation of which is described in the Preparation Examples in Synthesis Example 2 in Stage 1.

By way of example and additionally, the preparation of inventive compounds of the formula (I) and the specific inventive compounds of the formula (I-3) is explained in the Formula Schemes which follow. Reference is also made here to the Preparation Examples.

Formula Schemes 1 to 6 show, in general form, how the inventive compounds of the formula (I) can be obtained by the process according to the invention when W=O. The compounds of the general formula (I) where W=O are designated hereinafter by the general formula (I-1). The inventive compounds of the formula (I) where W=S can be obtained therefrom by reaction with a thionating reagent, for example Lawesson's reagent, ammonium sulphide or diphosphorus pentasulphide.

Formula Schemes 7 to 10 show how the compounds of the formula II can be obtained.

Formula Schemes 11 to 21 show how specific compounds of the general formula I can be obtained.

For the Formula Schemes and the explanation thereof, $Q^1$ to $Q^8$, $R^1$ to $R^6$, A, X, Y, V, m, and n hereinafter are each as defined above, unless a different definition is given in the explanation for the individual Formula Schemes.

Formula Scheme 1 (Preparation of Compounds of the General Formula I):

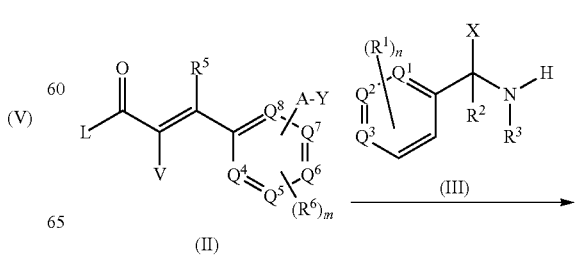

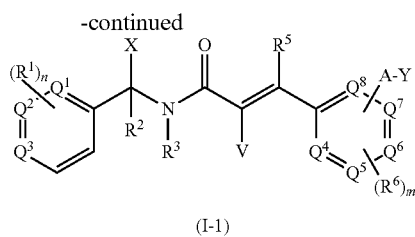

(I-1)

Inventive compounds of the general formula (I-1) can be obtained as shown in Formula Scheme 1, where L is halogen or hydroxyl, by the reaction of amines of the general structure (III) with activated carboxylic acid derivatives of the general structure (II). For (II), it is possible firstly to use an acid halide (e.g. L=chlorine) in the presence of a base, for example triethylamine or sodium hydroxide. Secondly, the carboxylic acid (L=OH) can also be employed, but using coupling reagents, for example dicyclohexylcarbodiimide, and additives such as 1-hydroxybenzotriazole [Chem. Ber. 1970. 788]. It is also possible to use coupling reagents such as 1-ethyl-3-(3-dimethylaminopropyl)carbodiimide, 1,1'-carbonyl-1H-imidazole and similar compounds. The coupling reagents employed to perform the preparation process may be all those suitable for preparing an ester or amide bond (cf. for example Bodansky et al., Peptide Synthesis, 2nd ed., Wiley & Sons, New York, 1976; Gross, Meienhofer, The Peptide: Analysis, Synthesis, Biology (Academic Press, New York, 1979). In addition, it is also possible to use mixed anhydrides for preparation of (I) [J. Am. Chem. Soc 1967, 5012]. In this process, it is possible to use different chloroformic esters, for example isobutyl chloroformate, isopropyl chloroformate. It is likewise possible for this purpose to use diethylacetyl chloride, trimethylacetyl chloride and the like.

Formula Scheme 2 (Preparation of Compounds of the General Formula I-2):

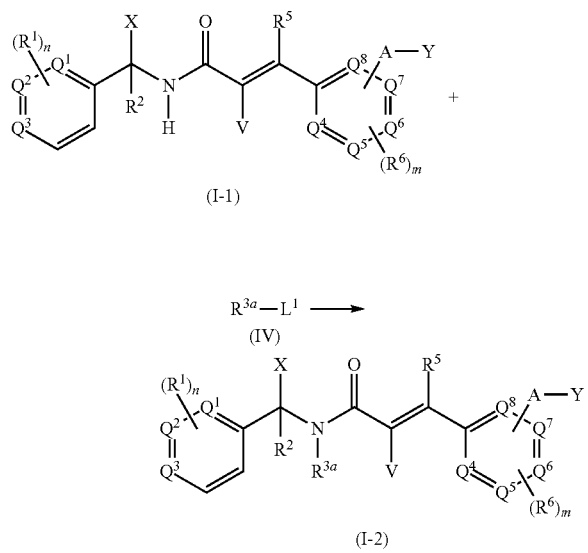

Inventive compounds of the (1-2) type can—as shown in Formula Scheme 2—also be prepared by the reaction of inventive compounds of the general structure (1-1) with an alkylating or acylating reagent of general structure (IV), for example methyl iodide in the presence of a suitable base, for example sodium hydride, where, in the formulae (I-1), (IV) and (1-2), $L^1$ is chlorine, bromine, iodine, tosylate or mesylate, and $R^{3a}$ is $C_1$-$C_4$-alkyl or $C_1$-$C_4$-alkylcarbonyl.

Formula Scheme 3 (Preparation of Compounds of the General Formula I-3)

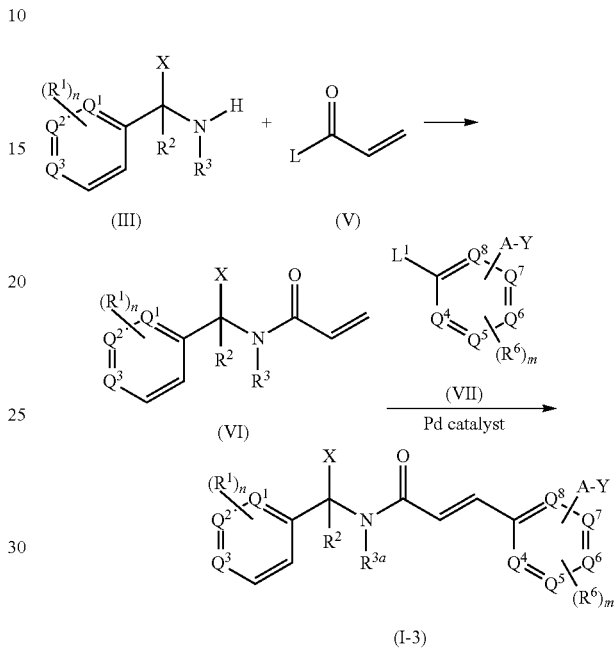

Compounds of the formula (I) can also be obtained in a two-stage process, as shown in Formula Scheme 3, where, in formula (VII), $L^1$ is chlorine, bromine, iodine or triflate.

In commonly known processes, amines of the formula (III) are first reacted here with acrylic acid derivatives of the formula (V) to give acrylamides of the formula (VI). Suitable reaction conditions for this reaction correspond to the reaction conditions specified for the reactions of carboxylic acid derivatives of the formula (II) with amines of the formula (III) in Formula Scheme 1.

Acrylamides of the formula (VI) can subsequently be reacted with halogen compounds of the formula (VII) by literature methods in a palladium-catalysed reaction to give the inventive compounds of the formula (I). The palladium catalyst used may, for example, be palladium acetate in the presence of triphenylphosphine (cf. for example Synlett 2006, 18, 2969-2972).

Formula Scheme 4 (Preparation of Compounds of the General Formula I-5 and I-6)

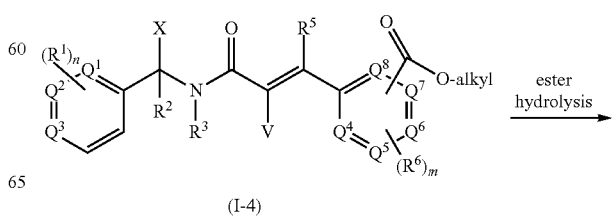

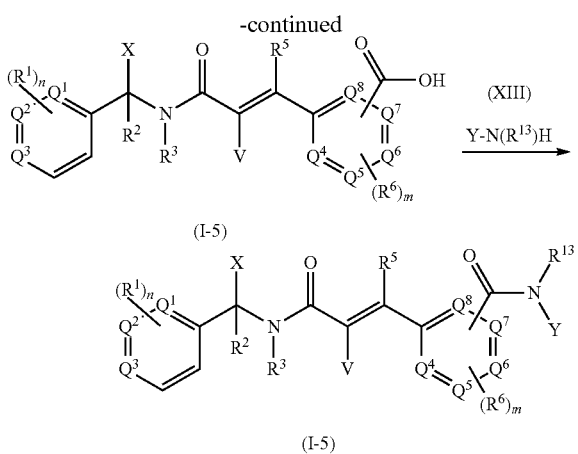

Compounds of the formula (I) can also be obtained by converting functional groups from other compounds of the formula (I), as shown in Formula Scheme 4.

For example, carboxylic ester derivatives of the formula (I-4), which can be synthesized by the methods indicated in Formula Schemes 1 or 3, can first be hydrolysed in analogy to methods which are common knowledge in the literature, in the presence of a base, for example lithium hydroxide, to give a carboxylic acid of the formula (I-5) (cf. for example J. Am. Chem. Soc. 1986, 108, 4603).

Carboxylic acids of the formula (I-5) can then be reacted with amines of the formula (XIII) to give carboxamide derivatives of the formula (I-6). The possible reaction conditions for this reaction have already been specified for the reactions of carboxylic acid derivatives of the formula (II) with amines of the formula (III) in Formula Scheme 1.

Formula Scheme 5 (Preparation of Compounds of the General Formula I-8, I-9)

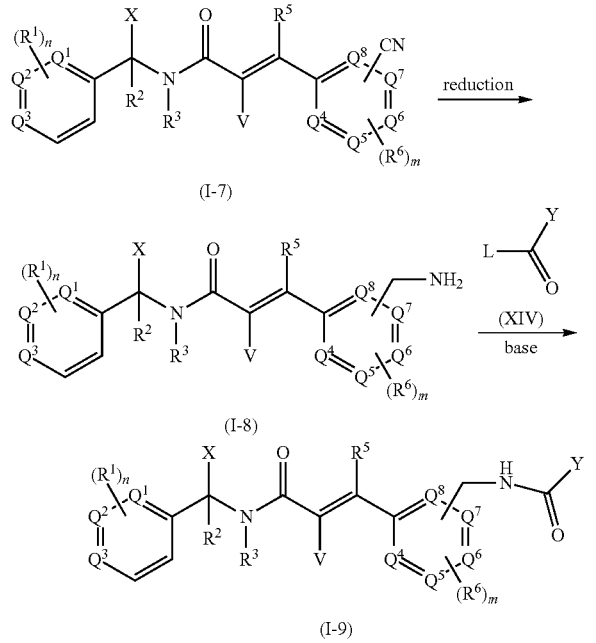

A further example for the conversion of compounds of the formula (I) by conversion of functional groups from other compounds of the formula (I) is shown in Formula Scheme 5.

For example, nitriles of the formula (I-7), which can be synthesized by the methods indicated in Formula Schemes 1 or 3, can first be reduced in analogy to methods which are common knowledge in the literature to give amines of the formula (I-8). Useful reducing agents include, for example hydrogen in the presence of catalyst, for example palladium on carbon (cf. for example J. Am. Chem. Soc. 1928, 50, 3370) or lithium aluminium hydride (cf. for example Org. Reac. 1951, 6, 469). Amines of the formula (I-8) can then be reacted with carboxylic acid derivatives of the formula (XIV) to give carboxamide derivatives of the formula (I-9). The possible reaction conditions for this reaction have already been specified for the reactions of carboxylic acid derivatives of the formula (II) with amines of the formula (III) in Formula Scheme 1.

Formula Scheme 6 (Preparation of Compounds of the General Formula I-11, I-12):

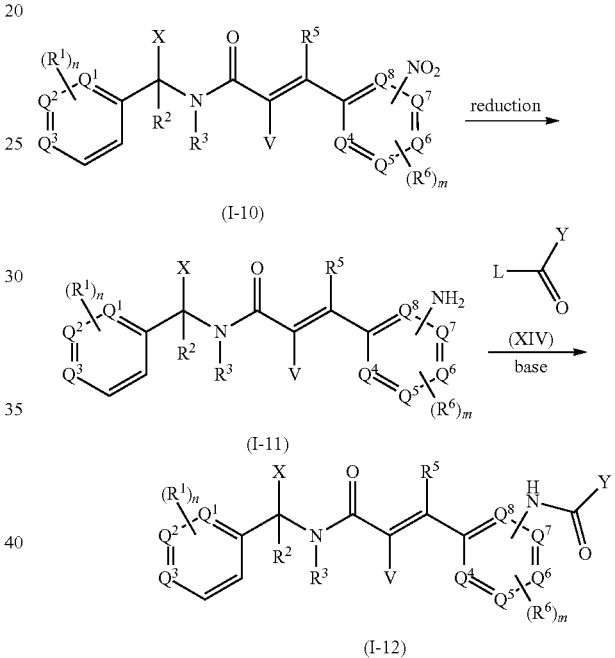

A further example for the conversion of compounds of the formula (I) by conversion of functional groups from other compounds of the formula (I) is shown in Formula Scheme 6.

Nitro compounds of the formula (I-10), which can be synthesized by the methods indicated in Formula Schemes 1 or 3, are first reduced in analogy to methods which are common knowledge in the literature to amines of the formula (I-11). Suitable processes for such reductions are in particular metal-mediated reactions, for example tin(II) chloride, iron powder, zinc powder and compounds similar thereto. The metal-mediated reductions, for example with tin(II) chloride, can be performed by a method described in Organic Syntheses Coll. Vol. (III), 453.

Amines of the formula (I-11) can then be reacted with carboxylic acid derivatives of the formula (XIV) to give carboxamide derivatives of the formula (I-12). The possible reaction conditions for this reaction have already been specified for the reactions of carboxylic acid derivatives of the formula (II) with amines of the formula (III) in Formula Scheme 1.

Formula Scheme 6a (Preparation of Compounds of the General Formula I-13 and I-14):

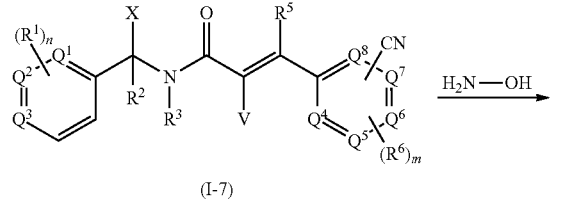
(I-7)

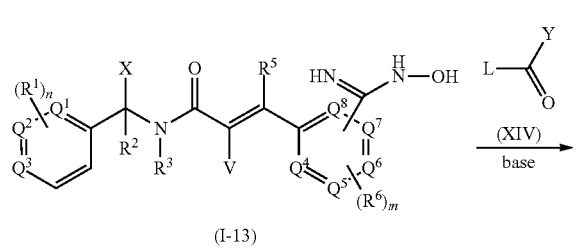
(I-13)

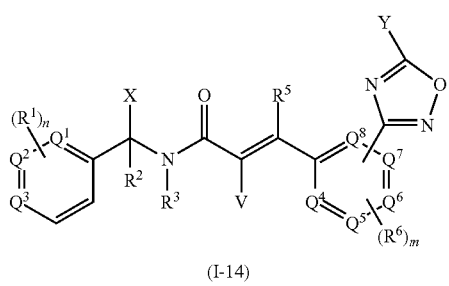
(I-14)

A further example for the conversion of compounds of the formula (I) by conversion of functional groups from other compounds of the formula (I) is shown in Formula Scheme 6a.

Cyano compounds of the formula (I-7), which can be synthesized by the methods indicated in Formula Scheme 1 or 3, are first reacted, in analogy to methods which are common knowledge in the literature, with hydroxylamine to give compounds of the formula (I-13).

Compounds of the formula (I-13) can then be reacted with carboxylic acid derivatives of the formula (XIV), for example carbonyl chlorides, in the presence of a base, for example pyridine, to give 1,3,4-oxadiazole derivatives of the formula (I-14).

Formula Scheme 6b (Preparation of Compounds of the General Formula I-15):

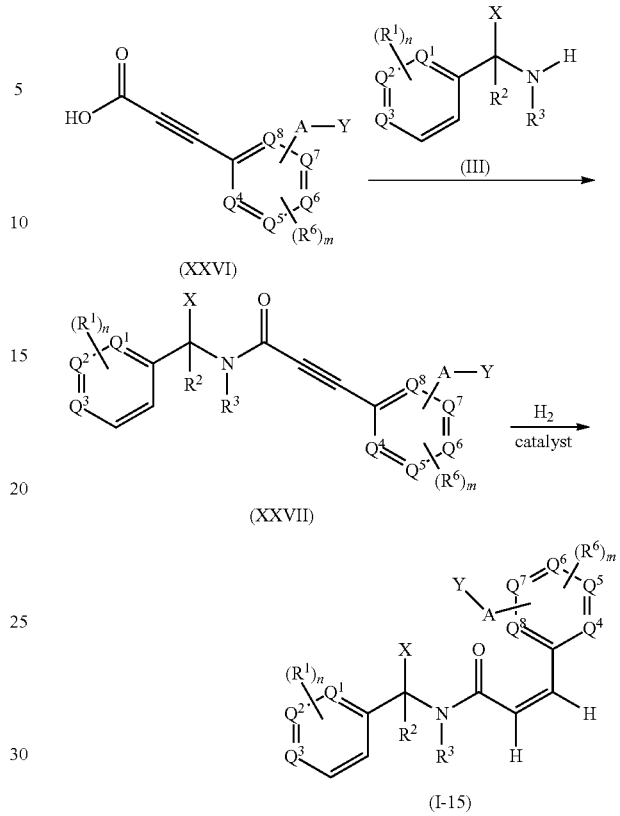

Z-Cinnamide derivatives of the formula (I-15) can be obtained as shown in Formula Scheme 6b.

In commonly known methods, compounds of the formula (VII) are first reacted here with propiolic acid of the formula (XXV) in the presence of a palladium catalyst, such as bis (triphenylphosphine)-palladium dichloride, and of copper salts, such as copper(I) iodide, to give alkynoic acids of the formula (XXVI) (lit.: WO2006/002981). Amines of the formula (III) can then be reacted with carboxylic acid derivatives of the formula (XXVI) to give carboxamide derivatives of the formula (XXVII). Suitable reaction conditions for this reaction correspond to the reaction conditions specified for the reactions of carboxylic acid derivatives of the formula (II) with amines of the formula (III) in Formula Scheme 1. The compounds of the formula (XXVII) can then be reacted with hydrogen in the presence of a suitable catalyst, for example of the Lindlar catalyst, selectively to give Z-cinnamides of the formula (I-15) (cf. for example Journal of Organic Chemistry 2003, 68, 2913-2920).

Formula Scheme 6c (Preparation of Compounds of the General Formula I-17):

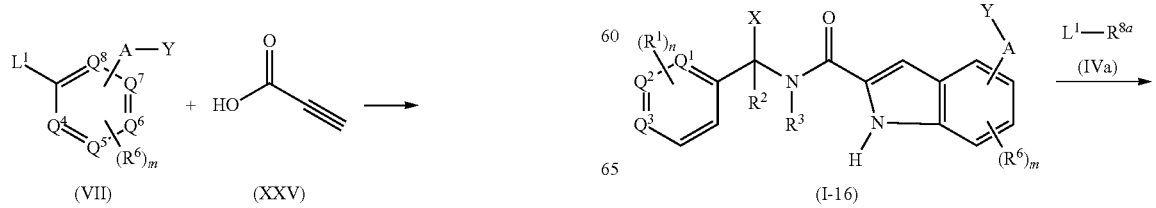
(I-16)

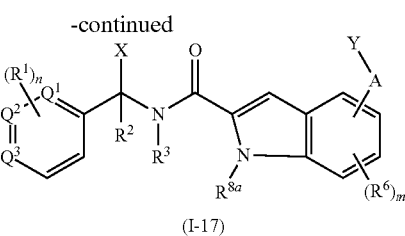

(I-17)

N-Substituted indole derivatives of the general formula (I-17) can be obtained as shown in Formula Scheme 6c, where
$R^{8a}$ is $R^8$ except hydrogen.

In this method, indoles of the general formula (I-16), which can be synthesized by the method indicated in Formula Scheme 1, are reacted with compounds of the general formula (IVa) in the presence of a base, for example potassium carbonate.

Carboxylic acids of the general formula (II) where L is OH are commercially available or known from the literature, or can be synthesized by methods known from the literature.

For instance, cinnamic acid derivatives of the formula (IIa)

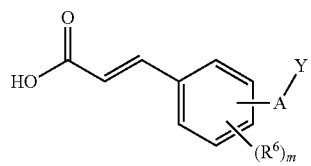

(IIa)

are obtained, for example, by a Heck reaction proceeding from commonly known bromo- or iodoaryl compounds, by reaction with 1-propenoic acid derivatives in the presence of a multitude of palladium catalysts, for example palladium acetate (the following references are cited here by way of example: Russian J. Org. Chem. 1995, 31, 439-444; Synth. Commun 2003, 33, 361-365; Chinese J. Org. Chem. 2004, 24, 59-62; Synthesis 1997, 1997, 521). It is also possible in the same way to use commonly known anilines, which are first converted to the diazonium salt in the presence of a diazotizing reagent, for example sodium nitrite, and then reacted with 1-propenoic acid derivatives in the presence of a palladium catalyst, for example palladium acetate (the following reference is cited here by way of example: Eur. J. Org. Chem. 1999, 1357-1366). Cinnamic acids of the formula (IIa) can also be obtained by reaction of aromatic aldehydes with malonic acid (the following literature is cited by way of example: Org. Synth. 1963, IV, 731; Synth. Comm. 1998, 28 (20), 3811-15)

Novel carboxylic acid derivatives of the general formula II (L=OH) can be obtained, for example, by the methods which follow.

Formula Scheme 7 (Preparation of Compounds of the General Formula II-1)

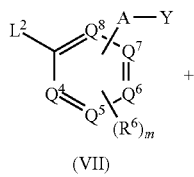

(VII)

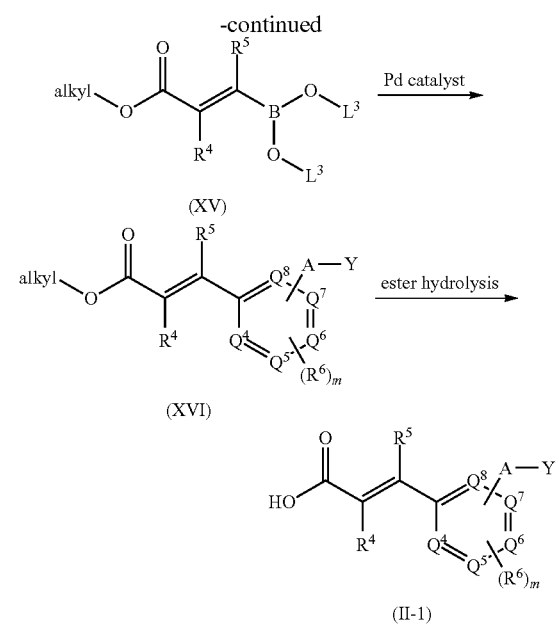

(XV)

(XVI)

(II-1)

Compounds of the formula (II-1) can be obtained as shown in Formula Scheme 7, where
alkyl is $C_1$-$C_4$-alkyl,
$L^2$ is chlorine, bromine, iodine or triflate and
$L^3$ is H or $C_1$-$C_4$-alkyl, where two $L^3$ substituents may also form a 5- or 6-membered ring.

As indicated in Formula Scheme 7, compounds of the formula (VII) are first reacted here with boronic acids or boronic esters of the formula (XV) in the presence of a palladium catalyst to give cinnamic esters of the formula (XVI). The catalytic palladium compound used may be a palladium (II) compound, for example bis(tricyclohexylphosphine)palladium(II) dichloride.

The carboxylic esters of the formula (XVI) are converted by commonly known methods, for example by alkaline hydrolysis with sodium hydroxide as a base, to the corresponding cinnamic acids of the formula (II-2), or can alternatively be obtained already as the free acids by varying the reaction conditions (for example the temperature or the reaction time) during the C—C coupling.

Formula Scheme 8 (Preparation of Compounds of the General Formula II-2)

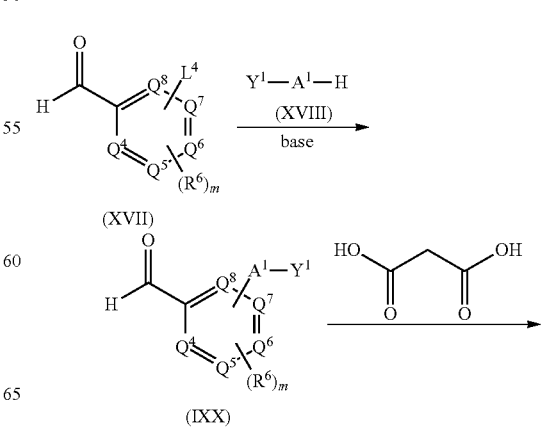

(XVII)

(IXX)

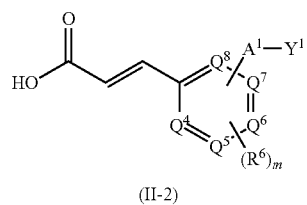

(II-2)

Compounds of the formula (II-2) can be obtained as shown in Formula Scheme 8, where $L^4$ is fluorine, chlorine or bromine, $Y^1$-$A^1$-H is an optionally substituted triazole, pyrazole, tetrazole or imidazole which bears a free N—H function, where useful substituents are the radicals specified in the general definition of A or Y.

Here, in analogy to known methods, aldehydes of the formula (XVII) are first reacted with heterocycles of the formula (XVIII), optionally in the presence of a base, to give aldehydes of the formula (IXX), some of which are known (cf. WO 2008019760; Tetrahedron (2001), 57(22), 4781-4785).

Aldehydes of the formula (IXX) can subsequently be reacted, in analogy to literature methods, with malonic acid in the presence of a nitrogen base, for example piperidine with decarboxylation to give cinnamic acids of the formula (II-2) (e.g. Bioorganic & Medicinal Chemistry Letters (2008), 18(5), 1663-1667; Journal of the Indian Chemical Society (2007), 84(6), 612-614; Journal of Chemical Research (2005), (6), 364-365).

Benzofurancarboxylic acids of the formula (IIb)

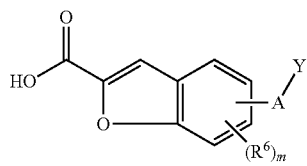

(IIb)

are likewise commercially available or known from the literature, or can be synthesized by literature methods. Examples include:

5-cyano-1-benzofuran-2-carboxylic acid, (Liebigs Annalen der Chemie 1982, 10. 1836-1869)

6-fluoro-1-benzofuran-2-carboxylic acid, (US005955495A)

6-fluoro-1-benzofuran-2-carboxylic acid, (JP2002/201193)

6-cyano-1-benzofuran-2-carboxylic acid, (WO2003/064411)

6-(trifluoromethyl)-1-benzofuran-2-carboxylic acid, (US005955495A)

5-chloro-6-methyl-1-benzofuran-2-carboxylic acid. (WO2005/080336)

Novel benzofurancarboxylic acids of the formula (II-3) can be obtained as shown in Formula Scheme 9, where $L^5$ is chlorine or bromine, ALK is a $C_1$-$C_4$-alkyl group.

Formula Scheme 9 (Preparation of Compounds of the General Formula II-3)

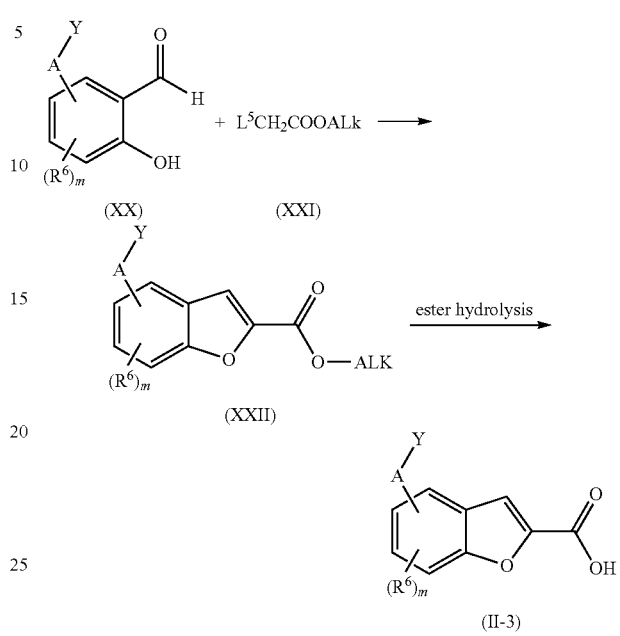

Here, in analogy to known methods (cf. for example DE 10115408), hydroxyaldehydes of the formula (XX) are first reacted with alkyl halocarboxylates, such as ethyl haloacetates, of the formula (XXI), in the presence of a base, for example potassium carbonate to give benzofurancarboxylic esters of the formula (XXII). The carboxylic esters of the formula (XXII) are then converted by commonly known methods, for example by alkaline hydrolysis with sodium hydroxide as a base, to the corresponding benzofurancarboxylic acids of the formula (II-3).

Indolecarboxylic acids of the formula (IIc)

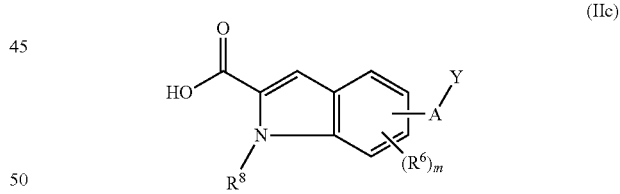

(IIc)

are likewise commercially available or known from the literature, or can be synthesized by literature methods. Examples include:

5-cyano-1H-indole-2-carboxylic acid (J. Org. Chem., 1953, 18, 345-357)

6-cyano-1H-indole-2-carboxylic acid (J. Med. Chem., 1997, 40. 2843-2857), 5-(methylsulphonyl)-1H-indole-2-carboxylic acid (WO2001/077101)

5,6-difluoro-1H-indole-2-carboxylic acid (WO2006/082400)

6-chloro-1H-pyrrolo[3,2-c]pyridine-2-carboxylic acid (WO2004/104001)

Novel indolecarboxylic acids of the formula (II-4) can be obtained as shown in Formula Scheme 10.

Formula Scheme 10 (Preparation of Compounds of the General Formula II-4)

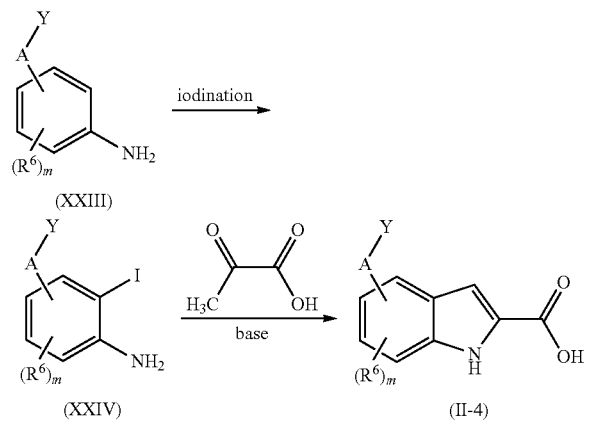

Here, in analogy to known methods (cf. for example Bioorg. Med. Chem. Lett. 2003, 13, 4385-4388), anilines of the formula (XXIII) are first converted to iodoanilines of the formula (XXIV) and then reacted with pyruvic acid in the presence of palladium acetate and of a base, for example 1,4-diazabicyclo[2.2.2]octane DABCO, to give benzofurancarboxylic esters of the formula (II-4).

Carbonyl halides, more preferably carbonyl chlorides, as likewise represented by the general structure (II) (L=halogen), can be prepared by the reaction of a carboxylic acid (L=OH) with halogenating reagents such as thionyl chloride, thionyl bromide, phosphoryl chloride, oxalyl chloride, phosphorus trichloride, etc. [Houben-Weyl, 1952, vol. VIII, p. 463 ff.].

Haloalkyl-substituted amines of the general formula (III) are commercially available or known from the literature, or can be synthesized by literature methods. For example, aryl halides can be reacted with haloalkyl carboxylates in the presence of magnesium in a Grignard reaction. The ketones thus formed can then be converted by a reductive amination to the corresponding amines (DE-A-2723464). 2,2,2-Trifluoro-1-(pyridin-4-yl)ethanamine is commercially available and can be synthesized analogously to the method in Angew. Chem. 1998, 110. 6, 880-881 and J. Mol. Cat. B: Enzymatic 30 (2004) 61-68.

Novel haloalkyl-substituted amines of the general formula (III) can be obtained, for example, by the methods which follow.

Formula Scheme 10a (Preparation of Compounds of the General Formula III-1)

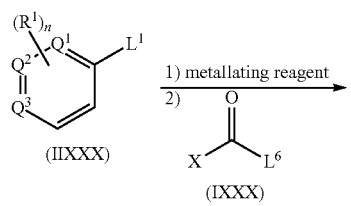

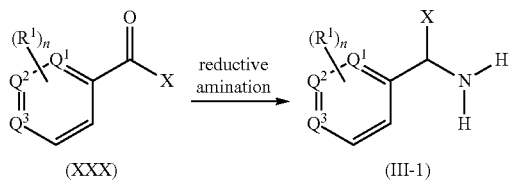

where $L^6$ is —C1-C4-alkoxy or —N(CH$_3$)—O—C$_1$-C$_4$-alkyl.

Novel compounds of the formula (III-1) can be obtained as shown in Formula Scheme 10a. It is possible here to react commercially available or literature compounds of the formula (IIXXX) first with a metallating reagent, for example magnesium, a Grignard compound, n-butyllithium or tert-butyllithium, to given an organometallic intermediate, which is subsequently reacted with a compound of the formula (IXXX) to obtain ketones of the formula (XXX). These can then be converted analogously to commonly known methods by reductive amination to amines of the formula (III-1). By reacting the ketones (XXX), for example, with hydroxylamine, it is possible here to form oxime intermediates, which are then reduced with a reducing agent, for example lithium aluminium hydride, to amines of the formula (III-1).

(Het)aryl halides of the formula (VII) are known or can be prepared by methods known in principle (see, for example, WO-A-2009055077, EP-A-1445253, EP-A-661258, U.S. Pat. No. 6,252,090, Chemical & Pharmaceutical Bulletin (1992), 40(7), 1789-92, Chemical & Pharmaceutical Bulletin (1994), 42(4), 913-16, Compt. rend. (1954), 237 357).

Novel (het)aryl halides of the general formula (VII) can be obtained, for example, by the methods which follow.

Formula Scheme 10b (Preparation of Compounds of the General Formula VII-1)

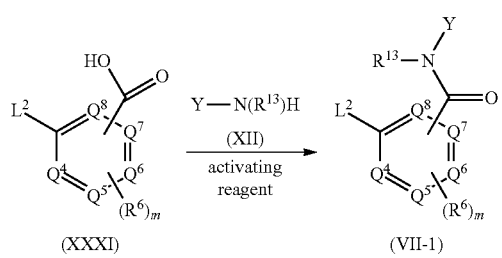

Novel compounds of the formula (VII-1) can be obtained as shown in Formula Scheme 10b. It is possible here to react commercially available or literature carboxylic acids of the formula (XXXI) with amines of the formula (XIII). The possible reaction conditions for this reaction have already been specified for the reactions of carboxylic acid derivatives of the formula (II) with amines of the formula (III) in Formula Scheme 1.

Formula Scheme 10c (Preparation of Compounds of the General Formula VII-2)

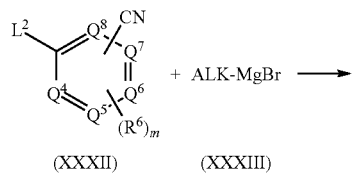

(XXXII)    (XXXIII)

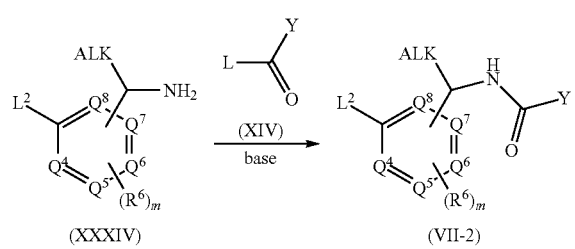

(XXXIV)    (VII-2)

As detailed in Formula Scheme 10c, in analogy to known methods, known nitrile derivatives of the formula (XXXII) are first reacted with alkyl-Grignard reagents of the formula (XXXIII) to obtain amines of the formula (XXXIV). Amines of the formula (XXXIV) can then be reacted with carboxylic acid derivatives of the formula (XIV) to give carboxamide derivatives of the formula (VII-1). The possible reaction conditions for this reaction have already been specified for the reactions of carboxylic acid derivatives of the formula (II) with amines of the formula (III) in Formula Scheme 1.

Formula Scheme 10d (Preparation of Compounds of the General Formula (VII-3)

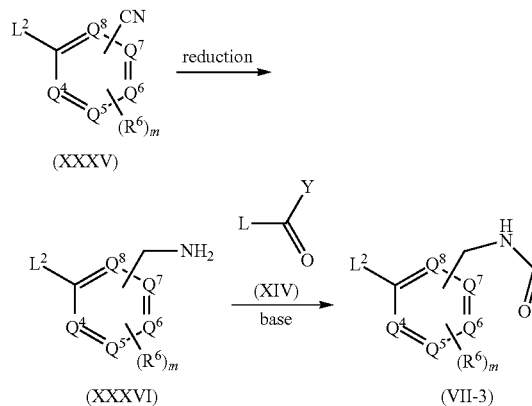

(XXXVI)    (VII-3)

As detailed in Formula Scheme 10d, in analogy to known methods, nitrile derivatives of the formula (XXXV) are first reacted with a reducing agent, for example lithium aluminium hydride, to give amines of the formula (XXXVI). Amines of the formula (XXXVI) can then be reacted with carboxylic acid derivatives of the formula (XIV) to give carboxamide derivatives of the formula (VII-3). The possible reaction conditions for this reaction have already been specified for the reactions of carboxylic acid derivatives of the formula (II) with amines of the formula (III) in Formula Scheme 1.

Formula Scheme 10e (Preparation of Compounds of the General Formula VII-4)

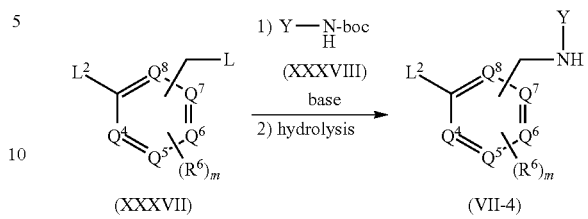

(XXXVII)    (VII-4)

As detailed in Formula Scheme 10e, in analogy to known methods, halogen derivatives of the formula (XXXVII) are reacted with a Boc-protected amine of the formula (XXXVIII) in the presence of a base, for example sodium hydride. Subsequently, the protecting group is detached to obtain secondary amines of the formula (VII-4).

Carboxylic acids of the general formula (II) where L is OH are commercially available or known from the literature, or can be synthesized by literature methods (Formula Schemes 7 to 10). The preparation of the carbonyl halides of the general formula (II) where L is halogen is explained after Formula Scheme 10.

Compounds of the formulae (IV), (IVa), (V), (XIII), (XIV), (XV), (XVII), (XVIII), (XX), (XXI), (XXIII), (XXV), (IIXXX), (XXX), (XXXI), (XXXII), (XXXIII), (XXXVI), (XXXVII) and (XXXVIII) are substances known from the literature or are commercially available.

The compounds of the general formulae I-1, I-2, I-4, I-7 and I-10 are obtainable according to Formula Scheme 1, the compounds of the general formula II-1 according to Formula Scheme 7.

The process according to the invention for preparing the novel compounds of the formula (I) is preferably performed using a diluent. Useful diluents for performing the process according to the invention may, in addition to water, be all inert solvents. Examples include: halohydrocarbons (e.g. chlorohydrocarbons, such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene), alcohols (e.g. methanol, ethanol, isopropanol, butanol), ethers (e.g. ethyl propyl ether, methyl tert-butyl ether, n-butyl ether, anisole, phenetole, cyclohexyl methyl ether, dimethyl ether, diethyl ether, dipropyl ether, diisopropyl ether, di-n-butyl ether, diisobutyl ether, diisoamyl ether, ethylene glycol dimethyl ether, tetrahydrofuran, dioxane, dichlorodiethyl ether, and polyethers of ethylene oxide and/or propylene oxide), amines (e.g. trimethyl-, triethyl-, tripropyl-, tributylamine, N-methylmorpholine, pyridine and tetramethylenediamine), nitrohydrocarbons (e.g. nitromethane, nitroethane, nitropropane, nitrobenzene, chloronitrobenzene, o-nitrotoluene; nitriles such as acetonitrile, propionitrile, butyronitrile, isobutyronitrile, benzonitrile, m-chlorobenzonitrile), tetrahydrothiophene dioxide, dimethyl sulphoxide, tetramethylene sulphoxide, dipropyl sulphoxide, benzyl methyl sulphoxide, diisobutyl sulphoxide, dibutyl sulphoxide, diisoamyl sulphoxide, sulphones (e.g. dimethyl, diethyl, dipropyl, dibutyl, diphenyl, dihexyl, methyl ethyl, ethyl propyl, ethyl isobutyl and pentamethylene sulphone), aliphatic, cycloaliphatic or aromatic hydrocarbons (e.g. pentane, hexane, heptane, octane, nonane and technical-grade hydrocarbons), and also "white spirits" comprising components having boiling points in the range from, for example, 40° C. to 250° C., cymene, petroleum fractions within a boiling range from 70° C. to 190° C., cyclohexane, methylcyclohexane, petroleum ether, ligroin, octane, benzene, toluene, chlorobenzene, bromobenzene, nitrobenzene, xylene, esters (e.g. methyl, ethyl, butyl, isobutyl acetate, dimethyl, dibutyl, ethylene carbonate); amides (e.g. hexamethylenephosphoramide, formamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2(1H)-pyrimidine, octylpyrrolidone, octylcaprolactam, 1,3-dimethyl-2-imidazolinedione, N-formylpiperidine, N,N'-1,4-diformylpiperazine), and ketones (e.g. acetone, acetophenone, methyl ethyl ketone, methyl butyl ketone).

It will be appreciated that the process according to the invention can also be performed in mixtures of the solvents and diluents mentioned.

When the process according to the invention is performed, the reaction temperatures can be varied within a relatively wide range. In general, the temperatures employed are between −30° C. and +150° C., preferably between −10° C. and +100° C.

The process according to the invention is generally performed under standard pressure. However, it is also possible to perform the process according to the invention under elevated or reduced pressure—generally at absolute pressures between 0.1 bar and 15 bar.

To perform the process according to the invention, the starting materials are generally used in approximately equimolar amounts. However, it is also possible to use one of the components in a greater excess. The reaction is generally performed in a suitable diluent in the presence of a reaction auxiliary, optionally also under a protective gas atmosphere (e.g. under nitrogen, argon or helium), and the reaction mixture is generally stirred at the required temperature for several hours. The workup is performed by customary methods (cf. the Preparation Examples).

The basic reaction auxiliaries used to perform the process according to the invention may be all suitable acid binders. Examples include: alkaline earth metal or alkali metal compounds (e.g. hydroxides, hydrides, oxides and carbonates of lithium, of sodium, of potassium, of magnesium, of calcium and of barium), amidine bases or guanidine bases (e.g. 7-methyl-1,5,7-triaza-bicyclo(4.4.0)dec-5-ene (MTBD); diazabicyclo(4.3.0)nonene (DBN), diazabicyclo(2.2.2)octane (DABCO), 1,8-diazabicyclo(5.4.0)undecene (DBU), cyclohexyltetrabutylguanidine (CyTBG), cyclohexyltetramethylguanidine (CyTMG), N,N,N,N-tetramethyl-1,8-naphthalenediamine, pentamethylpiperidine) and amines, especially tertiary amines (e.g. triethylamine, trimethylamine, tribenzylamine, triisopropylamine, tributylamine, tricyclohexylamine, triamylamine, trihexylamine, N,N-dimethylaniline, N,N-dimethyltoluidine, N,N-dimethyl-p-aminopyridine, N-methyl-pyrrolidine, N-methylpiperidine, N-methylimidazole, N-methylpyrazole, N-methylmorpholine, N-methylhexamethylenediamine, pyridine, 4-pyrrolidinopyridine, 4-dimethylaminopyridine, quinoline, α-picoline, β-picoline, pyrimidine, acridine, N,N,N',N'-tetramethylenediamine, N,N,N',N'-tetraethylenediamine, quinoxaline, N-propyldiisopropylamine, N-ethyl-diisopropylamine, N,N'-dimethylcyclohexylamine, 2,6-lutidine, 2,4-lutidine or triethyldiamine).

The acidic reaction auxiliaries used to perform the process according to the invention may be all mineral acids (e.g. hydrohalic acids such as hydrofluoric acid, hydrochloric acid, hydrobromic acid or hydriodic acid, and also sulphuric acid, phosphoric acid, phosphorous acid, nitric acid), Lewis acids (e.g. aluminium(III) chloride, boron trifluoride or the etherate thereof, titanium(V) chloride, tin(V) chloride, and organic acids (e.g. formic acid, acetic acid, propionic acid, malonic acid, lactic acid, oxalic acid, fumaric acid, adipic acid, stearic acid, tartaric acid, oleic acid, methanesulphonic acid, benzoic acid, benzenesulphonic acid or para-toluenesulphonic acid.

Formula Schemes 11-21 show, by way of example, the preparation of specific preferred inventive compounds of the general formula I.

Formula Scheme 11:

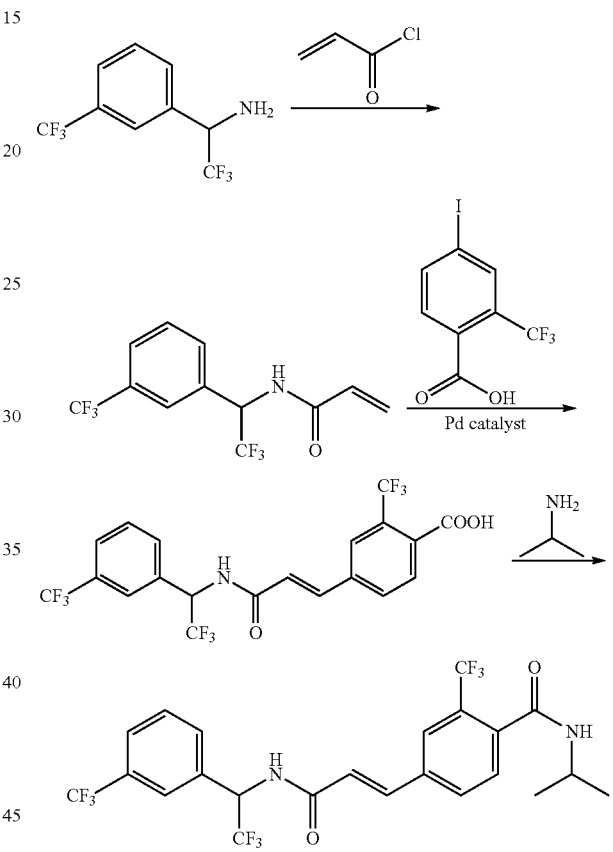

Formula Scheme 11a:

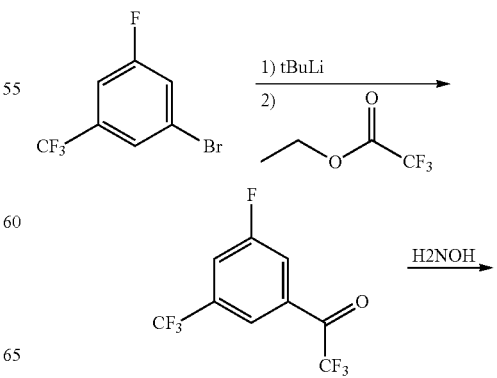

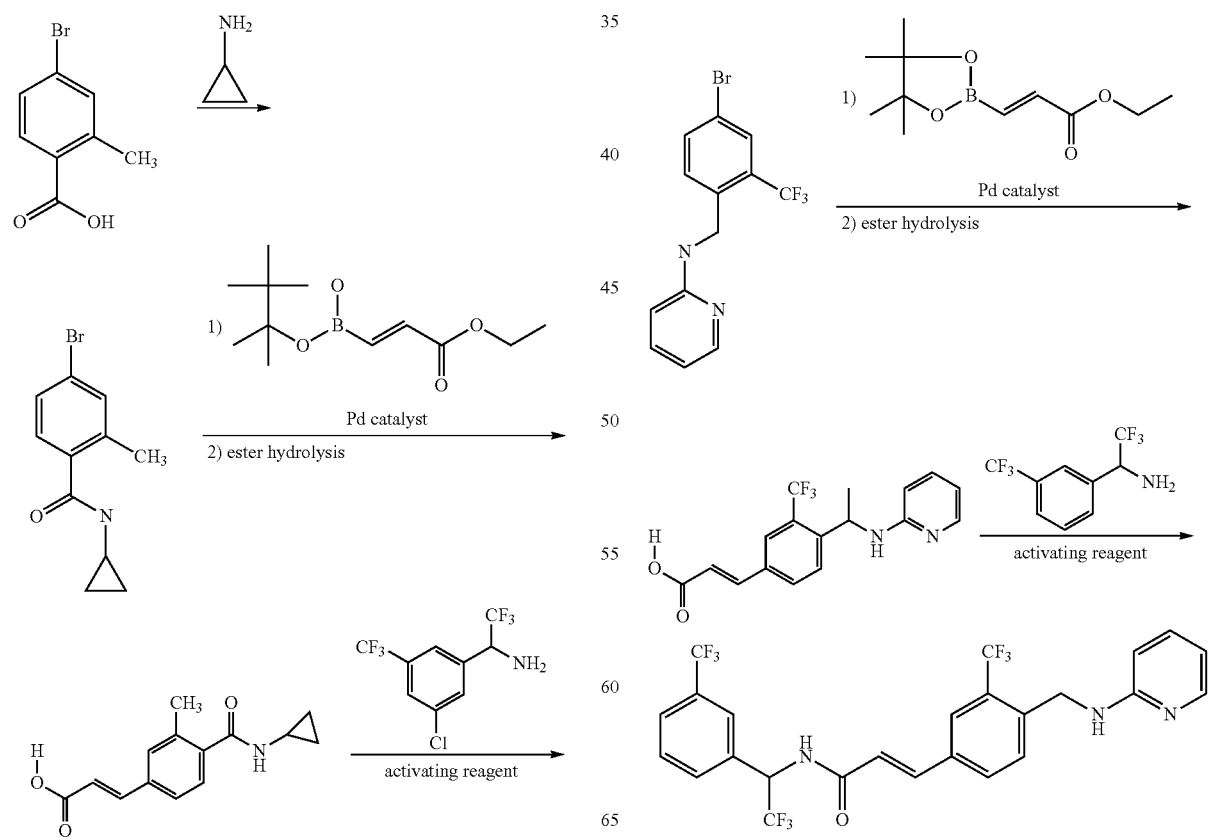

Formula Scheme 12b
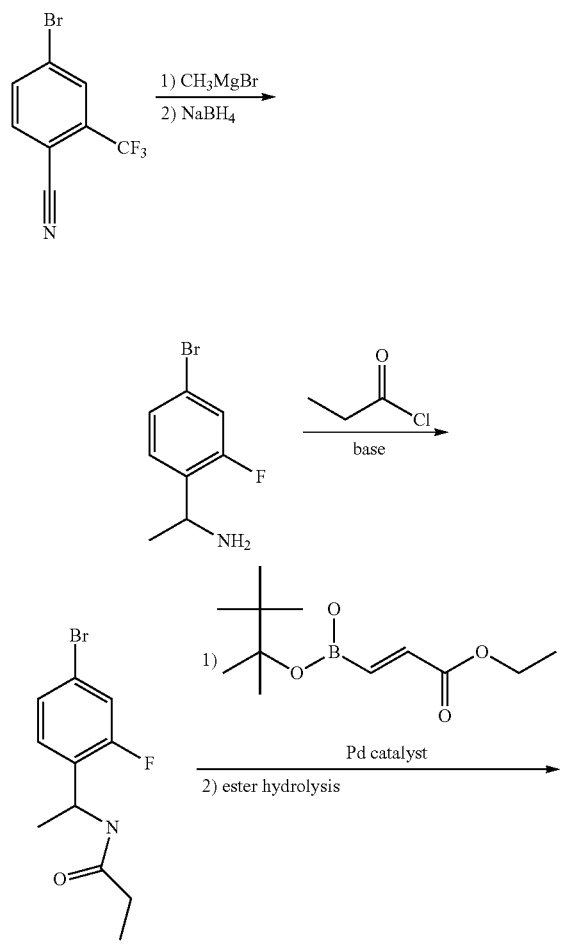
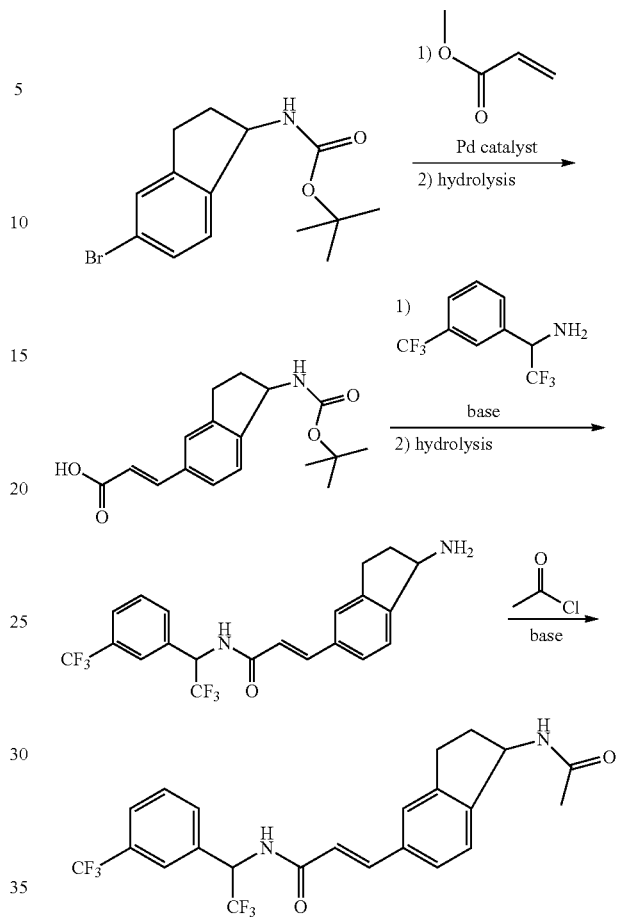
Formula Scheme 12d:
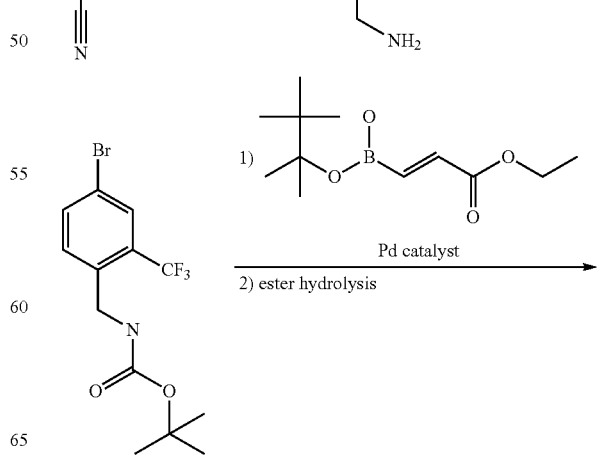
Formula Scheme 12c:
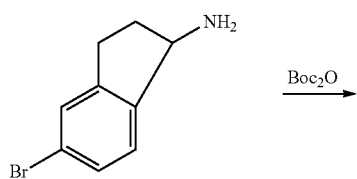
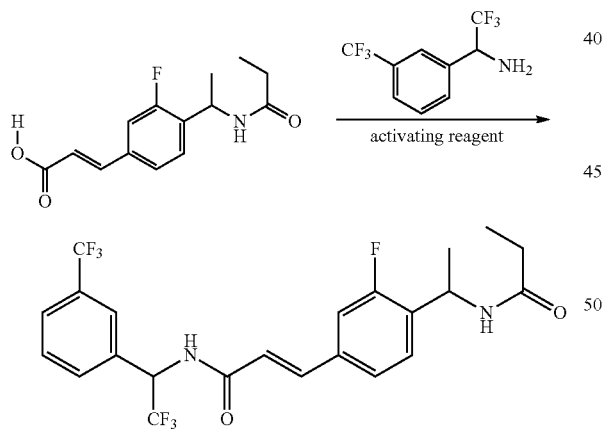

61
-continued
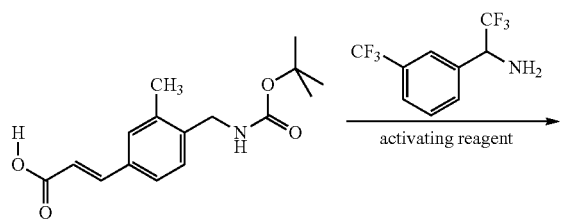
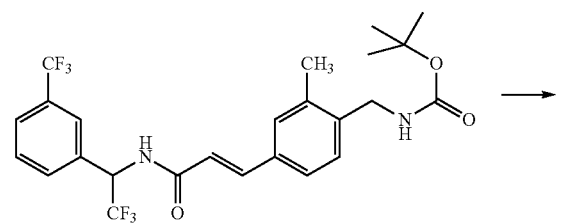
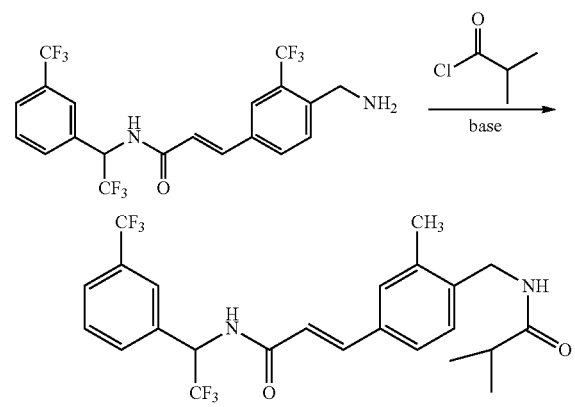
Formula Scheme 13:
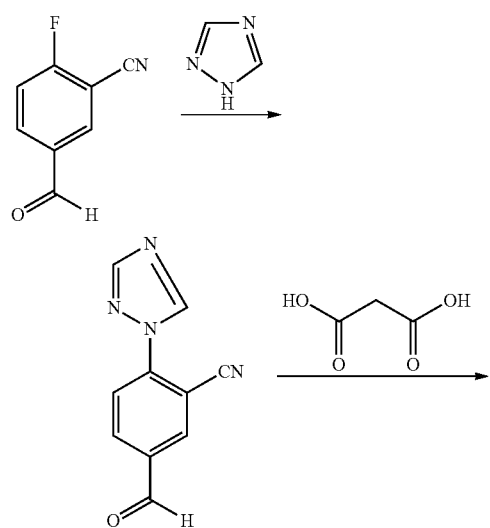
62
-continued
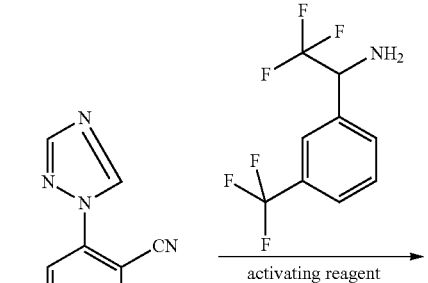
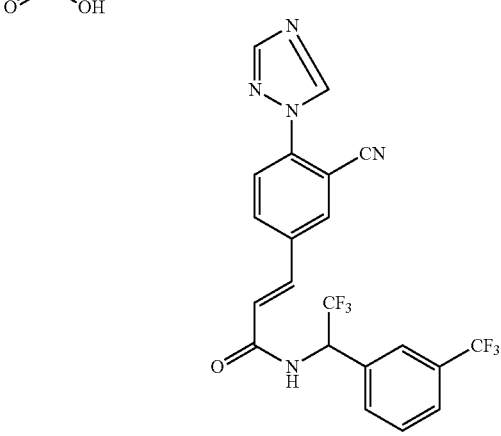
Formula Scheme 14:
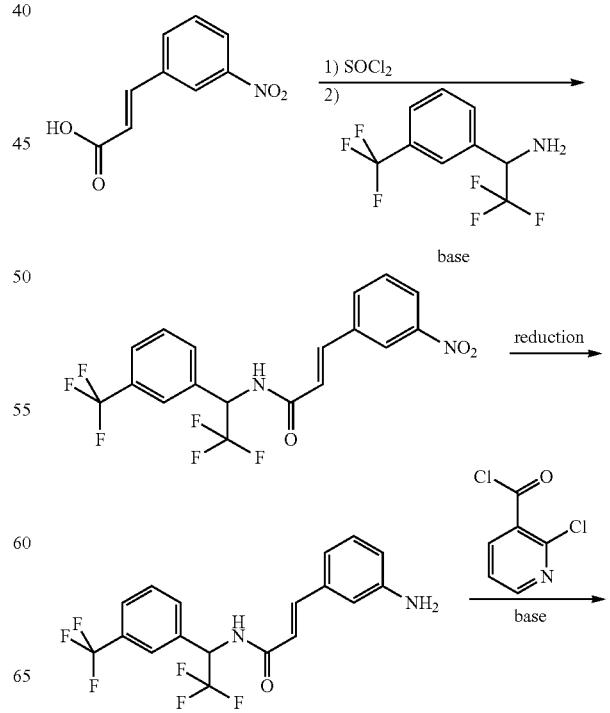

-continued
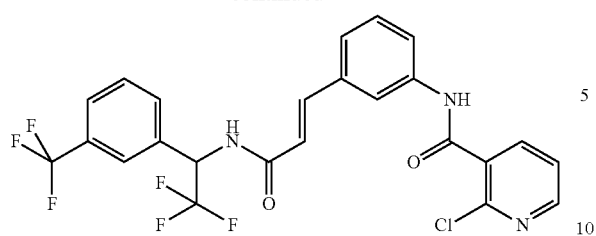
Formula Scheme 15:
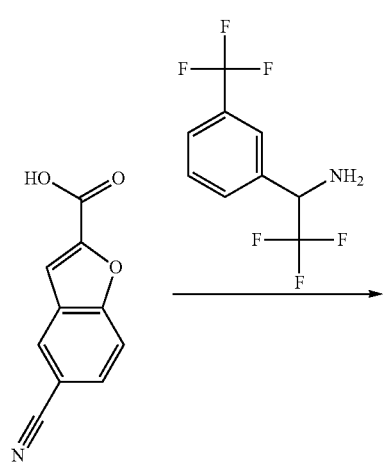
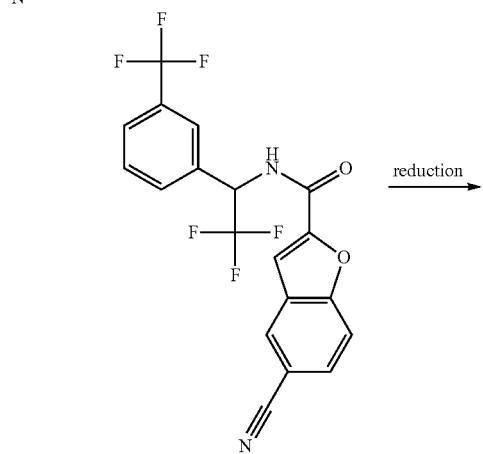
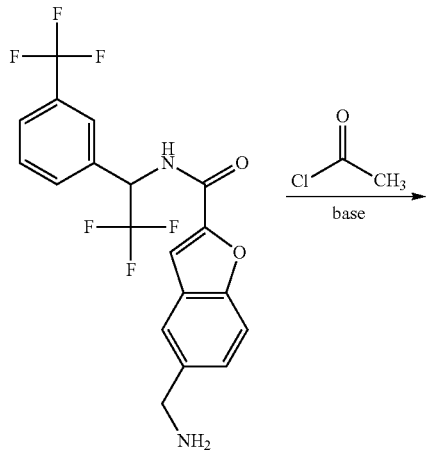
-continued
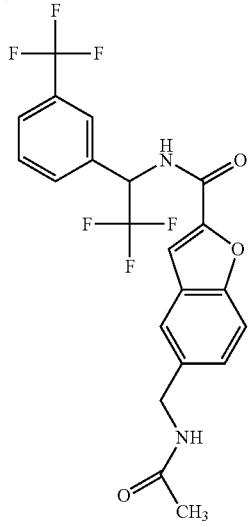 [SMILES: CC(=O)NCc1ccc2oc(C(=O)NC(c3cccc(C(F)(F)F)c3)C(F)(F)F)cc2c1]
Formula Scheme 16:
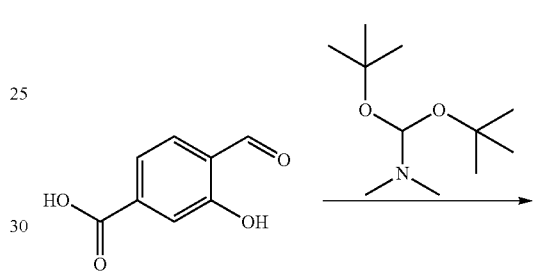
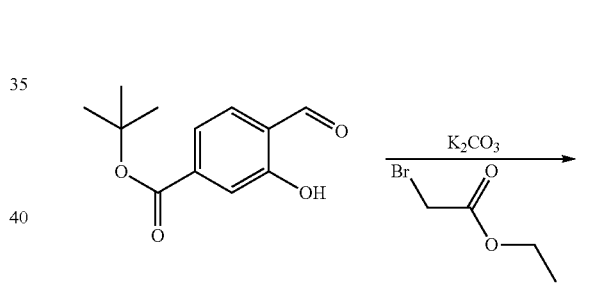
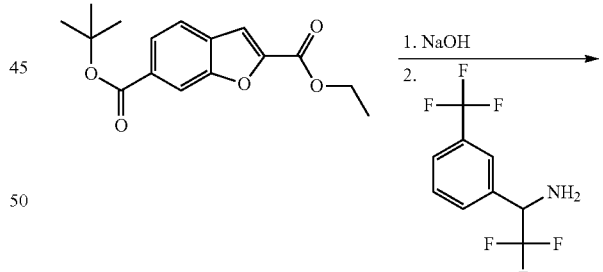
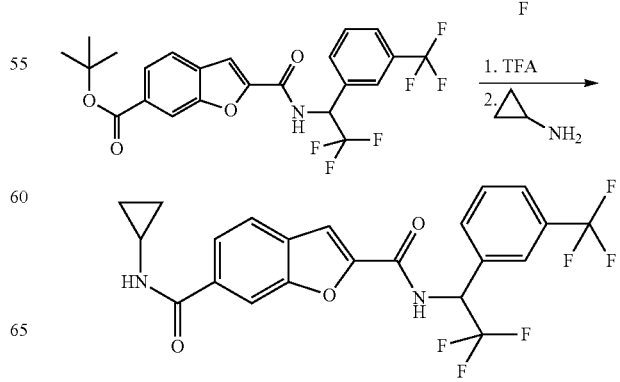

Formula Scheme 17:
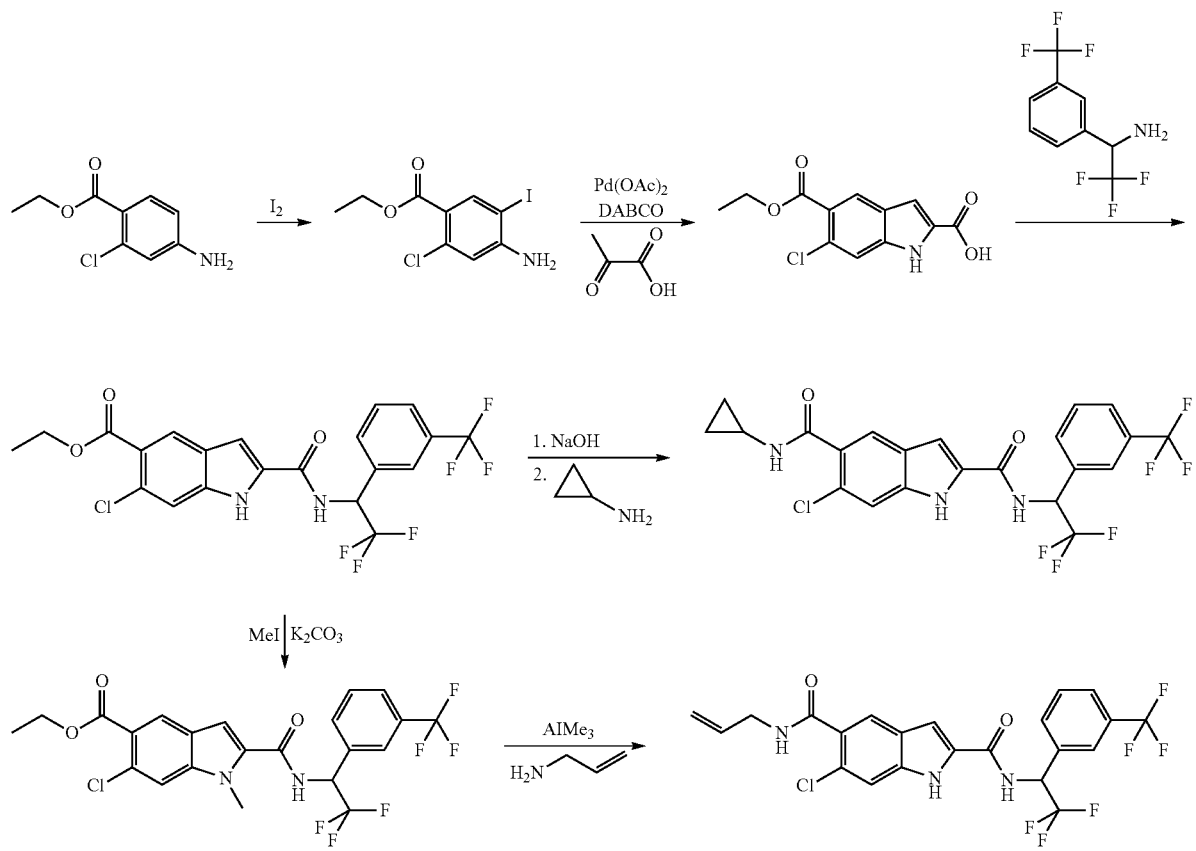
Formula Scheme 18:
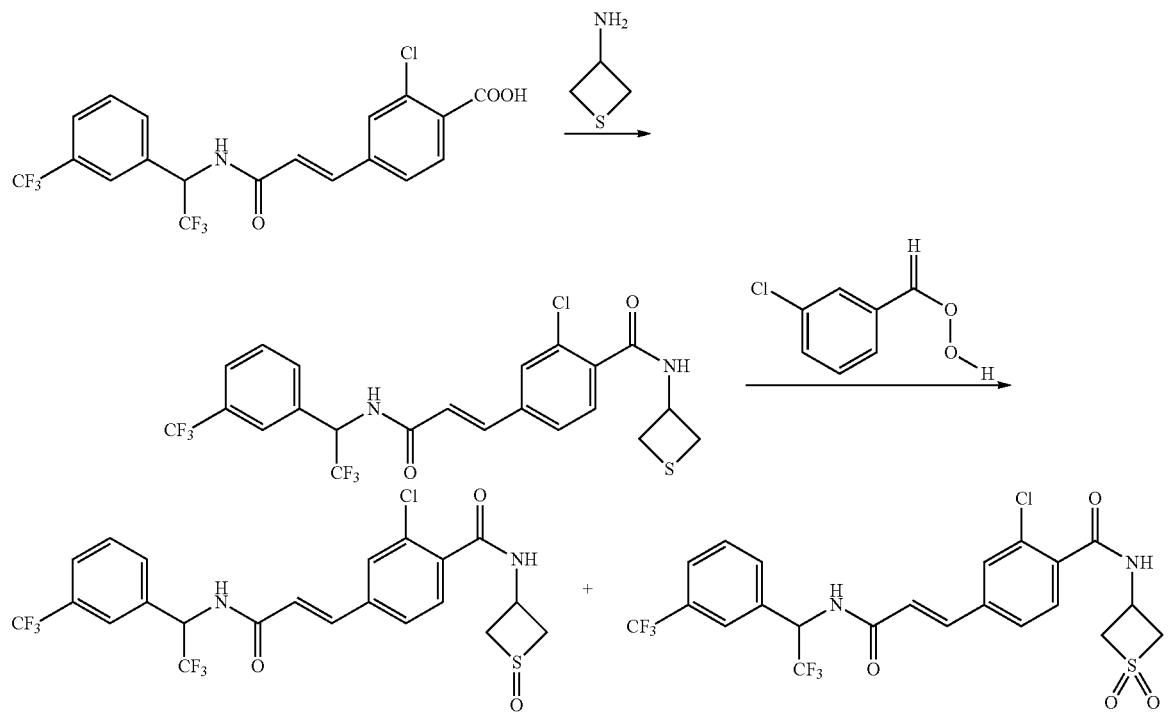

Formula Scheme 19:
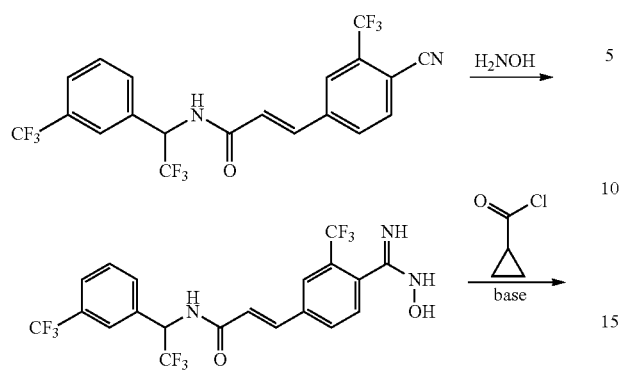
Formula Scheme 20
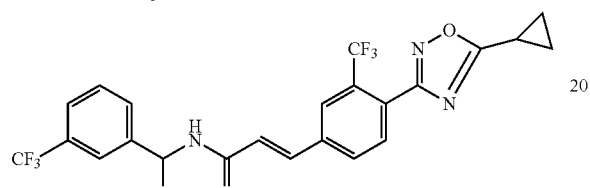
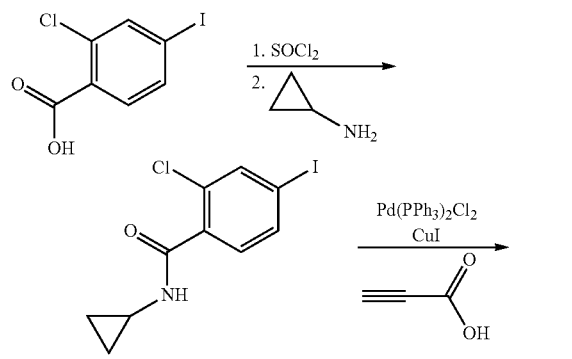
-continued
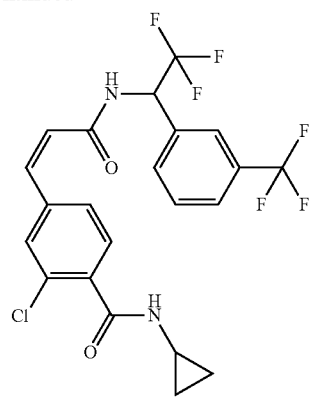
Formula Scheme 21
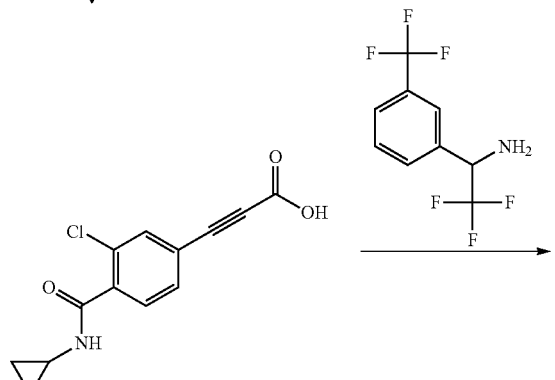
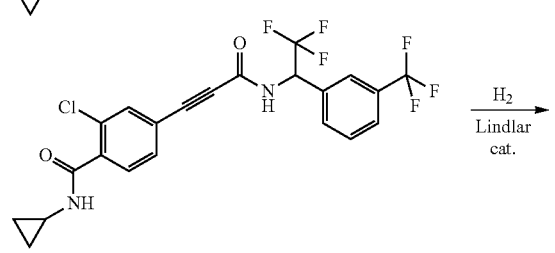

-continued

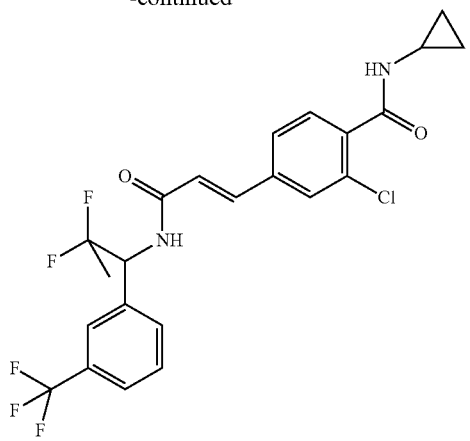

The Preparation and Use Examples which follow illustrate the invention without restricting it.

PREPARATION EXAMPLES

In the Examples which follow, RT means room temperature, i.e. 20° C., and the expression "1 eq" means 1 equivalent.

Synthesis Example 1 (Preparation of Compounds of the General Formula I-1 and I-2 According to Formula Schemes 1 and 2)

Stage 1

(2E)-3-(4-Cyanophenyl)-N-{2,2,2-trifluoro-1-[3-(trifluoromethyl)phenyl]ethyl}acrylamide (compound No. Ia-8 in Table 1)

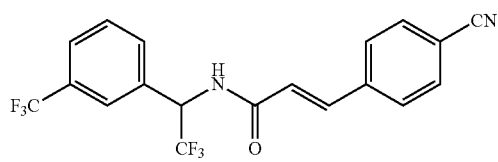 [SMILES: N#Cc1ccc(/C=C/C(=O)NC(c2cccc(C(F)(F)F)c2)C(F)(F)F)cc1]

280.8 mg (1.15 mmol) of 2,2-trifluoro-1-[3-(trifluoromethyl)phenyl]ethanamine (known from DE-A-2723464) and 128.6 mg (1.27 mmol) of triethylamine were initially charged in 2 ml of dichloromethane, and a solution of 221.3 mg (1.15 mmol) of (2E)-3-(4-cyanophenyl)acryloyl chloride (synthesis by reaction of (2E)-3-(4-cyanophenyl)acrylic acid with oxalyl chloride) was added. The reaction solution was stirred at room temperature for 18 hours, then diluted with dichloromethane, washed three times with water and dried over sodium sulphate. The solvent was distilled off under reduced pressure and the residue stirred with diisopropyl ether.

Yield: 280 mg (59.4% of theory).

$^1$H NMR (400 MHz, $d_6$-DMSO) δ=6.09 (m, 1H), 6.95 (d, 1H), 7.6 (d, 1H), 7.7 (m, 1H), 7.75 (m, 3H), 7.85 (m, 2H), 7.89 (m, 1H), 7.99 (m, 1H), 9.42 (d, 1H).

HPLC-MS: logP=3.54; mass (m/z): 399.0 (M+H)$^+$.

Stage 2

(2E)-3-(4-Cyanophenyl)-N-methyl-N-{2,2,2-trifluoro-1-[3-(trifluoromethyl)phenyl]ethyl}acrylamide (compound No. Ia-25 in Table 1)

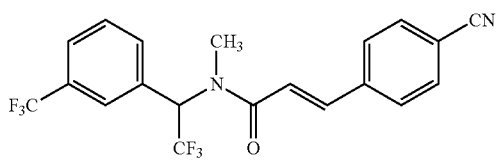 [SMILES: CN(C(=O)/C=C/c1ccc(C#N)cc1)C(c1cccc(C(F)(F)F)c1)C(F)(F)F]

120.0 mg (0.30 mmol) of (2E)-3-(4-cyanophenyl)-N-{2,2,2-trifluoro-1-[3-(trifluoromethyl)-phenyl]ethyl}acrylamide from Synthesis Example 1, Stage 1 were initially charged in 2 ml of N,N-dimethylformamide and admixed at 0° C. with 19.7 mg (0.45 mmol) of sodium hydride (55% oil dispersion). After addition of 64.1 mg (0.45 mmol) of methyl iodide, the mixture was stirred at room temperature for 18 hours. The reaction mixture was diluted with ethyl acetate, washed three times with water and dried over sodium sulphate. The solvent was distilled off under reduced pressure and the residue purified by preparative HPLC (solvent=water (A)+acetonitrile (B), gradient=40 min. from 10% B to 100% B, flow=18 ml/min).

Yield: 32 mg (25% of theory).

$^1$H NMR (400 MHz, $d_3$-acetonitrile) δ=3.00 (s, 3H), 6.75 (br. m, 1H), 7.20 (d, 1H), 7.6-7.8 (m, 9H).

HPLC-MS: logP=4.01; mass (m/z): 413.0 (M+H)$^+$.

Further compounds of the general formula (I) which were obtained in analogy to Synthesis Example 1 are listed in Tables 1 and 2.

Synthesis Example 2 (Preparation of Compounds of the General Formula I-3, I-5 and I-6 According to Formula Schemes 3 and 4)

Stage 1

N-{2,2,2-Trifluoro-1-[3-(trifluoromethyl)phenyl]ethyl}acrylamide

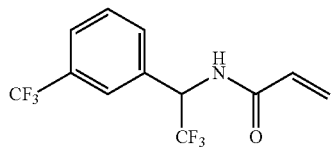 [SMILES: C=CC(=O)NC(c1cccc(C(F)(F)F)c1)C(F)(F)F]

20.0 g (82.2 mmol) of 2,2-trifluoro-1-[3-(trifluoromethyl)phenyl]ethanamine (lit. DE 2723464) were initially charged together with 7.80 g (98.7 mmol) of pyridine in 500 ml of dichloromethane, and 7.44 g (82.2 mmol) of acryloyl chloride were added dropwise thereto at 0° C. The reaction mixture was left to stir for another 4 hours while warming to room temperature. Subsequently, the mixture was washed repeatedly with water, the organic phase was dried over sodium sulphate and the solvent was distilled off under reduced pressure. The product was used without further purification in Stage 2.

Yield: 14.2 g (44.6% of theory)
$^1$H NMR (400 MHz, $d_6$-DMSO) δ=5.77 (m, 1H), 6.12 (m, 1H), 6.20 (m, 1H), 6.42 (m, 1H), 7.70 (m, 2H), 7.79 (m, 1H), 7.92 (m, 1H), 8.02 (s, 1H), 9.41 (d, 1H).
HPLC-MS: logP=2.75; mass (m/z): 298.0 (M+H)$^+$.

Stage 2

4-[(1E)-3-Oxo-3-({2,2,2-trifluoro-1-[3-(trifluoromethyl)phenyl]ethyl}amino)prop-1-en-1-yl]-2-(trifluoromethyl)benzoic acid

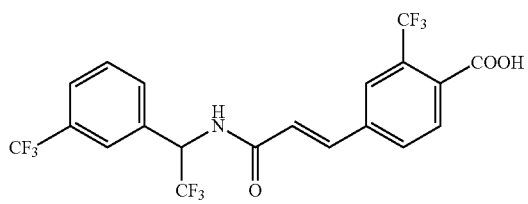 [SMILES: O=C(/C=C/c1ccc(C(=O)O)c(C(F)(F)F)c1)NC(c1cccc(C(F)(F)F)c1)C(F)(F)F]

Under argon, first 3.34 g (7.90 mmol) of N-{2,2,2-trifluoro-1-[3-(trifluoromethyl)phenyl]ethyl}-acrylamide from Example 2, Stage 1, and then 2.49 g (7.90 mmol) of 4-iodo-2-(trifluoromethyl)benzoic acid (commercially available, CAS Registry Number: 954815-11-3), 0.206 g (7.90 mmol) of triphenylphosphine, 88.4 mg (0.39 mmol) of palladium(II) acetate and 13.5 g (133 mmol) of triethylamine were initially charged in 67 ml of N,N-dimethylformamide, and the reaction mixture was stirred at 100° C. for 5 hours. After addition of water, the solution was extracted with ethyl acetate, and then the organic phase was washed three times with saturated sodium chloride solution and dried over sodium sulphate. The solvent was distilled off under reduced pressure and the residue was chromatographed on silica gel with ethyl acetate.
Yield: 2.57 g (60% of theory).
$^1$H NMR (400 MHz, $d_6$-DMSO) δ=6.10 (m, 1H), 6.93 (d, 1H), 7.6 (m, 1H), 7.69 (m, 1H), 7.75 (m, 2H), 7.85 (m, 1H), 7.95 (m, 1H), 7.99 (m, 1H), 9.38 (d, 1H).
HPLC-MS: logP=3.29; mass (m/z): 486.0 (M+H)$^+$.

In analogy to the method described in Synthesis Example 2, Stage 2, the following compounds of the general formula (I-5) were also obtained:

2-Methyl-4-[(1E)-3-oxo-3-({2,2,2-trifluoro-1-[3-(trifluoromethyl)phenyl]ethyl}amino)prop-1-en-1-yl]benzoic acid $^1$H NMR (400 MHz, $d_6$-DMSO) δ=2.55 (s, 3H), 6.09 (m, 1H), 6.89 (d, 1H), 7.6 (m, 1H), 7.50 (m, 3H), 7.7-7.9 (m, 3H), 8.00 (m, 1H), 9.34 (d, 1H).
HPLC-MS: logP=3.14; mass (m/z): 431.1 (M+H)$^+$.

2-Chloro-4-[(1E)-3-oxo-3-({2,2,2-trifluoro-1-[3-(trifluoromethyl)phenyl]ethyl}amino)prop-1-en-1-yl]benzoic acid $^1$H NMR (400 MHz, $d_6$-DMSO) δ=6.09 (m, 1H), 6.90 (d, 1H), 7.6 (m, 1H), 7.50 (m, 1H), 7.60 (m, 1H), 7.71 (m, 1H), 7.79 (m, 1H), 7.90 (m, 1H), 8.00 (s, 1H), 9.37 (d, 1H).
HPLC-MS: logP=3.10; mass (m/z): 452.0 (M+H)$^+$.

2-Bromo-4-[(1E)-3-oxo-3-({2,2,2-trifluoro-1-[3-(trifluoromethyl)phenyl]ethyl}amino)prop-1-en-1-yl]benzoic acid $^1$H NMR (400 MHz, $d_6$-DMSO) δ=6.09 (m, 1H), 6.91 (d, 1H), 7.6 (m, 1H), 7.50 (d, 1H), 7.62 (m, 1H), 7.70 (m, 2H), 7.79 (m, 1H), 7.90 (m, 1H), 7.99 (m, 1H), 9.36 (d, 1H).
HPLC-MS: logP=3.15; mass (m/z): 496.0 (M+H)$^+$.

Stage 3

N-(1-Fluoropropan-2-yl)-4-[(1E)-3-oxo-3-({2,2,2-trifluoro-1-[3-(trifluoromethyl)phenyl]-ethyl}amino)prop-1-en-1-yl]-2-(trifluoromethyl)benzamide (compound No. Ia-75 in Table 1)

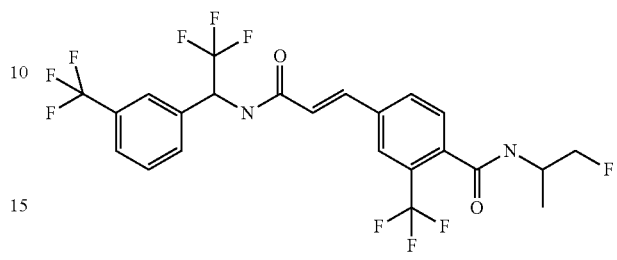

49 mg (1 eq, 0.1 mmol) of 4-[(1E)-3-oxo-3-({2,2,2-trifluoro-1-[3-(trifluoromethyl)phenyl]ethyl}-amino)prop-1-en-1-yl]-2-(trifluoromethyl)benzoic acid from Example 2, Stage 2 were dissolved in 1 ml of dichloromethane. Then 17 mg (1.0 eq, 0.10 mmol) of 6-chlorohydroxybenzotriazole, 23 mg (1.2 eq, 0.12 mmol) of N-(3-dimethylaminopropyl)-N'-ethylcarbodiimide hydrochloride and 26 mg (2 eq, 0.20 mmol) of N-ethyldiisopropylamine were added thereto, and the mixture was stirred at RT for 20 min. Subsequently, 11 mg (1.0 eq, 0.10 mmol) of 1-fluoropropan-2-amine hydrochloride were added and the reaction mixture was stirred at room temperature for 12 h. After this time, the reaction mixture was concentrated and the resulting crude product was purified by means of preparative HPLC (phenomenex Gemini C18 5 µm; 110A; AXIA 50×21.2 mm; gradient: 0-2 min 70% water, 30% MeOH, 2.5-6.0 min linear gradient to 5% water, 95% MeOH, 6.0-20.00 min 5% water, 95% MeOH; modifier: 20% HCOOH added at 2 ml/min). This gives 27 mg (37%) of N-(1-fluoropropan-2-yl)-4-[(1E)-3-oxo-3-({2,2,2-trifluoro-1-[3-(trifluoromethyl)phenyl]ethyl}amino)-prop-1-en-1-yl]-2-(trifluoromethyl)benzamide as a solid.
HPLC-MS: logP=3.37, mass (m/z): 544.96 (M+H)$^+$.
$^1$H NMR (400 MHz, d6-DMSO): δ=9.51 (d, 1H), 8.60 (d, 1H), 8.05 (s, 1H), 8.00 (s, 1H), 7.95 (m, 2H), 7.80 (d, 1H), 7.72 (t, 1H), 7.66 (d, 1H, J=16 Hz), 7.55 (d, 1H), 6.96 (d, 1H, J=16 Hz), 6.17 (m, 1H), 4.38 (dd, 2H, 1J(H,F)=47 Hz and J(H,H)=5 Hz), 4.20 (m, 1H), 1.15 (d, 3H)

Synthesis Example 3 (Preparation of Compounds of the General Formula I-11 and I-12 According to Formula Scheme 6)

Stage 1

(2E)-3-(3-Nitrophenyl)-N-{2,2,2-trifluoro-1-[3-(trifluoromethyl)phenyl]ethyl}acrylamide

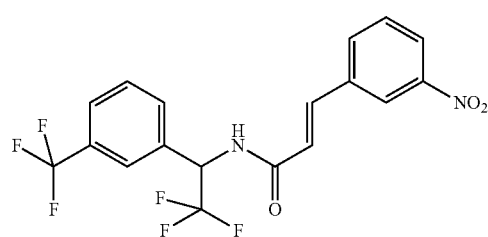 [SMILES: O=C(/C=C/c1cccc([N+](=O)[O-])c1)NC(c1cccc(C(F)(F)F)c1)C(F)(F)F]

300 mg (1.23 mmol) of 2,2-trifluoro-1-[3-(trifluoromethyl)phenyl]ethanamine (lit. DE 2723464) and 137 mg (1.35 mmol) of triethylamine were initially charged in 2 ml of dichloromethane, and a solution of 261 mg (1.23 mmol) of (2E)-3-(3-nitrophenyl)acryloyl chloride (synthesis by reaction of (2E)-3-(3-nitrophenyl)acrylic acid with oxalyl chloride) was added. The reaction solution was stirred at room temperature for 18 hours, then diluted with dichloromethane, washed three times with water and dried over sodium sulphate. The solvent was distilled off under reduced pressure and the residue stirred with diisopropyl ether.

Yield: 417 mg (69.5% of theory).

$^1$H NMR (400 MHz, $d_6$-DMSO) δ=6.10 (m, 1H), 7.00 (d, 1H), 7.6 (d, 1H), 7.75 (m, 1H), 7.8 (m, 3H), 7.85 (m, 2H), 7.89 (m, 1H), 7.99 (m, 1H), 9.43 (d, 1H).

HPLC-MS: logP=3.81; mass (m/z): 419.1 (M+H)$^+$.

Stage 2

(2E)-3-(3-Aminophenyl)-N-{2,2,2-trifluoro-1-[3-(trifluoromethyl)phenyl]ethyl}acrylamide

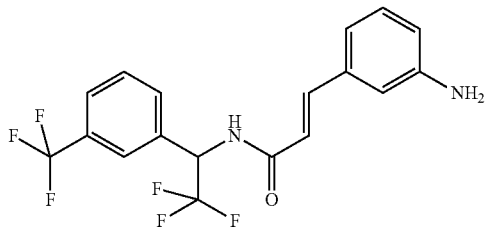

626 mg (3.30 mmol) of Sn(II)Cl$_2$ were initially charged in 5 ml of ethanol, and 350 mg (0.83 mmol) of (2E)-3-(3-nitrophenyl)-N-{2,2,2-trifluoro-1-[3-(trifluoromethyl)phenyl]ethyl}-acrylamide from Example 3, Stage 1 were added. The reaction solution was stirred at reflux temperature for 1 hour, cooled and admixed with 50 ml of water. While cooling with ice, the pH was adjusted to 9 with concentrated sodium hydroxide solution and the mixture was then extracted with dichloromethane. The organic phase was dried with sodium sulphate, the solvent distilled off under reduced pressure and the residue stirred with diisopropyl ether.

Yield: 279 mg (74.6% of theory).

$^1$H NMR (400 MHz, $d_6$-DMSO) δ=6.08 (m, 1H), 6.65 (m, 1H), 7.6 (d, 1H), 7.75 (m, 1H), 7.04 (m, 1H), 7.38 (m, 1H), 7.68 (m, 1H), 7.75 (m, 1H), 7.90 (m, 1H), 7.99 (m, 1H), 9.25 (m, 1H).

HPLC-MS: logP=2.88; mass (m/z): 389.1 (M+H)$^+$.

Stage 3

2-Chloro-N-{3-[(1E)-3-oxo-3-({2,2,2-trifluoro-1-[3-(trifluoromethyl)phenyl]ethyl}amino)prop-1-en-1-yl]phenyl}nicotinamide (compound Ia-5 in Table 1)

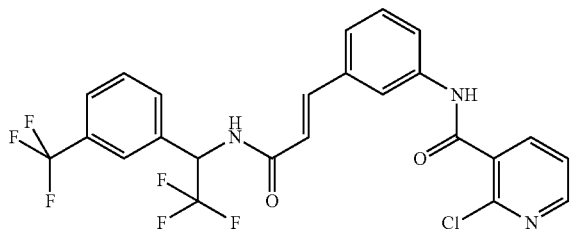 [SMILES: O=C(/C=C/c1cccc(NC(=O)c2cccnc2Cl)c1)NC(c1cccc(C(F)(F)F)c1)C(F)(F)F]

100 mg (0.25 mmol) of (2E)-3-(3-aminophenyl)-N-{2,2,2-trifluoro-1-[3-(trifluoromethyl)phenyl]-ethyl}acrylamide from Example 3, Stage 2 and 33.8 mg (0.33 mmol) of triethylamine were initially charged in 1 ml of trichloromethane, and a solution of 49.8 mg (0.33 mmol) of 2-chloronicotinyl chloride in 1 ml of trichloromethane was added. The reaction solution was stirred at room temperature for 18 hours, then diluted with dichloromethane, washed three times with water and dried over sodium sulphate. The solvent was distilled off under reduced pressure and the residue purified by preparative HPLC (solvent=water (A)+acetonitrile (B), gradient=40 min. from 10% B to 100% B, flow=18 ml/min).

Yield: 80.0 mg (58.9% of theory).

$^1$H NMR (400 MHz, $d_6$-DMSO) δ=6.08 (m, 1H), 6.83 (d, 1H), 7.36 (m, 1H), 7.40 (m, 1H), 7.52 (m, 2H), 7.72 (m, 1H), 7.75 (m, 1H), 7.89 (m, 1H), 7.99 (m, 1H), 8.05 (m, 1H), 8.12 (m, 1H), 8.52 (m, 1H), 9.38 (m, 1H).

HPLC-MS: logP=3.39; mass (m/z): 528.1 (M+H)$^+$.

Synthesis Example 4 (Preparation of Compounds of the General Formula I-1 and II-1 According to Formula Schemes 1 and 7)

Stage 1

1-[3-Chloro-5-(trifluoromethyl)phenyl]-2,2,2-trifluoroethanamine

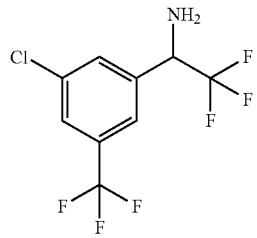 [SMILES: NC(c1cc(Cl)cc(C(F)(F)F)c1)C(F)(F)F]

In a 500 ml multineck flask with low-temperature thermometer, dropping funnel and argon balloon, 5.5 g (0.228 mol, 1.3 eq) of magnesium turnings (activated with dibromoethane and washed with diethyl ether) were blanketed with 120 ml of diethyl ether. At 0° C., 45.5 g of 3-bromo-5-chlorobenzotrifluoride (0.175 mol, 1 eq) in 120 ml of diethyl ether were slowly added dropwise. The reaction started up of its own accord after a few minutes, with a colour change (red-brown) and heating; the temperature was kept at about 0° C. during the addition. On completion of addition of the bromide, the mixture was stirred for a further 30 min.

A separate 2 l 3-neck flask with low-temperature thermometer, dropping funnel and argon balloon was initially charged with 32.4 g of ethyl trifluoroacetate (0.228 mol, 1.3 eq) in 250 ml of diethyl ether, and cooled to −80° C. At this temperature, the Grignard reagent (cooled to −10° C.) was slowly added dropwise. On completion of addition, the reaction mixture was stirred at −80° C. for a further 30 min. Thereafter, the reaction mixture was warmed to −10° C. and acidified with 10% hydrochloric acid. The resulting mixture was admixed with saturated NaCl solution, the phases were separated and the aqueous phase was washed with 200-300 ml of diethyl ether. The combined ethereal phases were dried over magnesium sulphate and the solvent was subsequently removed on a rotary evaporator.

The resulting crude product was purified by vacuum distillation (71° C. at 18 mbar). 37.7 g (78% of theory) of 1-[3-chloro-5-(trifluoromethyl)phenyl]-2,2,2-trifluoroethanone were obtained as a colourless oil. This was converted further without further purification.

To a solution of 24.5 g of 1-[3-chloro-5-(trifluoromethyl)phenyl]-2,2,2-trifluoroethanone (88 mmol, 1 eq) in 200 ml of toluene were added 13.6 g of m-(aminomethyl)benzylamine (100 mmol, 1.13 eq). After the addition of a catalytic amount of p-TsOH.H2O (~100 mg), the mixture was refluxed on a water separator for 12 h (approx. 5 ml of water were removed). Thereafter, another 5.5 g of m-(aminomethyl)benzylamine (40 mmol) were added and the mixture was boiled for a further 11 h. Subsequently, the toluene was distilled off (760 Torr). The resulting crude product was distilled under high vacuum (30-105° C. at 0.5 Ton). Further distillation by means of a Vigreux column (b.p. 105-108° C. at 25 Torr) gives 16.0 g of 1-[3-chloro-5-(trifluoromethyl)phenyl]-2,2,2-trifluoroethanamine (58 mmol, 65%) as a clear liquid.

HPLC-MS: logP=2.94, mass (m/z): 277.93 (M+H)

$^1$H NMR (400 MHz, $d_3$-CD$_3$CN): δ=7.75 (m, 3H), 4.60 (m, 1H), 2.10 (s, 2H, br).

In analogy to the method described in Stage 1 for 1-[3-chloro-5-(trifluoromethyl)phenyl]-2,2,2-trifluoroethanamine, the following compound was also obtained:

2,2,2-Trifluoro-1-(3,4,5-trichlorophenyl)ethanamine

HPLC-MS: logP=3.17; mass (m/z): 277.9; 279.9 (M+H)$^+$.

$^1$H NMR (400 MHz, d6-DMSO) δ=7.84 (s, 2H), 4.63 (m, 1H), 2.72 ppm (br. s, 2H).

Stage 2

4-Bromo-N-cyclopropyl-2-(trifluoromethyl)benzamide

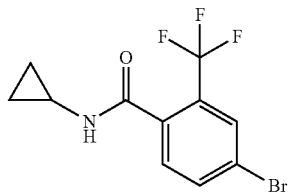 [SMILES: O=C(NC1CC1)c1ccc(Br)cc1C(F)(F)F]

1.50 g (1 eq, 5.57 mmol) of 4-bromo-2-(trifluoromethyl)benzoic acid (synthesis analogous to EP1445253 Yamanouchi Pharmaceutical Co. by bromination of the benzoic acid) were dissolved in 5 ml of dichloromethane. Then 954 mg (1.0 eq, 5.57 mmol) of 6-chlorohydroxybenzotriazole, 1.28 g (1.2 eq, 6.69 mmol) of N-(3-dimethylaminopropyl)-N'-ethylcarbodiimide hydrochloride and 1.45 ml (1.5 eq, 8.63 mmol) of N-ethyldiisopropylamine were added thereto, and the mixture was stirred at RT for 20 min. Subsequently, 477 mg (1.5 eq, 8.36 mmol) of cyclopropylamine were added thereto, and the reaction mixture was stirred at room temperature for 12 h. Thereafter, the mixture was concentrated under reduced pressure and the crude product dissolved in ethyl acetate (EA). The solution was washed 2× with buffer solution (0.5 M phosphate buffer pH=7) and then dried over MgSO$_4$. The purification was effected by means of silica gel chromatography with the eluent cyclohexane/ethyl acetate (EA) (0% EA to 100% EA). This gives 831 mg (48%) of 4-bromo-N-cyclopropyl-2-(trifluoromethyl)benzamide as a white solid.

HPLC-MS: logP=2.13; mass (m/z): 309.91 (M+H)$^+$.

$^1$H NMR (400 MHz, d3-CD3CN): δ=8.26 (s, 1H, br), 7.90 (s, 1H), 7.88 (d, 1H), 7.43 (d, 1H), 2.80 (m, 1H), 0.70 (m, 2H), 0.50 (m, 2H).

In analogy to the method described in Synthesis Example 4, Stage 1, the following compounds were also obtained:

4-Bromo-N-(pyridin-2-yl)-2-(trifluoromethyl)benzamide from 4-bromo-2-(trifluoromethyl)benzoic acid
HPLC-MS: logP=2.57; mass (m/z): 344.92 (M+H)$^+$.
$^1$H NMR (400 MHz, $d_3$-CD$_3$CN): δ=8.90 (s, 1H, br), 8.30 (d, 1H), 8.15 (d, 1H), 7.95 (s, 1H), 7.85 (d, 1H), 7.80 (dd, 1H), 7.60 (d, 1H), 7.13 (m, 1H).

N-Benzyl-4-bromo-2-(trifluoromethyl)benzamide proceeding from 4-bromo-2-(trifluoromethyl)benzoic acid
HPLC-MS: logP=2.89; mass (m/z): 359.85 (M+H)$^+$.
$^1$H NMR (400 MHz, $d_3$-CD$_3$CN): δ=7.90 (s, 1H), 7.80 (dd, 1H), 7.45 (d, 1H), 7.35 (m, 5H), 7.30 (m, 1H), 4.50 (d, 2H).

4-Bromo-N-(pyridin-2-ylmethyl)-2-(trifluoromethyl)benzamide proceeding from 4-bromo-2-(trifluoromethyl)benzoic acid
HPLC-MS: logP=1.56; mass (m/z): 360.91 (M+H)$^+$.
$^1$H NMR (400 MHz, $d_3$-CD$_3$CN): δ=8.50 (d, 1H), 7.90 (s, 1H), 7.85 (d, 1H), 7.73 (dd, 1H), 7.50 (d, 1H), 7.35 (d, 1H), 7.30 (s, 1H, br), 7.23 (m, 1H), 4.60 (d, 2H).

4-Bromo-2-methyl-N-(pyridin-2-ylmethyl)benzamide proceeding from 4-bromo-2-methylbenzoic acid.
HPLC-MS: logP=1.40; mass (m/z): 306.95 (M+H)$^+$.
$^1$H NMR (400 MHz, $d_3$-CD$_3$CN): δ=8.50 (t, 1H), 7.73 (t, 1H), 7.45 (s, 1H), 7.40 (d, 1H), 7.35 (m, 3H), 7.20 (dd, 1H), 4.60 (d, 2H), 2.40 (s, 3H).

4-Bromo-N-cyclopropyl-2-methylbenzamide proceeding from 4-bromo-2-methylbenzoic acid.
$^1$H NMR (400 MHz, $d_3$-CD$_3$CN): δ=7.45 (s, 1H), 7.35 (d, 1H), 7.20 (d, 1H), 6.80 (s, 1H, br), 2.80 (m, 1H), 2.40 (s, 3H), 0.70 (m, 2H), 0.55 (m, 2H).

Stage 3

(2E)-3-[4-(Cyclopropylcarbamoyl)-3-trifluoromethylphenyl]acrylic acid

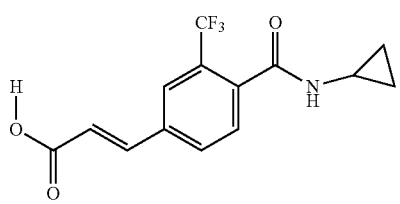 [SMILES: O=C(O)/C=C/c1ccc(C(=O)NC2CC2)c(C(F)(F)F)c1]

In a 30 ml microwave vessel, 1.18 g (1 eq, 3.84 mmol) of 4-bromo-N-cyclopropyl-2-(trifluoromethyl)benzamide and 868 mg (1 eq, 3.84 mmol) of ethyl (2E)-3-(4,4,5,5-tetramethyl-1,3,2-dioxaborolan-2-yl)acrylate were dissolved in 8 ml of 1,4-dioxane. To this were added 9 ml of Na$_2$CO$_3$ (2M in water) and 283 mg (0.1 eq, 0.38 mmol) of bis(tricyclohexylphosphine)-palladium(II) dichloride, and the reaction mixture was saturated with argon for 5 min. Then the reaction mixture was heated in the microwave (CEM Discover) at 150° C. (80 watts) for 10 min. Subsequently, the dioxane solution was decanted off, the residue was washed with 1,4-dioxane and the combined organic phases were concentrated under reduced pressure. The residue was dissolved in water and washed with a small amount of diethyl ether. Subsequently, the mixture was acidified to pH=3 with 1 M HCl, and the aqueous solution was extracted with ethyl acetate (EA). After drying the organic phase and concentrating, 412 mg (35%) of (2E,Z)-3-[4-(cyclopropylcarbamoyl)-3-(trifluoromethyl)phenyl]acrylic acid were obtained as a white solid.

HPLC-MS: logP=1.34, mass (m/z): 300.03 (M+H)$^+$.

$^1$H NMR (400 MHz, d3-CD3CN): δ=7.90 (s, 1H), 7.80 (d, 1H), 7.70 (d, 1H, J=16 Hz), 7.50 (d, 1H), 6.60 (s, 1H, br), 6.55 (d, 1H, J=16 Hz), 2.80 (m, 1H), 0.75 (m, 2H), 0.55 (m, 2H).

In analogy to the method described in Synthesis Example 4, Stage 2, the following compounds of the general formula II-1 were also obtained:

(2E)-3-[4-(Pyridin-2-yl)carbamoyl)-3-trifluoromethylphenyl]acrylic acid proceeding from 4-bromo-N-(pyridin-2-yl)-2-(trifluoromethyl)benzamide.

HPLC-MS: logP=1.69; mass (m/z): 337.04 (M+H)$^+$.

$^1$H NMR (400 MHz, d$_3$-CD$_3$CN): δ=8.30 (d, 1H, br), 8.15 (m, 2H), 8.00 (s, 1H), 7.90 (d, 1H), 7.80 (m, 1H), 7.60 (m, 2H), 7.10 (m, 1H), 6.60 (d, 1H, J=16 Hz).

(2E)-3-[4-(Phenylmethyl)carbamoyl)-3-trifluoromethylphenyl]acrylic acid proceeding from N-benzyl-4-bromo-2-(trifluoromethyl)benzamide.

HPLC-MS: logP=2.12, mass (m/z): 350.1 (M+H)$^+$.

$^1$H NMR (400 MHz, d$_3$-CD$_3$CN): δ=7.98 (s, 1H), 7.88 (d, 1H), 7.70 (d, 1H, J=16 Hz), 7.55 (d, 1H), 7.35 (m, 5H), 7.29 (m, 1H, br), 6.60 (d, 1H, J=16 Hz), 4.51 (d, 2H).

(2E)-3-[4-(Pyridin-2-ylmethyl)carbamoyl)-3-trifluoromethylphenyl]acrylic acid proceeding from 4-bromo-N-(pyridin-2-ylmethyl)-2-(trifluoromethyl)benzamide.

HPLC-MS: logP=0.91; mass (m/z): 350.9 (M+H)$^+$.

(2E)-3-[4-(Cyclopropylcarbamoyl)-3-methylphenyl]acrylic acid proceeding from 4-bromo-N-cyclopropyl-2-(methyl)benzamide.

HPLC-MS: logP=1.14, mass (m/z): 246.09 (M+H)$^+$.

$^1$H NMR (400 MHz, d$^3$-CD$_3$CN): δ=7.60 (d, 1H, J=16 Hz), 7.45 (m, 2H), 7.30 (d, 1H), 7.20 (d, 1H), 6.45 (d, 1H, J=16 Hz), 2.90 (m, 1H), 2.35 (s, 3H), 0.75 (m, 2H), 0.55 (m, 2H).

Stage 4

4-[(1E,Z)-3-({1-[3-Chloro-5-(trifluoromethyl)phenyl]-2,2,2-trifluoroethyl}amino)-3-oxoprop-1-en-1-yl]-N-cyclopropyl-2-(trifluoromethyl)benzamide (compound No. Ia-40 in Table 1)

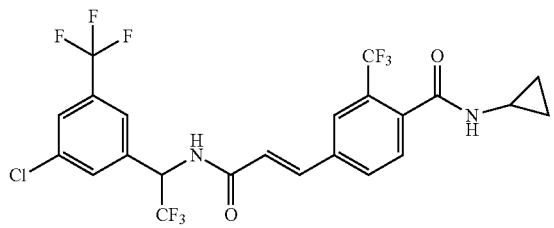 [SMILES: O=C(/C=C/c1ccc(C(=O)NC2CC2)c(C(F)(F)F)c1)NC(c1cc(Cl)cc(C(F)(F)F)c1)C(F)(F)F]

100 mg (1 eq, 0.29 mmol) of (2E,Z)-3-[4-(cyclopropylcarbamoyl)-3-(trifluoromethyl)phenyl]-acrylic acid were dissolved in 1 ml of dichloromethane. Then 50 mg (1.0 eq, 0.29 mmol) of 6-chlorohydroxybenzotriazole, 73 mg (1.3 eq, 0.38 mmol) of N-(3-dimethylaminopropyl)-N'-ethyl-carbodiimide hydrochloride and 102 µl (2 eq, 0.58 mmol) of N-ethyldiisopropylamine were added thereto, and the mixture was stirred at RT for 20 min. Subsequently, 98 mg (1.3 eq, 0.35 mmol) of 1-[3-chloro-5-(trifluoromethyl)phenyl]-2,2,2-trifluoroethanamine were added thereto, and the reaction mixture was stirred at room temperature for 12 h. Thereafter, the mixture was concentrated under reduced pressure and the crude product dissolved in ethyl acetate (EA). The solution was washed 2× with buffer solution (0.5M phosphate buffer pH=7) and then dried over MgSO$_4$. The purification was effected by means of silica gel chromatography with the eluent cyclohexane/ethyl acetate (EA) (0% EA to 100% EA). This gives 61 mg (37%) of 4-[(1E,Z)-3-({1-[3-chloro-5-(trifluoromethyl)phenyl]-2,2,2-trifluoroethyl}amino)-3-oxoprop-1-en-1-yl]-N-cyclopropyl-2-(trifluoromethyl)benzamide as a solid.

HPLC-MS: logP=3.68, mass (m/z): 558.97 (M+H)$^+$.

$^1$H NMR (400 MHz, d$_6$-DMSO): δ=9.51 (d, 1H), 8.55 (d, 1H), 8.12 (s, 1H), 8.08 (s, 1H), 8.03-7.95 (m, 2H), 7.93 (d, 1H), 7.66 (d, 1H, J=16 Hz), 7.54 (d, 1H), 6.93 (d, 1H, J=16 Hz), 6.26 (m, 1H), 2.79 (m, 1H), 0.70 (m, 2H), 0.50 (m, 2H)

Synthesis Example 5 (Preparation of Compounds of the General Formula I-1 and II-2 According to Formula Schemes 1 and 8)

Stage 1

(2E)-3-[3-Cyano-4-(1H-1,2,4-triazol-1-yl)phenyl]acrylic acid

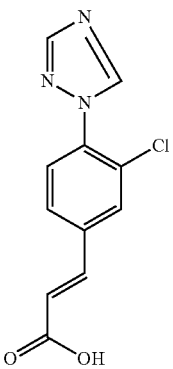 [SMILES: O=C(O)/C=C/c1ccc(-n2cncn2)c(Cl)c1]

2.05 g (10.3 mmol) of 5-formyl-2-(1H-1,2,4-triazol-1-yl)benzonitrile (lit.: WO-A-2008/019760), 1.60 g (16.6 mmol) of malonic acid and 176 mg (2.07 mmol) of piperidine were stirred in 20 ml of pyridine at 80° C. for 48 hours. The pyridine was distilled off under reduced pressure. The residue was added to ice-water and adjusted to pH 1 with concentrated hydrochloric acid. The aqueous phase was extracted repeatedly with ethyl acetate and dried over sodium sulphate, and the solvent was distilled off under reduced pressure.

Yield: 2.00 g (77% of theory).
HPLC-MS: logP=0.97; mass (m/z): 241.1 (M+H)+.

Stage 2

(2E)-3-[3-Cyano-4-(1H-1,2,4-triazol-1-yl)phenyl] acrylic acid (compound No. Ia-17 in Table 1)

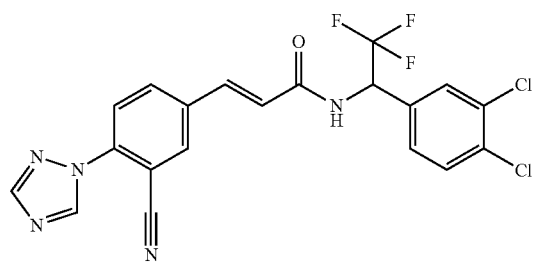 [SMILES: N#Cc1cc(/C=C/C(=O)NC(c2ccc(Cl)c(Cl)c2)C(F)(F)F)ccc1-n1cncn1]

100 mg (0.41 mmol) of 2(2E)-3-[3-cyano-4-(1H-1,2,4-triazol-1-yl)phenyl]acrylic acid from Example 5, Stage 1 and 96.0 mg (0.50 mmol) of EDC were initially charged in 2 ml of dioxane and stirred for 30 min. Then 101 mg (0.41 mmol) of 2,2,2-trifluoro-1-[3,4-dichlorophenyl]ethanamine (CAS Registry Number: 886369-74-0) were added and the mixture was stirred at room temperature for a further 18 hours. The dioxane was distilled off on a rotary evaporator, and the residue was taken up in water and extracted repeatedly with ethyl acetate. The organic phase was dried over sodium sulphate and the solvent distilled off on a rotary evaporator. The residue was chromatographed on silica gel with cyclohexane/ethyl acetate as the eluent (gradient=2 hours from 0% ethyl acetate to 100% ethyl acetate).

Yield: 69.0 mg (62% of theory).
$^1$H NMR (d$_6$-DMSO) δ=6.05 (m, 1H), 6.95 (d, 1H), 7.62 (m, 2H), 7.71 (m, 1H), 7.94 (m, 1H), 8.08 (m, 1H), 8.29 (m, 1H), 8.35 (m, 1H), 9.18 (s, 1H), 9.35 (d, 1H).
HPLC-MS: logP=3.22; mass (m/z): 466.0 (M+H)+

Synthesis Example 6 (Preparation of Compounds of the General Formula I-1 and I-9 According to Formula Schemes 1 and 5)

Stage 1

5-Cyano-N-{2,2,2-trifluoro-1-[3-(trifluoromethyl) phenyl]ethyl}-1-benzofuran-2-carboxamide (compound No. Ic-1 in Table 3)

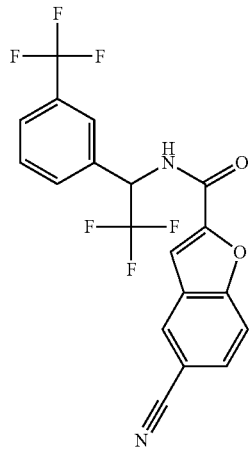 [SMILES: N#Cc1ccc2oc(C(=O)NC(c3cccc(C(F)(F)F)c3)C(F)(F)F)cc2c1]

A solution of 2,2,2-trifluoro-1-[3-trifluoromethylphenyl] ethanamine (400 mg, 1.64 mmol) in N,N-dimethylformamide (5 ml) was admixed with 5-cyanobenzofuran-2-carboxylic acid (400 mg, 2.13 mmol), HBTU (811 mg, 2.13 mmol) and N-methylmorpholine (549 mg, 2.13 mmol) and stirred at room temperature overnight. Subsequently, the reaction mixture was concentrated under reduced pressure, taken up in ethyl acetate and washed successively with a sodium hydrogencarbonate solution (10%) and a saturated sodium chloride solution. The organic phase was dried over sodium sulphate, filtered and concentrated under reduced pressure. The residue was chromatographed on silica gel with cyclohexane/ethyl acetate as the eluent (gradient=2 hours from 0% ethyl acetate to 20% ethyl acetate).

Yield: 467.6 mg (68% of theory).
HPLC-MS: logP=3.63; mass (m/z): 413.0 (M+H)+; $^1$H NMR (CD$_3$CN) 6.06-6.12 (m, 1H), 7.60 (s, 1H), 7.64-7.68 (m, 1H), 7.73-7.80 (m, 4H), 7.85-7.87 (m, 1H), 7.95 (m, 1H), 8.16 (m, 1H).

Stage 2

5-(Aminomethyl)-N-{2,2,2-trifluoro-1-[3-(trifluoromethyl)phenyl]ethyl}-1-benzofuran-2-carboxamide

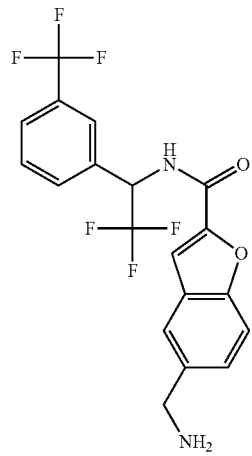 [SMILES: NCc1ccc2oc(C(=O)NC(c3cccc(C(F)(F)F)c3)C(F)(F)F)cc2c1]

A solution of 5-cyano-N-{2,2,2-trifluoro-1-[3-(trifluoromethyl)phenyl]ethyl}-1-benzofuran-2-carboxamide (273 mg, 0.66 mmol) in methanol (10 ml) was admixed with concentrated hydrochloric acid (0.42 ml) and palladium on carbon (10%; 50 mg) and stirred under a hydrogen atmosphere for 2 h. The reaction mixture was then filtered through Celite® and a silica gel pad.

Yield: 297.4 mg (107% of theory).
HPLC-MS: logP=2.02; mass (m/z): 415.1 (M—H)−; $^1$H NMR (CD$_3$CN) 3.90 (s, 1H), 6.09 (m, 1H), 7.42-7.68 (m, 6H), 7.74-8.07 (m, 5H).

Stage 3

5-(Acetamidomethyl)-N-{2,2,2-trifluoro-1-[3-(trifluoromethyl)phenyl]ethyl}-1-benzofuran-2-carboxamide (compound Ic-10 in Table 3)

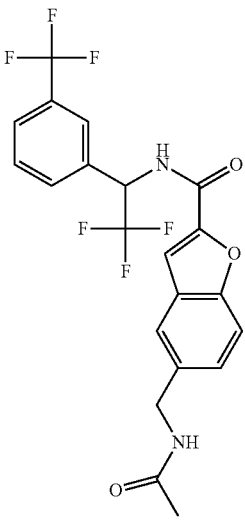 [SMILES: CC(=O)NCc1ccc2oc(C(=O)NC(c3cccc(C(F)(F)F)c3)C(F)(F)F)cc2c1]

A solution of 5-(aminomethyl)-N-{2,2,2-trifluoro-1-[3-(trifluoromethyl)phenyl]ethyl}-1-benzofuran-2-carboxamide (50 mg, 0.12 mmol) in dichloromethane (1 ml) was admixed with pyridine (0.01 ml) and cooled to 0° C. Then acetyl chloride (9 μl, 0.12 mmol) was added dropwise and the mixture was warmed up to room temperature overnight. The mixture was diluted with ethyl acetate and washed with hydrochloric acid (1 M). The organic phase was dried over sodium sulphate, filtered and concentrated under reduced pressure. The residue was chromatographed on a preparative HPLC with water/acetonitrile as the eluent (gradient=43 min from 10% acetonitrile in water to 100% acetonitrile).

Yield: 10.8 mg (19% of theory).

HPLC-MS: logP=2.80; mass (m/z): 459.1 (M+H)$^+$; $^1$H NMR (CD$_3$CN) 2.15 (s, 3H), 4.41 (d, 2H), 6.13 (quint, 1H), 6.88 (br. s, 1H), 7.40-7.42 (m, 1H), 7.51-7.56 (m, 2H), 7.62-7.69 (m, 2H), 7.76-7.78 (m, 1H), 7.88-7.90 (m, 1H), 7.97-7.99 (m, 1H), 8.21-8.23 (m, 1H).

Synthesis Example 7 (Preparation of Compounds of the General Formula I-6 and II-3 According to Formula Schemes 1, 4 and 9)

Stage 1 tert-Butyl 4-formyl-3-hydroxybenzoate

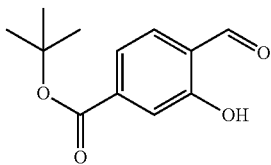 [SMILES: CC(C)(C)OC(=O)c1ccc(C=O)c(O)c1]

A solution of 4-formyl-3-hydroxybenzoic acid (1 g, 6.0 mmol) was dissolved in tetrahydrofuran (10 ml) and heated under reflux. Then N,N-dimethylformamide di-tert-butyl acetal was added dropwise (5.77 ml, 24.0 mmol) and the mixture was stirred at the temperature for 1.5 h. The cooled solution was concentrated under reduced pressure and the residue chromatographed on silica gel with cyclohexane/ethyl acetate as the eluent (gradient=1 hour from 0% ethyl acetate to 5% ethyl acetate).

Yield: 1.13 g (84% of theory).

HPLC-MS: logP=3.11; mass (m/z): 223.1 (M+H)$^+$; $^1$H NMR (CD$_3$CN) 1.58 (s, 9H), 7.48 (s, 1H), 7.57 (d, 1H), 7.76 (d, 1H).

Stage 2

6-tert-Butyl 2-ethyl 1-benzofuran-2,6-dicarboxylate

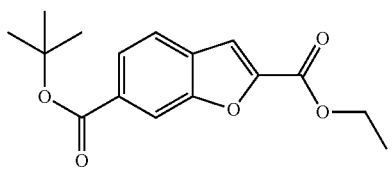 [SMILES: CCOC(=O)c1cc2ccc(C(=O)OC(C)(C)C)cc2o1]

A solution of tert-butyl 4-formyl-3-hydroxybenzoate (1.2 g, 5.40 mmol) and potassium carbonate (1726 mg, 12.4 mmol) in DMF (17 ml) was admixed dropwise with ethyl bromoacetate (0.56 ml, 5.0 mmol) and stirred at 80° C. for 6 h. Then ethyl bromoacetate (0.28 ml, 2.5 mmol) was added again and the mixture was stirred at 80° C. overnight. After cooling to room temperature, the reaction mixture was added to ice-water and extracted with ethyl acetate. The organic phases were dried over sodium sulphate, filtered and concentrated to dryness under reduced pressure.

Yield 497.3 mg (32% of theory).

HPLC-MS: logP=4.32; mass (m/z): 235.1 (M−C$_4$H$_9$+2H)$^+$; $^1$H NMR (CD$_3$CN) 1.38 (t, 3H), 1.60 (s, 9H), 4.40 (q, 2H), 7.59 (s, 1H), 7.79 (d, 1H), 7.93 (d, 1H), 8.19 (s, 1H).

Stage 3

6-(tert-Butoxycarbonyl)-1-benzofuran-2-carboxylic acid

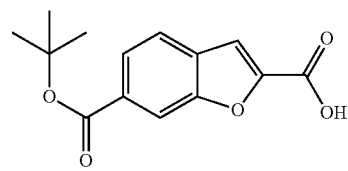 [SMILES: CC(C)(C)OC(=O)c1ccc2cc(C(=O)O)oc2c1]

A solution of 6-tert-butyl 2-ethyl 1-benzofuran-2,6-dicarboxylate (490 mg, 1.68 mmol) in ethanol (15 ml) was admixed with sodium hydroxide solution (3.36 ml, 1 M) and heated under reflux for 2 h. The cooled solution was added to ice-cooled hydrochloric acid (1 M), and the precipitate was filtered off with suction, washed with a little water and dried under reduced pressure.

Yield: 353 mg (80% of theory).

HPLC-MS: logP=2.58; mass (m/z): 261.1 (M+H)$^+$; $^1$H NMR (CD$_3$CN) 1.60 (s, 9H), 7.60 (s, 1H), 7.79 (d, 1H), 7.92-7.94 (m, 1H), 8.19 (s, 1H).

Stage 4 tert-Butyl 2-({2,2,2-trifluoro-1-[3-(trifluoromethyl)phenyl]ethyl}carbamoyl)-1-benzofuran-6-carboxylate

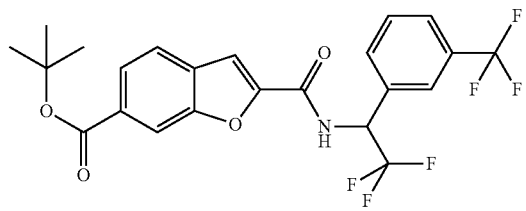 [SMILES: CC(C)(C)OC(=O)c1ccc2cc(C(=O)NC(c3cccc(C(F)(F)F)c3)C(F)(F)F)oc2c1]

A solution of 6-(tert-butoxycarbonyl)-1-benzofuran-2-carboxylic acid (350 mg, 1.33 mmol) and 2,2,2-trifluoro-1-[3-trifluoromethylphenyl]ethanamine (357 mg, 1.46 mmol) in N,N-dimethylformamide (5 ml) was admixed with 4-(4,6-dimethoxy[1.3.5]triazin-2-yl)-4-methylmorpholinium chloride hydrate (304 mg, 1.46 mmol) and stirred in a closed vessel at 50° C. overnight. The cooled reaction solution was admixed with hydrochloric acid (1 M) and extracted with ethyl acetate. The organic phase was washed with sat. sodium hydrogencarbonate solution and saturated sodium chloride solution, dried over sodium sulphate, filtered and concentrated to dryness under reduced pressure. This leaves 453 mg as a mixture of the tert-butyl ester and of the free acid, which was used for the next step without further purification.

Stage 5

2-({2,2,2-Trifluoro-1-[3-(trifluoromethyl)phenyl]ethyl}carbamoyl)-1-benzofuran-6-carboxylic acid

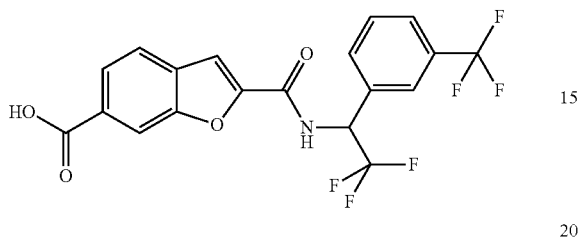

A solution of tert-butyl 2-({2,2,2-trifluoro-1-[3-(trifluoromethyl)phenyl]ethyl}carbamoyl)-1-benzofuran-6-carboxylate (450 mg, 1.04 mmol) in dichloromethane (4.5 ml) was admixed at 0° C. with trifluoroacetic acid (0.46 ml, 6.0 mmol) and stirred at room temperature overnight. Subsequently, the reaction mixture was washed with water, and the organic phase was dried over magnesium sulphate, filtered and concentrated under reduced pressure. The residue was filtered through silica gel, the filtercake was rinsed with ethyl acetate and methanol, and the filtrate was concentrated.

Yield: 266 mg (59% of theory).

HPLC-MS: logP=3.10; mass (m/z): 430.1 (M−H)−; $^1$H NMR (CD$_3$CN) 6.05-6.10 (m, 1H), 7.52-8.19 (m, 9H).

Stage 6

N$^6$-Cyclopropyl-N$^2$-{2,2,2-trifluoro-1-[3-(trifluoromethyl)phenyl]ethyl}-1-benzofuran-2,6-dicarboxamide (compound Ic-19 in Table 3)

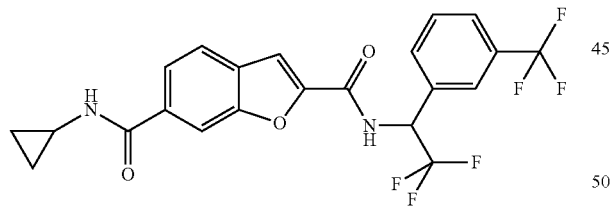

A solution of 2-({2,2,2-trifluoro-1-[3-(trifluoromethyl)phenyl]ethyl}carbamoyl)-1-benzofuran-6-carboxylic acid (100 mg, 0.21 mmol) in N,N-dimethylformamide (1 ml) was admixed with 4-(4,6-dimethoxy[1.3.5]triazin-2-yl)-4-methylmorpholinium chloride hydrate (100 mg, 0.46 mmol) and cyclopropylamine (36 mg, 0.63 mmol), and stirred in a closed vessel at 50° C. overnight. The cooled reaction solution was admixed with hydrochloric acid (1 M) and extracted with ethyl acetate. The organic phase was washed with sat. sodium hydrogencarbonate solution and saturated sodium chloride solution, dried over sodium sulphate, filtered and concentrated to dryness under reduced pressure. The residue was chromatographed on a preparative HPLC with water/acetonitrile as the eluent (gradient=43 min from 10% acetonitrile in water to 100% acetonitrile).

Yield: 18.2 mg (18% of theory).

HPLC-MS: logP=3.25; mass (m/z): 471.1 (M+H)+; $^1$H NMR (CD$_3$CN) 0.61-0.65 (m, 2H), 0.75-0.79 (m, 2H), 2.85-2.91 (m, 1H), 6.14 (quint, 1H), 7.18 (br. s, 1H), 7.58 (s, 1H), 7.69-7.79 (m, 4H), 7.89-7.91 (m, 1H), 7.97-7.99 (m, 2H), 8.28 (d, 1H).

Synthesis Example 8 (Preparation of Compounds of the General Formula I-6 and II-4 According to Formula Schemes 1, 4 and 10)

Stage 1

Ethyl 4-amino-2-chloro-5-iodobenzoate

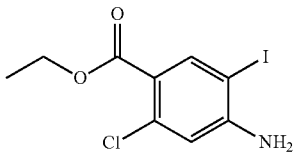

An iodine solution in ethanol was admixed with silver(I) sulphate and ethyl 4-amino-2-chlorobenzoate and then stirred at room temperature for 45 min. The reaction mixture was filtered through a frit and the filtrate was concentrated under reduced pressure. The residue was slurried in EtOAc and admixed with dilute sodium hydrogencarbonate solution. Once everything had gone into solution, the aqueous phase was removed and sodium thiosulphate was dissolved therein. The organic phase was washed again with the aqueous phase, and the aqueous phase was extracted with ethyl acetate. The combined organic phases were dried over sodium sulphate, filtered and concentrated under reduced pressure. Column chromatography purification on silica gel with cyclohexane/ethyl acetate as the eluent (gradient from 10% ethyl acetate to 33% ethyl acetate).

Yield: 1.85 g (74% of theory).

HPLC-MS: logP=2.95; mass (m/z): 326.0 (M+H)+; $^1$H NMR (CD$_3$CN) 1.32 (t, 3H), 4.27 (q, 2H), 5.01 (br. s, 2H), 6.80 (s, 1H), 8.16 (s, 1H).

Stage 2

6-Chloro-5-(ethoxycarbonyl)-1H-indole-2-carboxylic acid

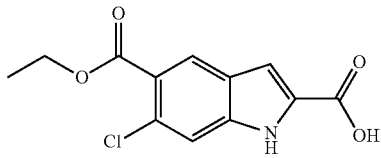 [SMILES: CCOC(=O)c1cc2cc(C(=O)O)[nH]c2cc1Cl]

A solution of ethyl 4-amino-2-chloro-5-iodobenzoate (1.82 g, 5.59 mmol) in N,N-dimethylformamide (18 ml) under argon was admixed with pyruvic acid (1.27 ml, 18.2 mmol) and 1,4-diazabicyclo[2.2.2]octane, evacuated and flooded with argon. Then argon was passed through the solution for 5 min, and then palladium(II) acetate (68 mg, 0.30 mmol) was added and the mixture was heated to 100° C. for 2 h. The cooled solution was filtered through Celite and the filtercake was rinsed with ethyl acetate (100 ml). The filtrate (suspension) was washed with hydrochloric acid (2 M; 2×25 ml) and with water (2×25 ml), dried over sodium sulphate and filtered. The filtrate was concentrated to dryness under reduced pressure and gives a red-brown solid (1.93 g, approx. 51% product), which was used for the next step without further purification.

Stage 3

Ethyl 6-chloro-2-({2,2,2-trifluoro-1-[3-(trifluoromethyl)phenyl]ethyl}carbamoyl)-1H-indole-5-carboxylate

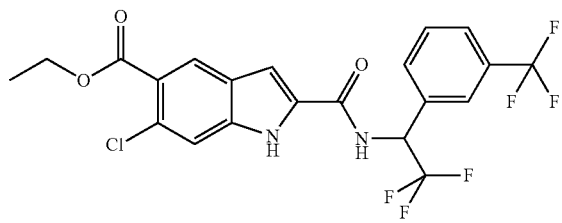 [SMILES: CCOC(=O)c1cc2cc(C(=O)NC(c3cccc(C(F)(F)F)c3)C(F)(F)F)[nH]c2cc1Cl]

A solution of the crude 6-chloro-5-(ethoxycarbonyl)-1H-indole-2-carboxylic acid product (1.9 g) and 2,2,2-trifluoro-1-[3-trifluoromethylphenyl]ethanamine (1.12 g, 4.60 mmol) in N,N-dimethylformamide (15 ml) was admixed with 4-(4,6-dimethoxy[1.3.5]triazin-2-yl)-4-methylmorpholinium chloride hydrate (953 mg, 4.60 mmol) and stirred at room temperature for 4 days. The reaction solution was admixed with hydrochloric acid (1 M) and extracted with ethyl acetate. The organic phase was washed with sat. sodium hydrogencarbonate solution and saturated sodium chloride solution, dried over sodium sulphate, filtered and concentrated to dryness under reduced pressure. Column chromatography purification on silica gel with cyclohexane/ethyl acetate as the eluent (gradient from 10% ethyl acetate to 25% ethyl acetate).

Yield: 603 mg (26% of theory over 2 stages).

HPLC-MS: logP=4.12; mass (m/z): 493.1 (M+H)$^+$; $^1$H NMR (CD$_3$CN) 1.38 (t, 3H), 4.35 (q, 2H), 6.16 (quint, 1H), 7.36 (s, 1H), 7.58 (s, 1H), 7.65-7.69 (m, 1H), 7.76-7.79 (m, 1H), 7.87-7.89 (m, 1H), 7.98 (s, 1H), 8.07-8.09 (m, 1H), 8.25 (s, 1H), 10.22 (s, 1H).

Stage 4

6-Chloro-N$^5$-cyclopropyl-N$^2$-{2,2,2-trifluoro-1-[3-(trifluoromethyl)phenyl]ethyl}-1H-indole-2,5-dicarboxamide (compound Ic-24 in Table 3)

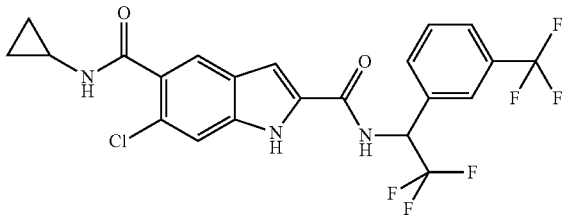 [SMILES: O=C(NC(c1cccc(C(F)(F)F)c1)C(F)(F)F)c1cc2cc(C(=O)NC3CC3)c(Cl)cc2[nH]1]

A solution of ethyl 6-chloro-2-({2,2,2-trifluoro-1-[3-(trifluoromethyl)phenyl]ethyl}carbamoyl)-1H-indole-5-carboxylate (590 mg, 1.18 mmol) in methanol (8 ml) was admixed with sodium hydroxide solution (1 M, 4.2 ml) and stirred under reflux overnight. The cooled solution was added to ice-cold hydrochloric acid (1 M) and the precipitate was filtered off with suction, washed with a little water and dried under reduced pressure. The remaining solid (366 mg) was used for the next step without further purification.

A portion of the acid thus obtained (121 mg) was dissolved in N,N-dimethylformamide (1.5 ml) and admixed with cyclopropylamine (12 mg, 0.20 mmol), HBTU (99 mg, 0.26 mmol) and N-methylmorpholine (67 mg, 0.66 mmol), and stirred at room temperature overnight. Subsequently, the reaction mixture was concentrated under reduced pressure, taken up in ethyl acetate and washed successively with a sodium hydrogencarbonate solution (10%) and a saturated sodium chloride solution. The organic phase was dried over sodium sulphate, filtered and concentrated under reduced pressure. The residue was chromatographed on a preparative HPLC with water/acetonitrile as the eluent (gradient=43 min from 10% acetonitrile in water to 100% acetonitrile).

Yield: 6.4 mg (3% of theory).

HPLC-MS: logP=3.08; mass (m/z): 504.1 (M+H)$^+$; $^1$H NMR (CD$_3$CN) 0.56-0.60 (m, 2H), 0.74-0.78 (m, 2H), 2.83-2.87 (m, 1H), 6.14 (quint, 1H), 6.86 (s, 1H), 7.29 (s, 1H), 7.52 (s, 1H), 7.64-7.68 (m, 1H), 7.76-7.77 (m, 2H), 7.88-7.90 (m, 1H), 7.97 (s, 1H), 8.08-8.01 (m, 1H), 10.19 (s, 1H).

Synthesis Example 9 (Preparation of Compounds of the General Formula I-14 According to Formula Scheme 6a and 19)

Stage 1

(2E)-3-[4-(N'-Hydroxycarbamimidoyl)-3-(trifluoromethyl)phenyl]-N-{2,2,2-trifluoro-1-[3-(trifluoromethyl)phenyl]ethyl}acrylamide

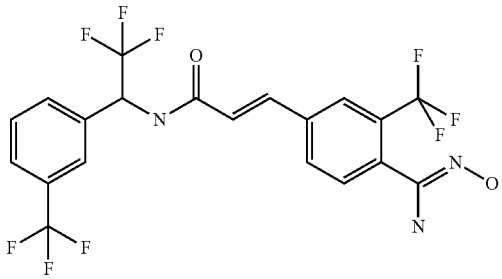 [SMILES: N/C(=N\O)c1ccc(/C=C/C(=O)NC(c2cccc(C(F)(F)F)c2)C(F)(F)F)cc1C(F)(F)F]

1.17 g (2.51 mmol) of (2E)-3-[4-cyano-3-(trifluoromethyl)phenyl]-N-{2,2,2-trifluoro-1-[3-(trifluoromethyl)phenyl]ethyl}acrylamide from Example Ia-46 were initially charged in a mixture of 11.7 ml of ethanol and 2.9 ml of water and admixed with 209.6 mg (3.01 mmol) of hydroxylammonium chloride and 399.5 mg (3.77 mmol) of sodium carbonate. The reaction mixture was heated under reflux for 18 hours and then admixed with water. After extracting repeatedly with ethyl acetate, the combined organic phases were dried over magnesium sulphate, the solvent was distilled off under reduced pressure and the residue was chromatographed using silica gel with cyclohexane/ethyl acetate as the eluent (gradient from 0% ethyl acetate to 100% ethyl acetate).

Yield: 95.0 mg (6.3% of theory)

$^1$H NMR (d$_6$-DMSO) δ=5.87 (s, 2H), 6.15 (m, 1H), 6.93 (d, 1H), 7.55-7.95 (m, 7H), 8.05 (d, 1H), 8.18 (s, 1H), 9.60 (d, 1H).

HPLC-MS: logP=2.55; mass (m/z): 498.1 (M+H)$^+$

Stage 2

(2E)-3-[4-(5-Cyclopropyl-1,2,4-oxadiazol-3-yl)-3-(trifluoromethyl)phenyl]-N-{2,2,2-trifluoro-1-[3-(trifluoromethyl)phenyl]ethyl}acrylamide (compound No. Ia-123 in Table 1)

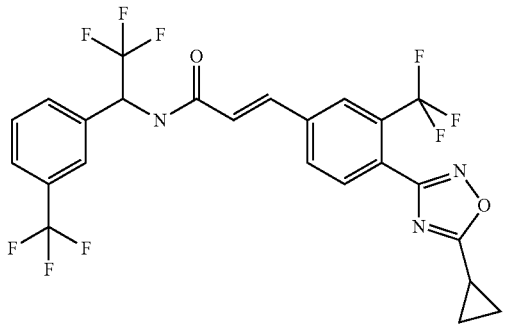 [SMILES: O=C(/C=C/c1ccc(-c2noc(C3CC3)n2)c(C(F)(F)F)c1)NC(c1cccc(C(F)(F)F)c1)C(F)(F)F]

80 mg (0.16 mmol) of (2E)-3-[4-(N'-hydroxycarbamimidoyl)-3-(trifluoromethyl)phenyl]-N-{2,2,2-trifluoro-1-[3-(trifluoromethyl)phenyl]ethyl}acrylamide from Stage 1 were initially charged in 2 ml of pyridine, admixed at room temperature with 16.7 mg (0.16 mmol) of cyclopropanecarbonyl chloride and heated under reflux for 18 hours. The pyridine was for the most part distilled off under reduced pressure, and the residue was admixed with water and extracted with ethyl acetate. After drying over magnesium sulphate, the solvent was distilled off under reduced pressure and the residue was chromatographed on silica gel with cyclohexane/ethyl acetate as the eluent (gradient from 0% ethyl acetate to 100% ethyl acetate).

Yield: 53.0 mg (58.5% of theory)

$^1$H NMR (d$_6$-DMSO) δ=0.78 (m, 4H), 1.49 (m, 1H), 6.18 (m, 1H), 7.03 (d, 1H), 7.70-7.80 (m, 3H), 7.87 (m, 2H), 7.91 (m, 1H), 8.04 (d, 1H), 8.18 (s, 1H), 9.60 (d, 1H).

HPLC-MS: logP=4.53; mass (m/z): 548.1 (M+H)$^+$

Synthesis Example 10 (Preparation of Sulphoxides and Sulphones According to Formula Scheme 18)

2-Chloro-N-(1,1-dioxidothietan-3-yl)-4-[(1E)-3-oxo-3-({2,2,2-trifluoro-1-[3-(trifluoromethyl)phenyl]ethyl}amino)prop-1-en-1-yl]benzamide (compound No. Ia-166 in Table 1) and 2-chloro-N-(1-oxidothietan-3-yl)-4-[(1E)-3-oxo-3-({2,2,2-trifluoro-1-[3-(trifluoromethyl)phenyl]ethyl}amino)prop-1-en-1-yl]benzamide (compound No. Ia-167 in Table 1)

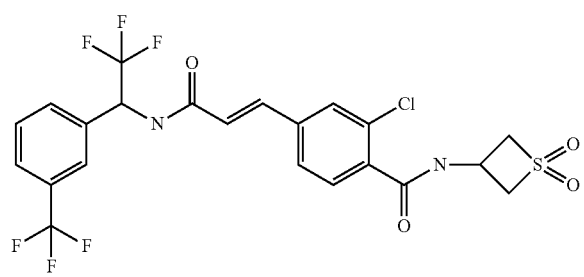

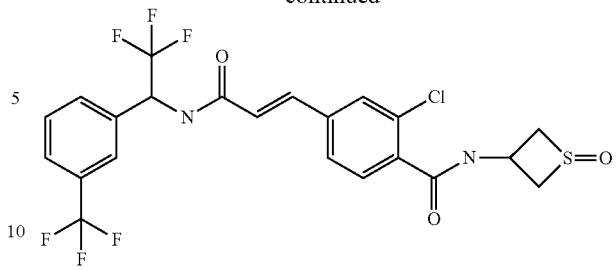

100 mg (0.19 mmol) of 4-[(1E)-3-oxo-3-({2,2,2-trifluoro-1-[3-(trifluoromethyl)phenyl]ethyl}-amino)prop-1-en-1-yl]-N-(thietan-3-yl)-2-(trifluoromethyl)benzamide (compound No. Ia-130, synthesized analogously to Synthesis Example 2) were initially charged in 5 ml of dichloromethane and admixed with a solution of 117.8 mg (0.47 mmol) of meta-chloroperbenzoic acid (content: 70%), and the mixture was stirred at 20° C. for 5 hours. The solution was admixed with saturated sodium hydrogencarbonate solution and extracted repeatedly with ethyl acetate. The combined organic phases were washed successively with sodium thiosulphate solution and with water and dried over magnesium sulphate, and the solvent was distilled off under reduced pressure. The residue was chromatographed on silica gel.

Yield:

28.0 mg (26.1%) of 2-chloro-N-(1,1-dioxidothietan-3-yl)-4-[(1E)-3-oxo-3-({2,2,2-trifluoro-1-[3-(trifluoromethyl)phenyl]ethyl}amino)prop-1-en-1-yl]benzamide $^1$H NMR (d$_6$-DMSO) δ=4.20 (m, 2H), 4.53 (m, 2H), 4.63 (m, 1H), 6.15 (m, 1H), 6.90 (d, 1H), 7.45-7.85 (m, 5H), 7.95 (m, 1H), 8.05 (s, 1H), 9.28 (d, 1H), 9.50 (d, 1H).

HPLC-MS: logP=2.93; mass (m/z): 555.2 (M+H)$^+$ 19.0 mg (18.3%) of 2-chloro-N-(1-oxidothietan-3-yl)-4-[(1E)-3-oxo-3-({2,2,2-trifluoro-1-[3-(trifluoromethyl)phenyl]ethyl}amino)prop-1-en-1-yl]benzamide.

$^1$H NMR (d$_6$-DMSO) δ=3.20 (m, 2H), 4.20 (m, 2H), 4.38 (m, 1H), 4.63 (m, 2H), 6.15 (m, 1H), 6.90 (d, 1H), 7.45-7.85 (m, 5H), 7.95 (m, 1H), 8.05 (s, 1H), 9.08 (d, 1H), 9.50 (d, 1H).

HPLC-MS: logP=2.63; mass (m/z): 539.2 (M+H)$^+$

Synthesis Example 11 (Preparation of Compounds of the General Formula I and II-1 According to Formula Scheme 1 and 7)

Stage 1

N-Cyclopropyl-6-iodo-4-(trifluoromethyl)nicotinamide

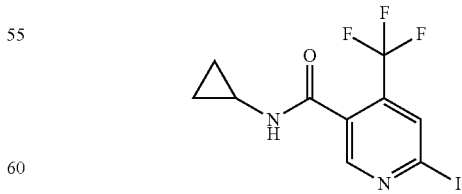

Cyclopropylamine (862 mg, 15.1 mmol) was dissolved in 4 ml of dichloromethane and admixed dropwise under argon with a solution of trimethylaluminium in toluene (2 M, 7.55 ml, 15.1 mmol). The mixture was stirred for 30 min, and then methyl 6-iodo-4-(trifluoromethyl)nicotinate (500 mg, 1.51 mmol) (synthesis analogous to J. Med. Chem., 2008, 51, 3133-3144 by esterification of nicotinic acid) dissolved in 3 ml of dichloromethane was added dropwise. The mixture was heated under reflux overnight and, after cooling to room temperature, water was added cautiously. The mixture was extracted with ethyl acetate, the organic phase washed with potassium sodium tartrate solution, dried over magnesium sulphate and filtered, and the filtrate concentrated under reduced pressure. The purification was effected by means of silica gel chromatography with the eluent cyclohexane/ethyl acetate (EA) (0% EA to 30% EA).

Yield: 288 mg (53% of theory).

HPLC-MS: logP=1.92; mass (m/z): 357.0 (M+H)$^+$; $^1$H NMR (CD$_3$CN) 0.54-0.59 (m, 2H), 0.72-0.79 (m, 2H), 2.79-2.82 (m, 1H), 7.07 (br. s, 1H), 8.11 (s, 1H), 8.48 (s, 1H).

Stage 2

(2E)-3-[5-(Cyclopropylcarbamoyl)-4-(trifluoromethyl)pyridin-2-yl]acrylic acid

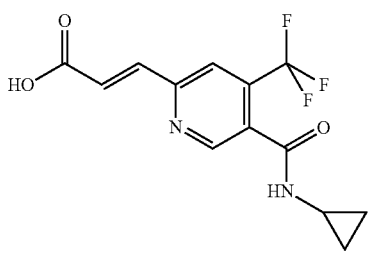 [SMILES: O=C(O)/C=C/c1cc(C(F)(F)F)c(C(=O)NC2CC2)cn1]

N-Cyclopropyl-6-iodo-4-(trifluoromethyl)nicotinamide (125 mg, 0.34 mmol) and ethyl (2E)-3-(4,4,5,5-tetramethyl-1,3,2-dioxaborolan-2-yl)acrylate (93 mg, 0.41 mmol) were dissolved in 2 ml of 1,4-dioxane and admixed under argon with sodium carbonate (180 mg, 1.72 mmol) and bis(tricyclohexylphosphine)palladium(II) dichloride. The reaction mixture was heated in a microwave (CEM Discover) at 120° C. (80 W) for 10 min. Then the reaction mixture was filtered through kieselguhr, and the filtrate was taken up in ethyl acetate, washed with hydrochloric acid (1 M), dried over magnesium sulphate, filtered and concentrated under reduced pressure. The residue was taken up in 1.5 ml of ethanol, admixed with sodium hydroxide solution (1M) and stirred at room temperature overnight. Then the reaction mixture was added to ice-cold dilute hydrochloric acid and extracted with ethyl acetate. The organic phase was dried over sodium sulphate, filtered and concentrated to dryness under reduced pressure.

Yield: 72 mg (70% of theory).

HPLC-MS: logP=1.26; mass (m/z): 301.1 (M+H)$^+$; $^1$H NMR (CD$_3$CN) 0.56-0.58 (m, 2H), 0.76-0.79 (m, 2H), 2.80-2.85 (m, 1H), 6.96 (d, 1H), 7.08 (br. s, 1H), 7.69 (d, 1H), 7.87 (s, 1H), 8.74 (s, 1H), 9.5 (br. s, 1H).

Stage 3

N-Cyclopropyl-6-[(1E)-3-oxo-3-({2,2,2-trifluoro-1-[3-(trifluoromethyl)phenyl]ethyl}amino)-prop-1-en-1-yl]-4-(trifluoromethyl)nicotinamide (compound No. If-2 in Table 6)

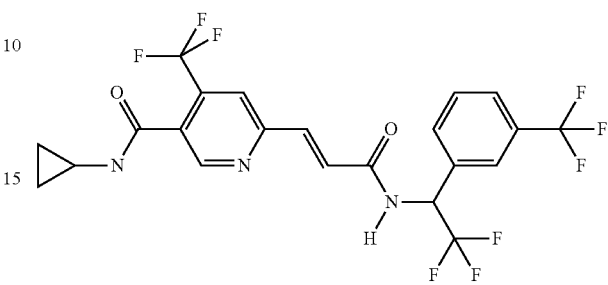

(2E)-3-[5-(Cyclopropylcarbamoyl)-4-(trifluoromethyl)pyridin-2-yl]acrylic acid (61 mg, 0.20 mmol) and 2,2,2-trifluoro-1-[3-trifluoromethylphenyl]ethanamine (46 mg, 0.19 mmol) were initially charged in N,N-dimethylformamide and admixed with HBTU (72 mg, 0.19 mmol) and N-methylmorpholine (57 mg, 0.57 mmol) and stirred at room temperature overnight. Subsequently, the reaction mixture was concentrated under reduced pressure, taken up in ethyl acetate and washed successively with a sodium hydrogencarbonate solution (10%) and a saturated sodium chloride solution. The organic phase was dried over sodium sulphate, filtered and concentrated under reduced pressure. The residue was chromatographed on a preparative HPLC with water/acetonitrile as the eluent (gradient=43 min from 10% acetonitrile in water to 100% acetonitrile).

Yield: 17 mg (16% of theory).

HPLC-MS: logP=3.27; mass (m/z): 526.1 (M+H)$^+$; $^1$H NMR (CD$_3$CN) 0.56-0.58 (m, 2H), 0.76-0.78 (m, 2H), 2.81-2.85 (m, 1H), 6.01 (quint, 1H), 7.08 (s, 1H), 7.28 (d, 1H), 7.65-7.68 (m, 2H), 7.76-7.81 (m, 3H

Synthesis Example 12 (Preparation of Compounds of the General Formula I-16 and I-17 According to Formula Scheme 4, 6c and 17)

Stage 1

Ethyl 6-chloro-1-methyl-2-({2,2,2-trifluoro-1-[3-(trifluoromethyl)phenyl]ethyl}carbamoyl)-1H-indole-5-carboxylate

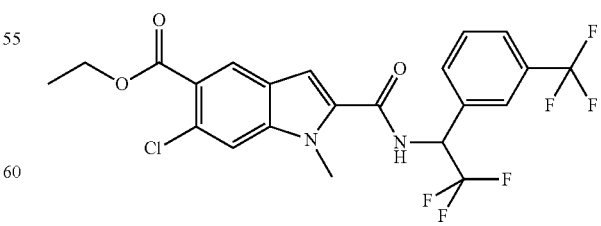

Ethyl 6-chloro-2-({2,2,2-trifluoro-1-[3-(trifluoromethyl)phenyl]ethyl}carbamoyl)-1H-indole-5-carboxylate (1.30 g, 2.63 mmol) (Synthesis Example 8, Stage 3) and potassium carbonate were initially charged in acetonitrile (39 ml) and admixed with iodomethane (561 mg, 3.95 mmol). The reaction mixture was heated under reflux overnight. After cooling to room temperature, the mixture was concentrated to dryness under reduced pressure, and the residue taken up in ethyl acetate and washed with water. The organic phase was dried over sodium sulphate, filtered and concentrated to dryness under reduced pressure.

Yield: 1.14 g (85% of theory).

HPLC-MS: logP=4.74; mass (m/z): 507.2 (M+H)⁺; $^1$H NMR (CD$_3$CN) 1.38 (t, 3H), 3.93 (s, 3H), 4.35 (q, 2H), 6.13 (quint, 1H), 7.25 (s, 1H), 7.59 (s, 1H), 7.65-7.69 (m, 1H), 7.77-7.79 (m, 1H), 7.88-7.90 (m, 1H), 7.98 (s, 1H), 8.08-8.11 (m, 1H), 8.21 (s, 1H).

Stage 2

N⁵-Allyl-6-chloro-1-methyl-N²-{2,2,2-trifluoro-1-[3-(trifluoromethyl)phenyl]ethyl}-1H-indole-2,5-dicarboxamide (compound No. Ic-32 in Table 3)

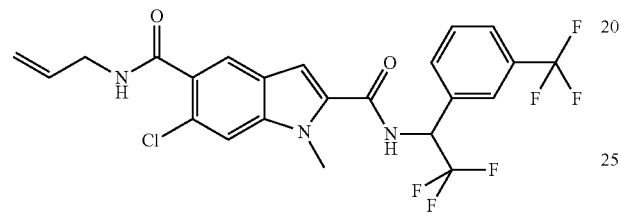

Allylamine (156 mg, 2.73 mmol) was dissolved in 3 ml of dichloromethane and admixed dropwise under argon with a solution of trimethylaluminium in toluene (2 M, 1.37 ml, 2.73 mmol). The mixture was stirred for 30 min, and then ethyl 6-chloro-1-methyl-2-({2,2,2-trifluoro-1-[3-(trifluoromethyl)phenyl]ethyl}carbamoyl)-1H-indole-5-carboxylate (165 mg, 0.27 mmol) dissolved in 3 ml of dichloromethane was added dropwise. The mixture was heated under reflux overnight and, after cooling to room temperature, water was added cautiously. The mixture was extracted with ethyl acetate, the organic phase washed with potassium sodium tartrate solution, dried over magnesium sulphate and filtered, and the filtrate concentrated under reduced pressure. The purification was effected by means of silica gel chromatography with the eluent cyclohexane/ethyl acetate (EA) (0% EA to 30% EA).

Yield: 74 mg (52% of theory).

HPLC-MS: logP=3.68; mass (m/z): 518.2 (M+H)⁺; $^1$H NMR (d$_6$-DMSO) 3.88-3.90 (m, 2H), 3.95 (s, 3H), 5.11-5.14 (m, 1H), 5.26-5.29 (m, 1H), 5.87-5.94 (m, 1H), 6.30 (quint, 1H), 7.42 (s, 1H), 7.71-7.73 (m, 1H), 7.78 (s, 1H), 7.82-7.83 (m, 2H), 8.07-8.08 (m, 1H), 8.22 (s, 1H), 8.56-8.58 (m, 1H) 9.79 (d, 1H).

Synthesis Example 13 (Preparation of Compounds of the General Formula I-15 According to Formula Scheme 6b and 20)

Stage 1

2-Chloro-N-cyclopropyl-4-iodobenzamide

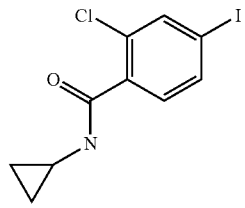 [SMILES: O=C(NC1CC1)c1ccc(I)cc1Cl]

2-Chloro-4-iodobenzoic acid (3.31 g, 11.7 mmol) was dissolved in ethyl acetate (23 ml), admixed with one drop of N,N-dimethylformamide and thionyl chloride (6.96 g, 59.0 mmol), and heated under reflux overnight. The cooled suspension was concentrated under reduced pressure and taken up in dichloromethane (60 ml). The solution was cooled to 0° C., and pyridine (925 mg, 11.7 mmol) and cyclopropylamine (668 mg, 11.7 mmol) were added dropwise. The reaction mixture was warmed up to room temperature and stirred overnight. Then it was washed with hydrochloric acid (1 M), dried over sodium sulphate, filtered and concentrated to dryness under reduced pressure.

Yield: 3.06 g (81% of theory).

HPLC-MS: logP=2.13; mass (m/z): 321.9 (M+H)⁺; $^1$H NMR (CD$_3$CN) 0.53-0.57 (m, 2H), 0.72-0.77 (m, 2H), 2.77-2.83 (m, 1H), 6.87 (br. s, 1H), 7.16 (d, 1H), 7.71 (d, 1H), 7.84 (s, 1H).

Stage 2

2-Chloro-N-cyclopropyl-4-[3-oxo-3-({2,2,2-trifluoro-1-[3-(trifluoromethyl)phenyl]ethyl}amino) prop-1-yn-1-yl]benzamide

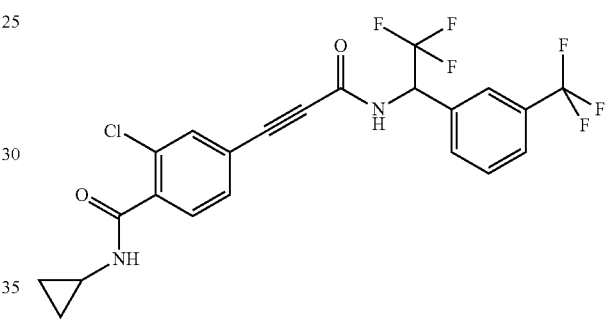

2-Chloro-N-cyclopropyl-4-iodobenzamide (1.0 g, 3.11 mmol) and propiolic acid (222 mg, 3.11 mmol) were dissolved in N,N-dimethylformamide (1.2 ml) and cooled to 0° C. Then bis(triphenylphosphine)palladium(II) dichloride (43 mg, 0.06 mmol) and copper(I) iodide (23 mg, 0.12 mmol) were added and the mixture was cooled to −10° C. After addition of diisopropylamine (786 mg, 7.77 mmol), the mixture was warmed slowly to room temperature and stirred overnight. The reaction mixture was diluted with ethyl acetate, washed successively with hydrochloric acid (2 M) and saturated sodium chloride solution, dried over magnesium sulphate, filtered and concentrated to dryness under reduced pressure. The residue was dissolved in N,N-dimethylformamide (1 ml) and admixed with 4-(4,6-dimethoxy [1.3.5]triazin-2-yl)-4-methylmorpholinium chloride hydrate (973 mg, 3.52 mmol) and 2,2,2-trifluoro-1-[3-trifluoromethylphenyl]ethanamine (780 mg, 3.20 mmol) and stirred at room temperature overnight. The reaction solution was admixed with hydrochloric acid (1 M) and extracted with ethyl acetate. The organic phase was washed with saturated sodium hydrogencarbonate solution and saturated sodium chloride solution, dried over sodium sulphate, filtered and concentrated to dryness under reduced pressure. The residue was purified by means of silica gel chromatography with the eluent cyclohexane/ethyl acetate (EA) (0% EA to 40% EA).

Yield: 462 mg (30% of theory).

HPLC-MS: logP=3.34; mass (m/z): 489.0 (M+H)⁺; $^1$H NMR (CD$_3$CN) 0.57-0.59 (m, 2H), 0.74-0.78 (m, 2H), 2.79-2.86 (m, 1H), 5.94 (quint, 1H), 6.93 (s, 1H), 7.45-7.47 (m, 1H), 7.55-7.57 (m, 1H), 7.65-7.69 (m, 2H), 7.74-7.78 (m, 1H), 7.90 (s, 1H), 8.30 (d, 1H).

Stage 3

2-Chloro-N-cyclopropyl-4-[(1Z)-3-oxo-3-({2,2,2-trifluoro-1-[3-(trifluoromethyl)phenyl]ethyl}-amino)prop-1-en-1-yl]benzamide (compound No. Ig-1 in Table 7)

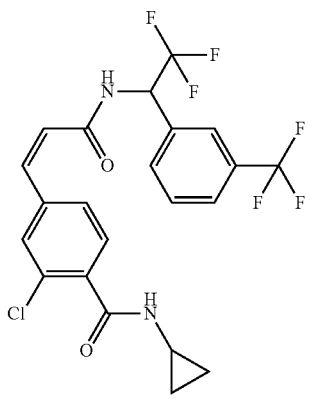 [SMILES: O=C(/C=C\c1ccc(C(=O)NC2CC2)c(Cl)c1)NC(c1cccc(C(F)(F)F)c1)C(F)(F)F]

2-Chloro-N-cyclopropyl-4-[3-oxo-3-({2,2,2-trifluoro-1-[3-(trifluoromethyl)phenyl]ethyl}amino)-prop-1-yn-1-yl]benzamide (110 mg, 0.20 mmol), quinoline (10 mg, 0.07 mmol) and palladium on calcium carbonate (5% Pd; 10 mg) were suspended in methanol and stirred for 4 days, in the course of which palladium on calcium carbonate (3×10 mg) was added again every 24 h. Then the reaction mixture was filtered through kieselguhr, and the filtrate concentrated to dryness under reduced pressure. The residue was purified by means of silica gel chromatography with the eluent cyclohexane/ethyl acetate (EA) (0% EA to 50% EA).

Yield: 72 mg (70% of theory).

HPLC-MS: logP=3.06; mass (m/z): 489.1 (M–H)$^-$; $^1$H NMR (CD$_3$CN) 0.54-0.57 (m, 2H), 0.73-0.76 (m, 2H), 2.79-2.83 (m, 1H), 5.93 (quint, 1H), 6.17 (d, 1H), 6.81 (d, 1H), 6.87 (s, 1H), 7.27-7.29 (m, 1H), 7.36-7.37 (m, 1H), 7.57 (s, 1H), 7.61-7.64 (m, 1H), 7.70-7.71 (m, 1H), 7.74-7.76 (m, 1H), 7.82-7.86 (m, 2H).

Synthesis Example 14 (Preparation of Compounds of the General Formulae I and III-1 According to Formula Scheme 10a and 21)

Stage 1

2,2-Difluoro-1-[3-(trifluoromethyl)phenyl]propan-1-one

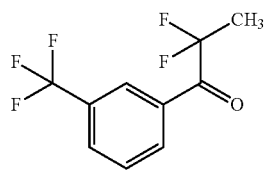 [SMILES: CC(F)(F)C(=O)c1cccc(C(F)(F)F)c1]

A solution of 2-propylmagnesium chloride in THF (1.3 M, 7.5 ml) was cooled to −15° C. and admixed with 1-iodo-3-(trifluoromethyl)benzene (2.80 g, 10.2 mmol). The reaction mixture was stirred at −15° C. for 1 h, warmed to room temperature and admixed dropwise with a solution of 2,2-difluoro-N-methoxy-N-methylpropanamide (1.43 g, 9.35 mmol; prepared according to Synth. Comm. 2008 (38), 1940-1945), and stirred at room temperature overnight. Then the mixture was added to ice-cold dilute hydrochloric acid and extracted with ethyl acetate. The combined organic phases were dried over sodium sulphate and concentrated under reduced pressure. The residue was purified by means of silica gel chromatography with the eluent cyclohexane/ethyl acetate (EA) (0% EA to 30% EA).

Yield: 1.19 g (53% of theory).

HPLC-MS: logP=3.61; $^1$H NMR (CD$_3$CN) 1.93 (t, 3H), 7.78 (t, 1H), 8.02 (d, 1H), 8.31-8.34 (m, 2H).

Stage 2

2-Chloro-N-cyclopropyl-4-[(1E)-3-({2,2-difluoro-1-[3-(trifluoromethyl)phenyl]propyl}amino)-3-oxo-prop-1-en-1-yl]benzamide (compound No. 1d-1 in Table 4)

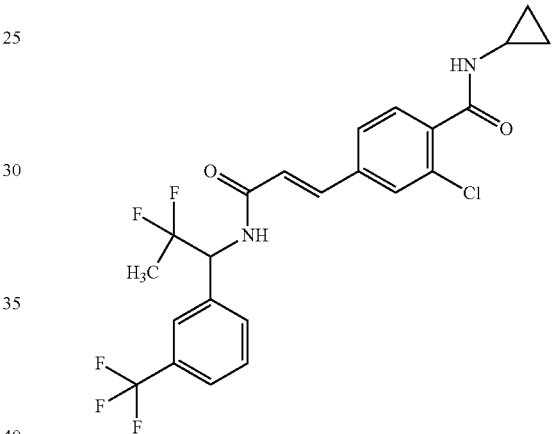

A solution of 2,2-difluoro-1-[3-(trifluoromethyl)phenyl]propan-1-one (1.19 g, 4.99 mmol) in ethanol (15 ml) was admixed with water (1.5 ml), hydroxylamine hydrochloride (695 mg, 10.0 mmol) and sodium acetate (922 mg, 11.2 mmol) and stirred at 75° C. for 21 h. The mixture, having been cooled to room temperature, was concentrated under reduced pressure, taken up in hydrochloric acid (1M) and extracted with ethyl acetate. The combined organic phases were dried over sodium sulphate and concentrated under reduced pressure. The remaining solid was dissolved in tetrahydrofuran (15 ml) and cooled to 0° C. under argon. Then lithium aluminium hydride (362 mg, 9.08 mmol) was added, and the mixture was first warmed up to room temperature and then heated under reflux for 2 h. Then the reaction mixture was cooled to 0° C. and first admixed with saturated ammonium chloride solution, diluted with sodium hydroxide solution (1 M) and extracted with ethyl acetate. The organic phase was dried over sodium sulphate, filtered and concentrated to dryness under reduced pressure. The residue was dissolved in N,N-dimethylformamide (7.5 ml) and admixed successively with (2E)-3-[3-chloro-4-(cyclopropylcarbamoyl)phenyl]acrylic acid (250 mg, 0.94 mmol) and 4-(4,6-dimethoxy[1.3.5]triazin-2-yl)-4-methylmorpholinium chloride hydrate (270 mg, 0.97 mmol) and stirred at room temperature overnight. The reaction solution was admixed with hydrochloric acid (1 M) and extracted with ethyl acetate. The organic phase was washed with saturated sodium hydrogencarbonate solution and saturated sodium chloride solution, dried over sodium sulphate, filtered and concentrated to dryness under reduced pressure. The residue was chromatographed on a preparative HPLC with water/acetonitrile as the eluent (gradient=43 min from 10% acetonitrile in water to 100% acetonitrile).

Yield: 108 mg (4% of theory).

HPLC-MS: logP=3.04; mass (m/z): 487.1 (M+H)$^+$; $^1$H NMR (CD$_3$CN) 0.56-0.59 (m, 2H), 0.73-0.77 (m, 2H), 0.92 (t, 3H), 2.81-2.84 (m, 1H), 4.91-4.92 (m, 1H), 6.65 (d, 1H), 6.93 (s, 1H), 7.16-7.17 (m, 1H), 7.39-7.42 (m, 2H), 7.47-7.65 (m, 6H).

Synthesis Example 15 (Preparation of Compounds of the General Formula I and II According to Formula Scheme 12c)

Stage 1 tert-Butyl (5-bromo-2,3-dihydro-1H-inden-1-yl)carbamate

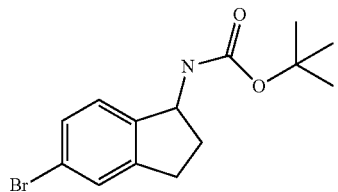 [SMILES: CC(C)(C)OC(=O)NC1CCc2cc(Br)ccc21]

A mixture of 16 g (75.4 mmol) of 5-bromoindan-1-amine, 12.8 g (320 mmol) of sodium hydroxide in water and 200 ml of THF was admixed at 0° C. with a solution of 32.9 g (151 mmol) of di-tert-butyl dicarbonate in THF, and stirred at 0° C. until conversion was complete. Extractive workup and chromatographic purification gave 18 g (57.7 mmol) of tert-butyl (5-bromo-2,3-dihydro-1H-inden-1-yl)carbamate (77%).

Stage 2

Methyl (2E)-3-{1-[(tert-butoxycarbonyl)amino]-2,3-dihydro-1H-inden-5-yl}acrylate

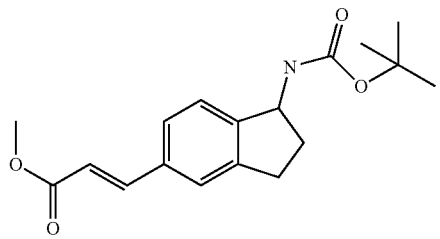 [SMILES: COC(=O)/C=C/c1ccc2c(c1)CCC2NC(=O)OC(C)(C)C]

A mixture of 25 g (80.1 mmol) of tert-butyl (5-bromo-2,3-dihydro-1H-inden-1-yl)carbamate, 975 mg (3.20 mmol) of tris(2-methylphenyl)phosphine, 179 mg (797 μmol) of palladium(II) acetate and 8.9 g (103 mmol) of methyl acrylate in 150 ml of triethylamine was stirred at 150° C. for five hours.

The precipitate was filtered off, and chromatographic purification afforded 19 g (59.9 mmol) of methyl (2E)-3-[1-[(tert-butoxycarbonyl)amino]-2,3-dihydro-1H-inden-5-yl]acrylate (75%).

Stage 3

(2E)-3-{1-[(tert-Butoxycarbonyl)amino]-2,3-dihydro-1H-inden-5-yl}acrylic acid

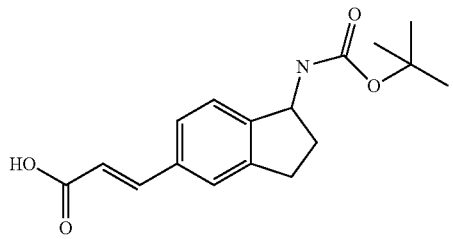 [SMILES: CC(C)(C)OC(=O)NC1CCc2cc(/C=C/C(=O)O)ccc21]

17 g (53.6 mmol) of methyl (2E)-3-[1-[(tert-butoxycarbonyl)amino]-2,3-dihydro-1H-inden-5-yl]acrylate were heated under reflux in 300 ml of dilute sodium hydroxide solution for one hour, and the resulting precipitate was filtered off, washed with diethyl ether and dried under reduced pressure. This gives 13.6 g (44.8 mmol) of (2E)-3-[1-[(tert-butoxycarbonyl)amino]-2,3-dihydro-1H-inden-5-yl]acrylic acid (84%).

$^1$H NMR (400 MHz, d$_6$-DMSO) δ=1.43 (s, 9H), 1.82 (m, 1H), 2.35 (m, 1H), 2.77 (m, 1H), 2.89 (m, 1H), 4.98 (m, 1H), 6.46 (d, 1H), 7.21 (t, 1H), 7.48 (d, 1H), 7.52 (s, 1H), 7.56 (d, 1H), 12.22 (br. s, 1H).

HPLC-MS: logP=2.47; mass (m/z): 248.1 (M-tBu)$^+$.

Stage 4 tert-Butyl {5-[(1E)-3-oxo-3-({2,2,2-trifluoro-1-[3-(trifluoromethyl)phenyl]ethyl}amino)prop-1-en-1-yl]-2,3-dihydro-1H-inden-1-yl}carbamate

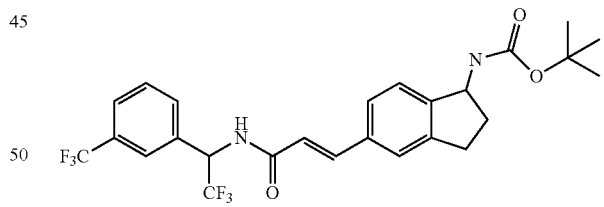

1.5 g (4.95 mmol) of (2E)-3-{1-[(tert-butoxycarbonyl)amino]-2,3-dihydro-1H-inden-5-yl}acrylic acid and 1.2 g (4.95 mmol) of 2,2,2-trifluoro-1-[3-(trifluoromethyl)phenyl]ethanamine were dissolved in 100 ml of DMF, 1.5 g (5.44 mmol) of 4-(4,6-dimethoxy-1,3,5-triazin-2-yl)-4-methylmorpholin-4-ium chloride were added, and the reaction mixture was heated to 50° C. overnight. The reaction solution was diluted with ethyl acetate, washed with sat. NaHCO$_3$ solution, 1N hydrochloric acid and sat. sodium chloride solution, dried over sodium sulphate, filtered and concentrated. Chromatographic purification gave 2.3 g (4.45 mmol) of tert-butyl {5-[(1E)-3-oxo-3-({2,2,2-trifluoro-1-[3-(trifluoromethyl)phenyl]ethyl}amino)prop-1-en-1-yl]-2,3-dihydro-1H-inden-1-yl}carbamate (87%).

¹H NMR (400 MHz, d₆-DMSO) δ=1.43 (s, 9H), 1.83 (m, 1H), 2.37 (m, 1H), 2.78 (m, 1H), 2.91 (m, 1H), 4.99 (m, 1H), 6.14 (p, 1H), 6.78 d, 1H), 7.23 (m, 2H), 7.43 (m, 2H), 7.53 (d, 1H), 7.71 (t, 1H), 7.80 (d, 1H), 7.94 (d, 1H), 8.04 (s, 1H), 9.39 ppm (d, 1H).

HPLC-MS: logP=4.44; mass (m/z): 529.2 (M+H)⁺.

Stage 5

(2E)-3-(1-Amino-2,3-dihydro-1H-inden-5-yl)-N-{2,2,2-trifluoro-1-[3-(trifluoromethyl)phenyl]-ethyl}acrylamide

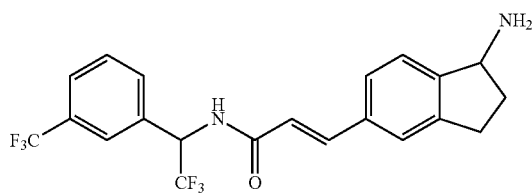 [SMILES: NC1CCc2cc(/C=C/C(=O)NC(c3cccc(C(F)(F)F)c3)C(F)(F)F)ccc21]

2.2 g of tert-butyl {5-[(1E)-3-oxo-3-({2,2,2-trifluoro-1-[3-(trifluoromethyl)phenyl]ethyl}-amino)prop-1-en-1-yl]-2,3-dihydro-1H-inden-1-yl}carbamate were dissolved in 40 ml of dioxane and admixed with 10 ml of semisaturated hydrochloric acid, and stirred at room temperature overnight. The reaction mixture was admixed with water and extracted with ethyl acetate. The combined organic phases were dried over sodium sulphate, filtered and concentrated. This gave 1.5 g of (2E)-3-(1-amino-2,3-dihydro-1H-inden-5-yl)-N-{2,2,2-trifluoro-1-[3-(trifluoromethyl)phenyl]-ethyl}-acrylamide (82%).

¹H NMR (400 MHz, d₆-DMSO) δ=2.02 (m, 1H), 2.49 (m, 1H), 2.92 (m, 1H), 3.09 (m, 1H), 4.74 (m, 1H), 6.15 (p, 1H), 6.78 (d, 1H), 7.52-7.67 (m, 4H), 7.71 (t, 1H), 7.82 (d, 1H), 7.97 (d, 1H), 8.06 (s, 1H), 8.45 (br. S, 2H), 9.53 (d, 1H).

HPLC-MS: logP=1.70; mass (m/z): 412.2 (M-NH₂)⁺.

Stage 6

(2E)-3-(1-Acetamido-2,3-dihydro-1H-inden-5-yl)-N-{2,2,2-trifluoro-1-[3-(trifluoromethyl)-phenyl]ethyl}acrylamide (compound No. Ie-1 in Table 5)

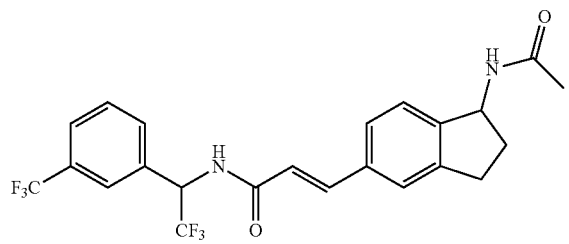 [SMILES: CC(=O)NC1CCc2cc(/C=C/C(=O)NC(c3cccc(C(F)(F)F)c3)C(F)(F)F)ccc21]

150 mg of (2E)-3-(1-amino-2,3-dihydro-1H-inden-5-yl)-N-{2,2,2-trifluoro-1-[3-(trifluoromethyl)-phenyl]ethyl}acrylamide were dissolved in 5 ml of dichloromethane, admixed with 71 mg of N-methylmorpholine and 36 mg of acetic anhydride, and stirred at room temperature overnight. The reaction mixture was concentrated on a rotary evaporator to obtain 165 mg of (2E)-3-(1-acetamido-2,3-dihydro-1H-inden-5-yl)-N-{2,2,2-trifluoro-1-[3-(trifluoromethyl)phenyl]ethyl}acrylamide (100%).

¹H NMR (400 MHz, d₆-DMSO): 1.78 (m, 1H), 1.87 (s, 3H), 2.40 (m, 1H), 2.82 (m, 1H), 2.93 (m, 1H), 5.27 (q, 1H), 6.14 (m, 1H), 6.80 (d, 1H), 7.24 (d, 1H), 7.44 (d, 1H), 7.48 (s, 1H), 7.54 (d, 1H), 7.71 (t, 1H), 7.81 (d, 1H), 7.95 (d, 1H), 8.05 (s, 1H), 8.21 (d, 1H), 9.41 (d, 1H).

HPLC-MS: logP=3.00; mass (m/z): 471.1 (M+H)⁺.

Synthesis Example 16 (Preparation of Compounds of the General Formula I-9 and VII-3 According to Formula Scheme 10d and 12d)

Stage 1

1-[4-Bromo-2-(trifluoromethyl)phenyl]methanamine

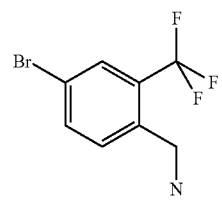 [SMILES: NCc1ccc(Br)cc1C(F)(F)F]

A solution of 18 ml of BH₃.Me₂S (180 mmol, 10M) was added slowly at 0° C. to a solution of 10.0 g (40.0 mmol) of 4-bromo-2-(trifluoromethyl)benzonitrile (Chem. Pharm. Bull. 2005, 53, 4, 402-409) in THF (110 ml). The mixture was stirred at 0° C. for 30 min, then warmed to 25° C. and stirred for 30 min. Subsequently, the mixture was heated under reflux for 30 min. After cooling to room temperature, the reaction mixture was admixed with 1M aqueous NaOH and extracted with ethyl acetate (3×150 ml). The combined organic phases were combined, dried over Na₂SO₄ and concentrated under reduced pressure. The resulting crude product was admixed at 0° C. with a solution of HCl in ethanol, and the mixture was stirred for 1 h. The mixture was concentrated under reduced pressure and the solid was washed with diethyl ether. 9.0 g (77%) of 1-[4-bromo-2-(trifluoromethyl)phenyl]methanamine hydrochloride were obtained.

HPLC-MS: logP=0.92, mass (m/z): =254.09 (M+H)⁺.

Stage 2 tert-Butyl [4-bromo-2-(trifluoromethyl)benzyl]carbamate

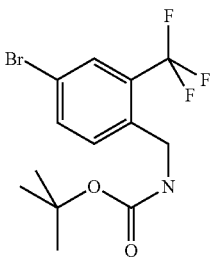 [SMILES: CC(C)(C)OC(=O)NCc1ccc(Br)cc1C(F)(F)F]

tert-Butyl [4-bromo-2-(trifluoromethyl)benzyl]carbamate was obtained by reaction of 1-[4-bromo-2-(trifluoromethyl)phenyl]methanamine hydrochloride with di-tert-butyl dicarbonate in analogy to tert-butyl (5-bromo-2,3-dihydro-1H-inden-1-yl)carbamate from Synthesis Example 15, Stage 1.

HPLC-MS: logP=4.13, mass (m/z): 297.9 (M+C4H9)+

$^1$H NMR (400 MHz, CD$_3$CN): δ=7.83 (m, 1H), 7.78 (d, 1H), 7.45 (d, 1H), 5.85 (s, 1H, br), 4.35 (d, 2H), 1.42 (s, 9H).

Stage 3

(2E)-3-[4-{[tert-Butoxycarbonyl)amino]methyl}-3-(trifluoromethyl)phenyl]acrylic acid

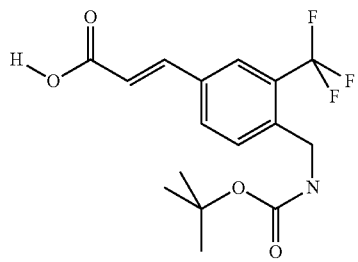 [SMILES: CC(C)(C)OC(=O)NCc1ccc(/C=C/C(=O)O)cc1C(F)(F)F]

(2E)-3-[4-{[(tert-Butoxycarbonyl)amino]methyl}-3-(trifluoromethyl)phenyl]acrylic acid was obtained by reaction of tert-butyl [4-bromo-2-(trifluoromethyl)benzyl]carbamate with ethyl (2E)-3-(4,4,5,5-tetramethyl-1,3,2-dioxaborolan-2-yl)acrylate in analogy to (2E)-3-[4-(cyclopropylcarbamoyl)-3-trifluoromethylphenyl]acrylic acid from Synthesis Example 4, Stage 3.

HPLC-MS: logP=2.67, mass (m/z): 290.1 (M+C4H9)$^+$ $^1$H NMR (400 MHz, CD$_3$CN): δ=7.90 (s, 1H), 7.84 (d, 1H), 7.68 (d, 1H, J=16 Hz), 7.57 (d, 1H), 6.55 (d, 1H, J=16 Hz), 5.83 (s, 1H, br), 4.42 (d, 2H), 1.42 (s, 9H).

Stage 4 tert-Butyl {4-[1E)-3-oxo-3-({2,2,2-trifluoro-1-[3-(trifluoromethyl)phenyl]ethyl}amino)prop-1-en-1-yl]-2-(trifluoromethyl)benzyl}carbamate

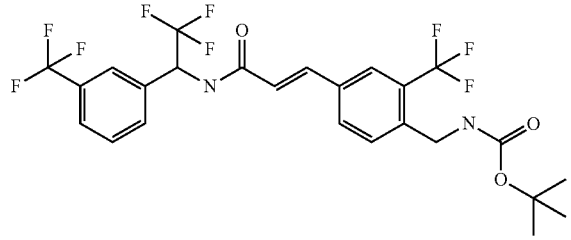 [SMILES: CC(C)(C)OC(=O)NCc1ccc(/C=C/C(=O)NC(c2cccc(C(F)(F)F)c2)C(F)(F)F)cc1C(F)(F)F]

To a solution of 980 mg (1 eq, 2.84 mmol) of (2E)-3-[4-{[(tert-butoxycarbonyl)amino]methyl}-3-(trifluoromethyl)phenyl]acrylic acid in 10 ml of dichloromethane were added 481 mg (1 eq, 2.84 mmol) of 6-chlorohydroxybenzotriazole and 707 mg (1.3 eq, 3.70 mmol) of 1-ethyl-3-(3-dimethylaminopropyl)carbodiimide hydrochloride (EDC) and 733 mg (2 eq, 5.68 mmol, 989 µl) of Huenig's base. The reaction mixture was stirred at room temperature for 20 min. Then 1.04 g (1.5 eq, 4.26 mmol) of 2,2,2-trifluoro-1-[3-(trifluoromethyl) phenyl]ethanamine as a solution in 1 ml of CH$_2$Cl$_2$ were added, and the mixture was stirred at room temperature for 16 h. The reaction mixture was concentrated under reduced pressure and partitioned between saturated Na$_2$CO$_3$ solution and ethyl acetate. After drying and concentrating the solvent, 2.108 g of tert-butyl {4-[(1E)-3-oxo-3-({2,2,2-trifluoro-1-[3-(trifluoromethyl)phenyl]ethyl}amino)prop-1-en-1-yl]-2-(trifluoromethyl)benzyl}carbamate were obtained as an oil, which was converted in the next step without further purification.

HPLC-MS: logP=4.40; mass (m/z): 571.40 (M+H)$^+$

Stage 5

(2E)-3-[4-(Aminomethyl)-3-(trifluoromethyl)phenyl]-N-{2,2,2-trifluoro-1-[3-(trifluoro-methyl)phenyl]ethyl}acrylamide

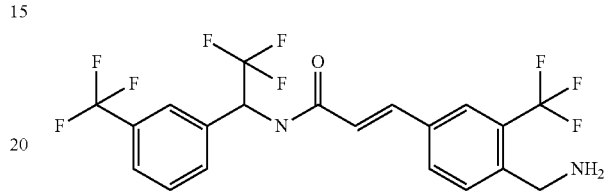

2 g (1 eq, 3.6 mmol) of N-Boc cinnamide were dissolved in 13.7 ml of 4M HCl in dioxane (15 eq, 55 mmol) and stirred at room temperature for 4 h. Subsequently, the crude mixture was concentrated under reduced pressure at a bath temperature of <30° C. The resulting crude product (1.7 g) was used as the hydrochloride in the next step without further purification.

HPLC-MS: logP=1.61, mass (m/z): 471.35 (M+H)$^+$

Stage 6

(2E)-3-{4-[(Isobutyrylamino)methyl]-3-(trifluoromethyl)phenyl}-N-{2,2,2-trifluoro-1-[3-(trifluoromethyl)phenyl]ethyl}acrylamide (compound Ia-266 in Table 1)

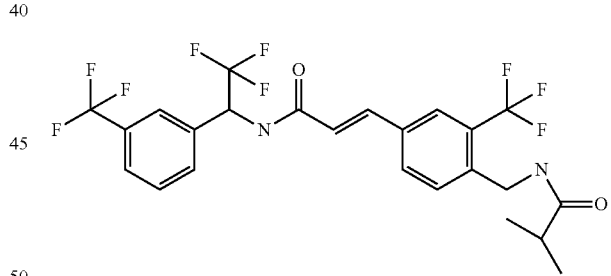

30 mg (1.2 eq, 0.28 mmol) of isobutyryl chloride were dissolved in 1 ml of dichloromethane. To this were added 113 mg (1.0 eq, 0.24 mmol) of the hydrochloride of (2E)-3-[4-(aminomethyl)-3-(trifluoromethyl)phenyl]-N-{2,2,2-trifluoro-1-[3-(trifluoromethyl)phenyl]ethyl}acrylamide from Stage 5 and 93 mg (3 eq) of Hünig's base. The mixture was stirred at room temperature for 16 h and then concentrated. The crude product was purified by means of preparative HPLC (Phenomenex Gemini C18 5 µm; 125A; Aqua 50×21.2 mm; gradient: 0-1.5 min 78% water, 20% acetonitrile, 1.5-10.0 min linear gradient to 18% water, 80% acetonitrile, 10.0-14.00 min 18% water, 20% acetonitrile; modifier: 10% NH4HCO3 added at 2 ml/min). This gives 57 mg (44%) of (2E)-3-{4-[(isobutyrylamino)methyl]-3-(trifluoromethyl)phenyl}-N-{2,2,2-trifluoro-1-[3-(trifluoro-methyl)phenyl]ethyl}acrylamide.

HPLC-MS: logP=3.78, mass (m/z): 541.2 (M+H)+.

1H NMR (400 MHz, d6-DMSO): δ=9.48 (d, 1H), 8.55 (t, 1H), 8.05 (s, 1H), 7.90 (m, 2H), 7.88 (d, 1H), 7.80 (d, 1H), 7.70 (t, 1H), 7.61 (d, 1H, J=16 Hz), 7.50 (d, 1H), 6.90 (d, 1H, J=16 Hz), 6.15 (m, 1H), 4.43 (d, 2H), 2.50 (m, 1H), 1.06 (d, 6H)

Synthesis Example 17 (Preparation of Compounds of the General Formula I-6, II-1, III-1, According to Formula Scheme 11a)

2,2,2-Trifluoro-1-[3-fluoro-5-(trifluoromethyl)phenyl]ethanone

Stage 1

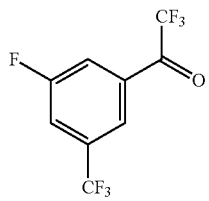

5.00 g (20.57 mmol) of 3-bromo-5-fluorobenzotrifluoride were stirred in 60 ml of dry ether and admixed dropwise at −78° C. under a protective gas atmosphere (argon) with 1.33 ml (20.75 mmol) of tert-butyllithium solution [cf. also trifluoroacylation: H. K. Nair, D. M. Quinn *Bioorganic & Medicinal Chemistry Letters* 3(12), 2619-22 (1993); G. J. Pork et al., *J. Org. Chem.* 22, 993 (1957)]. Subsequently, the reaction mixture was stirred at −78° C. for 45 minutes and then added dropwise, with the aid of a syringe, in portions at −78° C., to a solution of 3.71 g (26.17 mmol) of ethyl trifluoroacetate in 40 ml of dry ether. Thereafter, the entire reaction mixture was stirred first at −78° C. for 10 minutes and then at room temperature for one hour. For workup, the entire reaction mixture was added to water and extracted with ether. The organic phase was removed and dried at 40° C. under reduced pressure (not less than 10 mbar owing to the high volatility of the compound). This gave 4.06 g (75.9% of theory) of 2,2,2-trifluoro-1-[3-fluoro-5-(trifluoromethyl)phenyl]-ethanone, which was isolated as the hydrate.

HPLC-MS: logP=2.54, mass (m/z): 261.1 (M+H)+

Stage 2

2,2,2-Trifluoro-1-[3-fluoro-5-(trifluoromethyl)phenyl]ethanone oxime

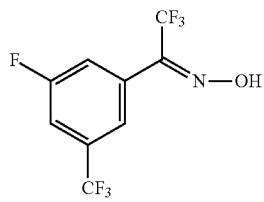

4.00 g (15.37 mmol) of 2,2,2-trifluoro-1-[3-fluoro-5-(trifluoromethyl)phenyl]ethanone hydrate from Stage 1 were stirred in a mixture of 37.3 ml of pyridine and 26.9 ml of ethanol, and stirred at reflux temperature for approx. 18 hours. After cooling, the entire reaction mixture was admixed with water and then concentrated under reduced pressure. The remaining residue was purified by means of column chromatography using silica gel (silica gel 60-Merck, particle size: 0.04 to 0.063 mm; cyclohexane/acetone gradient) to obtain 2.18 g (51.5% of theory) of 2,2,2-trifluoro-1-[3-fluoro-5-(trifluoromethyl)phenyl]ethanone oxime as a syn/anti isomer mixture.

HPLC-MS: logP=3.17; 3.21; mass (m/z): 275 (M)+

Stage 3

α,3-Bis(trifluoromethyl)-5-fluorobenzenemethanamine

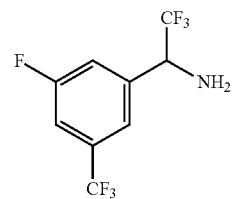

2.18 g (7.92 mmol) of 2,2,2-trifluoro-1-[3-fluoro-5-(trifluoromethyl)phenyl]ethanone oxime were stirred in 35.4 ml of isopropyl ether, and admixed with 3.54 g (93.35 mmol) of lithium aluminium hydride in portions [cf. also synthesis of aryltrifluoroethylamines: DE 2723464, 1977)]. Thereafter, the reaction mixture was stirred at reflux temperature for approx. 3 hours. For workup, the reaction mixture was cooled to 0° C. and admixed cautiously with saturated tartaric acid solution, in order to destroy excess lithium aluminium hydride. After the vigorous evolution of gas had ended, the mixture was admixed with 2N sodium hydroxide solution (alkaline) and the organic phase was removed. The aqueous phase was extracted twice more with isopropyl ether. Thereafter, the combined phases were dried over magnesium sulphate and concentrated under reduced pressure at 40° C. (not less than 50 mbar). This gave 1.55 g (71.7% of theory) of α,3-bis(trifluoromethyl)-5-fluorobenzenemethanamine, which was used for subsequent reactions without further purification.

HPLC-MS: logP=2.51; mass (m/z): 262.1 (M+H)+.

1H NMR (CD3CN, 400 MHz): δ=4.61 (q, 1H), 7.46, 7.52 (2d, 1H arom.), 7.64 (s, 1H arom.).

Stage 4

N-[α,3-Bis(trifluoromethyl)-5-fluorobenzenemethane]-3-trifluoromethyl-4-(N-cyclopropylcarbamoyl)cinnamide (compound No. Ia-229 in Table 1)

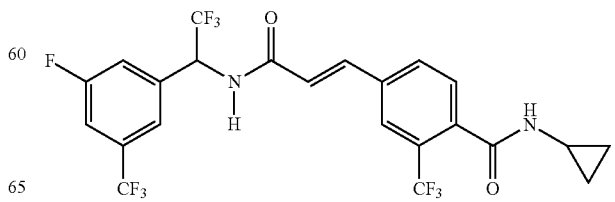

95.25 mg (0.31 mmol) of (2E,Z)-3-[4-(cyclopropylcarbamoyl)-3-(trifluoromethyl)phenyl]acrylic acid from Synthesis Example 4, Stage 3 and α,3-bis(trifluoromethyl)-5-fluorobenzenemethanamine were stirred in 7 ml of dichloromethane, admixed with 1-[bis(dimethylamino)methylene]-1H-1,2,3-triazolo-[4,5-b]pyridinium hexafluorophosphate 3-oxide (HATU) and N,N-diethyl-N-isopropylamine (Hünig's Base), and stirred at room temperature for 30 hours. Thereafter, the entire reaction mixture was washed with 1N hydrochloric acid, and the organic phase was removed and dried over sodium sulphate. After concentrating under reduced pressure, the remaining residue was purified twice by means of column chromatography using silica gel (silica gel 60-Merck, particle size: 0.04 to 0.063 mm; cyclohexane/acetone gradient). This gave 42.3 g (24.5% of theory) of N-[α,3-bis(trifluoromethyl)-5-fluorobenzenemethane]-3-trifluoromethyl-4-(N-cyclopropyl-carbamoyl)cinnamide.

HPLC-MS: logP=3.59; mass (m/z) 543.2 (M)+

Synthesis Example 18 (Preparation of Compounds of the General Formula (Vii-3) According to Formula Scheme 10d and 12b)

Stage 1

1-(4-Bromo-2-fluorophenyl)ethanamine

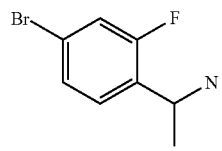

To a solution of 12 g of 4-bromo-2-fluorobenzonitrile (60 mM) in THF (120 ml) were added 75 ml (150 mM) of a 2 M solution of methylmagnesium bromide in diethyl ether at 0° C. The reaction mixture was stirred at 0° C. for 6 h. Then 200 ml of methanol were added gradually to the reaction mixture. Subsequently, 5.7 g (150 mM) of sodium borohydride were added in portions, and the mixture was stirred at room temperature for 16 h. Thereafter, the reaction mixture was concentrated under reduced pressure, and 200 ml of water were added. The pH was adjusted to pH=~1 with 2 M HCl, and the aqueous solution was extracted with chloroform. Subsequently, the pH was adjusted to pH=~9 with 2M NaOH, and extraction was effected with chloroform (2×100 ml). The combined chloroform extracts were dried, and the solvent was removed under reduced pressure. 7.3 g (44%) of 1-(4-bromo-2-fluorophenyl)ethanamine were obtained as a yellow oil.

$^1$H NMR (400 MHz, CDCl$_3$): δ=1.39 (d, 3H), 1.61 (s, 2H, br), 4.34 (m, 1H), 7.18 (m, 3H).

Stage 2

N-[1-(4-Bromo-2-fluorophenyl)ethyl]propanamide

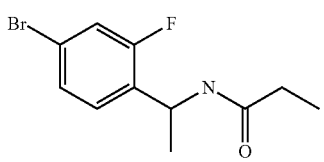

61 mg (1 eq, 0.24 mmol) of 1-(4-bromo-2-fluorophenyl)ethanamine from Stage 1 were dissolved in 4 ml of dichloromethane, and 24 mg (1.1 eq, 23 µl, 0.264 mmol) of propanoyl chloride and 70 mg (2.2 eq, 90 µl) of Hünig's base were added. The mixture was stirred at room temperature for 5 h and then concentrated. The crude product was dissolved in ethyl acetate and washed 1× with 1M HCl, 1× with sat. sodium carbonate solution and then with water, and dried over magnesium sulphate. After concentrating under reduced pressure, the resulting crude product was purified by means of chromatography on silica gel (eluent: cyclohexane/ethyl acetate). 50 mg (67%) of N-[1-(4-bromo-2-fluorophenyl)ethyl]propanamide were obtained.

HPLC-MS: logP=2.19, mass (m/z): 276.1 (M+H)+.

$^1$H NMR (400 MHz, DMSO-d$_6$): δ=8.25 (d, 1H, br), 7.46 (dd, 1H), 7.39 (dd, 1H), 7.30 (t, 1H), 5.05 (m, 1H), 2.10 (q, 2H), 1.31 (d, 3H), 0.97 (t, 3H).

Synthesis Example 19 (Preparation of Compounds of the General Formula (VII-4) According to Formula Scheme 10e and 12a)

N-[4-Bromo-2-(trifluoromethyl)benzyl]pyridin-2-amine

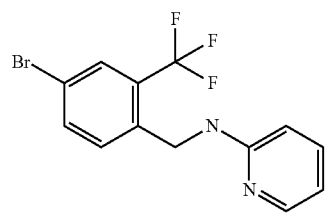 [SMILES: FC(F)(F)c1cc(Br)ccc1CNc1ccccn1]

To a solution of 0.61 g of tert-butyl pyridin-2-ylcarbamate (3.2 mmol) in 10 ml of dry DMF was added 0.18 g of NaH (60%, 4.4 mmol) in portions at 0° C., and the mixture was stirred at 0° C. for 30 min. Subsequently, 1.1 g (3.5 mmol) of 4-bromo-1-(bromomethyl)-2-(trifluoromethyl)benzene (WO2006/18725) were added as a solution in dry DMF (5.0 ml) at 0° C. The reaction mixture was warmed slowly to room temperature and stirred for 2 h. Thereafter, it was admixed with water and extracted with ethyl acetate. The organic phase was dried and concentrated under reduced pressure. The resulting crude product was purified by means of silica gel chromatography (n-hexane/ethyl acetate 30:1 to 10:1) to obtain 1.1 g (77%) of the N-Boc-protected amine.

This was dissolved in 20 ml of HCl-saturated ethyl acetate, and stirred at room temperature overnight. Subsequently, the solution was neutralized with aqueous K$_2$CO$_3$ solution and extracted with ethyl acetate. After drying and removal of the solvent, 0.8 g (75%) of N-[4-bromo-2-(trifluoromethyl)benzyl]pyridin-2-amine was obtained as a solid.

HPLC-MS: logP=1.57, mass (m/z): 333.0 (M+H)+.

$^1$H NMR (400 MHz, CD$_3$CN): δ=7.96 (dd, 1H), 7.78 (m, 1H), 7.68 (m, 1H), 7.50 (d, 1H), 7.43-7.39 (m, 1H), 6.58-6.56 (m, 1H), 6.50 (d, 1H), 5.68 (s, 1H, br), 4.68 (d, 2H).

The inventive compounds of the general formulae (Ia), (Ib), (Ic), (Id), (Ie), (If) and (Ig) described in Tables 1 to 7 are likewise preferred inventive compounds which are obtained according to or analogously to the Synthesis Examples described above.

TABLE 1

$$\text{(Ia)}$$

Structure: A benzyl-type compound with (R¹)ₙ on ring positions 2-6, bearing X and CF₃ at the benzylic carbon with R², attached via N(R³) to a C(=O)-C(R⁴)=C(R⁵)-phenyl ring with (R⁶)ₘ substituents and A-Y group.

where R², R⁴ and R⁵ are each H, X is CF₃ and (R¹)ₙ, R³, (R¹)ₘ, A and Y are each as defined in Table 1. The numbers 2 to 6 represent the positions on the aromatic rings.

| No. | (R¹)ₙ | R3 | (R⁶)ₙ | A | Y | HPLC-MS[a]; ¹H NMR (δ in ppm)[b] |
|---|---|---|---|---|---|---|
| Ia-1 | 3,5-Cl₂ | H | H | 4-(—NHCO—) | cyclopropyl | HPLC-MS: logP = 3.77; mass (m/z): 458.1 (M + H)⁺; ¹H NMR (d₄-methanol) 0.70 (m, 2H), 0.92 (m, 2H), 1.75 (m, 1H), 5.88 (m, 1H), 6.65 (d, 1H), 7.6 -7.7 (m, 8H). |
| Ia-2 | 3,5-Cl₂ | H | H | 4-(—NHCO—) | 2-chloropyridin-3-yl | HPLC-MS: logP = 3.69; mass (m/z): 529.1 (M + H)⁺; ¹H NMR (d₆-DMSO) 6.02 (m, 1H), 6.72 (d, 2H), 7.55 (m, 2H), 7.65 (m, 3H), 7.75 (m, 2H), 8.04 (m, 1H), 8.52 (m, 1H), 9.18 (m, 1H). |
| Ia-3 | 3-CF₃ | H | H | 4-(—NHCO—) | methyl | HPLC-MS: logP = 2.95; mass (m/z): 431.1 (M + H)⁺; ¹H NMR (d₆-DMSO) 2.03 (s, 3H), 6.08 (m, 1H), 6.70 (d, 1H), 7.56(m, 1H), 7.65 (m, 2H), 7.73 (m, 2H), 8.04 (m, 1H), 9.25 (m, 1H). |
| Ia-4 | 3-CF₃ | H | H | 3-(—NHCO—) | cyclopropyl | HPLC-MS: logP = 3.42; mass (m/z): 457.0 (M + H)⁺; ¹H NMR (d₆-DMSO) 0.80 (m, 4H), 1.78 (m, 1H), 6.10 (m, 1H), 6.78 (d, 1H), 7.20(m, 1H), 7.35 (m, 1H), 7.45 (m, 2H), 7.70 (m, 1H), 7.78 (m, 1H), 7.95 (m, 1H), 8.04 (m, 1H), 9.40 (m, 1H). |
| Ia-5 | 3-CF₃ | H | H | 3-(—NHCO—) | 2-chloropyridin-3-yl | See Synthesis Example 3, Stage 3 |
| Ia-6 | 3-CF₃ | H | H | 4-(—NHCO—) | 2,2,2-trifluoroethyl | HPLC-MS: logP = 3.43; mass (m/z): 499.1 (M + H)+; ¹H NMR (d₆-DMSO) 4.05 (m, 2H), 6.08 (m, 1H), 6.78 (d, 1H), 7.58 (m, 1H), 7.70 (m, 3H), 7.78 (m, 1H), 7.93 (m, 2H), 8.01 (m, 1H), 8.95 (m, 1H), 9.47 (m, 1H). |
| Ia-7 | 3-CF₃ | H | H | 4-(—CONH—) | pyridin-2-ylmethyl | HPLC-MS: logP = 2.45; mass (m/z): 508.1 (M + H)⁺; ¹H NMR (d₆-DMSO) 4.60 (m, 2H), 6.10 (m, 1H), 6.89 (d, 1H), 7.25 (m, 1H), 7.35 (m, 1H), 7.58 (m, 1H), 7.7 ? 7.8 (m, 3H), 7.9 ? 8.0 (m, 3H), 8.50 (m, 1H), 8.95 (m, 1H), 9.35 (d, 1H). |
| Ia-8 | 3-CF₃ | H | H | | 4-CN | See Synthesis Example 1, Stage 1 |
| Ia-9 | 3-CF₃ | H | 3-NO₂ | | 4-(1H-1,2,4-triazol-1-yl) | HPLC-MS: logP = 3.11; mass (m/z): 486,1 (M + H)⁺; ¹H NMR (d₃-acetonitrile) 6.05 (m, 1H), 6.85 (d, 1H), 7.6 -7.90 (m, 6H), 8.02 (m, 1H), 8.21 (m, 1H), 8.65 (m, 1H). |
| Ia-10 | 3-CF₃ | H | 3-CN | | 4-(1H-1,2,4-triazol-1-yl) | HPLC-MS: logP = 2.99; mass (m/z): 466.1 (M + H)+; ¹H NMR (d₃-acetonitrile) 6.06 (m, 1H), 6.87 (d, 1H), 7.6 -7.90 (m, 6H), 8.02 (m, 1H), 8.21 (m, 1H), 8.65 (m, 1H). |
| Ia-11 | 3-CF₃ | H | 3-CH₃ | 4-(—CONH—) | cyclopropyl | HPLC-MS: logP = 3.02; mass (m/z): 471.11 (M + H)⁺; 1H NMR ( d3-CD3CN) 7.86 (s, 1H), 7.80-7.70 (m, 3H), 7.66 (t, 1H), 7.57 (d, 1H, J= 16 Hz), 7.45-7.38 (m, 2H), 7.32 (d, 1H), 6.75 (s, 1H, br), 6.69 (d, 1H, J = 16 Hz), 5.99 |

TABLE 1-continued $$\text{(Ia)}$$

where $R^2$, $R^4$ and $R^5$ are each H, X is $CF_3$ and $(R^1)_n$, $R^3$, $(R^1)_m$, A and Y are each as defined in Table 1. The numbers 2 to 6 represent the positions on the aromatic rings.

| No. | $(R^1)_n$ | R3 | $(R^6)_n$ | A | Y | HPLC-MS[a]; $^1$H NMR (δ in ppm)[b] |
|---|---|---|---|---|---|---|
| Ia-12 | 3,5-Cl$_2$ | H | 3-CH$_3$ | 4-(—CONH—) | cyclopropyl | (m, 1H), 2.80 (m, 1H), 2.38 (s, 3H), 0.75 (m, 2H), 0.56 (m, 2H) HPLC-MS: logP = 3.33; mass (m/z): 473.03(M + H)+; 1H NMR (d3-CD3CN) 7.55-7.50 (m, 2H), 7.45-7.38 (m, 2H), 7.32 (d, 1H), 7.20 (d, 1H), 7.05 (s, 1H), 7.00 (d, 1H), 6.75 (s, 1H, br), 6.69 (d, 1H, J = 16 Hz), 5.90 (m, 1H), 2.80 (m, 1H), 2.38 (s, 3H), 0.75 (m, 2H), 0.56 (m, 2H) . |
| Ia-13 | 3-F | H | 3-CN | 4-(1H-1,2,4-triazol-1-yl) | | HPLC-MS: logP = 2.61; mass (m/z): 416.1 (M + H)$^+$; $^1$H NMR (d$_6$-DMSO) 5.98 (m, 1H), 6.95 (d, 1H), 7.25 (m, 1H), 7.48 (m, 1H), 7.62 (d, 2H), 7.91 (d, 2H), 8.10 (m, 1H), 8.30 (d, 2H), 9.15 (s, 1H), 9.30 (m, 1H). |
| Ia-14 | 4-CF$_3$ | H | 3-CN | 4-(1H-1,2,4-triazol-1-yl) | | HPLC-MS: logP = 3.08; mass (m/z): 466.1 (M + H)$^+$; $^1$H NMR (d$_6$-DMSO) 6.05 (m, 1H), 6.99 (d, 1H), 7.62 (m, 1H), 7.80 (s, 2H), 7.92 (d, 1H), 7.91 (d, 2H), 8.10 (m, 1H), 8.30 (d, 2H), 9.16 (s, 1H), 9.38 (m, 1H). |
| Ia-15 | 2,5-Cl$_2$ | H | 3-CN | 4-(1H-1,2,4-triazol-1-yl) | | HPLC-MS: logP = 3.19; mass (m/z): 467.1 (M + H)$^+$; $^1$H NMR (d$_6$-DMSO) 6.35 (m, 1H), 6.96 (d, 1H), 7.5 ? 7.6 (m, 3H), 7.90 (d, 2H), 8.13 (d, 1H), 8.32 (d, 2H), 8.10 (m, 1H), 8.30 (d, 2H), 9.16 (s, 1H), 9.45 (m, 1H). |
| Ia-16 | 3,5-Cl$_2$ | H | 3-CN | 4-(1H-1,2,4-triazol-1-yl) | | HPLC-MS: logP = 3.33; mass (m/z): 467.1 (M + H)$^+$; $^1$H NMR (d$_6$-DMSO) 6.05 (m, 1H), 6.95 (d, 1H), 7.62 (d, 2H), 7.92 (m, 1H), 8.10 (m, 1H), 8.32 (d, 2H), 8.10 (m, 1H), 8.30 (d, 2H), 9.15 (s, 1H), 9.45 (m, 1H). |
| Ia-17 | 3,4-Cl$_2$ | H | 3-CN | 4-(1H-1,2,4-triazol-1-yl) | | See Synthesis Example 5, Stage 2 |
| Ia-18 | 3-CF$_3$ | H | 3-CH$_3$ | 4-(—CONH—) | 2,2,2-trifluoroethyl | HPLC-MS: logP = 3.56; mass (m/z): 513.1 (M + H)$^+$; $^1$H NMR (d$_6$-DMSO) 2.39 (s, 3H), 4.05 (m, 2H), 6.08 (m, 1H), 6.85 (d, 1H), 7.38 (d, 2H), 7.4 ? 7.6 (m, 3H), 7.70 (m, 1H), 7.78 (m, 1H), 7.90 (m, 1H), (m, 1H), 8.02 (s, 1H), 8.82 (m, 1H), 9.30 (m, 1H). |
| Ia-19 | 3-CF$_3$ | H | 3-Cl | 4-(—CONH—) | 2,2,2-trifluoroethyl | HPLC-MS: logP = 3.56; mass (m/z): 530.9 (M + H)$^{+1}$H NMR (d$_6$-DMSO) 4.05 (m, 2H), 6.10 (m, 1H), 6.90 (d, 1H),7.5 ? 7.7 (m, 2H), 7.70 ? 7.8 (m, 2H), (m, 1H), 7.90 (m, 1H), 8.00 (s, 1H), 8.98 (m, 1H), 9.35 (m, 1H). |
| Ia-20 | 3,5-Cl$_2$ | H | 3-CH$_3$ | 4-(—CONH—) | 2,2,2-trifluoroethyl | HPLC-MS: logP = 3.90; mass (m/z): 513.9 (M + H)$^+$; $^1$H NMR (d$_6$-DMSO) 2.40 (s, 3H), 4.05 (m, 2H), 6.04 (m, 1H), 6.82 (d, 1H), 7.40 (d, 1H), 7.48 (m, 2H), 7.68 (s, 1H), 7.72 (s, 1H), 8.82 (m, 1H), 9.25 (m, 1H). |
| Ia-21 | 3-CF$_3$ | H | 3-Cl | 4-(—CONH—) | pyridin-2-ylmethyl | HPLC-MS: logP = 2.75; mass (m/z): 542.1 (M + H)$^+$; $^1$H NMR |

TABLE 1-continued (Ia)

where $R^2$, $R^4$ and $R^5$ are each H, X is $CF_3$ and $(R^1)_n$, $R^3$, $(R^1)_m$, A and Y are each as defined in Table 1. The numbers 2 to 6 represent the positions on the aromatic rings.

| No. | $(R^1)_n$ | R3 | $(R^6)_n$ | A | Y | HPLC-MS[a]; $^1$H NMR (δ in ppm)[b] |
|---|---|---|---|---|---|---|
| | | | | | | (d$_6$-DMSO) 4.54 (m, 2H), 6.10 (m, 1H), 6.90 (d, 1H), 7.25 (d, 1H), 7.42 (d, 1H), 7.5 ? 7.6 (m, 2H), 7.7 ? 7.8 (m, 2H) 7.90 (m, 1H), 7.98 (s, 1H)8.50 (m, 1H), 9.85 (m, 1H). |
| Ia-22 | 3-CF$_3$ | H | 3-CH$_3$ | 4-(—CONH—) | pyridin-2-ylmethyl | HPLC-MS: logP = 2.65; mass (m/z): 522.2 (M + H)$^+$; $^1$H NMR (d$_6$-DMSO) 2.39 (s, 3H), 4.56 (m, 2H), 6.10 (m, 1H), 6.85 (d, 1H), 7.25 (d, 1H), 7.35 (m, 1H), 7.48 (m, 1H), 7.55 (m, 1H) 7.6 7.7 (m, 2H), 7.90 (m, 1H), 7.98 (s, 1H), 8.50 (m, 1H), 8.70 (m, 1H), 9.30 (m, 1H). |
| Ia-23 | 3-CF$_3$ | H | 3-CF$_3$ | 4-(—CONH—) | cyclopropyl | HPLC-MS: logP = 3.18; mass (m/z): 525 (M + H)+; |
| Ia-24 | 3,5-Cl$_2$ | H | 3-CF$_3$ | 4-(—CONH—) | cyclopropyl | HPLC-MS: logP = 3.5; mass (m/z): 525 (M + H)+; 1H NMR (d3-CD3CN) 7.91 (s, 1H), 7.82 (d, 1H), 7.70 (m, 1H), 7.65 (d, 1H, J = 16 Hz), 7.55-7.50 (m, 4H), 6.90 (s, 1H, br), 6.75 (d, 1H, J = 16 Hz), 5.89 (m, 1H), 2.80 (m, 1H), 0.75 (m, 2H), 0.55 (m, 2H) |
| Ia-25 | 3-CF$_3$ | CH$_3$ | H | | 4-CN | See Synthesis Example 1, Stage 2 |
| Ia-26 | 3-CF$_3$ | H | 3-CH$_3$ | 4-(—COO—) | CH3 | HPLC-MS: logP = 4.09; mass (m/z): 446.1 (M + H)$^+$: $^1$H NMR (d$_3$-acetonitrile) 2.55 (s, 3H), 3.88 (s, 3H), 5.96 (m, 1H), 6.75 (d, 1H), 7.45 (m, 1H), 7.6 ? 7.7 (m, 2H), 7.7 ? 7.8 (m, 2H), 7.88 (s, 1H). |
| Ia-27 | 3-CF$_3$ | H | 3-CH$_3$ | 4-(—COO—) | H | HPLC-MS: logP = 3.14; mass (m/z): 432.1 (M + H)$^+$; $^1$H NMR (d$_6$-DMSO) 2.55 (s, 3H), 6.10 (m, 1H), 6.90 (d, 1H), 7.5-7.6 (m, 3H), 7.70 (m, 1H), 7.8-7.9 (m, 3H), 7.88 (s, 1H), 9.35 (m, 1H). |
| Ia-28 | 3-NO$_2$ | H | 3-CF$_3$ | 4-(—CONH—) | 3,3,3-trifluoro-propan-2-yl | HPLC-MS: logP = 3.83; mass (m/z): 558.96(M + H)+; 1H NMR (d$_6$-DMSO) 9.17 (d, 1H), 8.52 (s, 1H), 8.35 (dd, 1H), 8.28 (s, 1H), 8.19 (d, 1H), 8.12 (d, 1H), 7.98 (d, 1H, J= 16 Hz), 7.82 (t, 1H), 7.57 (d, 1H), 7.13 (d, 1H, J = 16 Hz), 6.93 (q, 1H), 4.77 (m, 1H), 1.31 (d, 3H). |
| Ia-29 | 2,6-F2 | H | 3-CF$_3$ | 4-(—CONH—) | 3,3,3-trifluoro-propan-2-yl | HPLC-MS: logP = 3.41; mass (m/z): 549.01 (M + H)+; 1H NMR (d$_6$-DMSO) 9.30 (d, 1H), 9.15 (d, 1H), 8.00 (s, 1H), 7.93 (d, 1H), 7.65 (d, 1H, J = 16 Hz), 7.58 (d, 1H), 7.26 (t, 2H), 7.17 (d, 1H, J = 16 Hz), 6.29 (m, 1H), 4.77 (m, 1H), 1.31 (d, 3H). |
| Ia-30 | 3-CF$_3$ | H | 3-CF$_3$ | 4-(—CONH—) | 3,3,3-trifluoro-propan-2-yl | HPLC-MS: logP = 3.58; mass (m/z): 580.97(M + H)+; 1H NMR (d$_6$-DMSO) 9.53 (d, 1H), 9.16 (d, 1H), 8.05 (d, 1H), 7.96 (t, 1H), 7.81 (d, 1H), 7.72 (t, 1H), 7.67 (d, 1H, J = 16 Hz), 7.57 (d, 1H), 6.98 (d, 1H, J = 16 Hz), 6.16 |

TABLE 1-continued (Ia)

where $R^2$, $R^4$ and $R^5$ are each H, X is $CF_3$ and $(R^1)_n$, $R^3$, $(R^1)_m$, A and Y are each as defined in Table 1. The numbers 2 to 6 represent the positions on the aromatic rings.

| No. | $(R^1)_n$ | R3 | $(R^6)_n$ | A | Y | HPLC-MS[a]; $^1$H NMR (δ in ppm)[b] |
|---|---|---|---|---|---|---|
| Ia-31 | 3-CF$_3$ | H | 3-CF$_3$ | 4-(—CONH—) | benzyl | (m, 1H), 4.77 (m, 1H), 1.31 (d, 3H). HPLC-MS: logP = 3.68; mass (m/z): 575.94(M + H)+; 1H NMR (d$_6$-DMSO) 9.52 (d, 1H), 9.07 (t, 1H), 8.05 (s, 1H), 8.02 (s, 1H), 7.94 (m, 2H), 7.81 (d, 1H), 7.72 (t, 1H), 7.66 (d, 1H, J = 16 Hz), 7.61 (d, 1H), 7.35 (m, 4H), 7.28 (m, 1H), 6.96 (d, 1H, J = 16 Hz), 6.15 (m, 1H), 4.44 (d, 2H). |
| Ia-32 | 3,4-Cl$_2$ | H | 3-CF$_3$ | 4-(—CONH—) | pyridin-2-ylmethyl | HPLC-MS: logP = 2.98; mass (m/z): 575.97(M + H)+; 1H NMR (d$_6$-DMSO) 9.45 (d, 1H), 9.15 (t, 1H), 8.53 (d, 1H), 8.03 (s, 1H), 7.96 (m, 2H), 7.70-7.60 (m, 3H), 7.60-7.50 (m, 3H), 7.39 (d, 1H), 7.29 (dd, 1H), 6.96 (d, 1H, J = 16 Hz), 6.09 (m, 1H), 4.54 (d, 2H). |
| Ia-33 | 3-NO$_2$ | H | 3-CF$_3$ | 4-(—CONH—) | pyridin-2-ylmethyl | HPLC-MS: logP = 2.93; mass (m/z): 553.99(M + H)+; 1H NMR (d$_6$-DMSO) 9.17 (t, 1H), 8.53 (m, 2H), 8.35 (dd, 1H), 8.27 (s, 1H), 8.19 (d, 1H), 8.12 (d, 1H), 7.98 (d, 1H, J = 16 Hz), 7.85-7.80 (m, 3H), 7.68 (d, 1H), 7.39 (d, 1H), 7.29 (dd, 1H), 7.13 (d, 1H, J = 16 Hz), 6.93 (q, 1H), 4.54 (d, 2H). |
| Ia-34 | 4-NO$_2$ | H | 3-CF$_3$ | 4-(—CONH—) | pyridin-2-ylmethyl | HPLC-MS: logP = 2.93; mass (m/z): 553.99(M + H)+; 1H NMR (d$_6$-DMSO) 9.17 (t, 1H), 8.53 (m, 1H), 8.35 (m, 2H), 8.27 (s, 1H), 8.19 (d, 1H), 8.00-7.90 (m, 3H), 7.80 (t, 1H), 7.69 (d, 1H), 7.39 (d, 1H), 7.29 (dd, 1H), 7.12 (d, 1H, J = 16 Hz), 6.88 (q, 1H), 4.54 (d, 2H). |
| Ia-35 | 2,6-F$_2$ | H | 3-CF$_3$ | 4-(—CONH—) | pyridin-2-ylmethyl | HPLC-MS: logP = 2.46; mass (m/z): 544.02(M + H)+; 1H NMR (d$_6$-DMSO) 9.29 (d, 1H), 9.14 (t, 1H), 8.52 (d, 1H), 7.99 (s, 1H), 7.93 (d, 1H), 7.80 (t, 1H), 7.70 (m, 1H), 7.65 (m, 1H), 7.39 (d, 1H), 7.25 (m, 2H), 7.17 (d, 1H, J = 16 Hz), 6.29 (m, 1H), 4.54 (d, 2H). |
| Ia-36 | 3-CF$_3$ | H | 3-CF$_3$ | 4-(—CONH—) | pyridin-2-ylmethyl | HPLC-MS: logP = 2.75; mass (m/z): 576.04(M + H)+; |
| Ia-37 | 3,4-Cl$_2$ | H | 3-CF$_3$ | 4-(—CONH—) | cyclopropyl | HPLC-MS: logP = 3.41; mass (m/z): 524.93(M + H)+; |
| Ia-38 | 2,6-F$_2$ | H | 3-CF$_3$ | 4-(—CONH—) | cyclopropyl | HPLC-MS: logP = 2.89; mass (m/z): 493(M + H)+; 1H NMR (d$_6$-DMSO) 9.27 (d, 1H), 8.54 (d, 1H), 7.96 (s, 1H), 7.88 (d, 1H), 7.65 (d, 1H, J = 16 Hz), 7.58 (d, 1H), 7.26 (t, 2H), 7.17 (d, 1H, J = 16 Hz), 6.29 (m, 1H), 2.78 (m, 1H), 0.70 (m, 2H), 0.50 (m, 2H) |
| Ia-39 | 3-CF$_3$, 5-Cl | H | 3-CH$_3$ | 4-(—CONH—) | cyclopropyl | HPLC-MS: logP = 3.47; mass (m/z): 506.98 (M + H)+; 1H NMR (d$_6$-DMSO) 9.45 (d, 1H), 8.30 (d, 1H), 8.11 (s, 1H), 8.08 (s, |

TABLE 1-continued (Ia)

where $R^2$, $R^4$ and $R^5$ are each H, X is $CF_3$ and $(R^1)_n$, $R^3$, $(R^1)_m$, A and Y are each as defined in Table 1. The numbers 2 to 6 represent the positions on the aromatic rings.

| No. | $(R^1)_n$ | R3 | $(R^6)_n$ | A | Y | HPLC-MS[a]; $^1$H NMR ($\delta$ in ppm)[b] |
|---|---|---|---|---|---|---|
| | | | | | | 1H), 8.00 (s, 1H), 7.52 (d, 1H, J = 16 Hz), 7.50-7.45 (m, 2H), 7.32 (d, 1H), 6.81 (d, 1H, J = 16 Hz), 6.25 (m, 1H), 2.82 (m, 1H), 0.70 (m, 2H), 0.50 (m, 2H). |
| Ia-40 | 3-$CF_3$, 5-Cl | H | 3-$CF_3$ | 4-(—CONH—) | cyclopropyl | See Synthesis Example 4, Stage 4 |
| Ia-41 | 3-$CF_3$ | H | 3-Br | 4-(—CONH—) | pyridin-2-ylmethyl | HPLC-MS: logP = 2.76; mass (m/z): 587.1 (M + H)$^+$; $^1$H NMR ($d_6$-acetonitrile) 4.63 (m, 2H), 5.95 (m, 1H), 6.73 (d, 1H), 7.22 (m, 1H), 7.35 (m, 1H), 7.9 ? 8.0 (m, 6H), 8.50 (m, 1H), 8.52 (m, 1H). |
| Ia-42 | 3-$CF_3$ | H | 3-Br | 4-(—CONH—) | cyclopropyl | HPLC-MS: logP = 3.23; mass (m/z): 536.1 (M + H)$^+$; $^1$H NMR ($d_6$-acetonitrile) 0.55 (m, 2H), 0.75 (m, 2H), 2.71 (m, 1H), 6.00 (m, 1H), 6.70 (d, 1H), 7.40 (m, 1H), 7.5 ? 7.7 (m, 6H), 9.18 (m, 1H). |
| Ia-43 | 3-$CF_3$ | H | 3-Cl | 4-(—CONH—) | cyclopropyl | HPLC-MS: logP = 3.22; mass (m/z): 491.1 (M + H)$^+$; $^1$H NMR ($d_6$-DMSO) 0.55 (m, 2H), 0.70 (m, 2H), 2.85 (m, 1H), 6.10 (m, 1H), 6.80 (d, 1H), 7.40 (m, 1H), 7.58 (m, 1H), 7.70 (m, 1H), 7.80 (m, 1H), 7.90 (m, 1H), 8.01 (m, 1H), 8.30 (s, 1H), 9.33 (m, 1H). |
| Ia-44 | 3-$CF_3$ | H | 3-Cl | | 4-CN | HPLC-MS: logP = 3.91; mass (m/z): 433.0 (M + H)$^+$; $^1$H NMR ($d_6$-DMSO) 6.08 (m, 1H), 6.86 (d, 1H), 7.50 (m, 2H), 7.59 (m, 1H), 7.70 (m, 2H), 7.90 (m, 1H), 8.02 (m, 1H), 9.34 (m, 1H). |
| Ia-45 | 3-$CF_3$ | H | 3-Br | 4-(—CONH—) | 2,2,2-trifluoroethyl | HPLC-MS: logP = 3.60; mass (m/z): 577.1 (M + H)$^+$; $^1$H NMR ($d_6$-DMSO) 4.05 (m, 2H), 6.10 (m, 1H), 6.90 (d, 1H), 7.5 ? 7.7 (m, 2H), 7.70 ? 7.8 (m, 2H), (m, 1H), 7.90 (m, 1H), 8.00 (s, 1H), 8.98 (m, 1H), 9.35 (m, 1H). |
| Ia-46 | 3-$CF_3$ | H | 3-$CF_3$ | | 4-CN | HPLC-MS: logP = 4.06; mass (m/z): 466.0 (M + H)$^+$; $^1$H NMR ($d_6$-DMSO) 6.09 (m, 1H), 6.88 (d, 1H), 7.50 (m, 2H), 7.59 (m, 1H), 7.70 (m, 2H), 7.90 (m, 1H), 8.02 (m, 1H), 9.33 (m, 1H). |
| Ia-47 | 3-$CF_3$ | H | 3-$CF_3$ | 4-(—CONH—) | 2-(2,2,2-trifluoro-ethoxy)ethyl | HPLC-MS: logP = 3.58; mass (m/z): 611.03(M + H)+; 1H NMR ($d_6$-DMSO) 9.53 (d, 1H), 8.65 (t, 1H), 8.05 (s, 1H), 8.00 (s, 1H), 7.94 (m, 2H), 7.80 (d, 1H), 7.71 (t, 1H), 7.65 (d, 1H, J = 16 Hz), 7.54 (d, 1H), 6.97 (d, 1H, J = 16 Hz), 6.16 (m, 1H), 4.11-4.04 (q, 2H, J(H,F)= 19Hz, J (H, H) = 10 Hz), 3.70 (t, 2H), 3.40 (t, 2H). |
| Ia-48 | 3-$CF_3$ | H | 3-$CF_3$ | 4-(—CONH—) | 4-fluorophenyl | HPLC-MS: logP = 3.89; mass (m/z): 578.99(M + H)+; 1H NMR ($d_6$-DMSO) 10.63 (s, 1H), 9.53 (d, 1H), 8.08 (s, 1H), 8.06 (s, 1H), 8.01 (d, 1H), 7.95 (d, 1H), 7.80 (d, 1H), 7.78-7.65 (m, 5H), |

TABLE 1-continued

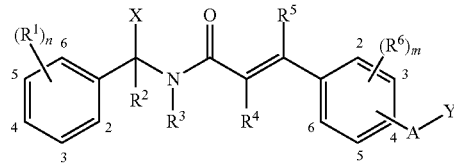

(Ia)

where $R^2$, $R^4$ and $R^5$ are each H, X is $CF_3$ and $(R^1)_n$, $R^3$, $(R^1)_m$, A and Y are each as defined in Table 1. The numbers 2 to 6 represent the positions on the aromatic rings.

| No. | $(R^1)_n$ | R3 | $(R^6)_n$ | A | Y | HPLC-MS[a]; $^1$H NMR (δ in ppm)[b] |
|---|---|---|---|---|---|---|
| Ia-49 | 3-$CF_3$ | H | 3-$CF_3$ | 4-(—CONH—) | pyridin-4-ylmethyl | 7.20 (t, 2H), 6.99 (d, 1H, J = 16 Hz), 6.16 (m, 1H). HPLC-MS: logP = 2; mass (m/z): 575.97(M + H)+; 1H NMR (d$_6$-DMSO) 9.53 (d, 1H), 9.17 (t, 1H), 8.53 (d, 2H), 8.05 (s, 1H), 8.03 (s, 1H), 7.95 (m, 2H), 7.80 (m, 1H), 7.72-7.65 (m, 3H), 7.34 (d, 2H), 6.98 (d, 1H, J = 16 Hz), 6.17 (m, 1H), 4.47 (d, 2H). |
| Ia-50 | 3-$CF_3$ | H | 3-$CF_3$ | 4-(—CONH—) | pyridin-3-ylmethyl | HPLC-MS: logP = 2.23; mass (m/z): 575.97(M + H)+; 1H NMR (d$_6$-DMSO) 9.53 (d, 1H), 9.12 (t, 1H), 8.55 (d, 1H), 8.47 (dd, 1H), 8.05 (s, 1H), 8.02 (s, 1H), 7.95 (m, 2H), 7.80 (d, 1H), 7.75-7.60 (m, 4H), 7.38 (dd, 1H), 6.97 (d, 1H, J = 16 Hz), 6.17 (m, 1H), 4.47 (d, 2H). |
| Ia-51 | 3-$CF_3$ | H | 3-$CF_3$ | 4-(—CONH—) | 2,2-bismethoxy-ethyl | HPLC-MS: logP = 3.18; mass (m/z): 573.11 (M + H)+; 1H NMR (d$_6$-DMSO) 9.52 (d, 1H), 8.65 (t, 1H), 8.05 (s, 1H), 8.00 (s, 1H), 7.95 (m, 2H), 7.80 (d, 1H), 7.70 (t, 1H), 7.68 (d, 1H, J = 16 Hz), 7.53 (d, 1H), 6.96 (d, 1H, J = 16 Hz), 6.16 (m, 1H), 4.47 (t, 1H). |
| Ia-52 | 3-$CF_3$ | H | 3-$CF_3$ | 4-(—CONHCH$_2$—) | tetrahydrofuran-2-yl | HPLC-MS: logP = 3.27; mass (m/z): 568.98 (M + H)+ |
| Ia-53 | 3-$CF_3$ | H | 3-$CF_3$ | 4-(—CONH—) | pyridin-3-yl | HPLC-MS: logP = 2.76; mass (m/z): 561.99(M + H)+ |
| Ia-54 | 3-$CF_3$ | H | 3-$CF_3$ | 4-(—CONH—) | pyridin-2-yl | HPLC-MS: logP = 3.58; mass (m/z): 561.99(M + H)+; 1H NMR (d3-CD3CN) 9.15 (s, 1H, br), 8.31 (d, 1H), 8.20 (d, 1H), 7.98 (s, 1H), 7.90-7.75 (m, 5H), 7.65 (m, 2H), 7.15 (dd, 1H), 6.82 (d, 1H, J = 16 Hz), 6.02 (m, 1H). |
| Ia-55 | 3-$CF_3$ | H | 3-$CF_3$ | 4-(—CONH—) | 2-methoxypropan-2-yl | HPLC-MS: logP = 3.37; mass (m/z): 557.01 (M + H)+; 1H NMR (d$_6$-DMSO) 9.51 (d, 1H), 8.41 (t, 1H), 8.05 (s, 1H), 7.99 (s, 1H), 7.94 (m, 2H), 7.80 (d, 1H), 7.72 (t, 1H), 7.65 (d, 1H, J = 16 Hz), 7.52 (d, 1H), 6.96 (d, 1H, J = 16 Hz), 6.17 (m, 1H), 4.11 (m, 1H), 3.40-3.30 (m, 5H), 1.10 (d, 3H). |
| Ia-56 | 3-$CF_3$ | H | 3-$CF_3$ | 4-(—CONH—) | 1-cyclopropylethyl | HPLC-MS: logP = 3.77; mass (m/z): 553.04(M + H)+; 1H NMR (d$_6$-DMSO) 9.51 (d, 1H), 8.45 (d, 1H), 8.05 (s, 1H), 8.00 (s, 1H), 7.95 (m, 2H), 7.80 (d, 1H), 7.70 (t, 1H), 7.68 (d, 1H, J = 16 Hz), 7.53 (d, 1H), 6.96 (d, 1H, J = 16 Hz), 6.17 (m, 1H), 3.46 (m, 1H), 1.18 (d, 3H), 0.90 (m, 1H), 0.50-0.20 (m, 4H). |
| Ia-57 | 3-$CF_3$ | H | 3-$CF_3$ | 4-(—CONH—) | 2,2-difluoroethyl | HPLC-MS: logP = 3.48; mass (m/z): 549.1 (M + H) |
| Ia-58 | 3-$CF_3$ | H | 3-$CF_3$ | 4-(—CONH—) | 2-methoxyethyl | HPLC-MS: logP = 3.12; mass (m/z): 542.99(M + H)+; 1H NMR (d$_6$-DMSO) 9.52 (d, 1H), 8.59 (t, 1H), 8.05 (s, 1H), 7.99 (s, |

TABLE 1-continued

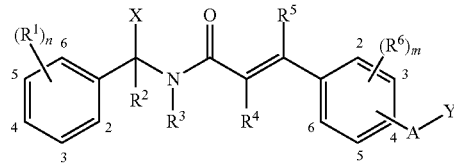

(Ia)

where $R^2$, $R^4$ and $R^5$ are each H, X is $CF_3$ and $(R^1)_n$, $R^3$, $(R^1)_m$, A and Y are each as defined in Table 1. The numbers 2 to 6 represent the positions on the aromatic rings.

| No. | $(R^1)_n$ | R3 | $(R^6)_n$ | A | Y | HPLC-MS[a]; $^1$H NMR (δ in ppm)[b] |
|---|---|---|---|---|---|---|
| | | | | | | 1H), 7.94 (m, 2H), 7.80 (d, 1H), 7.71 (t, 1H), 7.63 (d, 1H, J = 16 Hz), 7.54 (d, 1H), 6.96 (d, 1H, J = 16 Hz), 6.16 (m, 1H), 3.45-3.30 (m, 7H). |
| Ia-59 | 3-$CF_3$ | H | 3-$CF_3$ | 4-(—CONH—) | oxetan-3-yl | HPLC MS: logP = 2.89; mass (m/z): 540.98 (M + H)+. |
| Ia-60 | 3-$CF_3$ | H | 3-$CF_3$ | 4-(—CON($CH_3$)—) | cyclopropyl | HPLC-MS: logP = 3.62; mass (m/z): 538.98 (M + H)+; 1H NMR ($d_6$-DMSO) 9.51 (d, 1H), 8.05 (s, 1H), 8.02 (s, 1H), 7.94 (m, 2H), 7.80 (d, 1H), 7.71 (t, 1H), 7.65 (m, 2H), 6.97 (d, 1H, J = 16 Hz), 6.16 (m, 1H), 3.00 (s, 3H), 2.65 (m, 1H), 0.80-0.70 (m, 2H), 0.50 (m, 2H). |
| Ia-61 | 3-$CF_3$ | H | 3-$CF_3$ | 4-(—CONH—) | cyclobutyl | HPLC-MS: logP = 3.58; mass (m/z): 538.99(M + H)+; 1H NMR ($d_6$-DMSO) 9.50 (d, 1H), 8.72 (d, 1H), 8.02 (s, 1H), 8.00-7.85 (m, 3H), 7.80 (d, 1H), 7.70 (t, 1H), 7.68 (d, 1H, J = 16 Hz), 7.56 (d, 1H), 6.96 (d, 1H, J = 16 Hz), 6.17 (m, 1H), 4.34 (m, 1H), 2.23 (m, 2H), 2.00 (m, 2H), 1.68 (m, 6H). |
| Ia-62 | 3-$CF_3$ | H | 3-$CF_3$ | 4-(—CONH—) | isopropyl | HPLC-MS: logP = 3.41; mass (m/z): 526.99(M + H)+; 1H NMR ($d_6$-DMSO) 9.51 (d, 1H), 8.37 (d, 1H), 8.05 (s, 1H), 7.99 (s, 1H), 7.95 (m, 2H), 7.80 (d, 1H), 7.70 (t, 1H), 7.68 (d, 1H, J = 16 Hz), 7.53 (d, 1H), 6.96 (d, 1H, J = 16 Hz), 6.16 (m, 1H), 4.02 (m, 1H), 1.13 (d, 6H). |
| Ia-63 | 3-$CF_3$ | H | 3-$CF_3$ | 4-(—CONH—) | prop-2-yn-1-yl | HPLC-MS: logP = 3.36; mass (m/z): 523.1 (M + H)+; |
| Ia-64 | 3-$CF_3$ | H | 3-$CF_3$ | 4-(—CONH—) | ethyl | HPLC-MS: logP = 3.18; mass (m/z): 512.97(M + H)+; |
| Ia-65 | 3-$CF_3$ | H | 3-$CF_3$ | 4-(—CONH—) | 2-fluorocyclopropyl | HPLC-MS: logP = 3.33; mass (m/z): 543.10(M + H)+; |
| Ia-66 | 3-$CF_3$ | H | 3-$CF_3$ | 4-(—CONH—) | 2-chloropyridin-4-ylmethyl | HPLC-MS: logP = 3.41; mass (m/z): 609.95 (M + H)+; 1H NMR ($d_6$-DMSO) 9.53 (d, 1H), 9.20 (t, 1H), 8.38 (d, 1H), 8.05 (s, 2H), 7.96 (m, 2H), 7.81 (d, 1H), 7.70 (m, 3H), 7.44 (s, 1H), 7.37 (d, 1H), 6.98 (d, 1H, J = 16 Hz), 6.16 (m, 1H), 4.50 (d, 2H). |
| Ia-67 | 3-$CF_3$ | H | 3-$CF_3$ | 4-(—CON(cyclo-propyl)-) | tetrahydro-2H-pyran-4-yl | HPLC-MS: logP = 3.77; mass (m/z): 609.05 (M + H)+; |
| Ia-68 | 3-$CF_3$ | H | 3-$CF_3$ | 4-(—CONH—) | 1-ethoxycyclopropyl | HPLC-MS: logP = 3.52; mass (m/z): 569.04(M + H)+; 1H NMR ($d_6$-DMSO) 9.52 (d, 1H), 9.37 (s, 1H), 8.05 (s, 1H), 8.00 (s, 1H), 7.93 (m, 2H), 7.80 (d, 1H), 7.72 (t, 1H), 7.65 (d, 1H, J = 16 Hz), 7.56 (d, 1H), 6.96 (d, 1H, J = 16 Hz), 6.16 (m, 1H), 3.60 (q, 2H), 1.10 (t, 3H), 1.08 (m, 2H), 0.86 (m, 2H). |
| Ia-69 | 3-$CF_3$ | H | 3-$CF_3$ | 4-(—CONH—) | tetrahydro-2H-pyran-4-yl | HPLC-MS: logP = 3.12; mass (m/z): 569.04(M + H)+; 1H NMR ($d_6$-DMSO) 9.51 (d, 1H), 8.51 (d, 1H), 8.05 (s, 1H), 8.00 (s, |

TABLE 1-continued (Ia)

where R², R⁴ and R⁵ are each H, X is CF₃ and (R¹)ₙ, R³, (R¹)ₘ, A and Y are each as defined in Table 1. The numbers 2 to 6 represent the positions on the aromatic rings.

| No. | (R¹)ₙ | R3 | (R⁶)ₙ | A | Y | HPLC-MS[a]; ¹H NMR (δ in ppm)[b] |
|---|---|---|---|---|---|---|
| | | | | | | 1H), 7.94 (m, 2H), 7.81 (d, 1H), 7.71 (t, 1H), 7.65 (d, 1H, J = 16 Hz), 7.55 (d, 1H), 6.96 (d, 1H, J = 16 Hz), 6.17 (m, 1H), 3.96 (m, 1H), 3.90 (m, 2H), 3.50 (m, 2H), 1.76 (m, 2H), 1.50 (m, 2H) |
| Ia-70 | 3-CF₃ | H | 3-CF₃ | 4-(—CONH—) | 1-(pyridin-2-yl)-cyclopropyl | HPLC-MS: logP = 3.23; mass (m/z): 602.06(M + H)+; 1H NMR (d₆-DMSO) 9.53 (d, 1H), 9.32 (s, 1H), 8.45 (d, 1H), 8.05 (m, 2H), 8.00-7.90 (m, 3H), 7.80-7.65 (m, 4H), 7.51 (d, 1H), 6.99 (d, 1H, J = 16 Hz), 6.17 (m, 1H), 1.55 (m, 2H), 1.23 (m, 2H). |
| Ia-71 | 3-CF₃ | H | 3-CF₃ | 4-(—CONH—) | 2-phenylcyclo-propyl | HPLC-MS: logP = 4.22; mass (m/z): 601.1 (M + H)+; |
| Ia-72 | 3-CF₃ | H | 3-CF₃ | 4-(—CONH—) | 6-chloropyridin-3-yl | HPLC-MS: logP = 3.73; mass (m/z): 595.95 (M + H)+; 1H NMR (d₆-DMSO) 10.99 (s, 1H), 9.58 (d, 1H), 8.68 (d, 1H), 8.17 (dd, 1H), 8.06 (s, 1H), 8.00 (m, 2H), 7.95 (m, 1H), 7.80 (m, 2H), 7.72 (m, 3H), 7.55 (d, 1H), 7.03 (d, 1H, J = 16 Hz), 6.15 (m, 1H). |
| Ia-73 | 3-CF₃ | H | 3-CF₃ | 4-(—CONH—) | 5-fluoropyridin-2-yl | HPLC-MS: logP = 3.31; mass (m/z): 593.99(M + H)+; 1H NMR (d₆-DMSO) 9.52 (d, 1H), 9.04 (t, 1H), 8.40 (d, 1H), 8.05 (s, 1H), 8.00 (s, 1H), 7.94 (m, 2H), 7.81 (d, 1H), 7.70-7.63 (m, 3H), 7.43 (m, 1H), 6.98 (d, 1H, J = 16 Hz), 6.16 (m, 1H), 4.61 (d, 2H). |
| Ia-74 | 3-CF₃ | H | 3-CF₃ | 4-(—CONH—) | 2-fluorophenyl-methyl | HPLC-MS: logP = 3.77; mass (m/z): 593(M + H)+; 1H NMR (d₆-DMSO) 9.53 (d, 1H), 9.07 (t, 1H), 8.05 (s, 1H), 8.01 (s, 1H), 7.95 (m, 2H), 7.81 (d, 1H), 7.73-7.60 (m, 4H), 7.42 (t, 1H), 7.34 (m, 1H), 7.18 (m, 1H), 6.97 (d, 1H, J = 16 Hz), 6.16 (m, 1H), 4.48 (d, 2H). |
| Ia-75 | 3-CF₃ | H | 3-CF₃ | 4-(—CONH—) | 1-fluoropropan-2-yl | See Synthesis Example 2, Stage 3 |
| Ia-76 | 3-CF₃ | H | 3-CF₃ | 4-(—CONH—) | 1-methyl-1H-imidazol-4-yl | HPLC-MS: logP = 1.72; mass (m/z): 579(M + H)+; 1H NMR (d₆-DMSO) 9.52 (d, 1H), 8.82 (t, 1H), 8.05 (s, 1H), 7.99 (s, 1H), 7.93 (m, 2H), 7.81 (d, 1H), 7.71 (t, 1H), 7.65 (d, 1H, J = 16 Hz), 7.57 (d, 1H), 7.52 (s, 1H), 6.98 (s, 1H), 6.96 (d, 1H, J = 16 Hz), 6.16 (m, 1H), 4.28 (d, 2H), 3.62 (s, 3H). |
| Ia-77 | 3-CF₃ | H | 3-CF₃ | 4-(—CONH—) | 2-(trifluoromethyl)-cyclopentyl | HPLC-MS: logP = 3.93; mass (m/z): 620.98 (M + H)+; 1H NMR (d₆-DMSO) 9.53 (d, 1H), 8.65 (d, 1H), 8.05 (s, 1H), 8.00 (s, 1H), 7.96 (m, 2H), 7.81 (d, 1H), 7.71 (t, 1H), 7.65 (d, 1H, J = 16 Hz), 7.43 (d, 1H), 6.95 (d, 1H, J = 16 Hz), 6.17 (m, 1H), 4.64 (m, 1H), 2.95 (m, 1H), 1.93 (m, 2H), 1.83 (m, 2H), 1.00 (m, 2H) |

TABLE 1-continued (Ia)

where $R^2$, $R^4$ and $R^5$ are each H, X is $CF_3$ and $(R^1)_n$, $R^3$, $(R^1)_m$, A and Y are each as defined in Table 1. The numbers 2 to 6 represent the positions on the aromatic rings.

| No. | $(R^1)_n$ | R3 | $(R^6)_n$ | A | Y | HPLC-MS[a]; $^1$H NMR (δ in ppm)[b] |
|---|---|---|---|---|---|---|
| Ia-78 | 3-$CF_3$ | H | 3-$CF_3$ | 4-(—CONH—) | cyclopropylmethyl | HPLC-MS: logP = 3.52; mass (m/z): 539(M + H)+ |
| Ia-79 | 3-$CF_3$ | H | 3-$CF_3$ | 4-(—CONH—) | 2,2-difluoropropyl | HPLC-MS: logP = 3.65; mass (m/z): 563.1 (M + H)+; |
| Ia-80 | 3-$CF_3$ | H | 3-$CF_3$ | 4-(—CONH—) | (6-chloropyridin-3-pyridin-3-yl)methyl | HPLC-MS: logP = 3.65; mass (m/z): 610(M + H)+; |
| Ia-81 | 3-$CF_3$ 4-$COOCH_3$ | H | 3-$CF_3$ | 4-(—CONH—) | cyclopropyl | HPLC-MS: logP = 3.09; mass (m/z): 583.09(M + H)+ |
| Ia-82 | 3-Cl, 5-$CF_3$ | H | 3-$CF_3$ | 4-(—CONH—) | pyridin-2-yl | HPLC-MS: logP = 4.32; mass (m/z): 596.0(M + H)+ |
| Ia-83 | 3-$CF_3$ | H | 3-$CH_3$ | 4-(—CONH—) | oxetan-3-yl | HPLC-MS: logP = 2.69 mass (m/z): 487.1 (M + H)+; |
| Ia-84 | 3-$CF_3$ | H | 3-$CF_3$ | 4-(—CONH—) | pyridin-4-yl | HPLC-MS: logP = 1.99 mass (m/z): 562.2(M + H)+; |
| Ia-85 | 3-$CF_3$ | H | 3-$CH_3$ | 4-(—CONH—) | 1-ethoxycyclopropyl | HPLC-MS: logP = 3.27 mass (m/z): 515.2(M + H)+; |
| Ia-86 | 3-$CF_3$ | H | 3-$CH_3$ | 4-(—CONH—) | tetrahydro-2H-pyran-4-yl | HPLC-MS: logP = 2.89 mass (m/z): 515.2(M + H)+; |
| Ia-87 | 3-$CF_3$ | H | 3-$CH_3$ | 4-(—CONH—) | 5-fluoropyridin-2-ylmethyl | HPLC-MS: logP = 3.13 mass (m/z): 540.2(M + H)+; |
| Ia-88 | 3-$CF_3$ | H | 3-$CH_3$ | 4-(—CONH—) | pyridin-4-yl | HPLC-MS: logP = 1.87 mass (m/z): 508.2(M + H)+; |
| Ia-89 | 3-$CF_3$ | H | 3-Br | 4-(—CON(CH3)—) | pyridin-2-yl | HPLC-MS: logP = 3.47 mass (m/z): 586.4(M + H)+; |
| Ia-90 | 3-$CF_3$ | H | 3-Br | 4-(—CONH—) | 5-fluoropyridin-2-ylmethyl | HPLC-MS: logP = 3.23 mass (m/z): 606.1 (M + H)+; |
| Ia-91 | 3-$CF_3$ | H | 3-Br | 4-(—CONH—) | pyridin-4-yl | HPLC-MS: logP = 1.96 mass (m/z): 574.1 (M + H)+; |
| Ia-92 | 3-$CF_3$ | H | 3-Br | 4-(—CONH—) | pyridin-2-yl | HPLC-MS: logP = 3.47 mass (m/z): 574.1 (M + H)+; |
| Ia-93 | 3-$CF_3$ | H | 3-Br | 4-(—CONH—) | 1-cyclopropylethyl | HPLC-MS: logP = 3.42 mass (m/z): 565.1 (M + H)+; |
| Ia-94 | 3-$CF_3$ | H | 3-Br | 4-(—CONH—) | oxetan-3-yl | HPLC-MS: logP = 2.8 mass (m/z): 553.1 (M + H)+; |
| Ia-95 | 3-$CF_3$ | H | 3-Br | 4-(—CON(CH3)—) | cyclopropyl | HPLC-MS: logP = 3.58 mass (m/z): 551.1 (M + H)+; |
| Ia-96 | 3-$CF_3$ | H | 3-Cl | 4-(—CONH—) | 1-ethoxycyclopropyl | HPLC-MS: logP = 3.47 mass (m/z): 535.2(M + H)+; |
| Ia-97 | 3-$CF_3$ | H | 3-Cl | 4-(—CONH—) | tetrahydro-2H-pyran-4-yl | HPLC-MS: logP = 2.99 mass (m/z): 535.2(M + H)+; |
| Ia-98 | 3-$CF_3$ | H | 3-Cl | 4-(—CONH—) | pyridin-2-yl | HPLC-MS: logP = 3.47 mass (m/z): 528.2(M + H)+; |
| Ia-99 | 3-$CF_3$ | H | 3-$CH_3$ | 4-(—CONH—) | 4-fluorophenyl | HPLC-MS: logP = 3.78 mass (m/z): 525.1 (M + H)+; |
| Ia-100 | 3-$CF_3$ | H | 3-$CH_3$ | 4-(—CONH—) | 2,2-difluoroethyl | HPLC-MS: logP = 3.13 mass (m/z): 495.1 (M + H)+; |
| Ia-101 | 3-$CF_3$ | H | 3-$CH_3$ | 4-(—CONH—) | cyclobutyl | HPLC-MS: logP = 3.53 mass (m/z): 485.1 (M + H)+; |
| Ia-102 | 3-$CF_3$ | H | 3-$CH_3$ | 4-(—CONH—) | isopropyl | HPLC-MS: logP = 3.27 mass (m/z): 473.2(M + H)+; |
| Ia-103 | 3-$CF_3$ | H | 3-Br | 4-(—CONH—N($COOCH_3$)—) | methyl | HPLC-MS: logP = 2.89 mass (m/z): 584.0(M + H)+; |
| Ia-104 | 3-$CF_3$ | H | 3-Br | 4-(—CONH—) | 2,2-difluoroethyl | HPLC-MS: logP = 3.23 mass (m/z): 561.0(M + H)+; |
| Ia-105 | 3-$CF_3$ | H | 3-Br | 4-(—CONH—) | 1-propyn-2-yl | HPLC-MS: logP = 3.09 mass (m/z): 535.0(M + H)+; |
| Ia-106 | 3-$CF_3$ | H | 3-Cl | 4-(—CONH—) | 2-oxopiperidin-3-yl | HPLC-MS: logP = 2.61 mass (m/z): 548.1 (M + H)+; |
| Ia-107 | 3-$CF_3$ | H | 3-Cl | 4-(—$CONHCH_2CONH$—) | 2,2,2-trifluoroethyl | HPLC-MS: logP = 2.99 mass (m/z): 590.1 (M + H)+; |
| Ia-108 | 3-$CF_3$ | H | 3-Cl | 4-(—$CONHCH_2CONH$—) | methyl | HPLC-MS: logP = 2.72 mass (m/z): 536.1 (M + H)+; |
| Ia-109 | 3-$CF_3$ | H | 3-Cl | 4-(—CONH—N($COOCH_3$)—) | H | HPLC-MS: logP = 2.72 mass (m/z): 524.1 (M + H)+; |

TABLE 1-continued (Ia)

where $R^2$, $R^4$ and $R^5$ are each H, X is $CF_3$ and $(R^1)_n$, $R^3$, $(R^1)_m$, A and Y are each as defined in Table 1. The numbers 2 to 6 represent the positions on the aromatic rings.

| No. | $(R^1)_n$ | R3 | $(R^6)_n$ | A | Y | HPLC-MS[a]; $^1$H NMR (δ in ppm)[b] |
|---|---|---|---|---|---|---|
| Ia-110 | 3-$CF_3$ | H | 3-Cl | 4-(—CONH—) | 5-fluoropyridin-2-ylmethyl | HPLC-MS: logP = 3.42 mass (m/z): 546.1 (M + H)+; |
| Ia-111 | 3-$CF_3$ | H | 3-Cl | 4-(—CONH—) | 2,2-difluoropropyl | HPLC-MS: logP = 3.37 mass (m/z): 529.1 (M + H)+; |
| Ia-112 | 3-$CF_3$ | H | 3-Cl | 4-(—CONH—) | 1-fluoropropan-2-yl | HPLC-MS: logP = 3.25 mass (m/z): 511.1 (M + H)+; |
| Ia-113 | 3-$CF_3$ | H | 3-Cl | 4-(—CONH—) | pyridin-4-yl | HPLC-MS: logP = 1.92 mass (m/z): 528.2(M + H)+; |
| Ia-114 | 3-$CF_3$ | H | 3-Cl | 4-(—CONH—) | 1-cyclopropylethyl | HPLC-MS: logP = 3.68 mass (m/z): 519.2(M + H)+; |
| Ia-115 | 3-$CF_3$ | H | 3-$CH_3$ | 4-(—CONH—) | 2-cyclopropylethyl | HPLC-MS: logP = 3.61 mass (m/z): 499.2(M + H)+; |
| Ia-116 | 3-$CF_3$ | H | 3-$CH_3$ | 4-(—CON(CH3)—) | cyclopropyl | HPLC-MS: logP = 3.37 mass (m/z): 485.2(M + H)+; |
| Ia-117 | 3-$CF_3$ | H | H | 4-(—$SO_2$NH—) | cyclopropyl | HPLC-MS: logP = 3.33; mass (m/z): 493.1 (M + H)+; 1H NMR (CD3CN) 0.46 ? 0.56 (m, 4H), 2.10 ? 2.18 (m, 1H), 5.93 ? 6.05 (m, 2H), 6.80 (d, 1H), 7.64 7.69 (m, 2H), 7.75 ? 7.81 (m, 5H), 7.87 ? 7.89 (m, 3H). |
| Ia-118 | 3-$CF_3$ | H | 3-Cl | 4-(—CONH—) | cyclopropyl | HPLC-MS: logP = 3.24; mass (m/z): 491.1 (M + H)+; 1H NMR (CD3CN) 0.56 ? 0.59 (m, 2H), 0.75 ? 0.78 (m, 2H), 2.81 ? 2.85 (m, 1H), 5.99 (quint, 1H), 6.71 (d, 1H), 6.94 (s, 1H), 7.46 (d, 1H), 7.52-7.67 (m, 4H), 7.76-7.81 (m, 3H), 7.87 (s, 1H). |
| Ia-119 | 3-$CF_3$ | H | 3-$CF_3$ | 4-(—CONH—) | 1,3-pyrimidin-2-yl | HPLC-MS: logP = 3.11; mass (m/z): 563.1 (M + H)+; 1H NMR ($d_6$-DMSO) 6.17 (m, 1H), 6.98 (d, 1H), 7.20 (m, 1H), 7.60 (m, 1H), 7.70 (m, 1H), 7.82 (d, 1H), 7.93 (t, 1H), 8.01 (d, 1H), 8.61 (d, 1H), 8.42 (s, 1H), 9.55 (d, 1H), 11.3 (s, 1H). |
| Ia-120 | 3-$CF_3$ | H | 3-$CF_3$ | 4-(—CONH—) | 6-chloropyridin-2-yl | HPLC-MS: logP = 4.33; mass (m/z): 594(M + H)+; 1H NMR (CD3CN) 6.01 (m, 1H), 6.82 (d, 1H), 7.18 (d, 1H), 7.65-7.85 (m, 6H), 7.89 (d, 1H), 7.92 (s, 1H), 8.18 (d, 1H), 9.20 (d, 1H) |
| Ia-121 | 3-$CF_3$ | H | 3-$CF_3$ | 4-(—CONH—) | 4-chloropyridin-2-yl | HPLC-MS: logP = 4.3; mass (m/z): 594(M + H)+; 1H NMR ($d_6$-DMSO) 6.17 (m, 1H), 6.97 (d, 1H), 7.18 (d, 1H), 7.67-7.85 (m, 6H), 7.93 (m, 1H), 8.04 (s, 1H), 8.18 (d, 1H), 8.42 (s, 1H), 9.60 (d, 1H), 11.3 (s, 1H). |
| Ia-122 | 3-$CF_3$ | H | 3-$CF_3$ | 4-(—CONH—) | 5-chloropyridin-2-yl | HPLC-MS: logP = 4.3; mass (m/z): 594(M + H)+; 1H NMR ($d_6$-DMSO) 6.18 (m, 1H), 6.99 (d, 1H), 7.18 (d, 1H), 7.68 -7.86 (m, 6H), 7.96 (m, 1H), 8.06 (s, 1H), 8.19 (d, 1H), 8.41 (s, 1H), 9.59 (d, 1H), 11.4 (s, 1H). |
| Ia-123 | 3-$CF_3$ | H | 3-$CF_3$ | 5-cyclopropyl-(1,2,4-oxadiazol)-3-yl | | See Synthesis Example 9, Stage 2 |
| Ia-124 | 3-$CF_3$ | H | 3-$CF_3$ | 4-(—CONH—) | 1-methylpyrazol-3-yl | HPLC-MS: logP = 3.28; mass (m/z): 565.1 (M + H)+; 1H NMR ($d_6$-DMSO) 3.76 (s, 3H), 6.17 (m, 1H), 6.53 (s, 1H), 7.00 (d, 1H), 7.60 (s, 1H) ? 7.62 -7.69 (m, 3H), 7.81 (m, 2H), 7.95 (d, |

TABLE 1-continued

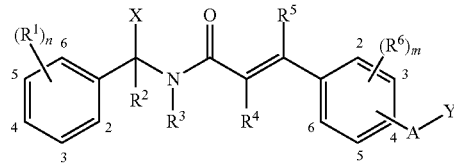

(Ia)

where $R^2$, $R^4$ and $R^5$ are each H, X is $CF_3$ and $(R^1)_n$, $R^3$, $(R^1)_m$, A and Y are each as defined in Table 1. The numbers 2 to 6 represent the positions on the aromatic rings.

| No. | $(R^1)_n$ | R3 | $(R^6)_n$ | A | Y | HPLC-MS[a]; $^1$H NMR (δ in ppm)[b] |
|---|---|---|---|---|---|---|
| Ia-125 | 3-$CF_3$ | H | 3-$CF_3$ | 4-(—CONH—) | 1,3-pyrimidin-4-yl | 1H), 8.04 (d, 1H), 8.18 (s, 1H), 9.58 (d, 1H), 11.00 (s, 1H). HPLC-MS: logP = 3.35; mass (m/z): 563.2(M + H)+; 1H NMR (d₆-DMSO) 6.18 (m, 1H), 6.99 (d, 1H), 7.54 -7.80 (m, 5H), 7.93 (m, 1H), 8.06 (m, 1H), 8.19 (m, 1H), 8.74 (d, 1H), 8.93 (s, 1H), 9.58 (d, 1H), 11.6 (s, 1H). |
| Ia-126 | 3-$CF_3$ | H | 3-$CF_3$ | 4-(—CONH—) | (4-chloropyridin-2-yl)methyl | HPLC-MS: logP = 3.68; mass (m/z): 610.1 (M + H)+; 1H NMR (d₆-DMSO) 4,55 (s, 2H), 6.17 (m, 1H), 6.98 (d, 1H), 7.49 (s, 1H), 7.65-7.74 (m, 3H), 7.82 (m, 2H), 8.01 (s, 1H), 8.12 (m, 1H), 8.52 (s, 1H), 9.20 (m, 1H), 9.58 (m, 1H). |
| Ia-127 | 3-$CF_3$ | H | 3-$CF_3$ | 4-(—CONH—) | (1,3-pyrimidin-2-yl)methyl | HPLC-MS: logP = 3.05; mass (m/z): 577.1 (M + H)+; 1H NMR (d₆-DMSO) 4.63 (s, 2H), 6.19 (m, 1H), 6.98 (d, 1H), 7.43 (s, 1H), 7.69 (d, 2H), 7.72 (m, 2H), 7.82 (m, 2H), 7.98 (m, 1H), 8.04 (s, 1H), 8.07 (s, 1H), 8.82 (s, 1H), 9.15 (m, 1H), 9.60 (m, 1H). |
| Ia-128 | 3-$CF_3$ | H | 3-$CF_3$ | 4-(—CONH—) | 1-(pyridin-2 -yl)-ethyl | HPLC-MS: logP = 3.22; mass (m/z): 590.2(M + H)+; 1H NMR (d₆-DMSO) 1.47 (d, 3H), 5.14 (s, 2H), 6.17 (m, 1H), 6.97 (d, 1H), 7.28 (m, 1H), 7.43 (d, 2H), 7.65 (m, 2H), 7.72 (m, 1H), 7.80 (m, 2H), 7.96 (m, 1H), 8.05 (d, 1H), 8.53 (d, 1H), 9.01 (m, 1H), 9.55 (m, 1H). |
| Ia-129 | 3-$CF_3$ | H | 3-$CF_3$ | 4-(—CONH—) | cyanomethyl | HPLC-MS: logP = 3.19; mass (m/z): 524.1 (M + H)+; 1H NMR (d₆-DMSO) 4.33 (d, 2H), 6.17 (m, 1H), 7.00 (d, 1H), 7.63 (m, 1H), 7.73 (d, 1H), 7.83 (m, 1H), 7.72 (m, 1H), 7.96 (m, 1H), 8.05 (s, 1H), 8.53 (d, 1H), 9.30(m, 1H), 9.56 (m, 1H). |
| Ia-130 | 3-$CF_3$ | H | 3-$CF_3$ | 4-(—CONH—) | thietan-3-yl | HPLC-MS: logP = 3.62; mass (m/z): 557.1 (M + H)+; 1H NMR (d₆-DMSO) 3.17 (m, 2H), 3.44 (m, 2H), 5.14 (m, 1H), 6.18 (m, 1H), 7.61 (d, 1H), 7.68 (d, 1H), 7.72 (m, 1H), 7.72 (m, 1H), 7.83 (m, 1H), 7.95 (m, 1H), 8.05 (d, 1H), 9.21 (m, 1H), 9.56 (m, 1H), 9.59 (m, 1H). |
| Ia-131 | 3-$CF_3$ | H | 3-$CF_3$ | 4-(—CONHNMe—) | methyl | HPLC-MS: logP = 3.05; mass (m/z): 528.1 (M + H)+; 1H NMR (d₆-DMSO) 2.55 (s, 6H), 6.18 (m, 1H), 6.96 (m, 1H), 7.54 (m, 1H), 7.63 -7.73 (m, 2H), 7.90-8.00 (m, 2H), 8.05 (s, 1H), 9.15 (s, 1H), 9.40 (s, 1H), 9.55 (m, 1H). |
| Ia-132 | 3-$CF_3$ | H | 3-$CF_3$ | 4-(—CONH—) | 1-(methoxy-carbonyl)ethyl | HPLC-MS: logP = 3.47; mass (m/z): 571.1 (M + H)+; 1H NMR (d₆-DMSO) 1.35 (s, 3H), 3.67 (s, 3H), 3.44 (m, 2H), 4.47 (m, 1H), 6.17 (m, 1H), 6.97 (d, 1H), |

TABLE 1-continued

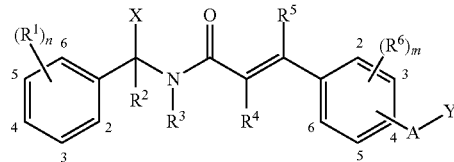

(Ia)

where $R^2$, $R^4$ and $R^5$ are each H, X is $CF_3$ and $(R^1)_n$, $R^3$, $(R^1)_m$, A and Y are each as defined in Table 1. The numbers 2 to 6 represent the positions on the aromatic rings.

| No. | $(R^1)_n$ | R3 | $(R^6)_n$ | A | Y | HPLC-MS[a]; $^1$H NMR (δ in ppm)[b] |
|---|---|---|---|---|---|---|
| Ia-133 | 3-$CF_3$ | H | 3-Br | 4-(—CONH—) | (1,3-pyrimidin-2-yl)methyl | 7.59 (d, 1H), 7.65 (s, 1H), 7.72 (m, 2H), 7.96 (m, 2H), 8.02 (s, 1H), 8.05 (s, 1H), 8.99(d, 1H), 9.56 (d, 1H). HPLC-MS: logP = 2.93; mass (m/z): 589(M + H)+; 1H NMR ($d_6$-DMSO) 4.64 (dd, 2H), 6.16 (m, 1H), 6.92 (d, 1H), 7.42 (m, 2H), 7.51 (m, 2H) 7.67 (m, 2H), 7.87 (m, 2H), 8.80(m, 1H), 9.01, (m, 1H), 9.56 (d, 1H). |
| Ia-134 | 3-$CF_3$ | H | 3-Br | 4-(—CONH—) | 1-(pyridin-2-yl)-ethyl | HPLC-MS: logP = 3.11; mass (m/z): 600.1 (M + H)+; 1H NMR ($d_6$-DMSO) 1.47 (d, 3H), 5.13 (m, 1H), 6.16 (m, 1H), 6.92 (d, 1H), 7.42 (m, 2H), 7.51 (m, 2H) 7.67 (m, 2H), 7.87 (m, 2H), 8.06 (s, 1H), 8.53 (m, 1H), 8.80(m, 1H), 9.01, (m, 1H), 9.56 (d, 1H). |
| Ia-135 | 3-$CF_3$ | H | 3-$CF_3$ | 4-(1H-pyrazol-1-yl) | | HPLC-MS: logP = 3.95; mass (m/z): 508.1 (M + H)+; 1H NMR ($d_6$-DMSO) 6.18 (m, 1H), 6.56 (m, 1H), 6.98 (d, 1H), 7.65-7.85 (m, 4H), 7.95 (d, 1H), 8.07 (m, 2H), 8.16 (s, 1H), 8.80(m, 1H), 9.58 (d, 1H). |
| Ia-136 | 3-$CF_3$ | H | 3-$CF_3$ | 4-(—CONH—) | 2-oxotetrahydro-furan-3-yl | HPLC-MS: logP = ; mass (m/z): (M + H)+; 1H NMR ($d_6$-DMSO) 2.28 (m, 2H), 4.26 (m, 2H), 4.40 (m, 2H), 4.75 (m, 1H), 6.18 (m, 1H), 6.98 (d, 1H), 7.55-7.85 (m, 4H), 7.70 (m, 1H), 8.04 (m, 2H), 9.06(m, 1H), 9.58 (d, 1H). |
| Ia-137 | 3-$CF_3$ | H | 3-$CF_3$ | 4-(—CONH—) | 5-chloro-1,3-pyrimidin-2-yl | HPLC-MS: logP = 3.62; mass (m/z): 597(M + H)+; 1H NMR ($d_6$-DMSO) 6.17 (m, 1H), 7.00 (d, 1H), 7.65-7.75 (m, 2H), 7.95 (d, 1H), 7.81 (d, 2H), 7.95 (d, 2H), 8.05 (s, 1H), 8.74(s, 1H), 9.55 (d, 1H), 11.50 (s, 1H) |
| Ia-138 | 3-$CF_3$ | H | 3-$CF_3$ | 4-(—CONH—) | but-3-yn-2-yl | HPLC-MS: logP = 3.58; mass (m/z): 537.1 (M + H)+; 1H NMR ($d_6$-DMSO) 1.37 (d, 3H), 3.19 (s, 1H), 4.77 (m, 1H), 6.18 (m, 1H), 6.96 (d, 1H), 7.55-7.75 (m, 4H), 7.80 (m, 1H), 7.93 (m, 1H), 8.04 (d, 2H), 9.01 (d, 1H), 9.55 (d, 1H). |
| Ia-139 | 3-$CF_3$ | H | 3-$CF_3$ | 4-(—CONH—) | 1-(pyrazol-1-yl)-propan-2-yl | HPLC-MS: logP = 3.42; mass (m/z): 593.2(M + H)+; 1H NMR ($d_6$-DMSO) 1.07 (d, 3H), 4.19 (m, 2H), 4.35 (m, 1H), 6.19 (m, 1H), 6.96 (d, 1H), 7.55-7.75 (m, 6H), 7.81 (m, 1H), 7.92 (m, 1H), 8.05 (d, 2H), 9.01 (d, 1H), 9.55 (d, 1H). |
| Ia-140 | 3-$CF_3$ | H | 3-$CF_3$ | 4-(—CONH—) | 1-cyanocyclo-propan-2-yl | HPLC-MS: logP = 3.37; mass (m/z): 550.1 (M + H)+; 1H NMR ($d_6$-DMSO) 1.23 (m, 2H), 1.57 (m, 2H), 4.19 (m, 2H), 4.35 (m, 1H), 6.19 (m, 1H), 6.98 (d, 1H), 7.60-7.80 (m, 5H), 7.95 (m, 1H), 8.05 (d, 2H), 9.01 (d, 1H), 9.55 (d, 1H). |

TABLE 1-continued (Ia)

where $R^2$, $R^4$ and $R^5$ are each H, X is $CF_3$ and $(R^1)_n$, $R^3$, $(R^1)_m$, A and Y are each as defined in Table 1. The numbers 2 to 6 represent the positions on the aromatic rings.

| No. | $(R^1)_n$ | R3 | $(R^6)_n$ | A | Y | HPLC-MS[a]; $^1$H NMR (δ in ppm)[b] |
|---|---|---|---|---|---|---|
| Ia-141 | 3-$CF_3$ | H | 3-$CF_3$ | 4-(—CONH—) | 1-cyanoethyl | HPLC-MS: logP = 3.39; mass (m/z): 538.1 (M + H)+; 1H NMR (d$_6$-DMSO) 1.49 (d, 2H), 4.93 (m, 1H), 6.16 (m, 1H), 6.98 (d, 1H), 7.60-7.85 (m, 5H), 7.96 (m, 1H), 8.09 (s, 1H), 9.01 (d, 1H), 9.35 (m, 1H), 9.55 (m, 1H). |
| Ia-142 | 3-$CF_3$ | H | 3-$CF_3$ | 4-(—CONH—) | H | HPLC-MS: logP = 2.89; mass (m/z): 485.1 (M + H)+; 1H NMR (d$_6$-DMSO) 6.16 (m, 1H), 6.98 (d, 1H), 7.55-7.75 (m, 5H), 7.82 (d, 1H), 7.80- 8.00 (m, 2H), 8.05 (s, 1H), 9.01 (d, 1H), 9.50 (m, 1H). |
| Ia-143 | 3-$CF_3$ | H | 3-$CF_3$ | 4-(—CONH—) | 1,3-difluoropropan-2-yl | HPLC-MS: logP = 3.48; mass (m/z): 563.1 (M + H)+; 1H NMR (d$_6$-DMSO) 4.03 (m, 1H), 4.47 (m, 2H), 4.61 (m, 2H), 6.17 (m, 1H), 6.97 (d, 1H), 7.60-7.75 (m, 5H), 7.82 (d, 1H), 7.95 (m, 1H), 8.05 (d, 1H), 8.92(d, 1H), 9.55 (m, 1H). |
| Ia-144 | 3-$CF_3$ | H | 3-$CF_3$ | 4-(—CONH—) | butan-2-yl | HPLC-MS: logP = 3.84; mass (m/z): 541.1 (M + H)+; 1H NMR (d$_6$-DMSO) 0.85 (m, 3H), 1.15 (d, 3H), 1.48 (m, 2H), 3.84 (m, 1H), 6.16 (m, 1H), 6.95 (d, 1H), 7.50-7.75 (m, 5H), 7.82 (d, 1H), 7.90- 8.10 (m, 2H), 8.35 (d, 1H), 9.55 (m, 1H). |
| Ia-145 | 3-$CF_3$ | H | 3-$CF_3$ | 4-(—CONH—) | 3-chloroprop-2-en-1-yl | HPLC-MS: logP = 3.69; mass (m/z): 559.1 (M + H)+; 1H NMR (d$_6$-DMSO) 3.87 (m, 1H), 5.95 (m, 1H), 1.48 (m, 2H), 3.84 (m, 1H), 6.16 (m, 1H), 6.43 (m, 1H), 6.95 (d, 1H), 7.60-7.85 (m, 5H), 7.95 (m, 1H), 8.05 (d, 2H), 8.75- 8.82 (m, 2H), 9.53 (d, 1H). |
| Ia-146 | 3-$CF_3$ | H | 3-$CF_3$ | 4-(—CONH—) | 2-methylbut-3-yn-2-yl | HPLC-MS: logP = 3.8; mass (m/z): 551.2(M + H)+; 1H NMR (d$_6$-DMSO) 1.56 (s, 6H), 2.51 (s, 1H), 6.17 (m, 1H), 6.98 (d, 1H), 7.60-7.75 (m, 3H), 7.83 (m, 1H), 7.94 (m, 2H), 8.09 (d, 1H), 8.65 (s, 1H), 9.01 (d, 1H), 9.55 (d, 1H). |
| Ia-147 | 3-$CF_3$ | H | 3-$CF_3$ | 4-(—CONH—) | methyl | HPLC-MS: logP = 3.09; mass (m/z): 499.1 (M + H)+; 1H NMR (d$_6$-DMSO) 2.75 (s, 3H), 6.17 (m, 1H), 6.96 (d, 1H), 7.55-7.85 (m, 4H), 7.83 (m, 1H), 7.95 (m, 1H), 8.05 (d, 1H), 8.41 (m, 1H), 9.01 (d, 1H), 9.50 (d, 1H). |
| Ia-148 | 3-$CF_3$ | H | 3-$CF_3$ | 4-(—CONH—) | 1-(cyclopropyl)-prop-2-yl | HPLC-MS: logP = 4.24; mass (m/z): 567.2(M + H)+; 1H NMR (d$_6$-DMSO) 0.45 (m, 4H), 0.76 (m, 1H), 1.15 (d, 3H), 1.23 (m, 1H), 1.45 (m, 1H), 4.20 (m, 1H), 6.17 (m, 1H), 6.95 (d, 1H), 7.55-7.85 (m, 4H), 7.83 (m, 1H), 7.95 (m, 1H), 8.05 (d, 1H), 8.35 (m, 1H), 9.50 (d, 1H). |

TABLE 1-continued

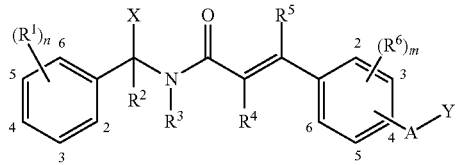

where $R^2$, $R^4$ and $R^5$ are each H, X is $CF_3$ and $(R^1)_n$, $R^3$, $(R^1)_m$, A and Y are each as defined in Table 1. The numbers 2 to 6 represent the positions on the aromatic rings.

| No. | $(R^1)_n$ | R3 | $(R^6)_n$ | A | Y | HPLC-MS[a]; $^1$H NMR (δ in ppm)[b] |
|---|---|---|---|---|---|---|
| Ia-149 | 3-$CF_3$ | H | 3-$CF_3$ | 4-(—CONH—O—) | propan-2-yl | HPLC-MS: logP = 3.48; mass (m/z): 543.1 (M + H)+; 1H NMR (d6 DMSO) 1.20 (d, 6H), 4.14 (m, 1H), 6.16 (m, 1H), 6.97 (d, 1H), 7.60-7.85 (m, 5H), 7.95 (m, 1H), 8.05 (d, 1H), 9.55 (d, 1H), 11.50 (s, 1H). |
| Ia-150 | 3-$CF_3$ | H | 3-Cl | 4-(—CONH—) | propan-2-yl | HPLC-MS: logP = 3.5; mass (m/z): 493.2(M + H)+; 1H NMR ($d_6$-DMSO) 1.14 (d, 6H), 4.03 (m, 1H), 6.15 (m, 1H), 6.89 (d, 1H), 7.40-7.85 (m, 5H), 7.95 (m, 1H), 8.05 (d, 1H), 8.31 (d, 1H), 9.55 (m, 1H). |
| Ia-151 | 3-$CF_3$ | H | 3-Cl | 4-(—CONH—) | prop-2-yn-1-yl | HPLC-MS: logP = 3.2; mass (m/z): 489.1 (M + H)+; 1H NMR ($d_6$-DMSO) 3.14 (s, 1H), 4.04 (m, 2H), 6.15 (m, 1H), 7.00 (d, 1H), 7.45-7.85 (m, 5H), 7.95 (m, 1H), 8.05 (d, 1H), 8.98 (m, 1H), 9.50 (d, 1H). |
| Ia-152 | 3-$CF_3$ | H | 3-Cl | 4-(—CONH—) | thietan-3-yl | HPLC-MS: logP = 3.51; mass (m/z): 523.1 (M + H)+; 1H NMR ($d_6$-DMSO) 3.43 (m, 4H), 5.16 (m, 1H), 6.15 (m, 1H), 6.90 (d, 1H), 7.45-7.85 (m, 5H), 7.95 (m, 1H), 8.05 (s, 1H), 9.10 (d, 1H), 9.50 (d, 1H). |
| Ia-153 | 3-$CF_3$ | H | 3-Cl | 4-(—CONH—) | 1,3-pyrimidin-2-ylmethyl | HPLC-MS: logP = 2.94; mass (m/z): 543.2(M + H)+; 1H NMR ($d_6$-DMSO) 4.63 (m,2H), 6.15 (m, 1H), 6.90 (d, 1H), 7.45-7.85 (m, 5H), 7.95 (m, 1H), 8.05 (s, 1H), 8.80 (m, 1H), 8.97 (m, 1H), 9.50 (d, 1H). |
| Ia-154 | 3-$CF_3$ | H | 3-Cl | 4-(—CONH—) | 1-(pyridin-2-yl)-ethyl | HPLC-MS: logP = 3.45; mass (m/z): 556.1 (M + H)+; 1H NMR ($d_6$-DMSO) 1.47 (d, 3H), 5.14 (m, 1H), 6.15 (m, 1H), 6.90 (d, 1H), 7.28 (m, 1H), 7.45-7.85 (m, 6H), 7.95 (m, 1H), 8.05 (s, 1H), 8.55 (m, 1H), 8.93 (m, 1H), 9.50 (d, 1H). |
| Ia-155 | 3-$CF_3$ | H | 3-Cl | 4-(—CONH—) | 1,3-difluoro-propan-2-yl | HPLC-MS: logP = 3.36; mass (m/z): 529.1 (M + H)+; 1H NMR ($d_6$-DMSO) 4.03 (m, 1H), 4.47 (m, 2H), 4.61 (m, 2H), 6.15 (m, 1H), 6.90 (d, 1H), 7.45-7.85 (m, 5H), 7.82 (d, 1H), 7.95 (m, 1H), 8.05 (d, 1H), 8.85 (d, 1H), 9.49 (m, 1H). |
| Ia-156 | 3-$CF_3$ | H | 3-Cl | 4-(—CONH—) | 2,2-difluoroethyl | HPLC-MS: logP = 3.34; mass (m/z): 515.1 (M + H)+; 1H NMR ($d_6$-DMSO) 3.65 (m, 2H), 6.15 (m, 1H), 6.90 (d, 1H), 7.45-7.85 (m, 5H), 7.95 (m, 1H), 8.05 (d, 1H), 8.85 (m, 1H), 9.50 (m, 1H). |
| Ia-157 | 3-$CF_3$ | H | 3-Cl | 4-(—CONH—) | H | HPLC-MS: logP = 2.75; mass (m/z): 451 (M + H)+; 1H NMR ($d_6$-DMSO)6.15 (m, 1H), 6.90 (d, 1H), 7.50-7.95 (m, 7H), 8.05 (d, 1H), 8.85 (m, 1H), 9.48 (m, 1H). |

TABLE 1-continued (Ia)

where $R^2$, $R^4$ and $R^5$ are each H, X is $CF_3$ and $(R^1)_n$, $R^3$, $(R^1)_m$, A and Y are each as defined in Table 1. The numbers 2 to 6 represent the positions on the aromatic rings.

| No. | $(R^1)_n$ | R3 | $(R^6)_n$ | A | Y | HPLC-MS[a]; 1H NMR (δ in ppm)[b] |
|---|---|---|---|---|---|---|
| Ia-158 | 3-$CF_3$ | H | 3-Cl | 4-(—CONH—) | 1,1,1-trifluoro-propan-2-yl | HPLC-MS: logP = 3.78; mass (m/z): 547.1 (M + H)+; 1H NMR (d$_6$-DMSO) 1.32 (d, 3H), 4.77 (m, 1H), 6.15 (m, 1H), 6.90 (d, 1H), 7.45-7.85 (m, 6H), 7.95 (m, 1H), 8.05 (d, 1H), 9.07 (d, 1H), 9.55 (m, 1H). |
| Ia-159 | 3-$CF_3$ | H | 3-Cl | 4-(—CONH—) | methyl | HPLC-MS: logP = 3.13; mass (m/z): 548.1 (M + H)+; 1H NMR (d$_6$-DMSO) 4.73 (m, 2H), 6.15 (1,3-thiazol-2-yl)- (m, 1H), 6.90 (d, 1H), 7.50-7.85 (m, 6H), 7.95 (m, 1H), 8.05 (d, 1H), 9.07 (d, 1H), 9.37 (m, 1H), 9.52 (m, 1H). |
| Ia-160 | 3-$CF_3$ | H | 3-Cl | 4-(—CONH—) | 1-cyanoethyl | HPLC-MS: logP = 3.23; mass (m/z): 504(M + H)+; 1H NMR (d$_6$-DMSO) 1.50 (d, 3H), 4.95 (m, 2H), 6.15 (m, 1H), 6.90 (d, 1H), 7.50-7.85 (m, 6H), 7.95 (m, 1H), 8.05 (d, 1H), 9.07 (d, 1H), 9.35 (m, 1H), 9.62 (m, 1H). |
| Ia-161 | 3-$CF_3$ | H | 3-Cl | 4-(—CONH—) | but-3-yn-2-yl | HPLC-MS: logP = 3.43; mass (m/z): 503.1 (M + H)+; 1H NMR (d$_6$-DMSO) 1.37 (d, 3H), 3.18 (m, 1H), 4.78 (m, 1H), 6.15 (m, 1H), 6.90 (d, 1H), 7.45-7.85 (m, 6H), 7.95 (m, 1H), 8.05 (d, 1H), 8.93 (d, 1H), 9.50 (d, 1H), 9.62 (m, 1H). |
| Ia-162 | 3-$CF_3$ | H | 3-Cl | 4-(—CONH—) | cyclobutyl | HPLC-MS: logP = 3.59; mass (m/z): 505.1 (M + H)+; 1H NMR (d$_6$-DMSO) 1.65 (m, 2H), 2.00 (m, 2H), 2.25 (m, 2H), 3.18 (m, 1H), 4.35 (m, 1H), 6.15 (m, 1H), 6.90 (d, 1H), 7.45-7.85 (m, 6H), 7.95 (m, 1H), 8.05 (d, 1H), 8.68 (d, 1H), 9.50 (d, 1H). |
| Ia-163 | 3-$CF_3$ | H | 3-Cl | 4-(—CONH—) | cyclopropylmethyl | HPLC-MS: logP = 3.54; mass (m/z): 505.1 (M + H)+; 1H NMR (d$_6$-DMSO), 1.02 (m, 4H), 3.17 (m, 2H), 4.35 (m, 1H), 6.15 (m, 1H), 6.90 (d, 1H), 7.45-7.85 (m, 6H), 7.95 (m, 1H), 8.05 (d, 1H), 8.51 (d, 1H), 9.50 (d, 1H). |
| Ia-164 | 3-$CF_3$ | H | 3-Cl | 4-(—CONH—) | 1-methoxypropan-2-yl | HPLC-MS: logP = 3.33; mass (m/z): 523.1 (M + H)+; 1H NMR (d$_6$-DMSO), 1.15 (d, 3H), 3.17 (m, 2H), 3.25 (s, 3H), 3.38 (m, 2H), 4.11 (m, 1H), 6.15 (m, 1H), 6.90 (d, 1H), 7.40-7.85 (m, 6H), 7.95 (m, 1H), 8.05 (d, 1H), 8.34 (d, 1H), 9.50 (d, 1H). |
| Ia-165 | 3-$CF_3$ | H | 3-Cl | 4-(—CONH—) | 4-chloropyridin-2-yl | HPLC-MS: logP = 4,23; mass (m/z): 562(M + H)+; 1H NMR (CD3CN) 6.02 (m, 1H), 6.78 (d, 1H), 7.20 (d, 1H), 7.55-7.90 (m, 8H), 8.25 (s, 1H), 8.35 (s, 1H), 9.31 (s, 1H), 9.55 (m, 1H). |
| Ia-166 | 3-$CF_3$ | H | 3-Cl | 4-(—CONH—) | 1,1-dioxidothietan-3-yl | See Synthesis Example 10 |
| Ia-167 | 3-$CF_3$ | H | 3-Cl | 4-(—CONH—) | 1-oxidothietan-3-yl | See Synthesis Example 10 |
| Ia-168 | 3-$CF_3$ | H | 3-Cl | 4-(—CONH—) | 5-chloropyridin-2-yl | HPLC-MS: logP = 4.28; mass (m/z): 562.2(M + H)+; 1H NMR |

TABLE 1-continued

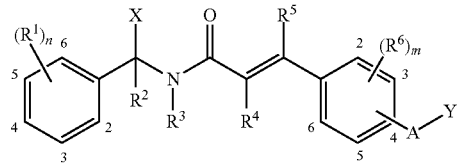

(Ia)

where $R^2$, $R^4$ and $R^5$ are each H, X is $CF_3$ and $(R^1)_n$, $R^3$, $(R^1)_m$, A and Y are each as defined in Table 1. The numbers 2 to 6 represent the positions on the aromatic rings.

| No. | $(R^1)_n$ | R3 | $(R^6)_n$ | A | Y | HPLC-MS[a]; $^1$H NMR (δ in ppm)[b] |
|---|---|---|---|---|---|---|
| | | | | | | (d$_6$-DMSO) 6.15 (m, 1H), 6.90 (d, 1H), 7.55-7.85 (m, 6H), 7.95 (m, 1H), 8.05 (s, 1H), 8.21 (m, 1H), 8.92 (d, 2H), 9.50 (d, 1H). |
| Ia-169 | 3-CF$_3$ | H | 3-CF$_3$ | 4-(—CONH—) | furan-2-ylmethyl | HPLC-MS: logP = 3.63; mass (m/z): 565.1 (M + H)+; 1H NMR (d$_6$-DMSO) 4.44 (m, 2H), 6.15 (m, 1H), 6.30 (m, 1H), 6.41 (m, 1H), 6.90 (d, 1H), 7.55-7.85 (m, 6H), 7.95 (m, 1H), 8.05 (s, 1H), 8.21 (m, 1H), 9.02 (m, 2H), 9.50 (d, 1H). |
| Ia-170 | 3-CF$_3$ | H | 3-CF$_3$ | 4-(—CONH—N(CO$_2$Me)—) | methyl | HPLC-MS: logP = 3.23; mass (m/z): 572.2(M + H)+; 1H NMR (d$_6$-DMSO) 3.15 (s, 3H), 3.65 (s, 3H), 6.15 (m, 1H), 6.30 (m, 1H), 6.41 (m, 1H), 6.90 (d, 1H), 7.60- 8.10 (m, 6H), 7.95 (m, 1H), 8.05 (s, 1H), 8.21 (m, 1H), 9.02 (m, 2H), 9.55 (d, 1H). |
| Ia-171 | 3-CF$_3$ | H | 3-CF$_3$ | 4-(—CONH—) | 1-(1-chlorocyclo-propyl)ethyl | HPLC-MS: logP = 4.18; mass (m/z): 587.2(M + H)+; 1H NMR (d$_6$-DMSO) 1.00 (m, 4H), 1.25 (d, 3H), 3.97 (m, 1H), 6.15 (m, 1H), 6.30 (m, 1H), 6.41 (m, 1H), 6.90 (d, 1H), 7.50-7.85 (m, 6H), 7.95 (m, 1H), 8.05 (s, 1H), 8.68 (d, 1H), 9.50 (d, 1H). |
| Ia-172 | 3-CF$_3$ | H | 3-CF$_3$ | 4-(—CONH—) | 1-cyano-1-cyclopropylethyl | HPLC-MS: logP = 3.74; mass (m/z): 578.3(M + H)+; 1H NMR (d$_6$-DMSO) 0.62 (m, 4H), 1.44 (m, 1H), 1.63 (s, 3H), 6.15 (m, 1H), 6.30 (m, 1H), 6.41 (m, 1H), 6.90 (d, 1H), 7.50-7.85 (m, 6H), 7.95 (m, 1H), 8.05 (s, 1H), 9.20 (s, 1H), 9.52 (d, 1H). |
| Ia-173 | 3-CF$_3$ | H | 3-Br | 4-(—CONH—) | 1-fluoropropan-2-yl | HPLC-MS: logP = 3.35; mass (m/z): 555.1 (M + H)+; 1H NMR (d$_6$-DMSO) 1.03 (d, 3H), 4.27 (m, 1H), 4.30 (m, 1H), 4,45 (m, 1H), 6.15 (m, 1H), 6.90 (d, 1H), 7.41 (d, 1H), 7.54 (d, 1H), 7.67 (m, 1H), 7.80 (d, 1H), 7.89 (d, 1H), 8.04 (s, 1H), 8.52 (d, 1H), 9.45 (d, 1H) |
| Ia-174 | 3-CF$_3$ | H | 3-Br | 4-(—CONH—) | propan-2-yl | HPLC-MS: logP = 3.48; mass (m/z): 539(M + H)+; 1H NMR (d$_6$-DMSO) 1.14 (d, 6H), 4.03 (m, 1H), 6.15 (m, 1H), 6.90 (d, 1H), 7.40-7.85 (m, 7H), 7.95 (m, 1H), 8.05 (s, 1H), 8.28 (d, 1H), 9.45 (d, 1H). |
| Ia-175 | 3-CF$_3$ | H | 3-Br | 4-(—CONH—) | 1,3-difluoropropan-2-yl | HPLC-MS: logP = 3.35; mass (m/z): 575.1 (M + H)+; 1H NMR (d$_6$-DMSO) 4.02 (m, 1H), 4.52 (m, 2H), 4.65 (m, 2H), 6.15 (m, 1H), 6.90 (d, 1H), 7.40-7.95 (m, 7H), 8.05 (s, 1H), 8.84 (d, 1H), 9.48 (d, 1H). |
| Ia-176 | 3-CF$_3$ | H | 3-Br | 4-(—CONH—) | 1,1,1-trifluoro-propan-2-yl | HPLC-MS: logP = 3.78; mass (m/z): 593.1 (M + H)+; 1H NMR (d$_6$-DMSO) 1.31 (d, 3H), 4.77 (m, 1H), 6.15 (m, 1H), 6.90 (d, |

TABLE 1-continued

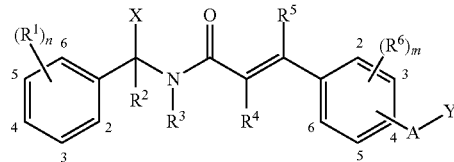

(Ia)

where $R^2$, $R^4$ and $R^5$ are each H, X is $CF_3$ and $(R^1)_n$, $R^3$, $(R^1)_m$, A and Y are each as defined in Table 1. The numbers 2 to 6 represent the positions on the aromatic rings.

| No. | $(R^1)_n$ | R3 | $(R^6)_n$ | A | Y | HPLC-MS[a]; $^1$H NMR (δ in ppm)[b] |
|---|---|---|---|---|---|---|
| Ia-177 | 3-$CF_3$ | H | 3-Br | 4-(—CONH—) | 1,3-thiazol-2-ylmethyl | 1H), 7.45-7.95 (m, 7H), 8.05 (s, 1H), 9.05 (d, 1H), 9.50 (d, 1H). HPLC-MS: logP = 3.14; mass (m/z): 592.1 (M + H)+; 1H NMR ($d_6$-DMSO) 4.73 (d, 2H), 6.15 (m, 1H), 6.90 (d, 1H), 7.45-7.95 (m, 7H), 8.05 (s, 1H), 9.35 (d, 1H), 9.50 (d, 1H). |
| Ia-178 | 3-$CF_3$ | H | 3-Br | 4-(—CONH—) | but-3-yn-2-yl | HPLC-MS: logP = 3.44; mass (m/z): 549(M + H)+; 1H NMR ($d_6$-DMSO) 1.38 (d, 3H), 3.18 (s, 1H), 4.76 (m, 1H), 6.15 (m, 1H), 6.90 (d, 1H), 7.45-7.95 (m, 7H), 8.06 (s, 1H), 8.91 (d, 1H), 9.45 (d, 1H). |
| Ia-179 | 3-$CF_3$ | H | 3-Br | 4-(—CONH—) | cyclobutyl | HPLC-MS: logP = 3.61; mass (m/z): 551.1 (M + H)+; 1H NMR ($d_6$-DMSO) 1.68 (m, 2H), 2.00 (m, 2H), 2.23 (m, 2H), 4.35 (m, 1H), 6.15 (m, 1H), 6.90 (d, 1H), 7.45-7.95 (m, 7H), 8.06 (s, 1H), 8.66 (d, 1H), 9.44 (d, 1H). |
| Ia-180 | 3-$CF_3$ | H | 3-Br | 4-(—CONH—) | cyclopropylmethyl | HPLC-MS: logP = 3.55; mass (m/z): 551.2(M + H)+; 1H NMR ($d_6$-DMSO) 0.5 (m, 2H), 0.80 (m, 2H), 1.00 (m, 1H), 3.13 (m, 2H), 4.35 (m, 1H), 6.15 (m, 1H), 6.90 (d, 1H), 7.45-7.95 (m, 7H), 8.06 (s, 1H), 8.50 (d, 1H), 9.45 (d, 1H). |
| Ia-181 | 3-$CF_3$ | H | 3-Br | 4-(—CONH—) | 3-methylthietan-3-yl | HPLC-MS: logP = 3.55; mass (m/z): 551.2(M + H)+; 1H NMR ($d_6$-DMSO) 1.72 (s, 3H), 2.94 (m, 2H), 3.76 (m, 2H), 4.35 (m, 1H), 6.15 (m, 1H), 6.90 (d, 1H), 7.50-7.95 (m, 7H), 8.06 (s, 1H), 8.71 (s, 1H), 9.44 (d, 1H). |
| Ia-182 | 3-$CF_3$ | H | 3-Cl | 4-(—CONH—) | 1-cyano-2-methyl-propan-1-yl | HPLC-MS: logP = 3.68; mass (m/z): 532.1 (M + H)+; 1H NMR ($d_6$-DMSO) 1.07 (m, 6H), 2.09 (m, 1H), 4.81 (m, 1H), 6.15 (m, 1H), 6.90 (d, 1H), 7.50-7.95 (m, 7H), 8.06 (s, 1H), 9.30 (d, 1H), 9.44 (d, 1H). |
| Ia-183 | 3-$CF_3$ | H | 3-Cl | 4-(—CONH—) | 3-chloropyridin-2-yl | HPLC-MS: logP = 3.44; mass (m/z): 562.1 (M + H)+; 1H NMR ($d_6$-DMSO) 6.16 (m, 1H), 6.91 (d, 1H), 7.38 (m, 1H), 7.50-7.95 (m, 9H), 8.06 (s, 1H), 8.42 (d, 1H), 9.50 (d, 1H). |
| Ia-184 | 3-$CF_3$ | H | 3-Cl | 4-(—CONH—) | 1,3-pyrimidin-4-yl | HPLC-MS: logP = 3.22; mass ($d_6$-DMSO) 6.16 (m, 1H), 6.91 (d, 1H), 7.55-7.95 (m, 8H), 8.06 (s, 1H), 8.17 (m, 1H), 8.73 (d, 1H), 8.92 (s, 1H), 9.50 (d, 1H). |
| Ia-185 | 3-$CF_3$ | H | 3-Cl | 4-(—CONH—) | 1,3-thiazol-2-yl | HPLC-MS: logP = 3.51; mass (m/z): 534.1 (M + H)+; 1H NMR ($d_6$-DMSO) 6.16 (m, 1H), 6.91 (d, 1H), 7.32 (d, 1H), 7.55-7.95 (m, 8H), 8.05 (s, 1H), 8.17 (m, 1H), 9.50 (d, 1H). |
| Ia-186 | 3-$CF_3$ | H | 3-Cl | 4-(—CONH—) | 1-methylpyrazol-3-ylmethyl | HPLC-MS: logP = 2.95; mass (m/z): 545.3(M + H)+; 1H NMR ($d_6$-DMSO) 3.78 (s, 3H), 4.36 |

TABLE 1-continued (Ia)

where R², R⁴ and R⁵ are each H, X is CF₃ and (R¹)ₙ, R³, (R¹)ₘ, A and Y are each as defined in Table 1. The numbers 2 to 6 represent the positions on the aromatic rings.

| No. | (R¹)ₙ | R3 | (R⁶)ₙ | A | Y | HPLC-MS[a]; ¹H NMR (δ in ppm)[b] |
|---|---|---|---|---|---|---|
| | | | | | | (m, 2H), 6.15 (m, 1H), 6.17 (d, 1H), 6.90 (d, 1H), 7.45-7.95 (m, 7H), 8.05 (s, 1H), 8.17 (m, 1H), 8.84 (t, 1H), 9.47 (d, 1H). |
| Ia-187 | 3-CF₃ | H | 3-Cl | 4-(—CONH—) | 1-(1,3-thiazol-2-yl)-ethyl | HPLC-MS: logP = 3.4; mass (m/z): 562.1 (M + H)+; 1H NMR (d6 -DMO) 1.58 (s, 3H), 5.38 (m, 1H),S 6.15 (m, 1H), 6.90 (d, 1H), 7.45-7.95 (m, 8H), 8.05 (s, 1H), 8.17 (m, 1H), 9.27 (t, 1H), 9.50 (d, 1H). |
| Ia-188 | 3-CF₃ | H | 3-Cl | 4-(—CONH—) | 1-methylpyrazol-5-yl | HPLC-MS: logP = 2.73; mass (m/z): 531.1 (M + H)+; 1H NMR (d₆-DMSO) 3.74 (s, 3H), 6.16 (m, 1H), 6.90 (d, 1H), 6.93 (d, 1H), 7.38 (d, 1H), 7.55-7.95 (m, 8H), 8.05 (s, 1H), 9.50 (d, 1H). |
| Ia-189 | 3-CF₃ | H | 3-Cl | 4-(—CONH—) | (1-methylpyrazol-5-yl)methyl | HPLC-MS: logP = 2.93; mass (m/z): 545.2(M + H)+; 1H NMR (d₆-DMSO) 3.82 (s, 3H), 4.50 (m, 2H), 6.16 (m, 1H), 6.21 (d, 1H), 6.90 (d, 1H), 7.31 (d, 1H), 7.55-7.95 (m, 7H), 8.05 (s, 1H), 8.97 (t, 1H), 9.47 (d, 1H). |
| Ia-190 | 3-CF₃ | H | 3-Cl | 4-(—CONH—NMe—) | methyl | HPLC-MS: logP = 2.93; mass (m/z): 545.2(M + H)+; 1H NMR (d₆-DMSO) 2.32 (s, 3H), 2.56 (s, 3H), 6.15 (m, 1H), 6.90 (d, 1H), 7.40-7.95 (m, 6H), 8.06 (s, 1H), 8.71 (s, 1H), 9.33 (s, 1H), 9.46 (d, 1H). |
| Ia-191 | 3-CF₃ | H | 3-Cl | 4-(—CONH—) | 1-(methoxy-carbonyl)ethyl | HPLC-MS: logP = 3.29; mass (m/z): 537.1 (M + H)+; 1H NMR (d₆-DMSO) 1.35 (s, 3H), 3.67 (s, 3H), 4.67 (m, 1H), 6.15 (m, 1H), 6.90 (d, 1H), 7.45-7.95 (m, 7H), 8.06 (s, 1H), 8.90 (s, 1H), 9.50 (d, 1H). |
| Ia-192 | 3-CF₃ | H | 3-Cl | 4-(—CONH—) | butan-2-yl | HPLC-MS: logP = 3.71; mass (m/z): 507.2(M + H)+; 1H NMR (d₆-DMSO) 0.90 (t, 3H), 1.12 (d, 3H), 1.48 (m, 2H), 3.86 (m, 1H), 6.15 (m, 1H), 6.90 (d, 1H), 7.45-7.95 (m, 7H), 8.06 (s, 1H), 8.25 (d, 1H), 9.46 (d, 1H). |
| Ia-193 | 3-CF₃ | H | 3-Cl | 4-(—CONH—) | 3-chloroprop-2-en-1-yl | HPLC-MS: logP = 3.58; mass (m/z): 525.2(M + H)+; 1H NMR (d₆-DMSO) 3.91 (m, 2H), 6.02 (m, 1H), 6.15 (m, 1H), 6.42 (m, 1H), 6.90 (d, 1H), 7.50-7.95 (m, 7H), 8.06 (s, 1H), 8.73 (m, 1H), 9.46 (d, 1H). |
| Ia-194 | 3-CF₃ | H | 3-Cl | 4-(—CONH—O—) | propan-2-yl | HPLC-MS: logP = 3.29; mass (m/z): 509.1 (M + H)+; 1H NMR (d6 DMSO)1.20 (d, 6H), 4.16 (m, 1H), 6.15 (m, 1H), 6.88 (d, 1H), 7.50-7.95 (m, 7H), 8.06 (s, 1H), 9.50 (d, 1H). |
| Ia-195 | 3-CF₃ | H | 3-Cl | 4-(—CONH—) | 1-cyano-1-methylethyl | HPLC-MS: logP = 3.34; mass (m/z): 518.1 (M + H)+; 1H NMR (d₆-DMSO) 1.66 (s, 6H), 6.15 (m, 1H), 6.88 (d, 1H), 7.50-7.95 (m, 7H), 8.06 (s, 1H), 9.06 (s, 1H), 9.47 (d, 1H). |

TABLE 1-continued (Ia)

where $R^2$, $R^4$ and $R^5$ are each H, X is $CF_3$ and $(R^1)_n$, $R^3$, $(R^1)_m$, A and Y are each as defined in Table 1. The numbers 2 to 6 represent the positions on the aromatic rings.

| No. | $(R^1)_n$ | R3 | $(R^6)_n$ | A | Y | HPLC-MS[a]; $^1$H NMR (δ in ppm)[b] |
|---|---|---|---|---|---|---|
| Ia-196 | 3-CF$_3$ | H | 3-Cl | 4-(—CONH—) | 1-methylprop-3-yn-1-yl | HPLC-MS: logP = 3.64; mass (m/z): 517(M + H)+; 1H NMR (d$_6$-DMSO) 1.57 (s, 6H), 3.30 (, 1H), 6.15 (m, 1H), 6.88 (d, 1H), 7.40-7.95 (m, 7H), 8.06 (s, 1H), 8.54 (s, 1H), 9.06 (s, 1H), 9.47 (d, 1H). |
| Ia-197 | 3-CF$_3$ | H | 3-Cl | 4-(—CONH—) | 1,3-pyrimidin-2-yl | HPLC-MS: logP = 2.95; mass (m/z): 529.1 (M + H)+; 1H NMR (d$_6$-DMSO) 6.16 (m, 1H), 6.88 (d, 1H), 7.20 (m, 1H), 7.55-7.95 (m, 7H), 8.06 (s, 1H), 8.62 (s, 1H), 9.06 (s, 1H), 9.50 (d, 1H). |
| Ia-198 | 3-CF$_3$ | H | 3-Br | 4-(4-cyano-1H-pyrazol-1-yl) | | HPLC-MS: logP = 2.95; mass (m/z): 529.1 (M + H)+; 1H NMR (d$_6$-DMSO) 6.17 (m, 1H), 6.93 (d, 1H), 7.20 (m, 1H), 7.55-7.95 (m, 6H), 8.06 (s, 1H), 8.38 (s, 1H), 9.03 (s, 1H), 9.55 (d, 1H). |
| Ia-199 | 3-CF$_3$ | H | 3-Cl | 4-(—CONH—) | 5-chloro-1,3-pyrimidin-2-yl | HPLC-MS: logP = 3.47; mass (m/z): 563(M + H)+; 1H NMR (d$_6$-DMSO) 6.16 (m, 1H), 6.90 (d, 1H), 7.20 (m, 1H), 7.55-7.95 (m, 7H), 8.06 (s, 1H), 8.75 (s, 1H), 9.50 (d, 1H). |
| Ia-200 | 3-CF$_3$ | H | 3-Cl | 4-(4-cyano-1H-pyrazol-1-yl) | | HPLC-MS: logP = 3.83; mass (m/z): 499(M + H)+; 1H NMR (d$_6$-DMSO) 6.17 (m, 1H), 6.93 (d, 1H), 7.20 (m, 1H), 7.55-7.95 (m, 6H), 8.06 (s, 1H), 8.39 (s, 1H), 9.03 (s, 1H), 9.55 (d, 1H). |
| Ia-201 | 3-CF$_3$ | H | 3-CN | 4-(1H-pyrazol-1-yl) | | HPLC-MS: logP = 3.5; mass (m/z): 465 (M + H)+; 1H NMR (d$_6$-DMSO) 6.17 (m, 1H), 6.66 (s, 1H), 6.97 (d, 1H), 7.20 (m, 1H), 7.55-7.95 (m, 6H), 8.06 (s, 1H), 8.24 (s, 1H), 8.47(s, 1H), 9.03 (s, 1H), 9.55 (d, 1H). |
| Ia-202 | 3-Cl, 4-F | H | 3-Cl | 4-(4-cyano-1H-pyrazol-1-yl) | | HPLC-MS: logP = 3.77; mass (m/z): 483(M + H)+; 1H NMR (d$_6$-DMSO) 6.07 (m, 1H), 6.90 (d, 1H), 7.20 (m, 1H), 7.50-7.95 (m, 6H), 8.00 (s, 1H), 8.40 (s, 1H), 9.06 (s, 1H), 9.45 (d, 1H). |
| Ia-203 | 3-CF$_3$ | H | 3-Cl | 4-(—CONH—) | 5-fluoropyridin-2-yl | HPLC-MS: logP = 3.84; mass (m/z): 546.1 (M + H)+; 1H NMR (d$_6$-DMSO) 6.17 (m, 1H), 6.92 (d, 1H), 7.18 (d, 1H), 7.60-7.69 (m, 6H), 7.78 (m, 1H), 7.90 (s, 1H), 8.22 (m, 1H), 9.55 (d, 1H), 11.2 (s, 1H). |
| Ia-204 | 3-CF$_3$ | H | 3-Cl | 4-(—CONH—) | 5-nitropyridin-2-yl | HPLC-MS: logP = 3.95; mass (m/z): 573(M + H)+; 1H NMR (d$_6$-DMSO) 6.19 (m, 1H), 6.95 (d, 1H), 7.57 (d, 1H), 7.69 (s, 1H), 7.81 (m, 2H), 7.94 (m, 1H), 8.05 (s, 1H), 8.42 (d, 1H), 8.57 (d, 1H), 9.21 (s, 1H), 9.55 (m, 1H), 11.8 (s, 1H). |

TABLE 1-continued (Ia)

where $R^2$, $R^4$ and $R^5$ are each H, X is $CF_3$ and $(R^1)_n$, $R^3$, $(R^1)_m$, A and Y are each as defined in Table 1. The numbers 2 to 6 represent the positions on the aromatic rings.

| No. | $(R^1)_n$ | R3 | $(R^6)_n$ | A | Y | HPLC-MS[a]; $^1$H NMR (δ in ppm)[b] |
|---|---|---|---|---|---|---|
| Ia-205 | 3-$CF_3$ | H | 3-Cl | 4-(—CONH—) | 5-cyanopyridin-2-yl | HPLC-MS: logP = 3.72; mass (m/z): 553.1 (M + H)+; 1H NMR (d$_6$-DMSO) 6.16 (m, 1H), 6.93 (d, 1H), 7.57 (d, 1H), 7.67 (s, 1H), 7.81 (m, 2H), 7.94 (m, 1H), 8.05 (s, 1H), 8.32 (s, 1H), 8.83 (s, 1H), 9.21 (s, 1H), 9.55 (m, 1H), 11.6 (s, 1H). |
| Ia-206 | 3-$CF_3$ | H | 3-CN | | 4-(4-chloro-1H-pyrazol-1-yl) | HPLC-MS: logP = 3.75; mass (m/z): 483(M + H)+; 1H NMR (d$_6$-DMSO) 6.07 (m, 1H), 6.92 (d, 1H), 7.20 (m, 1H), 7.55-7.95 (m, 5H), 8.00 (s, 1H), 8.39 (s, 1H), 9.06 (s, 1H), 9.45 (d, 1H). |
| Ia-207 | 3-$CF_3$ | H | 3-Br | | 4-(3-chloro-1H-1,2,4-triazol-1-yl) | HPLC-MS: logP = 3.75; mass (m/z): 483(M + H)+; 1H NMR (d$_6$-DMSO) 6.17 (m, 1H), 6.96 (d, 1H), 7.20 (m, 1H), 7.55-7.95 (m, 5H), 8.00 (s, 1H), 8.39 (s, 1H), 9.06 (s, 1H), 9.58 (d, 1H). |
| Ia-208 | 3-$CF_3$ | H | 3-$CF_3$ | | 4-(3-chloro-1H-1,2,4-triazol-1-yl) | HPLC-MS: logP = 4.02; mass (m/z): 543(M + H)+; 1H NMR (d$_6$-DMSO) 6.18 (m, 1H), 7.04 (d, 1H), 7.20 (m, 1H), 7.70-7.95 (m, 5H), 8.05 (s, 1H), 8.25 (s, 1H), 9.02 (s, 1H), 9.56 (d, 1H). |
| Ia-209 | 3-Cl, 4F | H | 3-Cl | | 4-(1-H-1,2,4-triazol-1-yl) | HPLC-MS: logP = 3.15; mass (m/z): 459(M + H)+; 1H NMR (d$_6$-DMSO) 6.07(m, 1H), 6.93 (d, 1H), 7.20 (m, 1H), 7.70-7.95 (m, 5H), 8.00 (s, 1H), 8.29 (s, 1H), 9.00 (s, 1H), 9.43 (d, 1H). |
| Ia-210 | 3-$CF_3$ | H | 3-$CF_3$ | 4-(—CONH—) | 5-fluoropyridin-2-yl | HPLC-MS: logP = 3.93; mass (m/z): 580.1 (M + H)+; 1H NMR (d$_6$-DMSO) 6.18 (m, 1H), 7.00 (d, 1H), 7.70-7.73 (m, 1H), 7.67 (s, 1H), 7.96 (m, 1H), 8.06 (s, 1H), 8.18 (m, 1H), 8.37 (m, 1H), 9.55 (d, 1H), 11.3 (s, 1H). |
| Ia-211 | 3-$CF_3$ | H | 3-$CF_3$ | 4-(—CONH—) | 5-cyanopyridin-2-yl | HPLC-MS: logP = 3.82; mass (m/z): 587.1 (M + H)+; 1H NMR (d$_6$-DMSO) 6.15 (m, 1H), 7.00 (d, 1H), 7.64 (d, 1H), 7.67 (s, 1H), 7.81 (m, 2H), 7.98 (m, 1H), 8.06 (d, 1H), 8.32 (m, 1H), 8.83 (s, 1H), 9.21 (s, 1H), 9.5 (d, 1H), 11.8 (s, 1H). |
| Ia-212 | 3-$CF_3$ | H | 3-Br | 4-(—CONH—) | 5-fluoropyridin-2-yl | HPLC-MS: logP = 3.87; mass (m/z): 590(M + H)+; 1H NMR (d$_6$-DMSO) 6.16 (m, 1H), 6.92 (d, 1H), 7.56 (s, 1H), 7.59 (m, 1H), 7.71 (m, 1H), 7.81 (m, 1H), 7.94 (m, 2H), 8.05 (s, 1H), 8.22 (m, 1H), 8.37 (m, 1H), 9.50(d, 1H), 11.1 (s, 1H). |
| Ia-213 | 3-$CF_3$ | H | 3-Br | 4-(—CONH—) | 5-chloropyridin-2-yl | HPLC-MS: logP = 4.25; mass (m/z): 591.9(M + H)+; 1H NMR (d$_6$-DMSO) 6.16 (m, 1H), 6.92 (d, 1H), 7.55 (s, 1H), 7.59 (m, 1H), 7.71 (m, 1H), 7.82 (m, 1H), 7.96 (m, 2H), 8.05 (s, 1H), |

TABLE 1-continued

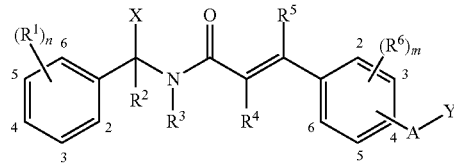

(Ia)

where $R^2$, $R^4$ and $R^5$ are each H, X is $CF_3$ and $(R^1)_n$, $R^3$, $(R^1)_m$, A and Y are each as defined in Table 1. The numbers 2 to 6 represent the positions on the aromatic rings.

| No. | $(R^1)_n$ | R3 | $(R^6)_n$ | A | Y | HPLC-MS[a]; $^1$H NMR (δ in ppm)[b] |
|---|---|---|---|---|---|---|
| Ia-214 | 3-$CF_3$ | H | 3-Br | 4-(—CONH—) | 5-cyanopyridin-2-yl | 8.21 (d, 1H), 8.41 (m, 1H), 9.52(d, 1H), 11.3 (s, 1H). HPLC-MS: logP = 3.75; mass (m/z): 599(M + H)+; 1H NMR ($d_6$-DMSO) 6.16 (m, 1H), 6.90 (d, 1H), 7.47 (d, 1H), 7.62 (m, 1H), 7.72 (m, 2H), 7.81 (m, 1H), 8.05 (s, 1H), 8.32 (m, 1H), 8.83 (s, 1H), 9.21 (s, 1H), 9.53 (d, 1H), 11.6 (s, 1H). |
| Ia-215 | 3-$CF_3$ | H | 3-Cl | 4-(—CONH—) | 5-nitropyridin-2-yl | HPLC-MS: logP = 3.97; mass (m/z): 619(M + H)+; 1H NMR ($d_6$-DMSO) 6.17 (m, 1H), 6.93 (d, 1H), 7.56 (d, 1H), 7.66 (d, 1H), 7.71 (m, 2H), 7.81 (m, 1H), 7.96 (s, 1H), 8.69 (d, 1H), 8.55 (d, 1H), 9.21 (s, 1H), 9.52 (m, 1H), 11.9 (s, 1H). |
| Ia-216 | 3-$CF_3$ | H | 3-Cl | 4-(—CONH—) | 1,4-pyrazin-2-yl | HPLC-MS: logP = 3.31; mass (m/z): 529.1 (M + H)+; 1H NMR (d, 1H), 7.50-7.95 ( (m, 7H)6.91, 7.96 ($d_6$-DMSO) 6.15 (m, 1H), 6.92 (s, 1H), 8.45 (m, 1H), 8.55 (d, 1H), 9.41 (s, 1H), 9.52 (m, 1H) |
| Ia-217 | 3-$CF_3$ | H | 3-Cl | 4-(—CONH—) | 1,2-pyridazin-3-yl | HPLC-MS: logP = 3.29; mass (m/z): 529(M + H)+; 1H NMR ($d_6$-DMSO) 6.15 (m, 1H), 6.92 (d, 1H), 7.50-7.95 (m, 7H), 7.96 (s, 1H), 8.46 (m, 1H), 8.55 (d, 1H), 9.40 (s, 1H), 9.52 (m, 1H) |
| Ia-218 | 3-$CF_3$ | H | 3-Cl | 4-(—CONH—) | 5-(methoxy-carbonyl)pyridin-2-yl | HPLC-MS: logP = 3.92; mass (m/z): 586.1 (M + H)+; 1H NMR ($d_6$-DMSO) 3.88 (s, 3H), 6.16 (m, 1H), 6.93 (d, 1H), 7.56 (s, 1H), 7.59 (m, 1H), 7.67 (s, 1H), 7.81 (s, 1H), 7.95 (m, 2H), 8.05 (s, 1H), 8.22 (m, 1H), 8.36 (m, 1H), 8.89 (s, 1H), 9.52 (d, 1H), 11.5 (s, 1H). |
| Ia-225 | 3-$CF_3$ | H | 3-$CF_3$ | 4-(—CONH—) | 1,2-pyridazin-3-yl | HPLC-MS: logP = 3.27; mass (m/z): 563(M + H)+; 1H NMR ($d_6$-DMSO) 6.18 (m, 1H), 7.00 (d, 1H), 7.65-8.00 (m, 8H), 8.10 (d, 1H), 8.36 (d, 1H), 9.05 (m, 1H), 9.55 (d, 1H). |
| Ia-226 | 3-$CF_3$ | H | 3-$CF_3$ | 4-(—CONH—) | 5-bromo-1,4-pyrazine | HPLC-MS: logP = 4.15; mass (m/z): 643(M + H)+; 1H NMR ($d_6$-DMSO) 6.18 (m, 1H), 7.00 (d, 1H), 7.65-8.00 (m, 7H), 8.10 (d, 1H), 8.67 (s, 1H), 9.20 (s, 1H), 9.55 (d, 1H). |
| Ia-227 | 3-$CF_3$ | H | 3-$CF_3$ | 4-(—CONH—) | 1-oxidothietan-3-yl | HPLC-MS: logP = 2.71; mass (m/z): 573.1 (M + H)+; 1H NMR ($d_6$-DMSO) 3.15 (m, 2H), 4.10 (m, 2H), 4.35 (m, 1H), 6.17 (m, 1H), 6.95 (d, 1H), 7.65- 8.00 (m, 7H), 8.05 (d, 1H), 9.16 (d, 1H), 9.50 (d, 1H). |
| Ia-228 | 3-$CF_3$ | H | 3-Cl | 4-(—CONH—) | 6-chloro-1,2-pyrazin-3-yl | HPLC-MS: logP = 3.7; mass (m/z): 563(M + H)+; 1H NMR ($d_6$-DMSO) 6.17 (m, 1H), 6.94 (d, 1H), 7.55-7.95 (m, 8H), 8.06 (d, 1H), 8.48 (d, 1H), 9.05 (m, 1H), 9.55 (d, 1H). |

TABLE 1-continued (Ia)

where $R^2$, $R^4$ and $R^5$ are each H, X is $CF_3$ and $(R^1)_n$, $R^3$, $(R^1)_m$, A and Y are each as defined in Table 1. The numbers 2 to 6 represent the positions on the aromatic rings.

| No. | $(R^1)_n$ | R3 | $(R^6)_n$ | A | Y | HPLC-MS[a]; $^1$H NMR (δ in ppm)[b] |
|---|---|---|---|---|---|---|
| Ia-229 | 3-CF$_3$, 5-F | H | 3-CF$_3$ | 4-(—CONH—) | cyclopropyl | See 4 |
| Ia-230 | 3-F | H | 3-CF$_3$ | 4-(—CONH—) | cyclopropyl | HPLC-MS: logP = 2.95; mass (m/z): 475.1 (M + H)+; 1 H NMR (d3-acetonitrile) 0.55 (m, 2H), 0.75 (m, 2H), 2.80 (m, 1H), 5.90 (m, 1H), 6.80 (d, 1H), 6.90 (br. s, 1H), 7.17-7.52 (m. 5H), 7.64 (d, 1H), 7.71-7.83 (m, 2H), 7.90 (s, 1H). |
| Ia-231 | 3-Cl | H | 3-CF$_3$ | 4-(—CONH—) | cyclopropyl | HPLC-MS: logP = 3.22; mass (m/z): 491.1 (M + H)+; 1 H NMR (d$_6$-DMSO) 0.50 (m, 2H), 0.69 (m, 2H), 2.80 (m, 1H), 6.01 (m, 1H), 6.95 (d, 1H), 7.47-7.64 (m, 4H), 7.70 (d, 1H), 7.73 (s, 1H), 7.91 (m, 1H), 7.98 (m, 1H), 8.53 (m, 1H), 9.40 (m, 1H). |
| Ia-232 | 3-CH$_3$ | H | 3-CF$_3$ | 4-(—CONH—) | cyclopropyl | HPLC-MS: logP = 3.17; mass (m/z): 471.1 (M + H)+; 1 H NMR (d$_6$-DMSO) 0.50 (m, 2H), 0.69 (m, 2H), 2.34 (s, 3H), 2.79 (m, 1H), 5.85 (m, 1H), 6.97 (d, 1H), 7.23 (m, 1H), 7.31-7.40 (m, 3H), 7.54 (m, 1H), 7.62 (d, 1H), 7.89 (m, 1H), 7.97 (s, 1H), 8.53 (m, 1H), 9.32 (m, 1H). |
| Ia-233 | 3-CF$_3$ | H | 2-Cl | 4-(—CONH—) | cyclopropyl | HPLC-MS: logP = 3.46; mass (m/z): 491.2(M + H)+; 1 H NMR (d$_3$-acetonitrile) 0.61 (m, 2H), 0.75 (m, 2H), 2.83 (m, 1H), 6.01 (m, 1H), 6.76 (d, 1H), 7.14 (br. s, 1H), 7.65-7.92 (m, 8H), 7.93 (m, 1H). |
| Ia-234 | 3-Cl | H | 2-Cl | 4-(—CONH—) | cyclopropyl | HPLC-MS: logP = 3.3; mass (m/z): 457.1 (M + H)+; 1 H NMR (d$_3$-acetonitrile) 0.60 (m, 2H), 0.75 (m, 2H), 2.84 (m, 1H), 5.90 (m, 1H), 6.75 (d, 1H), 7.14 (br. s, 1H), 7.44-7.48 (m, 3H), 7.57 (s, 1H), 7.14-7.84 (m, 4H), 7.93 (d, 1H). |
| Ia-235 | 3-Cl | H | 3-Cl | 4-(—CONH—) | cyclopropyl | HPLC-MS: logP = 3.03; mass (m/z): 457(M + H)+; 1 H NMR (d$_6$-DMSO) 0.53 (m, 2H), 0.69 (m, 2H), 2.82 (m, 1H), 6.01 (m, 1H), 6.88 (d, 1H), 7.43-7.61 (m, 6H), 7.73 (m, 2H), 8.49 (d, 1H), 9.38 (d, 1H). |
| Ia-236 | 3-CF$_3$ | H | 3-Cl | 4-(—CONH—) | (5-fluoropyridin-2-yl)methyl | HPLC-MS: logP = 3.15; mass (m/z): 560.22 (M + H)+; 1 H NMR (400 MHz, d3-CD3CN): 8.38 (m, 1H), 7.87 (s, 1H), 7.85-7.75 (m, 4H), 7.68-7.64 (m, 2H), 7.60-7.50 (m, 4H), 7.40-7.30 (m, 1H), 6.74 (d, 1H, J = 16 Hz), 6.00 (m, 1H), 4.72 (dd, 1H). |
| Ia-237 | 3-CF$_3$ | H | 3-Br | 4-(—CONH—) | 1-ethoxycyclo-propan-1-yl | HPLC-MS: logP = 3.42; mass (m/z): 579.34(M + H)+; |
| Ia-238 | 3-CF$_3$ | H | 3-CF$_3$ | 4-(—CH$_2$NHCO—) | ethyl | HPLC-MS: logP = 3.51; mass (m/z): 527.1 (M + H)+; 1 H NMR (d3-CD3CN) 7.86 (m, 2H), 7.80-7.70 (m, 4H), 7.68-7.63 (m, 2H), 7.55 (d, 1H), 6.80 (s, 1H, br), 6.74 (d, 1H, J = 16 Hz), 5.99 |

TABLE 1-continued (Ia)

where $R^2$, $R^4$ and $R^5$ are each H, X is $CF_3$ and $(R^1)_n$, $R^3$, $(R^1)_m$, A and Y are each as defined in Table 1. The numbers 2 to 6 represent the positions on the aromatic rings.

| No. | $(R^1)_n$ | R3 | $(R^6)_n$ | A | Y | HPLC-MS[a]; $^1$H NMR (δ in ppm)[b] |
|---|---|---|---|---|---|---|
| | | | | | | (m, 1H), 4.51 (d, 2H), 2.24 (q, 2H), 1.10 (t, 3H) |
| Ia-239 | 3-$CF_3$ | H | 3-$CF_3$ | 4-(—CON($CH_3$)—) | pyridin-2-yl | HPLC-MS: logP = 2.07; mass (m/z): 576.22 (M + H)+; 1H NMR (400 MHz, d3-CD3CN): 8.30 (d, 1H), 8.00 (d, 1H), 7.90 (m, 2H), 7.80-7.60 (m, 9H), 6.80 (m, 1H), 6.00 (m, 1H), 3.78 (m, 3H) |
| Ia-240 | 3-$CF_3$ | H | 3-$CF_3$ | 4-(—$CH_2$NHCO—) | cyclopropyl | HPLC-MS: logP = 3.76; mass (m/z): 539.15 (M + H)+; 1H NMR (400 MHz, d3-CD3CN): 7.90-7.75 (m, 5H), 7.70-7.60 (m, 3H), 7.55 (d, 1H), 7.09 (t, 1H, br), 6.75 (d, 1H, J = 16 Hz), 6.02 (m, 1H), 4.54 (d, 2H), 1.55 (m, 1H), 0.80 (m, 2H), 0.75 (m, 2H) |
| Ia-241 | 3-$CF_3$ | H | H | 4-(—$CH_2$NHCO—) | ethyl | HPLC-MS: logP = 2.8; mass (m/z): 459.17(M + H)+; 1H NMR (400 MHz, d3-CD3CN): 7.88 (s, 1H), 7.85-7.75 (m, 3H), 7.70-7.60 (m, 2H), 7.55 (d, 2H), 7.30 (d, 2H), 6.80 (s, 1H, br), 6.68 (d, 1H, J = 16 Hz), 6.00 (m, 1H), 4.38 (d, 2H), 3.30 (q, 2H), 1.10 (t, 3H) |
| Ia-242 | 3-$CF_3$ | H | 3-$CF_3$ | 4-(—CONH—) | cyclopropyl | HPLC-MS: logP = 2.07; mass (m/z): 519.45 (M + H)+; 1H NMR (400 MHz, $d_6$-DMSO): 9.60 (dd, 1H), 8.53 (m, 1H), 8.00-7.95 (m, 2H), 7.90 (d, 1H), 7.78 (m, 1H), 7.73 (m, 1H), 7.68-7.63 (m, 2H), 7.53 (m, 1H), 6.97 (m, 1H), 6.08 (m, 1H), 2.78 (m, 3H), 0.70 (m, 2H), 0.50 (m, 2H) |
| Ia-243 | 3-$SO_2CH_3$ | H | 3-$CF_3$ | 4-(—CONH—) | cyclopropyl | HPLC MS: logP = 2.31; mass (m/z): 535.47(M + H)+; |
| Ia-244 | 3-$SO_2CH_3$ | H | 3-$CF_3$ | 4-(—CONH—) | pyridin-2-yl | HPLC-MS: logP = 2.62; mass (m/z): 572.48 (M + H)+; 1H NMR (400 MHz, $d_6$-DMSO): 11.16 (s, 1H), 9.61 (d, 1H), 8.36 (s, 1H, br), 8.24 (s, 1H), 8.15 (m, 1H), 8.06 (s, 1H), 8.03-7.96 (m, 3H), 7.82 (m, 1H), 7.76-7.71 (m, 2H), 7.70 (d, 1H, J = 16 Hz), 7.18 (dd, 1H), 7.00 (d, 1H, J = 16 Hz), 6.20 (m, 1H), 3.27 (s, 3H) |
| Ia-245 | 3-$SOCH_3$ | H | 3-$CF_3$ | 4-(—$CH_2$NHCO—) | methyl | HPLC-MS: logP = 1.98; mass (m/z): 507.49 (M + H)+; |
| Ia-246 | 3-Cl | H | 3-$CF_3$ | 4-(—CONH—) | pyridin-2-yl | HPLC-MS: logP = 3.37; mass (m/z): 528.38 (M + H)+; 1H NMR (400 MHz, d3-CD3CN): 8.60 (d, 1H), 8.32 (d, 1H), 8.21 (d, 1H), 7.98 (s, 1H), 7.92 (d, 1H), 7.83 (m, 1H), 7.72 (d, 1H), 7.68 (d, 1H, J = 16 Hz), 7.61 (s, 1H), 7.51-7.45 (m, 4H), 7.16 (dd, 1H), 6.90 (d, 1H, J = 16 Hz), 5.90 (m, 1H) |
| Ia-247 | 3-$CF_3$ | H | 3-$CF_3$ | 4-(—$CH_2$NHCO—) | methyl | HPLC-MS: logP = 3.24; mass (m/z): 513.1 (M + H)+; 1H NMR (400 MHz, d3-CD3CN): 7.87 (m, 2H), 7.82-7.76 (m, 4H), 7.67-7.62 (m, 2H), 7.55 (d, 1H), 6.87 (s, 1H, br), 6.75 (d, 1H, |

TABLE 1-continued (Ia)

where $R^2$, $R^4$ and $R^5$ are each H, X is $CF_3$ and $(R^1)_n$, $R^3$, $(R^1)_m$, A and Y are each as defined in Table 1. The numbers 2 to 6 represent the positions on the aromatic rings.

| No. | $(R^1)_n$ | R3 | $(R^6)_n$ | A | Y | HPLC-MS[a]; $^1$H NMR (δ in ppm)[b] |
|---|---|---|---|---|---|---|
| Ia-248 | 3-$CF_3$ | H | 3-Cl | 4-(—$CH_2$NHCO—) | methyl | J = 16 Hz), 6.00 (m, 1H), 4.51 (d, 2H), 2.50 (s, 3H) HPLC-MS: logP = 3.06; mass (m/z): 479.1 (M + H)+; 1H NMR (400 MHz, d3-CD3CN): 7.82 (s, 1H), 7.80-7.75 (m, 3H), 7.65 (dd, 1H), 7.60 (s, 1H), 7.55 (d, 1H, J = 16 Hz), 7.50 (d, 1H), 7.38 (d, 1H), 6.85 (s, 1H, br), 6.69 (d, 1H, J = 16 Hz), 6.00 (m, 1H), 4.40 (d, 2H), 2.50 (s, 3H) |
| Ia-249 | 3-$CF_3$ | H | 3-$CH_3$ | 4-(—$CH_2$NHCO—) | methyl | HPLC-MS: logP = 2.9; mass (m/z): 459.1 (M + H)+; 1H NMR (400 MHz, d3-CD3CN): 7.86 (s, 1H), 7.80 (d, 1H), 7.77 (d, 1H), 7.72 (d, 1H), 7.66 (dd, 1H), 7.56 (d, 1H, J = 16 Hz), 7.39 (m, 2H), 7.25 (d, 1H), 6.71 (s, 1H, br), 6.64 (d, 1H, J = 16 Hz), 5.99 (m, 1H), 4.31 (d, 2H), 2.31 (s, 3H) |
| Ia-250 | 3-$CF_3$ | H | 3-F | 4-(—$CH_2$NH—) | pyridin-2-ylmethyl | HPLC-MS: logP = ; mass (m/z): 512.5 (M + H)+; 1H NMR (400 MHz, d3-CD3CN): 8.50 (d, 1H), 7.87 (s, 1H), 7.80-7.65 (m, 5H), 7.58 (d, 1H, J = 16 Hz), 7.50 (dd, 1H), 7.38 (m, 1H), 7.30 (d, 1H), 7.20 (dd, 1H), 6.67 (d, 1H, J = 16 Hz), 6.00 (m, 1H), 3.86 (m, 4H), 2.40-2.20 (s, 1H, br) |
| Ia-251 | 3-Cl, 4-F | H | 3-$CF_3$ | 4-(—$CH_2$NH—) | ethyl | HPLC-MS: logP = 3.47; mass (m/z): 511.1 (M + H)+; 1H NMR (d$_6$-DMSO) 9.39 (d, 1H), 8.36 (t, 1H), 7.90-7.85 (m, 2H), 7.70-7.60 (m, 2H), 7.53-7.49 (m, 2H), 6.88 (d, 1H, J = 16 Hz), 6.05 (m, 1H), 4.44 (d, 2H), 2.20 (q, 2H), 1.05 (t, 3H) |
| Ia-252 | 3-$CF_3$ | H | 3-F | 4-(—$CH_2$N(COCH$_3$)—) | pyridin-2-ylmethyl | HPLC-MS: logP = 2.72; mass (m/z): 554.49(M + H)+; 1H NMR (400 MHz, d3-CD3CN): 8.53 (d, 1H), 8.44 (d, 1H, rotamer), 7.87 (s, 1H), 7.80-7.65 (m, 5H), 7.55 (m, 1H), 7.40-7.20 (m, 5H), 6.70-6.65 (m, 1H), 5.99 (m, 1H), 4.69 (s, 2H, rotamer), 4.61-4.57 (m, 4H), 1.09 (s, 3H, isomer), 1.08 (s, 3H) |
| Ia-253 | 3-$CF_3$ | H | 3-F | 4-(—$CH_2$N(COiPr)—) | pyridin-2-ylmethyl | HPLC-MS: logP = 3.37; mass (m/z): 582.48 (M + H)+; 1H NMR (400 MHz, d3-CD3CN): 8.53 (m, 1H), 8.48 (m, 1H, rotamer), 7.85 (s, 1H), 7.70-7.50 (m, 7H), 7.30-7.20 (m, 4H), 6.65 (m, 1H), 6.00 (m, 1H), 4.71 (s, 2H, rotamer), 4.65-4.60 (m, 4H), 2.90 (m, 1H), 1.05 (m, 6H) |
| Ia-254 | 3-$CF_3$ | H | H | 4-(—$CH_2$N(COCH$_3$)—) | pyridin-2-ylmethyl | HPLC-MS: logP = 2.65; mass (m/z): 536.43(M + H)+; 1H NMR (400 MHz, d3-CD3CN): 8.53 (m, 1H), 8.47 (m, 1H, rotamer), 7.87 (s, 1H), 7.70-7.50 (m, 9H), 7.30-7.20 (m, 3H), 6.70-6.65 (m, 1H), 6.00 (m, 1H), 4.66 (s, 2H, rotamer), 4.57-4.59 (m, 4H), 1.08 (m, 3H) |

TABLE 1-continued

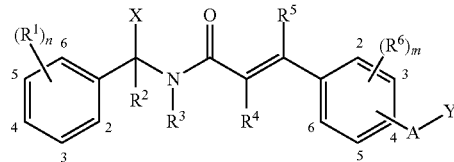

(Ia)

where $R^2$, $R^4$ and $R^5$ are each H, X is $CF_3$ and $(R^1)_n$, $R^3$, $(R^1)_m$, A and Y are each as defined in Table 1. The numbers 2 to 6 represent the positions on the aromatic rings.

| No. | $(R^1)_n$ | R3 | $(R^6)_n$ | A | Y | HPLC-MS[a]; $^1$H NMR (δ in ppm)[b] |
|---|---|---|---|---|---|---|
| Ia-255 | 3-$CF_3$ | H | 3-$CF_3$ | 4-(—CONH—) | 3-methylpyridin-2-yl | HPLC-MS: logP = 3.19; mass (m/z): 576.4(M + H)+; 1H NMR (400 MHz, d3-CD3CN): 8.80 (s, 1H, br), 8.22 (s, 1H), 8.00 (s, 1H), 7.90-7.85 (m, 3H), 7.80 (d, 1H), 7.75 (d, 1H), 7.70-7.65 (m, 4H), 7.20 (m, 1H), 6.83 (d, 1H, J = 16 Hz), 6.00 (m, 1H), 2.32 (s, 3H) |
| Ia-256 | 3-$SCF_3$ | H | 3-$CF_3$ | 4-(—CONH—) | cyclopropyl | HPLC-MS: logP = 3.51; mass (m/z): 557.3(M + H)+; 1H NMR (400 MHz, d3-CD3CN): 7.90 (m, 3H), 7.80-7.75 (m, 2H), 7.72 (d, 1H), 7.63 (d, 1H, J = 16 Hz), 7.60 (m, 1H), 7.45 (d, 1H), 6.97 (s, 1H), 6.79 (d, 1H, J = 16 Hz), 5.97 (m, 1H), 2.89 (m, 1H), 0.75 (m, 2H), 0.55 (m, 2H) |
| Ia-257 | 3-$CF_3$ | H | 3-$CF_3$ | 4-(—CON(Et)—) | cyclopropyl | HPLC-MS: logP = 3.89; mass (m/z): 553.4(M + H)+; 1H NMR (400 MHz, d3-CD3CN): 8.00 (d, 1H), 7.90 (s, 1H), 7.88 (s, 1H), 7.85-7.75 (m, 3H), 7.68 (m, 2H), 7.55 (d, 1H), 6.82 (d, 1H, J = 16 Hz), 6.00 (m, 1H), 3.52 (q, 2H), 1.50 (m, 1H), 1.20 (t, 3H), 0.93 (m, 1H), 0.55 (m, 4H) |
| Ia-258 | 3-$CF_3$ | H | 3-$CF_3$ | 4-(—CON(cPr)—) | pyridin-3-ylmethyl | HPLC-MS: logP = 2.8; mass (m/z): 616.4 (M + H)+; 1H NMR (400 MHz, d3-CD3CN): 8.61 (s, 1H), 8.52 (m, 1H), 8.20 (d, 1H), 7.93 (s, 1H), 7.89 (s, 1H), 7.85-7.80 (m, 2H), 7.75 (m, 2H), 7.65 (m, 2H), 7.50 (d, 1H), 7.35 (dd, 1H), 6.84 (d, 1H, J = 16 Hz), 6.00 (m, 1H), 4.75-4.70 (s, 2H, br), 1.40-1.30 (m, 1H), 0.50 (m, 4H) |
| Ia-259 | 3-$CF_3$ | H | 3-$CF_3$ | 4-(—CONH—) | 4-methylpyridin-2-yl | HPLC-MS: logP = 3.61; mass (m/z): 576.4(M + H)+; 1H NMR (400 MHz, d3-CD3CN): 9.40 (s, 1H, br), 8.09 (s, 1H), 8.05 (s, 1H), 7.95 (d, 1H), 7.90 (s, 1H), 7.86 (m, 2H), 7.80 (d, 1H), 7.75 (d, 1H), 7.65 (m, 2H), 7.59 (d, 1H), 6.96 (m, 1H), 6.81 (d, 1H, J = 16 Hz), 6.08 (m, 1H), 2.39 (s, 3H) |
| Ia-260 | 3-$CF_3$ | H | 3-$CF_3$ | 4-(—CONH—) | 4-cyanopyridin-2-yl | HPLC-MS: logP = 3.61; mass (m/z): 587.4(M + H)+; 1H NMR (400 MHz, d3-CD3CN): 9.43 (s, 1H, br), 8.50 (m, 2H), 8.00 (s, 1H), 7.93 (d, 1H), 7.88 (m, 2H), 7.80 (d, 1H), 7.75 (d, 1H), 7.73-7.65 (m, 3H), 7.45 (dd, 1H), 6.85 (d, 1H, J = 16 Hz), 6.02 (m, 1H) |
| Ia-261 | 3-$CF_3$ | H | 3-$CF_3$ | 4-(—CONH—) | trans-2-methyl-cyclopropyl | HPLC-MS: logP = 3.46; mass (m/z): 539.4(M + H)+; 1H NMR (400 MHz, d3-CD3CN): 7.90-7.78 (m, 6H), 7.65 (m, 3H), 7.50 (d, 1H), 6.90 (s, 1H), 6.78 (d, 1H, J = 16 Hz), 6.00 (m, 1H), 2.45 (m, 1H), 1.10 (d, 3H), 0.93 (m, 1H), 0.70 (m, 1H), 0.55 (m, 1H) |

TABLE 1-continued (Ia)

where $R^2$, $R^4$ and $R^5$ are each H, X is $CF_3$ and $(R^1)_n$, $R^3$, $(R^1)_m$, A and Y are each as defined in Table 1. The numbers 2 to 6 represent the positions on the aromatic rings.

| No. | $(R^1)_n$ | R3 | $(R^6)_n$ | A | Y | HPLC-MS[a]; $^1$H NMR (δ in ppm)[b] |
|---|---|---|---|---|---|---|
| Ia-262 | 3-$CF_3$ | H | 3-$CF_3$ | 4-(—CONHCH$_2$CONH—) | 2,2,2-trifluoroethyl | HPLC-MS: logP = 3.11; mass (m/z): 624.4(M + H)+; 1H NMR (400 MHz, d3-CD3CN): 7.94 (s, 1H), 7.88 (m, 2H), 7.85-7.75 (m, 3H), 7.70-7.60 (m, 3H), 7.20 (t, 1H), 7.00 (s, 1H, br), 6.80 (d, 1H, J = 16 Hz), 6.00 (m, 1H), 4.01 (d, 2H), 3.95 (m, 2H) |
| Ia-263 | 3-$CF_3$ | H | 3-$CF_3$ | 4-(—CH$_2$NH—) | pyridin-2-yl | HPLC-MS: logP = 2.2; mass (m/z): 548.4(M + H)+; 1H NMR (400 MHz, d3-CD3CN): 7.97 (d, 1H), 7.88 (s, 1H), 7.86 (s, 1H), 7.70-7.60 (m, 4H), 7.65-7.60 (m, 3H), 7.40 (dd, 1H), 6.73 (d, 1H, J = 16 Hz), 6.56 (dd, 1H), 6.53 (d, 1H), 6.02 (m, 1H), 5.72 (m, 1H, br), 4.73 (d, 2H) |
| Ia-264 | 3-$CF_3$ | H | 3-$CF_3$ | 4-(—CH$_2$NH—) | 4-chloropyridin-2-yl | HPLC-MS: logP = 4.28; mass (m/z): 582.3(M + H)+; 1H NMR (400 MHz, d3-CD3CN): 7.90-7.88 (m, 3H), 7.80-7.750 (m, 4H), 7.65-7.60 (m, 3H), 6.74 (d, 1H, J = 16 Hz), 6.60 (dd, 1H), 6.56 (d, 1H), 6.01 (m, 1H), 5.98 (t, 1H, br), 4.73 (d, 2H) |
| Ia-265 | 3-$CF_3$ | H | H | 4-(—CH$_2$NH—) | 4-chloropyridin-2-yl | HPLC-MS: logP = 3.15; mass (m/z): 514.4(M + H)+; 1H NMR (400 MHz, d3-CD3CN): 7.92 (d, 1H), 7.85 (d, 1H), 7.80-7.70 (m, 3H), 7.65 (t, 1H), 7.60 (d, 1H), 7.53 (d, 2H), 7.36 (d, 2H), 6.66 (d, 1H, J = 16 Hz), 6.57 (m, 1H), 6.49 (d, 1H), 6.02 (m, 1H), 5.92 (t, 1H), 4.53 (d, 2H) |
| Ia-266 | 3-$CF_3$ | H | 3-$CF_3$ | 4-(—CH$_2$NHCO—) | isopropyl | See Synthesis Example 16, Stage 6 |
| Ia-267 | 3-$CF_3$ | H | 3-$CF_3$ | 4-(—CH$_2$NHCO—) | cyclobutyl | HPLC-MS: logP = 3.9; mass (m/z): 553.2(M + H)+; 1H NMR (d$_6$-DMSO 9.49 (d, 1H), 8.25 (t, 1H), 8.05 (s, 1H), 7.95 (m, 2H), 7.87 (d, 1H), 7.81 (d, 1H), 7.70 (t, 1H), 7.61 (d, 1H, J = 16 Hz), 7.48 (d, 1H), 6.90 (d, 1H, J = 16 Hz), 6.15 (m, 1H), 4.43 (d, 2H), 3.10 (m, 1H), 2.20-2.00 (m, 4H), 1.90-1.80 (m, 2H) |
| Ia-268 | 3-$CF_3$ | H | 3-$CF_3$ | 4-(—CH$_2$NHCO—) | thien-3-yl | HPLC-MS: logP = 3.92; mass (m/z): 581.1 (M + H)+; 1H NMR (d$_6$-DMSO) 9.50 (d, 1H), 8.94 (t, 1H), 8.22 (dd, 1H), 8.05 (s, 1H), 7.95-7.87 (m, 3H), 7.81 (d, 1H), 7.70 (t, 1H), 7.62-7.58 (m, 2H), 7.55 (m, 2H), 6.90 (d, 1H, J = 16 Hz), 6.15 (m, 1H), 4.63 (d, 2H) |
| Ia-269 | 3-$CF_3$ | H | 3-$CF_3$ | 4-(—CH$_2$NHCO—) | 5-oxotetrahydro-furan-3-yl | HPLC-MS: logP = 3.34; mass (m/z): 583.1 (M + H)+; |
| Ia-270 | 3-$CF_3$ | H | 3-$CF_3$ | 4-(—CH$_2$NHCO—) | methylthiomethyl | HPLC-MS: logP = 3.84; mass (m/z): 599.2(M + H)+; 1H NMR (d$_6$-DMSO) 9.46 (d, 1H), 8.44 (t, 1H), 8.05 (s, 1H), 7.95 (m, 2H), 7.85-7.80 (m, 2H), 7.70 (t, 1H), 7.62 (d, 1H, J = 16 Hz), 7.50 (d, 1H), 6.90 (d, 1H, J = 16 Hz), |

TABLE 1-continued

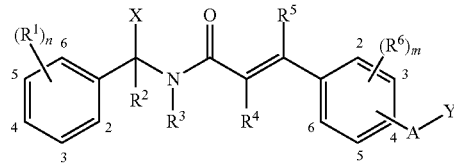

(Ia)

where $R^2$, $R^4$ and $R^5$ are each H, X is $CF_3$ and $(R^1)_n$, $R^3$, $(R^1)_m$, A and Y are each as defined in Table 1. The numbers 2 to 6 represent the positions on the aromatic rings.

| No. | $(R^1)_n$ | R3 | $(R^6)_n$ | A | Y | HPLC-MS[a]; $^1$H NMR (δ in ppm)[b] |
|---|---|---|---|---|---|---|
| Ia-271 | 3-CF$_3$ | H | 3-CF$_3$ | 4-(—CH$_2$NHSO$_2$—) | cyclopropyl | 6.16 (m, 1H), 4.44 (d, 2H), 2.04 (s, 3H), 1.53 (s, 6H) HPLC-MS: logP = 3.74; mass (m/z): 575.1 (M + H)+; 1H NMR (d$_6$-DMSO) 9.50 (d, 1H), 8.05 (s, 1H), 7.95 (m, 2H), 7.85-7.80 (m, 3H), 7.70 (t, 1H), 7.61 (d, 1H, J = 16 Hz), 6.90 (d, 1H, J = 16 Hz), 6.16 (m, 1H), 4.38 (d, 2H), 2.55 (m, 1H), 0.89 (m, 4H) |
| Ia-272 | 3-CF$_3$, 4-F | H | 3-CF$_3$ | 4-(—CH$_2$NHCO—) | ethyl | HPLC-MS: logP = 3.61; mass (m/z): 545.2(M + H)+; 1H NMR (d$_6$-DMSO) 9.49 (d, 1H), 8.36 (t, 1H), 8.12 (m, 1H), 8.05 (m, 1H), 7.94 (s, 1H), 7.88 (d, 1H), 7.67-7.60 (m, 2H), 7.53 (d, 1H), 6.88 (d, 1H, J = 16 Hz), 6.19 (m, 1H), 4.44 (d, 1H), 2.22 (q, 2H), 1.05 (t, 2H) |
| Ia-273 | 3-CF$_3$ | H | 3-F | 4-(—CH(CH$_3$)NHCO—) | ethyl | HPLC-MS: logP = 3.3; mass (m/z): 491.2(M + H)+; 1H NMR (d$_6$-DMSO) 9.47 (d, 1H), 8.28 (d, 1H), 8.05 (s, 1H), 7.95 (d, 1H), 7.80 (d, 1H), 7.70 (t, 1H), 7.52 (d, 1H, J = 16 Hz), 7.41-7.38 (m, 2H), 6.80 (d, 1H, J = 16 Hz), 6.15 (m, 1H), 5.10 (m, 1H), 2.13 (q, 2H), 0.98 (t, 2H) |
| Ia-274 | 3-Cl, 4-F | H | 3-F | 4-(—CH(CH$_3$)NHCO—) | ethyl | HPLC-MS: logP = 3.23; mass (m/z): 475.2(M + H)+; 1H NMR (d$_6$-DMSO) 9.37 (d, 1H), 8.28 (d, 1H), 7.90 (m, 1H), 7.68 (m, 1H), 7.55-7.49 (m, 2H), 7.40-7.35 (m, 3H), 6.78 (d, 1H, J = 16 Hz), 6.05 (m, 1H), 5.10 (m, 1H), 2.13 (q, 2H), 1.33 (d, 3H), 0.98 (t, 3H) |
| Ia-275 | 3-CF$_3$, 4-F | H | 3-F | 4-(—CH(CH$_3$)NHCO—) | ethyl | HPLC-MS: logP = 3.38; mass (m/z): 509.2(M + H)+; 1H NMR (d$_6$-DMSO) 9.46 (d, 1H), 8.28 (d, 1H), 8.13 (m, 1H), 8.05 (m, 1H), 7.64 (t, 1H), 7.52 (d, 1H, J = 16 Hz), 7.41-7.37 (m, 3H), 6.77 (d, 1H, J = 16 Hz), 6.19 (m, 1H), 5.10 (m, 1H), 2.13 (q, 2H), 1.33 (d, 3H), 0.98 (t, 3H) |
| Ia-276 | 3-CF$_3$ | H | 3-F | 4-(—CH$_2$NHCO—) | ethyl | HPLC-MS: logP = 3.12; mass (m/z): 477.2(M + H)+; 1H NMR (d$_6$-DMSO) 9.47 (d, 1H), 8.27 (t, 1H), 8.05 (s, 1H), 7.94 (d, 1H), 7.80 (d, 1H), 7.71 (t, 1H), 7.52 (d, 1H, J = 16 Hz), 7.40 (m, 2H), 7.35 (t, 1H), 6.80 (d, 1H, J = 16 Hz), 6.15 (m, 1H), 4.29 (d, 2H), 2.15 (q, 2H), 1.02 (t, 3H) |
| Ia-277 | 3-Cl, 4-F | H | 3-F | 4-(—CH$_2$NHCO—) | ethyl | HPLC-MS: logP = 3.06; mass (m/z): 461.2(M + H)+; 1H NMR (d$_6$-DMSO) 9.37 (d, 1H), 8.27 (t, 1H), 7.90 (d, 1H), 7.65 (m, 1H), 7.54-7.50 (m, 2H), 7.43-7.39 (m, 2H), 7.35 (t, 1H), 6.79 (d, 1H, J = 16 Hz), 6.05 (m, 1H), 4.30 (d, 2H), 2.15 (q, 2H), 1.02 (t, 3H) |

TABLE 1-continued (Ia)

$$\text{(R}^1)_n \text{—C}_6\text{H}_3\text{—CX(R}^2)\text{—N(R}^3)\text{—C(=O)—C(R}^4)=\text{C(R}^5)\text{—C}_6\text{H}_3\text{—(R}^6)_m\text{—A—Y}$$

where $R^2$, $R^4$ and $R^5$ are each H, X is $CF_3$ and $(R^1)_n$, $R^3$, $(R^1)_m$, A and Y are each as defined in Table 1. The numbers 2 to 6 represent the positions on the aromatic rings.

| No. | $(R^1)_n$ | R3 | $(R^6)_n$ | A | Y | HPLC-MS[a]; $^1$H NMR (δ in ppm)[b] |
|---|---|---|---|---|---|---|
| Ia-278 | 3-$CF_3$, 4-F | H | 3-$CF_3$ | 4-(—$CH_2$NHCO—) | ethyl | HPLC-MS: logP = 3.21; mass (m/z): 495.1 (M + H)+; 1H NMR ($d_6$-DMSO) 9.46 (d, 1H), 8.27 (t, 1H), 8.12 (d, 1H), 8.02 (m, 1H), 7.62 (t, 1H), 7.52 (d, 1H, J = 16 Hz), 7.41-7.38 (m, 2H), 7.31 (t, 1H), 6.79 (d, 1H, J = 16 Hz), 6.19 (m, 1H), 4.29 (d, 2H), 2.15 (q, 2H), 1.01 (t, 3H) |
| Ia-279 | 3-Cl, 4-F | H | 3-$CF_3$ | 4-(—CONH—) | cyclopropyl | HPLC-MS: logP = 3.33; mass (m/z): 509.1 (M + H)+; 1H NMR ($d_6$-DMSO) 9.42 (d, 1H), 8.55 (d, 1H), 8.00 (s, 1H), 7.90 (m, 2H), 7.65-7.60 (m, 2H), 7.55-7.50 (m, 2H), 6.93 (d, 1H, J = 16 Hz), 6.05 (m, 1H), 2.75 (m, 1H), 0.70 (m, 2H), 0.50 (m, 2H) |
| Ia-280 | 3-$CF_3$, 4-F | H | 3-$CF_3$ | 4-(—CONH—) | cyclopropyl | HPLC-MS: logP = 3.46; mass (m/z): 543.1 (M + H)+; 1H NMR ($d_6$-DMSO) 9.50 (d, 1H), 8.55 (d, 1H), 8.12 (m, 1H), 8.05 (m, 1H), 8.00 (s, 1H), 7.92 (d, 1H), 7.67-7.60 (m, 2H), 7.54 (d, 1H), 6.93 (d, 1H, J = 16 Hz), 6.19 (m, 1H), 2.78 (m, 1H), 0.70 (m, 2H), 0.50 (m, 2H) |
| Ia-281 | 3-$CF_3$, 4-F | H | 3-$CF_3$ | 4-(—CON($CH_3$)—) | pyridin-2-yl | HPLC-MS: logP = 3.63; mass (m/z): 594.03(M + H)+; 1H NMR (400 MHz, d3-CD3CN): 8.30 (s, 1H, br), 7.90 (m, 2H), 7.83 (m, 1H), 7.75 (m, 2H), 7.70-7.50 (m, 5H, br), 7.41 (dd, 1H), 7.12 (s, 1H, br), 6.72 (d, 1H, br), 5.97 (m, 1H), 3.40 (s, 3H, br) |
| Ia-282 | 3-$CF_3$, 4-F | H | H | 4-(—$CH_2$NHCO—) | ethyl | HPLC-MS: logP = 3.11; mass (m/z): 476.99(M + H)+; 1H NMR (400 MHz, $d_6$-DMSO): 9.45 (d, 1H), 8.31 (t, 1H), 8.14 (d, 1H), 8.05 (m, 1H), 7.65 (t, 1H), 7.57-7.52 (m, 3H), 7.29 (d, 2H), 6.76 (d, 1H, J = 16 Hz), 6.20 (m, 1H), 4.28 (d, 2H), 2.16 (q, 2H), 1.03 (t, 3H). |
| Ia-283 | 3,4,5-$Cl_3$ | H | 3-$CF_3$ | 4-(CONH—) | cyclopropyl | HPLC-MS: logP = 4.1; mass (m/z): 559.1 (M + H)+; 1H NMR ($d_6$-DMSO): 0.50 (m, 2H), 0.69 (m, 2H), 2.78 (m, 1H), 6.15 (p, 1H), 6.92 (d, 1H), 7.55 (d, 1H), 7.66 (d, 1H), 7.93 (br. d, 1H), 8.01 (m, 3H), 8.54 (d, 1H), 9.43 ppm (d, 1H). |
| Ia-284 | 3-Br | H | 3-$CF_3$ | 4-(CONH—) | cyclopropyl | HPLC-MS: logP = 3.35; mass (m/z): 535 (M + H)+; 1H NMR ($d_6$-DMSO): 0.50 (m, 2H), 0.69 (m, 2H), 2.78 (m, 1H), 6.01 (p, 1H), 6.95 (d, 1H), 7.42 (t, 1H), 7.54 (d, 1H), 7.65 (m, 3H), 7.87 (m, 1H), 7.91 (d, 1H), 7.99 (m, 1H), 8.54 (d, 1H), 9.40 (d, 1H). |

TABLE 2

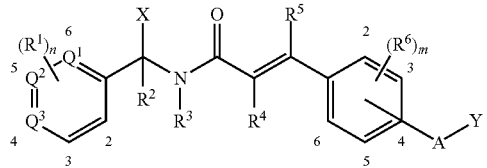

(Ib)

where $R^2$, $R^3$, $R^4$ and $R^5$ are each H, X is $CF_3$ and $Q^1$, $Q^2$, $Q^3$, $(R^1)_n$, $(R^6)_m$, A and Y are each as defined in Table 2. The numbers 2 to 6 represent the positions on the aromatic rings.

| No. | $(R^1)_n$ | $Q^1$ | $Q^2$ | $Q^3$ | $(R^6)_m$ | A | Y | HPLC-MS [a]; $^1H$ NMR ($\delta$ in ppm) [b] |
|---|---|---|---|---|---|---|---|---|
| Ib-1 | H | CH | CH | N | 3-$CF_3$ | 4-(—CONH—) | benzyl | HPLC-MS: logP = 3.02 mass (m/z): 509.0 (M + H)+; 1H NMR (400 MHz, $d_6$-DMSO): 9.09 (t, 1H), 8.71 (m, 2H), 8.26 (s, 1H), 8.17 (d, 1H), 7.97 (d, 1H, J = 16 Hz), 7.70-7.60 (m, 3H), 7.45 (m, 4H), 7.28 (m, 1H), 7.10 (d, 1H, J = 16 Hz), 6.73 (q, 1H), 4.46 (d, 2H) |
| Ib-2 | 3-$CF_3$ | CH | N | CH | 3-$CF_3$ | 4-(—CONH—) | pyridin-2-yl | HPLC-MS: logP = 3.02 mass (m/z): 563.2 (M + H)+; 1H NMR (400 MHz, d3-CD3CN): 9.28 (s, 1H, br), 8.97 (m, 2H), 8.90 (d, 1H), 8.28 (m, 1H), 8.20 (m, 2H), 7.97 (m, 2H), 7.90 (d, 1H), 7.85 (m, 1H), 7.70-7.65 (m, 2H), 7.15 (dd, 1H), 6.82 (d, 1H, J = 16 Hz), 6.13 (m, 1H) |
| Ib-3 | 3-$CF_3$ | CH | N | CH | 3-$CF_3$ | 4-(—CONH—) | cyclopropyl | HPLC-MS: logP = 2.83; mass (m/z): 526.51 (M + H)+; 1H NMR (400 MHz, d6-DMSO): 9.60 (d, 1H), 9.19 (s, 1H), 9.09 (s, 1H), 8.59 (d, 1H), 8.55 (s, 1H), 8.02 (s, 1H), 7.93 (dd, 1H), 7.67 (d, 1H, J = 16 Hz), 7.55 (d, 1H), 6.90 (d, 1H, J = 16 Hz), 6.38 (m, 1H), 0.70 (m, 2H), 0.50 (m, 2H) |
| Ib-4 | 3-$CF_3$ | CH | N | CH | 3-$CF_3$ | 4-(—$CH_2$NHCO—) | cyclopropyl | HPLC-MS: logP = 3.11; mass (m/z): 540.49 (M + H)+; 1H NMR (400 MHz, d6-DMSO): 9.60 (d, 1H), 9.19 (s, 1H), 9.08 (s, 1H), 8.70 (m, 1H), 8.56 (s, 1H), 7.96 (s, 1H), 7.93 (dd, 1H), 7.64 (d, 1H), 7.54 (d, 1H), 6.88 (d, 1H, J = 16 Hz), 6.35 (m, 1H), 4.47 (d, 1H), 1.70 (m, 2H), 0.70 (m, 4H) |

TABLE 3

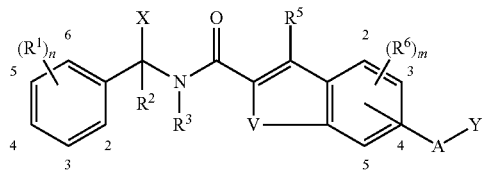

(Ic)

where $R^2$ and $R^5$ are each H, X is CF3 and $(R^1)_n$, $R^3$, V, $(R^6)_m$, A and Y are each as defined in Table 3. The numbers 2 to 6 or 2 to 5 represent the positions on the aromatic rings.

| No. | $(R^1)_n$ | $R^3$ | V | $(R^6)_m$ | A | Y | HPLC-MS [a]; $^1H$ NMR ($\delta$ in ppm) [b] |
|---|---|---|---|---|---|---|---|
| Ic-1 | 3-$CF_3$ | H | O | H | | 3-CN | See Synthesis Example 6, Stage 1 |
| Ic-2 | 3-$CF_3$ | H | O | H | 3-(—S—) | $CF_3$ | HPLC-MS: logP = 4.94; mass (m/z): 488.0 (M + H)+; 1H NMR (CD3CN) 6.13 (m, 1H), 7.60-7.90 (m, 5H), 7.97-7.98 (m, 1H), 8.15 (m, 1H), 8.24-8.27 (m, 1H). |
| Ic-3 | 3-$CF_3$ | H | O | H | | 4-CN | HPLC-MS: logP = 3.72; mass (m/z): 413.1 (M + H)+; 1H NMR (CD3CN) 6.13 (m, 1H), 7.57-8.05 (m, 8H), 8.33-8.35 (m, 1H). |

TABLE 3-continued

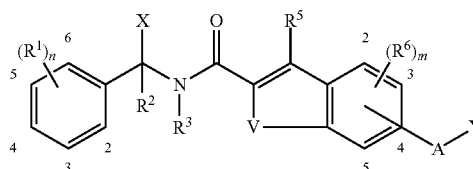

(Ic)

where $R^2$ and $R^5$ are each H, X is CF3 and $(R^1)_n$, $R^3$, V, $(R^6)_m$, A and Y are each as defined in Table 3. The numbers 2 to 6 or 2 to 5 represent the positions on the aromatic rings.

| No. | $(R^1)_n$ | $R^3$ | V | $(R^6)_m$ | A | Y | HPLC-MS [a]; $^1$H NMR (δ in ppm) [b] |
|---|---|---|---|---|---|---|---|
| Ic-4 | 3-CF$_3$ | H | NH | H | | 3-CN | HPLC-MS: logP = 3.48; mass (m/z): 412.1 (M + H)$^+$; $^1$H NMR (CD$_3$CN) 6.12 (m, 1H), 7.35 (s, 1H), 7.50-7.53 (m, 1H), 7.59-7.67 (m, 2H), 7.74-7.76 (m, 1H), 7.85-7.90 (m, 1H), 7.94 (m, 1H), 8.14 (m, 1H), 10.22 (s, 1H). |
| Ic-5 | 3,4-Cl$_2$ | H | O | H | | 3-CN | HPLC-MS: logP = 3.95; mass (m/z): 413.0 (M + H)$^+$; $^1$H NMR (CD$_3$CN) 5.99 (m, 1H), 7.51-7.53 (m, 1H), 7.58-7.61 (m, 2H), 7.72-7.80 (m, 3H), 8.03-8.05 (m, 1H), 8.16 (m, 1H). |
| Ic-6 | 3-CF$_3$ | H | O | H | 3-(—CONH—) | H | HPLC-MS: logP = 2.69; mass (m/z): 431.1 (M + H)$^+$; $^1$H NMR (CD$_3$CN) 6.03 (br. s, 1H), 6.13 (m, 1H), 6.81 (br. s, 1H), 7.63-7.99 (m, 7H), 8.24-8.25 (m, 2H). |
| Ic-7 | 2,4-Cl$_2$ | H | O | H | | 3-CN | HPLC-MS: logP = 4.04; mass (m/z): 413.0 (M + H)$^+$; $^1$H NMR (CD$_3$CN) 6.48 (m, 1H), 7.48-7.50 (m, 1H), 7.62-7.63 (m, 2H), 7.74-7.82 (m, 3H), 8.19-8.22 (m, 2H). |
| Ic-8 | 3-CF$_3$ | H | NH | H | | 4-CN | HPLC-MS: logP = 3.51; mass (m/z): 412.0 (M + H)$^+$; $^1$H NMR (CD$_3$CN) 6.16 (quint, 1H), 7.33-7.40 (m, 2H), 7.63-7.69 (m, 2H), 7.77-7.79 (m, 1H), 7.84-7.97 (m, 3H), 8.07-8.09 (m, 1H), 10.34 (s, 1H). |
| Ic-9 | 3-CF$_3$ | H | NH | 5-SO$_2$CH$_3$ | 3-(—SO$_2$—) | CH$_3$ | HPLC-MS: logP = 2.92; mass (m/z): 465.0 (M + H)$^+$; $^1$H NMR (CD$_3$CN) 3.05 (s, 3H), 6.13 (quint, 1H), 7.43-7.44 (m, 1H), 7.64-7.68 (m, 2H), 7.75-7.78 (m, 2H), 7.86-7.88 (m, 1H), 7.95-8.00 (m, 2H), 8.34 (m, 1H), 10.10 (s, 1H). |
| Ic-10 | 3-CF$_3$ | H | O | H | 3-(—CH$_2$NHCO—) | CH$_3$ | See Synthesis Example 6, Stage 3 |
| Ic-11 | 3-Cl, 5-CF$_3$ | H | NH | H | | 3-CN | HPLC-MS: logP = 3.90; mass (m/z): 446.0 (M + H)$^+$; $^1$H NMR (CD$_3$CN) 6.16 (quint, 1H), 7.37-7.38 (m, 1H), 7.53-7.55 (m, 1H), 7.61-7.64 (m, 1H), 7.82 (s, 1H), 7.91-7.93 (m, 1H), 8.03-8.05 (m, 1H), 8.17-8.18 (m, 1H), 10.34 (s, 1H). |
| Ic-12 | 3-CF$_3$ | H | O | H | 3-(—CH$_2$NHCO—) | pyridin-2-yl | HPLC-MS: logP = 3.62; mass (m/z): 522.1 (M + H)$^+$; $^1$H NMR (CD$_3$CN) 4.69 (d, 2H), 6.13 (quint, 1H), 7.49-7.56 (m, 3H), 7.64-7.78 (m, 3H), 7.87-7.98 (m, 3H), 8.11-8.13 (m, 1H), 8.19-8.22 (m, 1H), 8.56-8.59 (m, 1H), 8.69 (br. s, 1H). |
| Ic-13 | 3-CF$_3$ | H | O | H | 3-(—CH$_2$NHCO—) | 2-propen-1-yl | HPLC-MS: logP = 3.24; mass (m/z): 485.1 (M + H)$^+$; $^1$H NMR (CD$_3$CN) 1.77-1.83 (m, 1H), 2.97-2.99 (m, 1H), 4.42 (d, 1H), 4.47 (d, 2H), 5.11-5.19 (m, 1H), 5.92-6.01 (m, 1H), 6.13 (quint, 1H), 6.72-6.77 (m, 1H), 6.90 (br. s, 1H), 7.39-7.42 (m, 1H), 7.50-7.55 (m, 2H), 7.61-7.69 (m, 2H), 7.76-7.78 (m, 1H), 7.88-7.90 (m, 1H), |

TABLE 3-continued

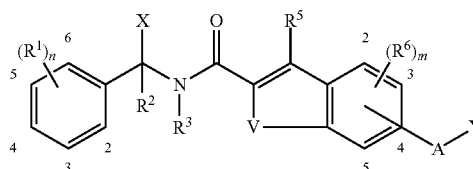

(Ic)

where $R^2$ and $R^5$ are each H, X is CF3 and $(R^1)_n$, $R^3$, V, $(R^6)_m$, A and Y are each as defined in Table 3. The numbers 2 to 6 or 2 to 5 represent the positions on the aromatic rings.

| No. | $(R^1)_n$ | $R^3$ | V | $(R^6)_m$ | A | Y | HPLC-MS [a]; $^1$H NMR ($\delta$ in ppm) [b] |
|---|---|---|---|---|---|---|---|
| Ic-14 | 3-CF$_3$ | H | O | H | 3-(—CH$_2$NHCO—) | ethyl | 7.97-7.99 (m, 1H), 8.21-8.23 (m, 1H). HPLC-MS: logP = 3.09; mass (m/z): 473.1 (M + H)$^+$; $^1$H NMR (d$_6$-DMSO) 1.03 (t, 3H), 2.15. (q, 2H), 4.36 (d, 2H), 6.30 (quint, 1H), 7.38-7.41 (m, 1H), 7.66-7.83 (m, 5H), 8.06-8.08 (m, 1H), 8.24 (s, 1H), 8.32-8.35 (m, 1H), 9.93-9.95 (m, 1H). |
| Ic-15 | 3-CF$_3$ | H | NH | H | | 4-CN | HPLC-MS: logP = 3.57; mass (m/z): 430.1 (M + H)$^+$; $^1$H NMR (CD$_3$CN) 6.15 (quint, 1H), 7.36-7.39 (m, 2H), 7.65-7.69 (m, 1H), 7.76-7.78 (m, 1H), 7.87-7.89 (m, 1H), 7.97 (m, 1H), 8.05-8.08 (m, 1H), 8.13-8.15 (m, 1H), 10.41 (s, 1H). |
| Ic-16 | 3-CF$_3$ | H | O | 6-F | 3-(—CONH—) | H | HPLC-MS: logP = 2.88; mass (m/z): 449.1 (M + H)$^+$; $^1$H NMR (CD$_3$CN) 6.12 (quint, 1H), 6.32 (br. s, 1H), 6.77 (br. s, 1H), 7.48 (d, 1H), 7.61 (s, 1H), 7.65-7.69 (m, 1H), 7.77-7.79 (m, 1H), 7.98 (m, 1H), 8.22-8.29 (m, 2H). |
| Ic-17 | 3-CF$_3$ | H | NH | H | 3-(SO$_2$—) | CF3 | HPLC-MS: logP = 4.19; mass (m/z): 517.1 (M + H)+; 1H NMR (CD$_3$CN) 6.13-6.19 (m, 1H), 7.55 (s, 1H), 7.66-7.70 (m, 1H), 7.77-7.90 (m, 3H), 7.98 (s, 1H), 8.23 (br. s, 1H), 8.58-8.59 (m, 1H), 10.69 (s, 1H). |
| Ic-18 | 3-CF$_3$ | H | NH | 5-Cl | 4-(—CONH—) | cyclo-propyl | HPLC-MS: logP = 2.98; mass (m/z): 504.02; 1H NMR (d6-DMSO) 11.80 (s, 1H), 9.50 (s, 1H, br), 8.63 (d, 1H), 7.99 (s, 1H), 7.89 (d, 1H), 7.75 (m, 2H), 7.67 (t, 1H), 7.51 (s, 1H), 7.30 (s, 1H), 6.15 (m, 1H), 2.88 (m, 1H), 0.81 (m, 2H), 0.64 (m, 2H). |
| Ic-19 | 3-CF$_3$ | H | O | H | 4-(—CONH—) | cyclo-propyl | See Synthesis Example 7, Stage 6 |
| Ic-20 | 3-CF$_3$, 5-Cl | H | NH | 5-Cl | 4-(—CONH—) | cyclo-propyl | HPLC-MS: logP = 3.47; mass (m/z): 537.98; 1H NMR (400 MHz, d6-DMSO): 9.64 (d, 1H), 8.44 (d, 1H), 8.30-8.20 (m, 3H), 7.99 (s, 1H), 7.84 (s, 1H), 7.50 (s, 1H), 7.41 (s, 1H), 6.42 (m, 1H), 2.82 (m, 1H), 0.70 (m, 2H), 0.50 (m, 2H). |
| Ic-21 | 3,4-Cl$_2$ | H | NH | 5-Cl | 4-(—CONH—) | cyclo-propyl | HPLC-MS: logP = 3.28; mass (m/z): 505.91 |
| Ic-22 | 3,5-Cl$_2$ | H | NH | 5-Cl | 4-(—CONH—) | cyclo-propyl | HPLC-MS: logP = 3.42; mass (m/z): 505.95; 1H NMR (400 MHz, d$_6$-DMSO): 9.55 (d, 1H), 8.44 (d, 1H), 8.30-8.20 (m, 2H), 7.92 (s, 1H), 7.83 (s, 1H), 7.75 (m, 1H), 7.49 (s, 1H), 7.41 (s, 1H), 6.29 (m, 1H), 2.82 (m, 1H), 0.70 (m, 2H), 0.50 (m, 2H). |
| Ic-23 | 3-CF$_3$ | H | NH | 6-Cl | 3-(—CONH—) | pyridin-2-ylmethyl | HPLC-MS: logP = 2.49; mass (m/z): 555.1 (M + H)$^+$; $^1$H NMR (CD$_3$CN) 4.65-4.66 (m, 2H), 6.15 (quint, 1H), 7.24-7.27 (m, 1H), 7.32 (s, 1H), 7.43-7.50 (m, 2H), 7.57 (s, 1H), 7.69-7.67 (m, 1H), |

TABLE 3-continued

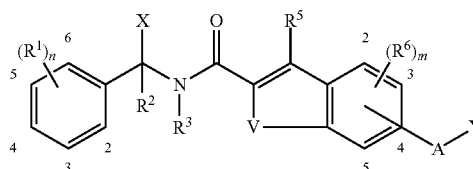

(Ic)

where $R^2$ and $R^5$ are each H, X is CF3 and $(R^1)_n$, $R^3$, V, $(R^6)_m$, A and Y are each as defined in Table 3. The numbers 2 to 6 or 2 to 5 represent the positions on the aromatic rings.

| No. | $(R^1)_n$ | $R^3$ | V | $(R^6)_m$ | A | Y | HPLC-MS [a]; $^1$H NMR (δ in ppm) [b] |
|---|---|---|---|---|---|---|---|
| Ic-24 | 3-CF$_3$ | H | NH | 6-Cl | 3-(—CONH—) | cyclo-propyl | 7.73-7.78 (m, 2H), 7.81-7.97 (m, 3H), 8.07-8.09 (m, 1H), 8.53-8.55 (m, 1H), 10.19 (s, 1H). See Sythesis Example 8, Stage 4 |
| Ic-25 | 3-CF$_3$ | H | N-Me | 3-Cl | 3-(—CONH—) | cyclo-propyl | HPLC-MS: logP = 3.5; mass (m/z): 518.1 (M + H)+; 1H NMR (CD3CN) 0.58-0.61 (m, 2H), 0.74-0.78 (m, 2H), 2.84-2.87 (m, 1H), 3.93 (s, 3H), 6.15 (m, 1H), 6.83 (m, 1H), 7.21 (s, 1H), 7.56 (s, 1H), 7.67-7.78 (m, 3H), 7.88-7.90 (m, 1H), 7.97 (s, 1H), 8.08-8.10 (m, 1H). |
| Ic-26 | 3-CF$_3$ | H | N-Et | 3-Cl | 3-(—CONH—) | cyclo-propyl | HPLC-MS: logP = 3.8; mass (m/z): 532.2 (M + H)+; 1H NMR (CD3CN) 0.58-0.60 (m, 2H), 0.75-0.78 (m, 2H), 1.27 (t, 3H), 2.85-2.87 (m, 1H), 4.45 (q, 2H), 6.14 (quint, 1H), 6.84 (m, 1H), 7.17 (s, 1H), 7.54 (s, 1H), 7.66-7.69 (m, 1H), 7.72 (s, 1H), 7.77-7.79 (m, 1H), 7.90-7.92 (m, 1H), 7.99 (s, 1H), 8.23-8.25 (m, 1H). |
| Ic-27 | 3-CF$_3$ | H | N-CH$_2$OEt | 3-Cl | 3-(—CONH—) | cyclo-propyl | HPLC-MS: logP = 3.81; mass (m/z): 562.2 (M + H)+; 1H NMR (CD3CN) 0.58-0.61 (m, 2H), 0.75-0.78 (m, 2H), 0.99 (t, 3H), 2.84-2.89 (m, 1H), 3.29-3.37 (m, 2H), 5.78 (s, 1H), 6.09-6.14 (m, 1H), 6.91-6.92 (m, 1H), 7.18 (s, 1H), 7.51 (s, 1H), 7.66-7.70 (m, 2H), 7.77-7.79 (m, 1H), 7.91-7.92 (m, 1H), 7.98 (s, 1H), 8.53 (d, 1H). |
| Ic-28 | 3-CF$_3$ | H | N-CH$_2$Ph | 3-Cl | 3-(—CONH—) | cyclo-propyl | HPLC-MS: logP = 4.25; mass (m/z): 594.2 (M + H)+; 1H NMR (CD3CN) 0.56-0.59 (m, 2H), 0.74-0.77 (m, 2H), 2.83-2.86 (m, 1H), 5.70 (s, 2H), 6.08 (quint, 1H), 6.83 (s, 1H), 6.97-7.00 (m, 2H), 7.16-7.21 (m, 3H), 7.28 (s, 1H), 7.49 (s, 1H), 7.63-7.66 (m, 1H), 7.76-7.77 (m, 2H), 7.82-7.84 (m, 1H), 7.93 (s, 1H), 8.18 (d, 1H). |
| Ic-29 | 3-CF$_3$ | H | N-prop-2-en-1-yl | 3-Cl | 3-(—CONH—) | cyclo-propyl | HPLC-MS: logP = 3.86; mass (m/z): 544.1 (M + H)+; 1H NMR (CD3CN) 0.58-0.59 (m, 2H), 0.75-0.77 (m, 2H), 1.93-1.97 (m, 1H), 4.73-4.76 (m, 1H), 5.00-5.02 (m, 1H), 5.07-5.08 (m, 2H), 5.89-5.97 (m, 1H), 6.10 (quint, 1H), 6.87 (s, 1H), 7.22 (s, 1H), 7.49 (s, 1H), 7.66-7.68 (m, 1H), 7.74 (s, 1H), 7.77-7.78 (m, 1H), 7.88-7.90 (m, 1H), 7.97 (s, 1H), 8.23 (d, 1H). |
| Ic-30 | 3-CF$_3$ | H | N-Me | 3-Cl | 3-(—CONH—) | methyl | HPLC-MS: logP = 3.2; mass (m/z): 492.1 (M + H)+; )+; 1H NMR (CD3CN) 2.89 (d, 3H), 3.88 (s, 3H), 6.12 (quint, 1H), 6.74-6.75 (m, 1H), 7.10 (s, 1H), 7.44 (s, 1H), 7.66-7.69 (m, 2H), 7.77-7.79 (m, 1H), 7.92-7.93 (m, 1H), 8.04 (s, 1H), 8.54 (d, 1H). |
| Ic-31 | 3-CF$_3$ | H | N-Me | 3-Cl | 3-(—CONH—) | but-3-yn-2-yl | HPLC-MS: logP = 3.73; mass (m/z): 530.1 (M + H)+; 1H NMR (CD3CN) 1.47 (d, 3H), 2.57 (d, 1H), |

TABLE 3-continued (Ic)

where R² and R⁵ are each H, X is CF3 and (R¹)$_n$, R³, V, (R⁶)$_m$, A and Y are each as defined in Table 3. The numbers 2 to 6 or 2 to 5 represent the positions on the aromatic rings.

| No. | (R¹)$_n$ | R³ | V | (R⁶)$_m$ | A | Y | HPLC-MS [a]; ¹H NMR (δ in ppm) [b] |
|---|---|---|---|---|---|---|---|
| | | | | | | | 3.92 (s, 3H), 4.88-4.93 (m, 1H), 6.13 (quint, 1H), 7.11 (d, 1H), 7.21 (s, 1H), 7.55 (s, 1H), 7.65-7.67 (m, 1H), 7.75-7.79 (m, 2H), 7.88-7.91 (m, 1H), 7.98 (s, 1H), 8.17 (d, 1H). |
| Ic-32 | 3-CF₃ | H | N-Me | 3-Cl | 3-(—CONH—) | prop-2-en-1-yl | See Synthesis Example 12, Stage 2 |
| Ic-33 | 3-CF₃ | H | N-Me | 3-Cl | 3-(—CONH—) | thietan-3-yl | HPLC-MS: logP = 3.82; mass (m/z): 550 (M + H)+; 1H NMR (CD3CN) 3.34-3.37 (m, 2H), 3.51-3.54 (m, 2H), 3.93 (s, 3H), 5.29-5.34 (m, 1H), 6.13 (quint, 1H), 7.21 (s, 1H), 7.37 (d, 1H), 7.57 (s, 1H), 7.66-7.69 (m, 1H), 7.77-7.79 (m, 2H), 7.89-7.90 (m, 1H), 7.98 (s, 1H), 8.14 (d, 1H). |
| Ic-34 | 3-CF₃ | H | N-CH₂-O-benzyl | 3-Cl | 3-(—CONH—) | cyclo-propyl | HPLC-MS: logP = 4.31; mass (m/z): 624.2 (M + H)+; 1H NMR (CD3CN) 0.58-0.60 (m, 2H), 0.75-0.78 (m, 2H), 2.83-2.88 (m, 1H), 4.36-4.42 (m, 2H), 5.91-5.95 (m, 2H), 6.12 (quint, 1H), 6.87 (s, 1H), 7.10-7.14 (m, 2H), 7.20-7.27 (m, 4H), 7.63-7.66 (m, 2H), 7.75-7.78 (m, 2H), 7.85-7.86 (m, 1H), 7.95-7.97 (m, 1H), 8.26 (d, 1H). |
| Ic-35 | 3-CF₃ | H | N-CH₂—COOMe | 3-Cl | 3-(—CONH—) | cyclo-propyl | HPLC-MS: logP = 3.42; mass (m/z): 576.1 (M + H)+; 1H NMR (CD3CN) 0.56-0.60 (m, 2H), 0.74-0.79 (m, 2H), 2.83-2.88 (m, 1H), 3.63 (s, 3H), 5.19 (s, 2H), 6.07 (quint, 1H), 6.84 (s, 1H), 7.34 (s, 1H), 7.55 (s, 1H), 7.65-7.68 (m, 1H), 7.76-7.79 (m, 2H), 7.85-7.87 (m, 1H), 7.95 (s, 1H), 8.10 (d, 1H). |
| Ic-36 | 3-CF₃ | H | N-CH₂-CN | 3-Cl | 3-(—CONH—) | cyclo-propyl | HPLC-MS: logP = 3.29; mass (m/z): 543.1 (M + H)+; 1H NMR (CD3CN) 0.58-0.60 (m, 2H), 0.76-0.78 (m, 2H), 2.85-2.86 (m, 1H), 5.48 (s, 2H), 6.15 (quint, 1H), 6.89 (s, 1H), 7.40 (s, 1H), 7.67-7.69 (m, 2H), 7.77-7.81 (m, 2H), 7.90-7.91 (m, 1H), 7.99 (s, 1H), 8.24 (d, 1H). |
| Ic-37 | 3-CF₃ | H | N-CH₂-ethynyl | 3-Cl | 3-(—CONH—) | cyclo-propyl | HPLC-MS: logP = 3.59; mass (m/z): 542.1 (M + H)+; 1H NMR (CD3CN) 0.57-0.60 (m, 2H), 0.75-0.78 (m, 2H), 2.51 (t, 1H), 2.84-2.87 (m, 1H), 5.32 (d, 2H), 6.14 (quint, 1H), 6.86 (s, 1H), 7.27 (s, 1H), 7.62 (s, 1H), 7.66-7.69 (m, 1H), 7.76-7.79 (m, 2H), 7.89-7.91 (m, 1H), 7.98 (s, 1H), 8.22 (d, 1H). |
| Ic-38 | 3-CF₃ | H | N-CH₂-ethynyl | 3-Cl | 3-(—CONH—) | cyclo-propyl | HPLC-MS: logP = 2.59; mass (m/z): 561.2 (M + H)+; 1H NMR (CD3CN) 0.56-0.60 (m, 2H), 0.74-0.79 (m, 2H), 2.83-2.87 (m, 1H), 5.07 (s, 2H), 5.81 (s, 1H), 6.10 (quint, 1H), 6.33 (s, 1H), 6.86 (s, 1H), 7.30 (s, 1H), 7.52 (s, 1H), 7.65-7.70 (m, 1H), 7.76-7.78 (m, 2H), |

TABLE 3-continued

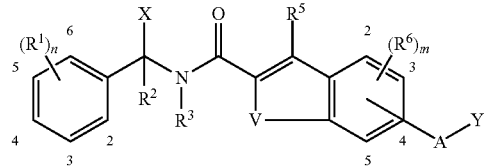

(Ic)

where $R^2$ and $R^5$ are each H, X is CF3 and $(R^1)_n$, $R^3$, V, $(R^6)_m$, A and Y are each as defined in Table 3. The numbers 2 to 6 or 2 to 5 represent the positions on the aromatic rings.

| No. | $(R^1)_n$ | $R^3$ | V | $(R^6)_m$ | A | Y | HPLC-MS [a]; $^1$H NMR (δ in ppm) [b] |
|---|---|---|---|---|---|---|---|
| Ic-39 | 3-CF$_3$ | H | N-CH$_2$-C(O)NH$_2$ | 3-Cl | 3-(—CONH—) | propan-2-yl | 7.86-7.88 (m, 1H), 7.96 (s, 1H), 8.22 (d, 1H). HPLC-MS: logP = 4.07; mass (m/z): 534.1 (M + H)+; 1H NMR (CD3CN) 1.22 (d, 6H), 1.28 (t, 3H), 4.13-4.18 (m, 1H), 4.47 (q, 2H), 6.13 (quint, 1H), 6.64 (d, 1H), 7.21 (s, 1H), 7.58 (s, 1H), 7.65-7.69 (m, 1H), 7.75-7.79 (m, 2H), 7.88-7.90 (m, 1H), 7.98 (s, 1H), 8.13 (d, 1H). |
| Ic-40 | 3-CF$_3$ | H | N-Et | 3-Cl | 3-(—CONH—) | cyclobutyl | HPLC-MS: logP = 4.22; mass (m/z): 546.1 (M + H)+; 1H NMR (d6-DMSO) 1.20 (t, 3H), 1.65-1.71 (m, 2H), 1.99-2.07 (m, 2H), 2.22-2.27 (m, 2H), 4.35-4.41 (m, 1H), 4.51 (q, 2H), 6.29 (quint, 1H), 7.36 (s, 1H), 7.64-7.87 (m, 4H), 8.04-8.06 (m, 1H), 8.20 (s, 1H), 8.55 (d, 1H), 9.78 (d, 1H). |
| Ic-41 | 3-CF$_3$ | H | N-Et | 3-Cl | 3-(—CONH—) | 2,2-difluoro-ethyl | HPLC-MS: logP = 3.87; mass (m/z): 556.1 (M + H)+; 1H NMR (CD3CN) 1.29 (t, 3H), 3.73-3.79 (m, 2H), 4.47 (q, 2H), 5.95-6.17 m, 2H), 7.09-7.11 (m, 1H), 7.21 (s, 1H), 7.60 (s, 1H), 7.66-7.69 (m, 1H), 7.77-7.79 (m, 1H), 7.81 (s, 1H), 7.89-7.90 (m, 1H), 7.98 (s, 1H), 8.16 (d, 1H). |
| Ic-42 | 3-CF$_3$ | H | N-Et | 3-Cl | 3-(—CONH—) | but-3-yn-2-yl | HPLC-MS: logP = 3.99; mass (m/z): 544.1 (M + H)+; 1H NMR (CD3CN) 1.29 (t, 3H), 1.47 (d, 3H), 2.56-2.57 (m, 1H), 4.48 (q, 2H), 4.87-4.94 (m, 1H), 6.13 (quint, 1H), 7.09-7.12 (m, 1H), 7.23 (s, 1H), 7.62 (s, 1H), 7.65-7.69 (m, 1H), 7.77-7.79 (m, 2H), 7.88-7.89 (m, 1H), 7.97 (s, 1H), 8.08 (d, 1H). |
| Ic-43 | 3-CF$_3$ | H | N-Et | 3-Cl | 3-(—CONH—) | pyridin-2-yl | HPLC-MS: logP = 4.22; mass (m/z): 569.1 (M + H)+; 1H NMR (CD3CN) 1.31 (t, 3H), 4.50 (q, 2H), 6.15 (quint, 1H), 7.11-7.14 (m, 1H), 7.27 (s, 1H), 7.66-7.70 (m, 2H), 7.77-7.90 (m, 3H), 7.97-7.99 (m, 2H), 8.09 (d, 1H), 8.28-8.31 (2H), 9.07 (s, 1H). |
| Ic-44 | 3-CF$_3$ | H | N-Et | 3-Cl | 3-(—CONH—) | cyclo-propyl | HPLC-MS: logP = 4.31; mass (m/z): 546.1 (M + H)+; 1H NMR (CD3CN) 0.37-0.38 (m, 2H), 0.50-0.53 (m, 2H), 1.30 (t, 3H), 2.68-2.70 (m, 1H), 3.06 (s, 3H), 4.49 (q, 2H), 6.14 (quint, 1H), 7.21 (s, 1H), 7.59-7.69 (m, 3H), 7.77-7.79 (m, 1H), 7.87-7.89 (m, 1H), 7.97 (s, 1H), 8.06 (d, 1H). |
| Ic-45 | 3-CF$_3$ | H | NH | 3-Cl | 3-(—CONH—) | pyridin-2-yl | HPLC-MS: logP = 3.37; mass (m/z): 541.1(M + H)+; 1H NMR (CD3CN) 6.16 (quint, 1H), 7.11-7.14 (m, 1H), 7.35 (m, 1H), 7.59 (s, 1H), 7.65-7.69 (m, 1H), 7.76-7.97 (m, 3H), 8.00 (s, 1H), 8.04 (s, 1H) 8.04 (d, 1H), 8.28-8.31 (m, 2H), 9.10 (m, 1H), 10.19 (s, 1H). |

TABLE 3-continued (Ic)

where $R^2$ and $R^5$ are each H, X is CF3 and $(R^1)_n$, $R^3$, V, $(R^6)_m$, A and Y are each as defined in Table 3. The numbers 2 to 6 or 2 to 5 represent the positions on the aromatic rings.

| No. | $(R^1)_n$ | $R^3$ | V | $(R^6)_m$ | A | Y | HPLC-MS [a]; $^1$H NMR (δ in ppm) [b] |
|---|---|---|---|---|---|---|---|
| Ic-46 | 3-CF$_3$ | H | NH | 3-Cl | 4-(—CONH—) | pyridin-2-ylmethyl | HPLC-MS: logP = 2.5; mass (m/z): 555.12 (M + H)+; 1H NMR (d3-CD3CN) 10.4 (s, 1H), 8.55 (s, 1H, br), 8.20 (d, 1H), 7.98 (s, 1H), 7.88 (dd, 1H), 7.80-7.75 (m, 3H), 7.70-7.65 (m, 2H), 7.55 (s, 1H), 7.48 (s, 1H), 7.25 (m, 2H), 6.15 (m, 1H), 4.56 (d, 2H) |
| Ic-47 | 3-CF$_3$ | H | NH | 3-Cl | 4-(—CONH—) | 2,2-difluoro-ethyl | |
| Ic-48 | 3-CF$_3$ | H | N-Me | 3-Cl | 4-(—CONH—) | cyclo-propyl | HPLC-MS: logP = 3.33; mass (m/z): 518.38 (M + H)+; 1H NMR (400 MHz, d3-CD3CN): 8.20 (d, 1H), 7.99 (s, 1H), 7.90 (d, 1H), 7.78 (d, 1H), 7.70 (m, 2H), 7.55 (s, 1H), 7.10 (s, 1H), 6.89 (s, 1H), 6.13 (m, 1H), 3.94 (s, 3H), 2.86 (m, 1H), 0.77 (m, 2H), 0.60 (m, 2H) |

TABLE 4

(Id)

where $R^2$, $R^3$, $R^4$ are each H, and X, $(R^1)_n$, $R^5$, $(R^6)_m$, A and Y are each as defined in Table 4. The numbers 2 to 6 represent the positions on the aromatic rings.

| No. | $(R^1)_n$ | X | $R^5$ | $(R^6)_m$ | A | Y | HPLC-MS [a]; $^1$H NMR (δ in ppm) [b] |
|---|---|---|---|---|---|---|---|
| Id-1 | 3-CF$_3$ | CF$_2$(CH$_3$) | H | 3-Cl | 4-(—CONH—) | cyclopropyl | See Synthesis Example 14, Stage 2 |
| Id-2 | 3-F | CHF$_2$ | H | 3-CF$_3$ | 4-(—CONH—) | cyclopropyl | HPLC-MS: logP = 2.68; mass (m/z): 457.1 (M + H)+; 1H NMR (d6-DMSO) 0.50 (m, 2H), 0.71 (m, 2H), 2.79 (m, 1H), 5.56 (m, 1H), 6.33 (m, 1H), 6.98 (d, 1H), 7.20 (m, 1H), 7.33-7.66 (m, 5H), 7.89 (m, 1H), 7.97 (s, 1H), 8.54 (d, 1H), 9.07 (d, 1H). |
| Id-3 | 3-Cl | CHF$_2$ | H | 3-CF$_3$ | 4-(—CONH—) | cyclopropyl | HPLC-MS: logP = 2.92; mass (m/z): 473.1 (M + H)+; 1H NMR (d6-DMSO) 0.50 (m, 2H), 0.69 (m, 2H), 2.80 (m, 1H), 5.55 (m, 1H), 6.33 (m, 1H), 6.99 (d, 1H), 7.44 (m, 3H), 7.53-7.62 (m, 3H), 7.90 (m, 1H), 8.01 (m, 1H), 8.54 (d, 1H), 9.08 (d, 1H). |
| Id-4 | 3-CF$_3$ | CF$_3$ | CH$_3$ | 3-CF$_3$ | 4-(—CONH—) | propan-2-yl | HPLC-MS: logP = 3.75; mass (m/z): 541.4 (M + H)+; 1H NMR (d3-CD3CN) 7.88 (m, 2H), 7.80-7.75 (m, 4H), 7.68-7.63 (t, 1H), 7.50 (d, 1H), 6.74 (d, 1H, br), 6.35 (s, 1H), 5.99 (m, 1H), |

TABLE 4-continued

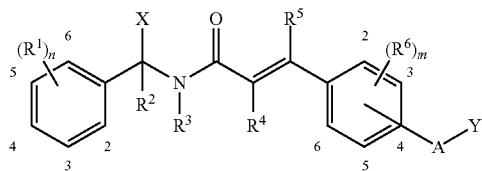

(Id)

where $R^2$, $R^3$, $R^4$ are each H, and X, $(R^1)_n$, $R^5$, $(R^6)_m$, A and Y are each as defined in Table 4. The numbers 2 to 6 represent the positions on the aromatic rings.

| No. | $(R^1)_n$ | X | $R^5$ | $(R^6)_m$ | A | Y | HPLC-MS [a]; $^1$H NMR (δ in ppm) [b] |
|---|---|---|---|---|---|---|---|
| | | | | | | | 4.10 (d, 2H), 1.94 (m, 3H), 1.20 (d, 6H) |

TABLE 5

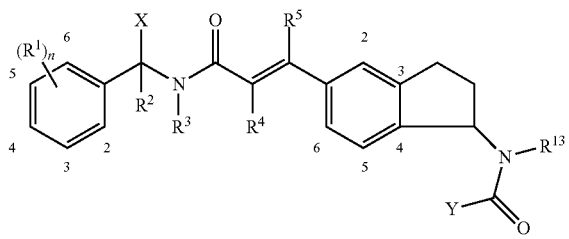

(Ie)

where $R^2$, $R^3$, $R^4$ and $R^5$ are each H, X is $CF_3$ and $(R^1)_n$, $R^{13}$ and Y are each as defined in Table 5. The numbers 2 to 6 represent the positions on the aromatic rings

| No. | $(R^1)_n$ | $R^{13}$ | Y | HPLC-MS [a]; $^1$H NMR (δ in ppm) [b] |
|---|---|---|---|---|
| Ie-1 | 3-$CF_3$ | H | methyl | See Synthesis Example 15, Stage 6 |
| Ie-2 | 3-$CF_3$ | H | cyclopropylmethyl | HPLC-MS: logP = 3.54; mass (m/z): 511.2 (M + H)+; 1H NMR (d6-DMSO) 0.15 (m, 2H), 0.47 (m, 2H), 1.02 (m, 1H), 1.80 (m, 1H), 2.04 (d, 2H), 2.41 (m, 1H), 2.73 (m, 1H), 2.94 (m, 1H), 5.29 (q, 1H), 6.14 (m, 1H), 6.80 (d, 1H), 7.23 (d, 1H), 7.45 (d, 1H), 7.47 (s, 1H), 7.54 (d, 1H), 7.71 (t, 1H), 7.81 (d, 1H), 7.94 (d, 1H) 8.04 (s, 1H), 8.09 (d, 1H), 9.40 (d, 1H). |
| Ie-3 | 3-$CF_3$ | H | ethyl | HPLC-MS: logP = 3.27; mass (m/z): 585.2 (M + H)+; 1H NMR (d6-DMSO) 1.05 (t, 3H), 1.79 (m, 1H), 2.13 (m, 2H), 2.38 (m, 1H), 2.82 (m, 1H), 2.94 (m, 1H), 5.28 (q, 1H), 6.14 (m, 1H), 6.80 (d, 1H), 7.22 (d, 1H), 7.44 (d, 1H), 7.47 (d, 1H), 7.54 (d, 1H), 7.71 (t, 1H), 7.81 (d, 1H), 7.94 (d, 1H), 8.05 (s, 1H), 8.13 (d, 1H), 9.42 (d, 1H). |

TABLE 6

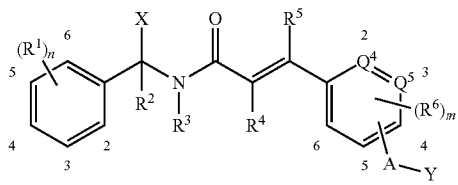

(If)

where $R^2$, $R^3$, $R^4$ and $R^5$ are each H, X is $CF_3$ and $Q^4$, $Q^5$, $(R^1)_n$, $(R^6)_m$, A and Y are each as defined in Table 6. The numbers 2 to 6 represent the positions on the aromatic rings.

| No. | $(R^1)_n$ | $Q^4$ | $Q^5$ | $(R^6)_m$ | A | Y | HPLC-MS [a]; 1H NMR ($\delta$ in ppm) [b] |
|---|---|---|---|---|---|---|---|
| If-1 | 3-$CF_3$ | CH | N | H | 4-(—$CH_2$NHCO—) | cyclopropyl | HPLC-MS: logP = 2.44; mass (m/z): 472.07 (M + H)+; 1H NMR (400 MHz, d3-CD3CN): 8.52 (d, 1H), 8.01-7.99 (m, 2H), 7.81 (d, 1H), 7.76 (d, 1H), 7.70-7.65 (m, 2H), 7.60 (d, 1H, J = 16 Hz), 7.45 (d, 1H), 7.14 (d, 1H, J = 16 Hz), 7.08 (s, 1H, br), 6.00 (m, 1H), 4.36 (d, 2H), 1.50 (m, 1H), 0.70 (m, 2H), 0.80 (m, 2H) |
| If-2 | 3-$CF_3$ | N | CH | 3-$CF_3$ | 4-(—CONH—) | cyclopropyl | See Synthesis Example 11, Stage 3 |
| If-3 | 3-$CF_3$ | N | CH | H | 4-(—CH($CH_3$)NHCO—) | cyclopropyl-methyl | HPLC-MS: logP = 3; mass (m/z): 500.15 (M + H)+; 1H NMR (400 MHz, d6-DMSO): 9.56 (d, 1H), 8.73 (s, 1H), 8.25 (d, 1H), 8.07 (s, 1H), 7.98 (d, 1H), 7.95 (d, 1H), 7.80 (d, 1H), 7.70 (m, 1H), 7.69 (d, 1H, J = 16Hz), 7.39 (dd, 1H), 6.87 (d, 1H, J = 16 Hz), 6.18 (m, 1H), 4.95 (m, 1H), 2.05 (d, 2H), 1.36 (d, 3H), 0.95 (m, 1H), 0.43 (m, 1H), 0.13 (m, 1H) |

TABLE 7

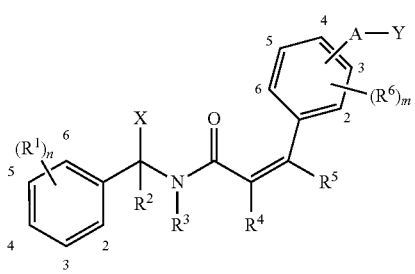

(Ig)

where $R^2$, $R^3$, $R^4$ and $R^5$ are each H, X is $CF_3$ and $(R^1)_n$, $(R^6)_m$, A and Y are each as defined in Table 7. The numbers 2 to 6 represent the positions on the aromatic rings.

| No. | $(R^1)_n$ | $(R^6)_m$ | A | Y | HPLC-MS [a]; $^1$H NMR ($\delta$ in ppm) [b] |
|---|---|---|---|---|---|
| Ig-1 | 3-CF3 | 3-Cl | 4-(—CONH—) | cyclopropyl | See Synthesis Example 13, Stage 3 |

[a] M+ is determined by LC-MS in the acidic range at pH 2.7; acetonitrile (contains 0.1% formic acid) and water as the eluent; linear gradient from 10% acetonitrile to 95% acetonitrile; instrument: Agilent 1100 LC-System, Agilent MSD System, HTS PAL.

The logP values reported in the above Tables and Preparation Examples were determined according to EEC Directive 79/831 Annex V.A8 by HPLC (High Performance Liquid Chromatography) on a reverse-phase column (C18). Temperature 43° C. Calibration is effected with unbranched alkan-2-ones (having 3 to 16 carbon atoms), the logP values of which are known.

b) The $^1$H NMR data are determined with a Bruker Avance 400, with tetramethylsilane as the reference (0.0), and the solvents $CD_3CN$, $CDCl_3$, $[D_6]$-DMSO. The signal splitting is characterized by s=singlet, br. s=broad singlet, d=doublet, t=triplet, q=quartet, quint=quintet, m=multiplet, dd=double doublet.

APPLICATION EXAMPLES

The following examples show the insecticidal and acaricidal action of the inventive compounds. The inventive compounds mentioned relate to the compounds listed in Tables 1 to 7 with the corresponding reference symbols, e.g. Ia-1:

Example 1

*Boophilus microplus* Test (BOOPMI Injection)

Solvent: dimethyl sulphoxide

To prepare an active ingredient formulation, 10 mg of active ingredient are mixed with 0.5 ml of solvent and the concentrate is diluted with water to the desired concentration. The active ingredient solution was injected into the abdomen (*Boophilus microplus*), and the animals were transferred to dishes and stored in a climate-controlled room. The efficacy was assessed by the number of fertile eggs laid.

After 7 days, the efficacy in % is determined. 100% means that no tick laid fertile eggs.

In this test, the following inventive compounds exhibit the stated effect:

100% efficacy at an application rate of 20 µg/animal:
Ia-5, Ia-8, Ia-22, Ia-23, Ia-24, Ia-29, Ia-30, Ia-31, Ia-32, Ia-40, Ia-41, Ia-42, Ia-43, Ia-44, Ia-45, Ia-46, Ia-58, Ia-60, Ia-73, Ia-76, Ia-77, Ia-80.

Example 2

*Ctenocephalides felis* Oral (CTECFE)

Solvent: 1 part by weight of dimethyl sulphoxide

For the purpose of preparing an active ingredient formulation, 10 mg of active ingredient are mixed with 0.5 ml of dimethyl sulphoxide. A portion of the concentrate was diluted with citrated cow's blood and the desired concentration was prepared.

20 unfed adult fleas (*Ctenocephalides felis*) are placed into a chamber sealed at the top and bottom with gauze. A metal cylinder with its lower end sealed with Parafilm is placed onto the chamber. The cylinder contains the blood-active ingredient preparation, which can be consumed by the fleas through the Parafilm membrane.

After 2 days, the kill rate in % is determined. 100% means that all fleas were killed; 0% means that no fleas were killed.

In this test, the following inventive compounds exhibit the stated effect:

95% efficacy at an application rate of 20 ppm:
Ia-73; Ia-31

In this test, the following inventive compounds exhibit the stated effect:

98% efficacy at an application rate of 20 ppm:
Ia-45; Ia-58

In this test, the following inventive compounds exhibit the stated effect:

100% efficacy at an application rate of 20 ppm:
Ia-22, Ia-23, Ia-24, Ia-30, Ia-32, Ia-40, Ia-41, Ia-42, Ia-43, Ia-60, Ia-80

Example 3

*Lucilia cuprina* Test (LUCICU)

Solvent: dimethyl sulphoxide

To prepare an active ingredient formulation, 10 mg of active ingredient are mixed with 0.5 ml of dimethyl sulphoxide, and the concentrate is diluted with water to the desired concentration. Vessels containing horsemeat which has been treated with the active ingredient formulation of the desired concentration are populated with *Lucilia cuprina* larvae.

After 2 days, the kill rate in % is determined. 100% means that all larvae were killed; 0% means that no larvae were killed.

In this test, the following inventive compounds exhibit the stated effect:

80% efficacy at an application rate of 20 ppm:
Ia-24

In this test, the following inventive compounds exhibit the stated effect:

90% efficacy at an application rate of 20 ppm:
Ia-22, Ia-40, Ia-41, Ia-60

In this test, the following inventive compounds exhibit the stated effect:

100% efficacy at an application rate of 20 ppm:
Ia-23, Ia-30, Ia-42, Ia-43, Ia-45

Example 4

*Musca domestica* Test (MUSCDO)

Solvent: dimethyl sulphoxide

To prepare an active ingredient formulation, 10 mg of active ingredient are mixed with 0.5 ml of dimethyl sulphoxide, and the concentrate is diluted with water to the desired concentration. Vessels containing a sponge which has been treated with the active ingredient formulation of the desired concentration are populated with *Musca domestica* adults.

After 2 days, the kill rate in % is determined. 100% means that all flies were killed; 0% means that no flies were killed.

In this test, the following inventive compounds exhibit the stated effect:

85% efficacy at an application rate of 20 ppm:
Ia-30

Example 5

Myzus Test (MYZUPE Spray Treatment)

Solvent: 78 parts by weight of acetone
1.5 parts by weight of dimethylformamide
Emulsifier: 0.5 part by weight of alkylaryl polyglycol ether To prepare an active ingredient formulation, 1 part by weight of active ingredient is mixed with the stated amounts of solvent and emulsifier, and the concentrate is diluted with emulsifier-containing water to the desired concentration. Leaf discs from china cabbage (*Brassica pekinensis*) infested by all stages of the green peach aphid (*Myzus persicae*) are sprayed with an active ingredient formulation of the desired concentration.

After 6 days, the efficacy in % is determined. 100% means that all aphids were killed; 0% means that no aphids were killed.

In this test, the following inventive compounds exhibit the stated effect:

80% efficacy at an application rate of 20 g/ha:
Ia-75

In this test, the following inventive compounds exhibit the stated effect:

90% efficacy at an application rate of 20 g/ha:
Ia-115

In this test, the following inventive compounds exhibit the stated effect:

100% efficacy at an application rate of 20 g/ha:
Ia-41; Ia-112

Example 6

*Spodoptera frugiperda* Test (SPODFR Spray Treatment)
Solvent: 78.0 parts by weight of acetone
   1.5 parts by weight of dimethylformamide
Emulsifier: 0.5 part by weight of alkylaryl polyglycol ether To prepare an active ingredient formulation, 1 part by weight of active ingredient was mixed with the stated amounts of solvent and emulsifier, and the concentrate was diluted with emulsifier-containing water to the desired concentration. Leaf discs from maize (*Zea mays*) are sprayed with an active ingredient formulation of the desired concentration and, after drying, populated with caterpillars of the armyworm (*Spodoptera frugiperda*).

After 7 days, the efficacy in % is determined. 100% means that all caterpillars were killed; 0% means that no caterpillars were killed.

In this test, the following inventive compounds exhibit the stated effect:
83% efficacy at an application rate of 20 g/ha:
Ia-23; Ia-72; Ia-82

In this test, the following inventive compounds exhibit the stated effect:
100% efficacy at an application rate of 20 g/ha:
Ia-54

Example 7

Phaedon Test (PHAECO Spray Treatment)
Solvent: 78.0 parts by weight of acetone
   1.5 parts by weight of dimethylformamide
Emulsifier: 0.5 part by weight of alkylaryl polyglycol ether To prepare an active ingredient formulation, 1 part by weight of active ingredient is mixed with the stated amounts of solvent and emulsifier, and the concentrate is diluted with emulsifier-containing water to the desired concentration. Leaf discs from china cabbage (*Brassica pekinensis*) are sprayed with an active ingredient formulation of the desired concentration and, after drying, populated with larvae of the mustard beetle (*Phaedon cochleariae*).

After 7 days, the efficacy in % is determined. 100% means that all beetle larvae were killed; 0% means that no beetle larvae were killed.

In this test, the following inventive compounds exhibit the stated effect:
100% efficacy at an application rate of 20 g/ha:
Ia-21, Ia-22, Ia-23, Ia-37, Ia-41, Ia-43, Ia-47, Ia-48, Ia-51,
  Ia-54, Ia-56, Ia-57, Ia-58, Ia-59, Ia-60, Ia-61, Ia-62, Ia-63,
  Ia-64, Ia-65, Ia-66, Ia-67, Ia-68, Ia-69, Ia-70, Ia-71, Ia-72,
  Ia-73, Ia-74, Ia-75, Ia-76, Ia-78, Ia-79, Ia-80, Ia-82, Ia-83,
  Ia-84, Ia-86, Ia-87, Ia-88, Ia-89, Ia-90, Ia-91, Ia-92, Ia-93,
  Ia-94, Ia-95, Ia-96, Ia-97, Ia-98, Ia-99, Ia-100, Ia-101,
  Ia-102, Ia-103, Ia-104, Ia-105, Ia-106, Ia-107, Ia-108,
  Ia-109, Ia-110, Ia-111, Ia-112, Ia-113, Ia-114, Ia-115,
  Ic-18, Ic-18, Ic-20, Ic-21, Ic-22, Ic-23, Ic-24

Example 8

*Tetranychus* Test, OP-resistant (TETRUR Spray Treatment)
Solvent: 78.0 parts by weight of acetone
   1.5 parts by weight of dimethylformamide
Emulsifier: 0.5 part by weight of alkylaryl polyglycol ether To prepare an active ingredient formulation, 1 part by weight of active ingredient is mixed with the stated amounts of solvent and emulsifier, and the concentrate is diluted with emulsifier-containing water to the desired concentration. Leaf discs from the common bean (*Phaseolus vulgaris*) infested by all stages of the red spider mite (*Tetranychus urticae*) are sprayed with an active ingredient formulation of the desired concentration.

After 6 days, the efficacy in % is determined. 100% means that all spider mites were killed; 0% means that no spider mites were killed.

In this test, the following inventive compounds exhibit the stated effect:
80% efficacy at an application rate of 20 g/ha:
Ia-63, Ia-77, Ia-90, Ia-92, Ia-94, Ia-95, Ia-96, Ia-99, Ia-100,
  Ic-18

In this test, the following inventive compounds exhibit the stated effect:
90% efficacy at an application rate of 20 g/ha:
Ia-23, Ia-47, Ia-48, Ia-49, Ia-51, Ia-57, Ia-58, Ia-60, Ia-65,
  Ia-66, Ia-74, Ia-78, Ia-79, Ia-93, Ia-115

In this test, the following inventive compounds exhibit the stated effect:
100% efficacy at an application rate of 20 g/ha:
Ia-23, Ia-36, Ia-41, Ia-50, Ia-52, Ia-54, Ia-55, Ia-56, Ia-59,
  Ia-61, Ia-62, Ia-68, Ia-69, Ia-70, Ia-73, Ia-75, Ia-112,
  Ia-113, Ia-114

Example 9

*Amblyomma hebaraeum* Test (AMBYHE)
Solvent: dimethyl sulphoxide

To prepare an appropriate active ingredient formulation, 10 mg of active ingredient are mixed with 0.5 ml of dimethyl sulphoxide, and the concentrate is diluted with water to the desired concentration.

Tick nymphs (*Amblyomma hebraeum*) are placed into perforated plastic cups and immersed in the desired concentration for one minute. The ticks are transferred onto filter papers in a Petri dish and stored in a climate-controlled cabinet.

After 42 days, the kill rate in % is determined. 100% means that all ticks were killed; 0% means that no ticks were killed.

In this test, for example, the following compounds from the Preparation Examples exhibit an efficacy of 100% at an application rate of 100 ppm: Ia-161, Ia-162

Example 10

*Boophilus microplus* Test (DIP)
Test animals: adult engorged *Boophilus microplus* females of the SP-resistant Parkhurst strain
Solvent: dimethyl sulphoxide 10 mg of active ingredient are dissolved in 0.5 ml of dimethyl sulphoxide. For the purpose of preparing a suitable formulation, the active ingredient solution is diluted with water to the concentration desired in each case.

This active ingredient formulation is pipetted into tubes. 8-10 ticks are transferred into a further tube with holes. The tube is immersed into the active ingredient formulation, and all ticks are completely wetted. After the liquid has run out, the ticks are transferred onto filter discs in plastic dishes and stored in a climate-controlled room. The efficacy is assessed after 7 days by the number of fertile eggs laid. Eggs whose fertility is not outwardly visible are stored in glass tubes in a climate-controlled cabinet until the larvae hatch. Efficacy of 100% means that none of the ticks has laid any fertile eggs.

In this test, for example, the following compounds from the Preparation Examples exhibit an efficacy of 100% at an application rate of 100 ppm: Ia-112, Ia-162

In this test, for example, the following compounds from the Preparation Examples exhibit an efficacy of 98% at an application rate of 100 ppm: Ia-161

In this test, for example, the following compounds from the Preparation Examples exhibit an efficacy of 90% at an application rate of 100 ppm: Ia-155

In this test, for example, the following compounds from the Preparation Examples exhibit an efficacy of 85% at an application rate of 100 ppm: Ia-114

Example 11

*Boophilus microplus* Test (BOOPMI Injection)
Solvent: dimethyl sulphoxide

To prepare an appropriate active ingredient formulation, 10 mg of active ingredient are mixed with 0.5 ml of solvent and the concentrate is diluted with solvent to the desired concentration. The active ingredient solution is injected into the abdomen (*Boophilus microplus*), and the animals are transferred to dishes and stored in a climate-controlled room. The efficacy was assessed by the number of fertile eggs laid.

After 7 days, the efficacy in % is determined. 100% means that none of the ticks has laid any fertile eggs.

In this test, for example, the following compounds from the Preparation Examples exhibit an efficacy of 100% at an application rate of 20 μg/animal: Ia-5, Ia-8, Ia-18, Ia-19, Ia-21, Ia-22, Ia-23, Ia-24, Ia-29, Ia-30, Ia-31, Ia-32, Ia-36, Ia-40, Ia-41, Ia-42, Ia-43, Ia-44, Ia-45, Ia-46, Ia-54, Ia-57, Ia-58, Ia-60, Ia-73, Ia-75, Ia-76, Ia-77, Ia-80, Ia-82, Ia-94, Ia-112, Ia-114, Ia-121, Ia-122, Ia-123, Ia-124, Ia-125, Ia-126, Ia-127, Ia-128, Ia-129, Ia-130, Ia-132, Ia-134, Ia-135, Ia-136, Ia-138, Ia-139, Ia-140, Ia-141, Ia-142, Ia-143, Ia-144, Ia-145, Ia-146, Ia-147, Ia-148, Ia-149, Ia-150, Ia-151, Ia-152, Ia-153, Ia-154, Ia-155, Ia-156, Ia-157, Ia-158, Ia-159, Ia-161, Ia-162, Ia-163, Ia-164, Ia-237, Ic-18, Ic-24, Ic-25

Example 12

*Ctenocephalides felis* Oral (CTECFE)
Solvent: 1 part by weight of dimethyl sulphoxide For the purpose of preparing an appropriate active ingredient formulation, 10 mg of active ingredient are mixed with 0.5 ml of dimethyl sulphoxide. A portion of the concentrate is diluted with citrated cow's blood and the desired concentration is established.

About 20 unfed adult fleas (*Ctenocephalides felis*) are placed into a chamber sealed at the top and bottom with gauze. A metal cylinder with its lower end sealed with Parafilm is placed onto the chamber. The cylinder contains the blood-active ingredient preparation, which can be consumed by the fleas through the Parafilm membrane. After 2 days, the kill rate in % is determined. 100% means that all fleas were killed; 0% means that no fleas were killed.

In this test, for example, the following compounds from the Preparation Examples exhibit an efficacy of 100% at an application rate of 100 ppm:

| Ia-19 | Ia-60  | Ia-124 | Ia-138 | Ia-149 | Ia-159 |
| Ia-21 | Ia-73  | Ia-125 | Ia-139 | Ia-150 | Ia-161 |
| Ia-22 | Ia-75  | Ia-126 | Ia-140 | Ia-151 | Ia-162 |
| Ia-23 | Ia-80  | Ia-127 | Ia-141 | Ia-152 | Ia-163 |
| Ia-24 | Ia-82  | Ia-128 | Ia-142 | Ia-153 | Ia-164 |
| Ia-30 | Ia-94  | Ia-129 | Ia-143 | Ia-154 | Ia-237 |
| Ia-43 | Ia-112 | Ia-130 | Ia-144 | Ia-155 | Ic-18  |
| Ia-45 | Ia-114 | Ia-132 | Ia-145 | Ia-156 | Ic-24  |
| Ia-57 | Ia-121 | Ia-134 | Ia-147 | Ia-157 | Ic-25  |
| Ia-58 | Ia-122 | Ia-136 | Ia-148 | Ia-158 |        |

In this test, for example, the following compounds from the Preparation Examples exhibit an efficacy of 98% at an application rate of 100 ppm: Ia-18

In this test, for example, the following compounds from the Preparation Examples exhibit an efficacy of 95% at an application rate of 100 ppm: Ia-54

In this test, for example, the following compounds from the Preparation Examples exhibit an efficacy of 90% at an application rate of 100 ppm: Ia-146

In this test, for example, the following compounds from the Preparation Examples exhibit an efficacy of 80% at an application rate of 100 ppm: Ia-5, Ia-76

Example 13

*Lucilia cuprina* Test (LUCICU)
Solvent: dimethyl sulphoxide

To prepare an appropriate active ingredient formulation, 10 mg of active ingredient are mixed with 0.5 ml of dimethyl sulphoxide, and the concentrate is diluted with water to the desired concentration. Vessels containing horsemeat which has been treated with the active ingredient formulation of the desired concentration are populated with about 20 *Lucilia cuprina* larvae.

After 2 days, the kill rate in % is determined. 100% means that all larvae were killed; 0% means that no larvae were killed.

In this test, for example, the following compounds from the Preparation Examples exhibit an efficacy of 100% at an application rate of 100 ppm:

Ia-18
Ia-19
Ia-21
Ia-22
Ia-23
Ia-24
Ia-25
Ia-30
Ia-32
Ia-36
Ia-40
Ia-41
Ia-42
Ia-43
Ia-45
Ia-46
Ia-54
Ia-57
Ia-60
Ia-75
Ia-77
Ia-82
Ia-112
Ia-114
Ia-121
Ia-122
Ia-123
Ia-124
Ia-125
Ia-126
Ia-127
Ia-129
Ia-132
Ia-136
Ia-138
Ia-140

Ia-141
Ia-143
Ia-144
Ia-145
Ia-146
Ia-148
Ia-149
Ia-150
Ia-151
Ia-153
Ia-154
Ia-155
Ia-156
Ia-158
Ia-159
Ia-161
Ia-162
Ia-163
Ia-237
Ic-18
Ic-24
Ic-25

In this test, for example, the following compounds from the Preparation Examples exhibit an efficacy of 95% at an application rate of 100 ppm: Ia-94

In this test, for example, the following compounds from the Preparation Examples exhibit an efficacy of 90% at an application rate of 100 ppm: Ia-31, Ia-128, Ia-134, Ia-142, Ia-152

In this test, for example, the following compounds from the Preparation Examples exhibit an efficacy of 80% at an application rate of 100 ppm: Ia-29, Ia-73, Ia-80, Ia-139, Ia-147

Example 14

*Musca domestica* Test (MUSCDO)

Solvent: dimethyl sulphoxide

To prepare an appropriate active ingredient formulation, 10 mg of active ingredient are mixed with 0.5 ml of dimethyl sulphoxide, and the concentrate is diluted with water to the desired concentration. Vessels containing a sponge which has been treated with the active ingredient formulation of the desired concentration are populated with *Musca domestica* adults.

After 2 days, the kill rate in % is determined. 100% means that all flies were killed; 0% means that no flies were killed.

In this test, for example, the following compounds from the Preparation Examples exhibit an efficacy of 100% at an application rate of 100 ppm: Ia-19, Ia-23, Ia-30, Ia-45, Ia-57, Ia-140, Ia-141, Ia-149, Ia-158, Ia-163, Ic-25

In this test, for example, the following compounds from the Preparation Examples exhibit an efficacy of 95% at an application rate of 100 ppm: Ia-60

In this test, for example, the following compounds from the Preparation Examples exhibit an efficacy of 90% at an application rate of 100 ppm: Ia-18, Ia-122, Ia-142, Ia-148, Ia-156

In this test, for example, the following compounds from the Preparation Examples exhibit an efficacy of 85% at an application rate of 100 ppm: Ia-40

In this test, for example, the following compounds from the Preparation Examples exhibit an efficacy of 80% at an application rate of 100 ppm: Ia-151, Ia-161

Example 15

*Spodoptera frugiperda* Test (SPODFR Spray Treatment)

Solvent: 78.0 parts by weight of acetone
1.5 parts by weight of dimethylformamide Emulsifier: 0.5 part by weight of alkylaryl polyglycol ether To prepare an appropriate active ingredient formulation, 1 part by weight of active ingredient is mixed with the stated amounts of solvent and emulsifier, and the concentrate is diluted with emulsifier-containing water to the desired concentration. Leaf discs from maize (*Zea mays*) are sprayed with an active ingredient formulation of the desired concentration and, after drying, populated with caterpillars of the armyworm (*Spodoptera frugiperda*).

After 7 days, the efficacy in % is determined. 100% means that all caterpillars were killed; 0% means that no caterpillars were killed.

In this test, for example, the following compounds from the Preparation Examples exhibit efficacy of 100% at an application rate of 500 g/ha:

Ia-3
Ia-8
Ia-10
Ia-11
Ia-17
Ia-21
Ia-22
Ia-23
Ia-24
Ia-44
Ia-46
Ia-68
Ia-71
Ia-72
Ia-73
Ia-74
Ia-75
Ia-78
Ia-79
Ia-80
Ia-82
Ia-85
Ia-87
Ia-89
Ia-90
Ia-91
Ia-92
Ia-93
Ia-95
Ia-96
Ia-98
Ia-99
Ia-100
Ia-101
Ia-102
Ia-103
Ia-104
Ia-107
Ia-108
Ia-109
Ia-110
Ia-111
Ia-112
Ia-113
Ia-114
Ia-116
Ia-120
Ia-122
Ia-123
Ia-229
Ia-231
Ia-233
Ia-236
Ia-237
Ia-238

|  |
|---|
| Ia-240 |
| Ia-241 |
| Ia-246 |
| Ia-255 |
| Ic-1 |
| Ic-12 |
| Ic-18 |
| Ic-21 |
| Ic-23 |
| Ic-24 |
| Ic-25 |
| Ic-31 |
| Ic-32 |
| Ic-34 |
| Ic-36 |
| Ic-37 |
| Ic-39 |
| Ic-41 |
| Ic-42 |
| Ic-44 |
| Ic-45 |

In this test, for example, the following compounds from the Preparation Examples exhibit efficacy of 83% at an application rate of 500 g/ha: Ia-7, Ia-15, Ia-28, Ia-32, Ia-47, Ia-55, Ia-56, Ia-58, Ia-59, Ia-64, Ia-70, Ia-235, Ib-2, Ic-4, Ic-43

In this test, for example, the following compounds from the Preparation Examples exhibit efficacy of 100% at an application rate of 100 g/ha: Ia-119, Ia-124, Ia-125, Ia-127, Ia-129, Ia-131, Ia-137, Ia-138, Ia-140, Ia-141, Ia-143, Ia-146, Ia-147, Ia-148, Ia-149, Ia-156, Ia-158, Ia-161, Ia-165, Ia-168, Ia-172, Ia-176, Ia-178, Ia-190, Ia-195, Ia-200, Ia-203, Ia-204, Ia-205, Ia-206, Ia-207, Ia-208, Ia-210, Ia-211, Ia-212, Ia-213, Ia-214, Ia-215, Ia-219, Ia-225, Ia-226, Ia-239, Ia-247, Ia-248, Ia-251, Ia-251, Ia-252, Ia-253, Ia-256, Ia-257, Ia-258, Ia-259, Ia-260, Ia-264, Ia-266, Ia-267, Ia-270, Ia-271, Ia-272, Ia-273, Ia-274, Ia-275, Ia-276, Ia-277, Ia-278, Ia-278, Ia-279, Ia-280, Ia-281, Ia-282, Ia-282, Ia-284, Ic-26, Ic-27, Ic-29, Ie-1, Ie-2, Ie-3, If-3

In this test, for example, the following compounds from the Preparation Examples exhibit efficacy of 83% at an application rate of 100 g/ha: Ia-155, Ia-170, Ia-175, Ia-179, Ia-183, Ia-196, Ia-198, Ia-209, Ia-223, If-2

Example 16

*Phaedon* Test (PHAECO Spray Treatment)
Solvent: 78.0 parts by weight of acetone
    1.5 parts by weight of dimethylformamide
Emulsifier: 0.5 part by weight of alkylaryl polyglycol ether
    To prepare an appropriate active ingredient formulation, 1 part by weight of active ingredient is mixed with the stated amounts of solvent and emulsifier, and the concentrate is diluted with emulsifier-containing water to the desired concentration. Leaf discs from china cabbage (*Brassica pekinensis*) are sprayed with an active ingredient formulation of the desired concentration and, after drying, populated with larvae of the mustard beetle (*Phaedon cochleariae*).
    After the desired time, the efficacy in % is determined. 100% means that all beetle larvae were killed; 0% means that no beetle larvae were killed.
    In this test, for example, the following compounds from the Preparation Examples exhibit efficacy of 100% at an application rate of 500 g/ha:

| Ia-2 | Ia-54 | Ia-84 | Ia-114 | Ic-3 | Ic-42 |
|---|---|---|---|---|---|
| Ia-3 | Ia-55 | Ia-85 | Ia-115 | Ic-4 | Ic-43 |
| Ia-4 | Ia-56 | Ia-86 | Ia-116 | Ic-5 | Ic-44 |
| Ia-5 | Ia-57 | Ia-87 | Ia-117 | Ic-6 | Ic-45 |
| Ia-6 | Ia-58 | Ia-88 | Ia-120 | Ic-7 | Ic-46 |
| Ia-7 | Ia-59 | Ia-89 | Ia-121 | Ic-8 | Ic-47 |
| Ia-8 | Ia-60 | Ia-90 | Ia-122 | Ic-9 | Id-1 |
| Ia-9 | Ia-61 | Ia-91 | Ia-123 | Ic-10 | Id-3 |
| Ia-10 | Ia-62 | Ia-92 | Ia-229 | Ic-13 | |
| Ia-11 | Ia-63 | Ia-93 | Ia-230 | Ic-14 | |
| Ia-12 | Ia-64 | Ia-94 | Ia-231 | Ic-15 | |
| Ia-13 | Ia-65 | Ia-95 | Ia-232 | Ic-16 | |
| Ia-14 | Ia-66 | Ia-96 | Ia-233 | Ic-17 | |
| Ia-15 | Ia-67 | Ia-97 | Ia-234 | Ic-18 | |
| Ia-16 | Ia-68 | Ia-98 | Ia-235 | Ic-19 | |
| Ia-17 | Ia-69 | Ia-99 | Ia-236 | Ic-20 | |
| Ia-18 | Ia-70 | Ia-100 | Ia-237 | Ic-21 | |
| Ia-19 | Ia-71 | Ia-101 | Ia-238 | Ic-22 | |
| Ia-20 | Ia-72 | Ia-102 | Ia-240 | Ic-23 | |
| Ia-21 | Ia-73 | Ia-103 | Ia-241 | Ic-24 | |
| Ia-44 | Ia-74 | Ia-104 | Ia-242 | Ic-25 | |
| Ia-45 | Ia-75 | Ia-105 | Ia-243 | Ic-31 | |
| Ia-46 | Ia-76 | Ia-106 | Ia-244 | Ic-32 | |
| Ia-47 | Ia-77 | Ia-107 | Ia-245 | Ic-33 | |
| Ia-48 | Ia-78 | Ia-108 | Ia-246 | Ic-34 | |
| Ia-49 | Ia-79 | Ia-109 | Ia-255 | Ic-37 | |
| Ia-50 | Ia-80 | Ia-110 | Ib-1 | Ic-38 | |
| Ia-51 | Ia-81 | Ia-111 | Ib-2 | Ic-39 | |
| Ia-52 | Ia-82 | Ia-112 | Ib-4 | Ic-40 | |
| Ia-53 | Ia-83 | Ia-113 | Ic-1 | Ic-41 | |

In this test, for example, the following compounds from the Preparation Examples exhibit efficacy of 83% at an application rate of 500 g/ha: Ia-1, Ia-27, Ib-3, Ic-11, Ic-2

In this test, for example, the following compounds from the Preparation Examples exhibit efficacy of 100% at an application rate of 100 g/ha:

|  |
|---|
| Ia-124 |
| Ia-125 |
| Ia-126 |
| Ia-127 |
| Ia-128 |
| Ia-129 |
| Ia-130 |
| Ia-131 |
| Ia-132 |
| Ia-133 |
| Ia-134 |
| Ia-135 |
| Ia-136 |
| Ia-137 |
| Ia-138 |
| Ia-139 |
| Ia-140 |
| Ia-141 |
| Ia-142 |
| Ia-143 |
| Ia-144 |
| Ia-145 |
| Ia-146 |
| Ia-147 |
| Ia-148 |
| Ia-149 |
| Ia-150 |
| Ia-151 |
| Ia-152 |
| Ia-153 |
| Ia-154 |
| Ia-155 |
| Ia-156 |
| Ia-158 |
| Ia-159 |
| Ia-160 |
| Ia-161 |
| Ia-162 |
| Ia-163 |
| Ia-164 |

| | |
|---|---|
| Ia-165 | Ia-263 |
| Ia-166 | Ia-264 |
| Ia-167 | Ia-265 |
| Ia-168 | Ia-266 |
| Ia-169 | Ia-267 |
| Ia-170 | Ia-268 |
| Ia-171 | Ia-269 |
| Ia-172 | Ia-270 |
| Ia-173 | Ia-271 |
| Ia-174 | Ia-272 |
| Ia-175 | Ia-273 |
| Ia-176 | Ia-274 |
| Ia-177 | Ia-275 |
| Ia-178 | Ia-276 |
| Ia-179 | Ia-277 |
| Ia-180 | Ia-278 |
| Ia-181 | Ia-279 |
| Ia-182 | Ia-280 |
| Ia-183 | Ia-281 |
| Ia-184 | Ia-282 |
| Ia-185 | Ia-283 |
| Ia-186 | Ia-284 |
| Ia-187 | Ib-3 |
| Ia-188 | Ic-26 |
| Ia-189 | Ic-27 |
| Ia-190 | Ic-29 |
| Ia-191 | Ic-30 |
| Ia-192 | Ic-48 |
| Ia-193 | Id-4 |
| Ia-194 | Ie-1 |
| Ia-195 | Ie-2 |
| Ia-196 | Ie-3 |
| Ia-197 | If-1 |
| Ia-198 | If-2 |
| Ia-199 | If-3 |
| Ia-200 | Ig-1 |
| Ia-201 | |
| Ia-202 | |
| Ia-203 | |
| Ia-204 | |
| Ia-205 | |
| Ia-205 | |
| Ia-206 | |
| Ia-208 | |
| Ia-209 | |
| Ia-210 | |
| Ia-211 | |
| Ia-212 | |
| Ia-213 | |
| Ia-214 | |
| Ia-215 | |
| Ia-216 | |
| Ia-217 | |
| Ia-219 | |
| Ia-220 | |
| Ia-221 | |
| Ia-222 | |
| Ia-223 | |
| Ia-224 | |
| Ia-225 | |
| Ia-226 | |
| Ia-227 | |
| Ia-228 | |
| Ia-239 | |
| Ia-247 | |
| Ia-248 | |
| Ia-249 | |
| Ia-250 | |
| Ia-251 | |
| Ia-252 | |
| Ia-253 | |
| Ia-254 | |
| Ia-256 | |
| Ia-257 | |
| Ia-258 | |
| Ia-259 | |
| Ia-260 | |
| Ia-261 | |
| Ia-262 | |

Example 17

*Myzus* Test (MYZUPE Spray Treatment)

Solvent: 78 parts by weight of acetone
  1.5 parts by weight of dimethylformamide
Emulsifier: 0.5 part by weight of alkylaryl polyglycol ether To prepare an appropriate active ingredient formulation, 1 part by weight of active ingredient is mixed with the stated amounts of solvent and emulsifier, and the concentrate is diluted with emulsifier-containing water to the desired concentration. Leaf discs from china cabbage (*Brassica pekinensis*) infested by all stages of the green peach aphid (*Myzus persicae*) are sprayed with an active ingredient formulation of the desired concentration.

After 6 days, the efficacy in % is determined. 100% means that all aphids were killed; 0% means that no aphids were killed.

In this test, for example, the following compounds from the Preparation Examples exhibit efficacy of 100% at an application rate of 500 g/ha: Ia-21, Ia-22, Ia-23, Ia-57, Ia-58, Ia-59, Ia-60, Ia-64, Ia-65, Ia-75, Ia-112

In this test, for example, the following compounds from the Preparation Examples exhibit efficacy of 90% at an application rate of 500 g/ha: Ia-36, Ia-41, Ia-55, Ia-63, Ia-67, Ia-69, Ia-78, Ia-79, Ic-37, Ic-44

In this test, for example, the following compounds from the Preparation Examples exhibit efficacy of 80% at an application rate of 500 g/ha: Ia-36, Ia-43, Ia-61, Ia-62, Ic-12

In this test, for example, the following compounds from the Preparation Examples exhibit efficacy of 100% at an application rate of 100 g/ha: Ia-115, Ia-130, Ia-131, Ia-136, Ia-141, Ia-142, Ia-143, Ia-150, Ia-153, Ia-155, Ia-156, Ia-160, Ia-162, Ia-163, Ia-164, Ia-169, Ia-170, Ia-174, Ia-175, Ia-184, Ia-190, Ia-195, Ia-252, Ia-256, Ia-276, Ia-277, Ia-278, Ia-279, Ia-280, Ic-26, If-2

In this test, for example, the following compounds from the Preparation Examples exhibit efficacy of 90% at an application rate of 100 g/ha: Ia-127, Ia-140, Ia-154, Ia-161, Ia-179, Ia-180, Ia-194, Ia-197, Ia-239, Ia-242, Ia-282, Ic-44, Id-4

In this test, for example, the following compounds from the Preparation Examples exhibit efficacy of 80% at an application rate of 100 g/ha: Ia-132, Ia-138, Ia-152, Ia-158, Ia-167, Ia-168, Ia-187, Ia-251, Ia-254

Example 18

*Tetranychus* Test; OP-Resistant (TETRUR Spray Treatment)
Solvent: 78.0 parts by weight of acetone
1.5 parts by weight of dimethylformamide
Emulsifier: 0.5 part by weight of alkylaryl polyglycol ether To prepare an appropriate active ingredient formulation, 1 part by weight of active ingredient is mixed with the stated amounts of solvent and emulsifier, and the concentrate is diluted with emulsifier-containing water to the desired concentration. Leaf discs from the common bean (*Phaseolus vulgaris*) infested by all stages of the red spider mite (*Tetranychus urticae*) are sprayed with an active ingredient formulation of the desired concentration.

After 6 days, the efficacy in % is determined. 100% means that all spider mites were killed; 0% means that no spider mites were killed.

In this test, for example, the following compounds from the Preparation Examples exhibit an efficacy of 100% at an application rate of 500 g/ha:

Ia-19
Ia-21
Ia-22
Ia-23
Ia-30
Ia-36
Ia-37
Ia-41
Ia-42
Ia-45
Ia-48
Ia-49
Ia-50
Ia-51
Ia-52
Ia-53
Ia-54
Ia-55
Ia-56
Ia-57
Ia-58
Ia-59
Ia-60
Ia-61
Ia-62
Ia-63
Ia-64
Ia-68
Ia-69
Ia-70
Ia-71
Ia-74
Ia-75
Ia-78
Ia-79
Ia-85
Ia-87
Ia-90
Ia-93
Ia-94
Ia-96
Ia-99
Ia-100
Ia-112
Ia-113
Ia-114
Ia-116
Ia-120
Ia-229
Ia-231
Ia-232
Ia-235
Ia-237
Ia-238
Ia-240
Ia-242
Ia-244
Ic-18
Ic-24
Ic-25
Ic-32
Ic-33
Ic-36
Ic-37
Ic-42
Ic-46

In this test, for example, the following compounds from the Preparation Examples exhibit an efficacy of 90% at an application rate of 500 g/ha:

Ia-18
Ia-31
Ia-32
Ia-43
Ia-65
Ia-73
Ia-80
Ia-83
Ia-88
Ia-91
Ia-92
Ia-95
Ia-97
Ia-98
Ia-103
Ia-104
Ia-106
Ia-110
Ia-111
Ia-115
Ia-122
Ia-236
Ia-241
Ia-245
Ic-31

In this test, for example, the following compounds from the Preparation Examples exhibit an efficacy of 80% at an application rate of 500 g/ha:

| | | | | | |
|---|---|---|---|---|---|
| Ia-47 | Ia-86 | Ia-101 | Ia-105 | Ia-108 | Ia-230 |
| Ia-84 | Ia-89 | Ia-102 | Ia-107 | Ia-109 | Ia-255 |

In this test, for example, the following compounds from the Preparation Examples exhibit an efficacy of 100% at an application rate of 100 g/ha:

| Ia-119 | Ia-132 | Ia-138 | Ia-144 | Ia-148 | Ia-152 | Ia-156 | Ia-162 | Ia-170 | Ia-178 | Ia-182 |
| Ia-124 | Ia-133 | Ia-139 | Ia-145 | Ia-149 | Ia-153 | Ia-158 | Ia-163 | Ia-173 | Ia-179 | Ia-183 |
| Ia-128 | Ia-134 | Ia-141 | Ia-146 | Ia-150 | Ia-154 | Ia-159 | Ia-164 | Ia-174 | Ia-180 | Ia-184 |
| Ia-129 | Ia-136 | Ia-143 | Ia-147 | Ia-151 | Ia-155 | Ia-161 | Ia-168 | Ia-176 | Ia-181 | Ia-185 |
| Ia-186 | Ia-192 | Ia-196 | Ia-214 | Ia-227 | Ia-252 | Ia-270 | Ia-274 | Ia-278 | Ia-282 | If-2 |
| Ia-188 | Ia-193 | Ia-203 | Ia-220 | Ia-239 | Ia-253 | Ia-271 | Ia-275 | Ia-279 | Ic-29 | |
| Ia-190 | Ia-194 | Ia-211 | Ia-222 | Ia-246 | Ia-257 | Ia-272 | Ia-276 | Ia-280 | Ic-31 | |
| Ia-191 | Ia-195 | Ia-213 | Ia-226 | Ia-247 | Ia-261 | Ia-273 | Ia-277 | Ia-281 | Ic-45 | |

In this test, for example, the following compounds from the Preparation Examples exhibit an efficacy of 90% at an application rate of 100 g/ha:

| Ia-137 | Ia-189 | Ia-205 | Ia-251 | Ia-284 | Ie-2 |
| Ia-175 | Ia-199 | Ia-215 | Ia-266 | Ia-66 | If-3 |
| Ia-187 | Ia-204 | Ia-224 | Ia-267 | Ie-1 | |

In this test, for example, the following compounds from the Preparation Examples exhibit an efficacy of 80% at an application rate of 100 g/ha:

Ia-18
Ia-32
Ia-126
Ia-127
Ia-130
Ia-131
Ia-140
Ia-160
Ia-169
Ia-171
Ia-172
Ia-210
Ia-212
Ia-219
Ia-259
Ia-264
Ie-3
Ig-1

The invention claimed is:

1. A compound of formula (I) or a diastereomer, enantiomer, E/Z isomer, or salt thereof

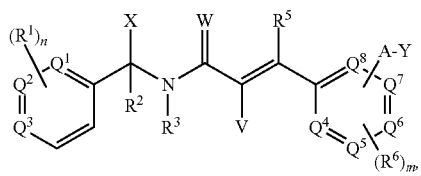

(I)

where
$R^1$ is hydrogen, halogen, nitro, cyano, optionally monosubstituted or identically or differently polysubstituted $C_1$-$C_4$-alkyl, $C_2$-$C_6$-alkenyl, $C_2$-$C_4$-alkynyl, $C_1$-$C_4$-alkoxy, $C_1$-$C_4$-alkylthio, $C_1$-$C_4$-alkylsulphinyl, $C_1$-$C_4$-lkylsulphonyl, $C_3$-$C_4$-cycloalkyl, $C_1$-$C_4$-alkylcarbonyl, $C_1$-$C_4$-alkoxycarbonyl, $C_1$-$C_4$-alkylaminocarbonyl, $C_1$-$C_4$-dialkylaminocarbonyl or $C_1$-$C_4$-alkylaminosulphonyl,
where the substituents are each independently halogen, cyano, nitro, hydroxyl, $C_1$-$C_4$-alkyl, $C_1$-$C_4$-alkoxy, $C_3$-$C_4$-cycloalkyl, $C_1$-$C_4$-haloalkoxy or $C_1$-$C_4$-alkylthio,
n is 1, 2 or 3,
$R^2$ is hydrogen, cyano, hydroxyl, amino, optionally monosubstituted to identically or differently trisubstituted $C_1$-$C_4$-alkyl, $C_2$-$C_4$-alkenyl, $C_2$-$C_4$-alkynyl, $C_1$-$C_4$-alkoxy or $C_3$-$C_6$-cycloalkyl,
where the substituents are each independently halogen, cyano, nitro, hydroxyl, amino, $C_1$-$C_4$-alkyl or $C_1$-$C_4$-alkoxy,
$R^3$ is hydrogen, optionally monosubstituted or identically or differently polysubstituted $C_1$-$C_4$-alkyl, $C_2$-$C_4$-alkenyl, $C_2$-$C_4$-alkynyl, $C_3$-$C_4$-cycloalkyl, aryl-$C_1$-$C_4$-alkyl, $C_1$-$C_4$-alkylcarbonyl, $C_1$-$C_4$-alkylsulphonyl, arylcarbonyl, hetarylcarbonyl, $C_1$-$C_4$-alkoxycarbonyl or aryloxycarbonyl,
where the substituents are each independently halogen, cyano, nitro, hydroxyl, $C_1$-$C_6$-alkyl, $C_1$-$C_6$-alkoxy, $C_3$-$C_6$-cycloalkyl, $C_1$-$C_6$-haloalkoxy, $C_1$-$C_6$-alkylthio, $C_1$-$C_4$-alkoxycarbonyl, aminocarbonyl, $C_1$-$C_4$-alkylaminocarbonyl or $C_1$-$C_4$-dialkylaminocarbonyl,
V is $R^4$,
where
$R^4$ is hydrogen, halogen or optionally monosubstituted or identically or differently polysubstituted $C_1$-$C_4$-alkyl,
where the substituents are each independently halogen, $C_1$-$C_4$-alkyl or $C_1$-$C_4$-alkoxy,
$R^5$ is hydrogen, halogen or optionally monosubstituted or identically or differently polysubstituted $C_1$-$C_4$-alkyl,
where the substituents are each independently halogen or $C_1$-$C_4$-alkyl,
$R^6$ is hydrogen, halogen, nitro, cyano, amino, hydroxyl, optionally monosubstituted or identically or differently polysubstituted $C_1$-$C_4$-alkyl, $C_2$-$C_4$-alkenyl, $C_2$-$C_4$-alkynyl, $C_3$-$C_5$-cycloalkyl, $C_1$-$C_4$-alkoxy, ($C_1$-$C_4$-alkoxy)carbonyl, $C_1$-$C_4$-alkylamino, formyl, ($C_1$-$C_4$-alkyl)carbonyl, $C_1$-$C_4$alkoxyimino-$C_1$-$C_4$-alkyl, $C_1$-$C_4$-dialkylamino, ($C_1$-$C_4$-alkylamino)carbonyl, ($C_1$-$C_4$-dialkylamino)carbonyl, $C_1$-$C_4$-alkylthio, $C_1$-$C_4$-alkylsulphinyl, $C_1$-$C_4$-alkylsulphonyl, $C_1$-$C_4$-alkylaminosulphonyl or $C_1$-$C_4$-alkylsulphonylamino,
where the substituents are each independently halogen, cyano, nitro, hydroxyl, amino, $C_1$-$C_6$-alkyl, $C_1$-$C_6$-alkoxy, $C_3$-$C_6$-cycloalkyl, $C_1$-$C_6$-haloalkoxy or $C_1$-$C_6$-alkylthio,
m is 0, 1, 2, or 3,
X is unsubstituted $C_1$-$C_4$-haloalkyl,
W is O,
A-Y together are cyano or are optionally monosubstituted heterocyclyl or oxoheterocyclyl selected from the group consisting of pyrrolyl, oxazolyl, isoxazolyl, thiazolyl, isothiazolyl, pyrazolyl, imidazolyl, 1,2,3-triazolyl, 1,2,4-triazolyl, 1,2,3-oxadiazolyl, 1,2,4-oxadiazolyl, 1,3,4-oxadiazolyl, 1,2,3-thiadiazolyl, 1,2,4-thiadiazolyl, 1,3,4-thiadiazolyl, tetrazolyl, pyridyl, pyrimidinyl, pyridazinyl, pyrazinyl, 1,2,4-triazinyl, 1,3,5-triazinyl, pyrrolidinyl, isoxazolidinyl, pyrazolidinyl, oxazolidinyl, thiazolidinyl, imidazolidinyl, imidazolidinyl, 1,2,4-oxadiazolidinyl, 1,2,4-thiadiazolyl, 1,2,4-triazolidinyl, 1,3,4-oxadiazolidinyl, 1,3,4-thiadiazolidinyl, 1,3,4-triazolidinyl, pyrrolinyl, isoxazolinyl, 2,3-dihydropyrazolyl, 3,4-dihydropyrazolyl, 4,5-dihydropyrazolyl, 2,3-dihydrooxazolyl, 3,4-dihydrooxazolyl, piperidinyl, oxopyrrolidinyl, 3-oxo-1,2,4-triazolidinyl, 5-oxo-1,2,4-triazolidinyl, dioxopyrrolidinyl, oxomorpholinyl, oxopiperidinyl and oxopiperazinyl, where the substituents are halogen, nitro, cyano, amino, hydroxyl, $C_1$-$C_6$-alkyl, $C_1$-$C_6$-alkoxy, $C_1$-$C_6$-alkoxy-$C_1$-$C_6$alkyl, $C_1$-$C_6$-alkylcarbonyl, $C_2$-$C_6$-alkenyl, $C_2$-$C_6$-alkynyl, $C_3$-$C_6$-cycloalkyl, $C_1$-$C_6$-alkylthio, $C_1$-$C_6$-alkylsulphinyl, $C_1$-$C_6$-alkylsulphonyl, $C_1$-$C_6$-alkoxycarbonyl or $C_1$-$C_6$-alkylaminocarbonyl, or A is a bivalent chemical moiety which is —NR$^{13}$C(=O)—, —C(R$^{11}$)(R$^{12}$)NR$^{13}$C(=O)—, —C(=O)NR$^{13}$—, —C(=O)N(R$^{13}$)—O—, —C(=O)NR$^{13}$CH$_2$—, —C(=O)O—, —C(=O)NR$^{13}$CH$_2$C(=O)NR$^{14}$—, —C(=O)NR$^{14}$—, —C(R$^{11}$)(R$^{12}$)NR$^{13}$—, —S(=O)$_2$NR$^{13}$—, or —C(R$^{11}$)(R$^{12}$)NR$^{13}$S(=O)$_2$—, where the first (left-hand) connection site in the bivalent chemical moieties in each case is connected to the ring at one of positions Q$^4$ to Q$^8$ and the second (right-hand) connection site in each case to Y, where R$^{11}$ and R$^{12}$ are each independently hydrogen, cyano or optionally monosubstituted to identically or differently trisubstituted $C_1$-$C_4$-alkyl or $C_3$-$C_6$-cycloalkyl, where the substituents are each independently selected from halogen, cyano, nitro, hydroxyl, $C_1$-$C_6$-alkyl or $C_1$-$C_6$-alkoxy, and where R$^{13}$ and R$^{14}$ are each independently hydrogen, optionally monosubstituted or identically or differently polysubstituted $C_1$-$C_4$-alkyl or $C_3$-$C_6$-cycloalkyl, $C_1$-$C_4$-alkylcarbonyl, $C_1$-$C_4$-alkoxycarbonyl or aryloxycarbonyl, where the substituents are each independently halogen, cyano, nitro, hydroxyl, $C_1$-$C_4$-alkyl or $C_1$-$C_4$-alkoxy, Y is hydrogen or optionally monosubstituted $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkenyl, is an optionally monosubstituted phenyl, or Y is an optionally monosubstituted heterocycle selected from the group consisting of thienyl, furanyl, pyrrolyl, oxazolyl, isoxazolyl, thiazolyl, isothiazolyl, pyrazolyl, imidazolyl, 1,2,3-triazolyl, 1,2,4,-triazolyl, 1,2,3-oxadiazolyl, 1,2,4-oxadiazolyl, 1,3,4-oxadiazolyl, 1,2,3-thiadiazolyl, 1,2,4-thiadiazolyl, 1,3,4-thiadiazolyl, tetrazolyl, pyridinyl, pyrimidinyl, pyridazinyl, pyrazinyl, 1,2,4-triazinyl, 1,3,5-triazinyl, pyrrolidinyl, isoxazolidinyl, pyrazolidinyl, oxazolidinyl, thiazolidinyl, imidazolidinyl, 1,2,4-oxadiazolidinyl, 1,2,4-thiadiazolidinyl, 1,2,4-triazolidinyl, 1,3,4-oxadiazolidinyl, 1,3,4-thiadiazolidinyl, 1,3,4-triazolidinyl, pyrrolinyl, isoxazolinyl, 2,3-dihydropyrazolyl, 3,4-dihydropyrazolyl, 4,5-dihydropyrazolyl, 2,3-dihydrooxazolyl, 3,4-dihydrooxazolyl, piperidinyl, tetrahydrothienyl, piperazinyl, morpholinyl, thiomorpholinyl, dihydropyranyl, tetrahydropyranyl, tetrahydrothienyl, 1,4-dioxanyl, 1,3-dioxanyl, dioxolanyl, dioxolyl, tetrahydrofuranyl, dihydrofuranyl, oxetanyl, thietanyl, oxidothietanyl, dioxidothietanyl, oxiranyl, azetidinyl, oxazetidinyl, oxaziridinyl, oxazepanyl, oxazinanyl, azepanyl, 5 oxopyrrolidinyl, dioxopyrrolidinyl, oxomorpholinyl, oxopiperidinyl, oxopiperazinyl and oxotetrahydrofuranyl, where the substituents are halogen, nitro, cyano, hydroxyl, amino, $C_1$-$C_6$-alkyl, $C_1$-$C_6$-alkoxy, $C_1$-$C_6$-alkylcarbonyl, $C_2$-$C_6$-alkenyl, $C_2$-$C_6$-alkynyl, $C_3$-$C_6$-cycloalkyl, $C_1$-$C_6$-alkylthio, $C_1$-$C_6$-alkylsulphinyl, $C_1$-$C_6$-alkylsulphonyl, or $C_1$-$C_6$-alkoxycarbonyl, Q$^1$ to Q$^3$ are each independently a carbon atom which is substituted by hydrogen or by R$^1$, Q$^4$ is a carbon atom which is substituted by hydrogen or R$^6$, and Q$^5$ to Q$^8$ are each independently a carbon atom which is substituted by hydrogen, R$^6$ or A-Y, where exactly one of Q$^5$, Q$^6$, Q$^7$, Q$^8$ is substituted by A-Y.

2. A compound of formula (I) or a diastereomer, enantiomer, E/Z isomer, or salt thereof according to claim 1, where R$^1$ is hydrogen, halogen, nitro, cyano, optionally monosubstituted or identically or differently polysubstituted $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_1$-$C_4$-alkylcarbonyl, $C_1$-$C_4$-alkoxycarbonyl, $C_1$-$C_4$-alkylaminocarbonyl, $C_1$-$C_4$-dialkylaminocarbonyl or $C_1$-$C_4$-alkylaminosulphonyl, where the substituents are each independently halogen, cyano, nitro, hydroxyl, $C_1$-$C_4$-alkyl, $C_1$-$C_4$-alkoxy, $C_3$-$C_4$-cycloalkyl, $C_1$-$C_4$-haloalkoxy or $C_1$-$C_4$-alkylthio, n is 1,2 or 3, R$^2$ is hydrogen, cyano, hydroxyl, optionally monosubstituted to identically or differently trisubstituted $C_1$-$C_4$-alkyl or $C_1$-$C_4$-alkoxy, where the substituents are each independently halogen, cyano, nitro, hydroxyl, amino, $C_1$-$C_4$-alkyl or $C_1$-$C_4$-alkoxy, R$^3$ is hydrogen, optionally monosubstituted or identically or differently polysubstituted $C_1$-$C_4$-alkyl, $C_2$-$C_4$-alkenyl, $C_2$-$C_4$-alkynyl, $C_1$-$C_4$-alkylcarbonyl, $C_1$-$C_4$-alkylsulphonyl, $C_1$-$C_4$-alkoxycarbonyl or aryloxycarbonyl, where the substituents are each independently halogen, cyano, nitro, hydroxyl. $C_1$-$C_6$-alkyl, $C_1$-$C_6$-alkoxy or $C_1$-$C_4$-alkoxycarbonyl, V is R$^4$, where R$^4$ is hydrogen or optionally monosubstituted to identically or differently trisubstituted $C_1$-$C_4$-alkyl, where the substituents are each independently halogen, $C_1$-$C_4$-alkyl or $C_1$-$C_4$-alkoxy, R$^6$ is hydrogen, halogen, nitro, cyano, optionally monosubstituted or identically or differently polysubstituted $C_1$-$C_4$-alkyl, $C_2$-$C_4$-alkynyl, $C_1$-$C_4$-alkoxy, ($C_1$-$C_4$-alkyl)carbonyl, ($C_1$-$C_4$-alkylamino)carbonyl, ($C_1$-$C_4$-dialkylamino)carbonyl, $C_1$-$C_4$-alkylthio, $C_1$-$C_4$-alkylsulphinyl, $C_1$-$C_4$-alkylsulphonyl, $C_1$-$C_4$-alkylaminosulphonyl or $C_1$-$C_4$-alkylsulphonylamino, where the substituents are each independently halogen, cyano, nitro, $C_1$-$C_6$-alkyl, $C_1$-$C_6$-alkoxy, $C_1$-$C_6$-haloalkoxy or $C_1$-$C_6$-alkylthio, m is 0, 1, 2, or 3, X is unsubstituted $C_1$-$C_4$-haloalkyl, W is O, A-Y together are cyano or are optionally monosubstituted heterocyclyl selected from the group consisting of pyrrolyl, oxazolyl, isoxazolyl, thiazolyl, isothiazolyl, pyrazolyl, imidazolyl, 2-imidazolinyl, 1,2,3-triazolyl, 1,2,4-triazolyl, 1,2,3-oxadiazolyl, 1,2,4-oxadiazolyl, 1,3,4-oxadiazolyl, 1,2,3-thiadiazolyl, 1,2,4-thiadiazolyl, 1,3,4-thiadiazolyl, tetrazolyl, pyridyl, pyrimidinyl, pyridazinyl, pyrazinyl, 1,2.4-triazinyl and 1,3,5-triazinyl, where the substituents are halogen, nitro, cyano, hydroxyl, amino, $C_1$-$C_4$-alkyl, C -$C_4$-alkoxy, $C_1$-$C_4$-alkoxy-$C_1$-

$C_4$-alkyl, $C_2$-$C_4$-alkynyl, $C_1$-$C_6$-alkylthio, $C_1$-$C_6$-alkylsulphinyl, $C_1$-$C_6$-alkylsulphonyl, or $C_3$-$C_6$-cycloalkyl,
or
A is a bivalent chemical moiety which is —NR$^{13}$C(=O)—, —C(R$^{11}$)(R$^{12}$)NR$^{13}$C(=O)—, —C(=O)-O—, —C(=O)NR$^{13}$—, —C(=O)N(R$^{13}$)—O—, —C(=O)NR$^{13}$CH$_2$—, —C(=O)NR$^{13}$CH$_2$C(=O)NR$^{14}$—, —C(=O)NR$^{13}$NR$^{14}$—, —C(R$^{11}$)(R$^{12}$)NR$^{13}$—, —S(=O)$_2$NR$^{13}$—, or —C(R$^{11}$)(R$^{12}$)NR$^{13}$S(=O)$_2$—,
where the first (left-hand) connection site in the bivalent chemical moieties in each case is connected to the ring at one of positions $Q^4$ to $Q^8$ and the second (right-hand) connection site in each case to Y, where
R$^{11}$ and R$^{12}$ are each independently hydrogen, $C_1$-$C_4$-alkyl or $C_1$-$C_4$-haloalkyl,
and where R$^{13}$ and R$^{14}$ are each independently hydrogen, optionally monosubstituted or identically or differently polysubstituted $C_1$-$C_4$-alkyl or $C_3$-$C_6$-cycloalkyl, $C_1$-$C_4$-alkylcarbonyl, aryloxycarbonyl or $C_1$-$C_4$-alkoxycarbonyl, where the substituents are each independently halogen, cyano, $C_1$-$C_4$-alkyl or $C_1$-$C_4$-alkoxy,
Y is hydrogen or optionally monosubstituted $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkenyl, is an optionally monosubstituted phenyl,
or Y is an optionally monosubstituted heterocycle selected from the group consisting of thienyl, furanyl, pyrrolyl, oxazolyl, isoxazolyl, thiazolyl, isothiazolyl, pyrazolyl, imidazolyl, 1,2,3-triazolyl, 1,2,4-triazolyl, 1,2,3-oxadiazolyl, 1,2,4-oxadiazolyl, 1,3,4-oxadiazolyl, 1,2,3-thiadiazolyl, 1,2,4-thiadiazolyl, 1,3,4-thiadiazolyl, tetrazolyl, pyridinyl, pyrimidinyl, pyridazinyl, pyrazinyl, 1,2,4-triazinyl, 1,3,5-triazinyl, piperazinyl, morpholinyl, tetrahydropyranyl, 1,4-dioxanyl, 1,3-dioxanyl, dioxolanyl, dioxolyl, tetrahydrofuranyl, dihydrofuranyl, oxetanyl, thietanyl, oxidothietanyl, dioxidothietanyl, oxiranyl, azetidinyl, oxazetidinyl, oxazepanyl, oxazinanyl, azepanyl, 5-oxopyrrolidinyl, dioxopyrrolidinyl, oxomorpholinyl, oxopiperidinyl, oxopiperazinyl and oxotetrahydrofuranyt
where the substituents are halogen, nitro, cyano, hydroxyl, amino, $C_1$-$C_6$-alkyl, $C_1$-$C_6$-alko $C_1$-$C_6$-alkylcarbonyl, $C_2$-$C_6$-alkenyl, $C_2$-$C_6$-alkynyl, $C_3$-$C_6$-cycloalkyl, $C_1$-$C_6$-alkylsulphinyl, $C_1$-$C_6$-alkylsulphonyl, $C_1$-$C_6$-alkylthio, or $C_1$-$C_6$-alkoxycarbonyl,
$Q^1$ to $Q^3$ are each independently a carbon atom which is substituted by hydrogen or by R$^1$,
$Q^4$ is a carbon atom which is substituted by hydrogen or R$^6$, and
$Q^5$ to $Q^8$ are each independently a carbon atom which is substituted by hydrogen, R$^6$ or A-Y,
where exactly one of $Q^5$, $Q^6$, $Q^7$, $Q^8$ is substituted by A-Y.
3. A compound of formula (I) or a diastereomer, enantiomer, E/Z isomer, or salt thereof according to claim 1, where
R$^1$ is hydrogen, nitro, cyano, fluorine, chlorine, bromine, iodine, methyl, ethyl, n-or ipropyl, fluoromethyl, chloromethyl, trichloromethyl, difluoromethyl, dichlorofluoromethyl, chlorodifluoromethyl, trifluoromethyl, fluoroethyl, chloroethyl, difluoroethyl, dichloroethyl, trifluoroethyl, chlorofluoroethyl, chlorodifluoroethyl, dichlorofluoroethyl, tetrafluoroethyl, pentafluoroethyl, chlorotetrafluoroethyl, trichloroethyl, heptafluoro-n-propyl, heptafluoroisopropyl, methoxy, ethoxy, n- or i-propoxy, fluoromethoxy, difluoromethoxy, trifluoromethoxy, methylthio, ethylthio, difluoromethylthio, trifluoromethylthio, chlorodifluoromethylthio, methylsulphinyl, trifluoromethylsulphinyl, trifluoromethylsulphonyl, methylsulphonyl, ethylsulphonyl, acetyl, propionyl, methoxycarbonyl, ethoxycarbonyl, methylaminocarbonyl, dimethylaminocarbonyl or ethylaminocarbonyl,
n is 1,2 or 3,
R$^2$ is hydrogen, methyl or ethyl,
R$^3$ is hydrogen, methyl, ethyl, 2-ethynyl, 2-propenyl, methoxymethyl, ethoxymethyl, methylcarbonyl, ethylcarbonyl, methoxycarbonyl, ethoxycarbonyl, npropoxycarbonyl, i-propoxycarbonyl, n-butoxycarbonyl, t-butoxycarbonyl or phenoxycarbonyl,
V is R$^4$, where
R$^4$ is hydrogen or methyl,
R$^5$ is hydrogen,
R$^6$ is hydrogen, nitro, cyano, fluorine, chlorine, bromine, iodine, methyl, ethyl, n- or ipropyl, n- ,i- ,s- or t-butyl, ethynyl, propynyl, fluoromethyl, chloromethyl, trichloromethyl, difluoromethyl, dichlorofluoromethyl, chlorodifluoromethyl, trifluoromethyl, fluoroethyl, chloroethyl, difluoroethyl, dichloroethyl, trifluoroethyl, chlorofluoroethyl, chlorodifluoroethyl, fluorodichloroethyl, tetrafluoroethyl, pentafluoroethyl, chlorotetrafluoroethyl, trichloroethyl, heptafluoro-n-propyl, heptafluoroisopropyl, methoxy, ethoxy, n- or i-propoxy, fluoromethoxy, difluoromethoxy, trifluoromethoxy, methylthio, ethylthio, difluoromethylthio, trifluoromethylthio, chlorodifluoromethylthio, methylsulphinyl, trifluoromethylsulphinyl, trifluoromethylsulphonyl, methylsulphonyl, ethylsulphonyl, acetyl, propionyl, methoxycarbonyl, ethoxycarbonyl, methylaminocarbonyl, ethylaminocarbonyl or dimethylaminocarbonyl,
m is 0, 1 or 2,
X is trifluoromethyl, difluoromethyl, fluoromethyl, chlorodifluoromethyl, dichlorofluoromethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2-chloro-2,2-difluoroethyl, 1,1-difluoroethyl, pentafluoroethyl, heptafluoro-n-propyl or nonafluoro-n-butyl,
W is O,
A-Y together are cyano or are optionally monosubstituted heterocyclyl selected from the group consisting of 1,2,4-oxadiazol-3-yl, 1H-imidazol-1-yl, 1H-pyrazol-1-yl, 1H-1,2,4-triazol-1-yl, 1H-1,2,3-triazol-1-yl, 1H-1,2,3,4-tetrazol-1-yl, and 2H-1,2,3,4-tetrazol-1-yl,
where the substituents are fluorine, chlorine, cyano, hydroxyl, amino, methyl, ethyl, n- or i-propyl, cyclopropyl, methoxy, ethoxy, n- or i-propoxy, methylthio, methylsulphinyl, methylsulphonyl, ethylthio, ethylsulphinyl, ethylsulphonyl, methoxycarbonyl, ethoxycarbonyl, or methylaminocarbonyl,
or
A is a bivalent chemical moiety which is —NR$^{13}$C(=O)—, —C(R$^{11}$)(R$^{12}$)NR$^{13}$C(=O)—, —C(R$^{11}$)(R$^{12}$)NR$^{13}$S(=O)NR$^{13}$—, —C(=O)N(R$^{13}$)—O—,—C(=O)NR$^{13}$CH$_2$—, —S(=O)$_2$NR$^{13}$—, —C(=O)O—, —C(=O)NR$^{13}$CH$_2$C(=O) NR$^{14}$—, —C(R$^{11}$)(R$^{12}$)NR$^{13}$—, or —C(=O)NR$^{13}$NR$^{14}$—, where the first (left-hand) connection site in the bivalent chemical moieties in each case is connected to the ring at one of positions $Q^4$ to $Q^8$ and the second (right-hand) connection site in each case to Y, where
R$^{11}$ and R$^{12}$ are each hydrogen or methyl,
R$^{13}$ and R$^{14}$ are each hydrogen, methyl, ethyl, cyclopropyl, cyanoethyl, methoxymethyl, ethoxymethyl, methylcarbonyl, ethylcarbonyl, npropylcarbonyl, i-propylcarbonyl, n-butylcarbonyl, t-butylcarbonyl, methoxycarbonyl, ethoxycarbonyl, n-propoxycarbonyl, i-propoxycarbonyl, n-butoxycarbonyl, t-butoxycarbonyl or phenoxycarbonyl, Y is hydrogen or optionally monosubstituted methyl, ethyl, n- or i-propyl, n-, i-, s- or t-butyl, n-, i-, s-, t- or neopentyl, cyclopropyl, cyclobutyl, cyclopentyl, cyclohexyl, ethenyl, propenyl, butenyl, pentenyl, ethynyl, propynyl, butynyl or pentynyl, where the substituents are fluorine, chlorine, bromine, cyano, nitro, hydroxyl, amino, cyclopropyl, methoxy, ethoxy, n- or i-propoxy, methylthio, methylsulphinyl, methylsulphonyl, ethylthio, ethylsulphinyl , ethylsulphonyl, methoxycarbonyl or ethoxycarbonyl, or Y is an optionally mono- to trisubstituted oxetan-3-yi, thietan-3-yl, 1-oxidothietan-3-yl, 1,1-dioxidothietan-3-yl, tetrahydrofuran-2-yl, tetrahydrofuran-3-yl, tetrahydropyran-2-yl, tetrahydropyran-3-yl, tetrahydropyran-4-yl, 1,3-dioxan-2-yl, 1,3-dioxin -3-yl, 1,3-dioxan-4-yl, 1,4-dioxan-2-yl, morpholin-l-yl, phenyl, pyridin-2-yl, pyridin-3-yl, pyridin-4-yl, pyrimidin-2-yl, pyrimidin-4-yl, pyrimidin-5-yl, pyridazin-3-yl, pyrazin-2-yl, furan-2-yl, furan-3-yl, thiophen-2-yl, thiophen-3-yl, pyrrol-2-yl, thiazol-2-yl, thiazol-4-yl, thiazol-5-yl, 1,2,4-thiadiazol-5-yl, oxazol-2-yl, oxazol-4-yl, oxazol-5-yl, isoxazol-3-yl, isoxazol-4-yl, 1,2,3-oxdiazol-4-yl, 1,3,4-oxdiazol-2-yl, 1H-imidazol-2-yl, 1H-imidazol-4-yl, 1H-imidazol-5-yl, 1H-pyrazol-3-yl, 1H-pyrazol-4-yl, 1H-pyrazol-5-yl, 1H-1,2,4-triazol-3-yl, 1H-1,2,4-triazol-5-yl, 1H-1,2,3-triazol-4-yl, 1H-1,2,3-triazol-5-yl, 2H-1,2,3-triazol-2-yl, 2H-1,2,3-triazol-4-yl, 1H-1,3,4-triazol-2-yl, 1H-1,2,3,4-tett azol-5-yl, 2-oxopiperidin-3-yl, 2-oxotetrahydrofuran-3-yl or 5-oxotetrahydrofuran-2-yl, where the substituents may be fluorine, chlorine, bromine, cyano, nitro, hydroxyl, amino, methyl, ethyl, difluoromethyl, trifluoromethyl, pentafluoroethyl, n- or i-propyl, cyclopropyl, methoxy, ethoxy, n- or i-propoxy, fluoromethoxy, difluoromethoxy, trifluoromethoxy, fluoroethoxy, difluoroethoxy, trifluoroethoxy, methylthio, methylsulphinyl, methylsulphonyl, ethylthio, ethylsulphinyl, ethylsuiphonyl, methoxycarbonyl, ethoxycarbonyl, methylaminocarbonyl or dimethylaminocarbonyl, $Q^1$ to $Q^3$ are each independently a carbon atom which is substituted by hydrogen or by $R^1$, $Q^4$ is a carbon atom which is substituted by hydrogen or $R^6$, $Q^5$ to $Q^8$ are each independently a carbon atom which is substituted by hydrogen, $R^6$ or A-Y, where exactly one of $Q^5$, $Q^6$, $Q^7$, $Q^8$ is substituted by A-Y.

4. A compound of formula (I) or a diastereomer, enantiomer, E/Z isomer, or salt thereof according to claim 3, where $R^4$ is hydrogen, and $R^5$ is hydrogen.

5. A pesticide comprising at least one compound of formula (I) and/or a salt thereof according to claim 1 in biologically active contents of 0.00000001 up to 95% by weight, based on the weight of the pesticide.

6. A pesticide according to claim 5, comprising a further active agrochemical ingredient.

7. A compound of formula (I) or a diastereomer, enantiomer, E/Z isomer, or salt thereof according to claim 1, where $R^2$, $R^4$ and $R^5$ are each H and X is $CF_3$.

8. A compound of formula (I) or a diastereomer, enantiomer, E/Z isomer, or salt thereof

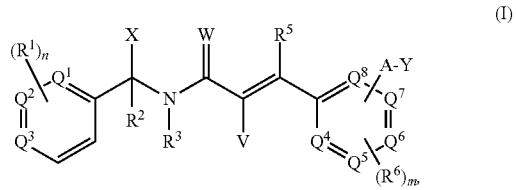

(I)

where $R^1$ is hydrogen, halogen, nitro, cyano, optionally monosubstituted or identically or differently polysubstituted $C_1$-$C_4$-alkyl, $C_2$-$C_6$-alkenyl, $C_2$-$C_4$-alkynyl, $C_1$-$C_4$-alkoxy, $C_1$-$C_4$-alkylthio, $C_1$-$C_4$-alkylsulphinyl, $C_1$-$C_4$-alkylsulphonyl, $C_3$-$C_4$-cycloalkyl, $C_1$-$C_4$-alkylcarbonyl, $C_1$-$C_4$-alkoxycarbonyl, $C_1$-$C_4$-alkylaminocarbonyl, $C_1$-$C_4$-dialkylaminocarbonyl or $C_1$-$C_4$-alkylaminosulphonyl, where the substituents are each independently halogen, cyano, nitro, hydroxyl, $C_1$-$C_4$-alkyl, $C_1$-$C_4$-alkoxy, $C_3$-$C_4$-cycloalkyl, $C_1$-$C_4$-haloalkoxy or $C_1$-$C_4$-alkylthio, n is 1, 2 or 3, $R^2$ is hydrogen, cyano, hydroxyl, amino, optionally monosubstituted to identically or differently trisubstituted $C_1$-$C_4$-alkyl, $C_2$-$C_4$-alkenyl, $C_2$-$C_4$-alkynyl, $C_1$-$C_4$-alkoxy or $C_3$-$C_6$-cycloalkyl, where the substituents are each independently halogen, cyano, nitro, hydroxyl, amino, $C_1$-$C_4$-alkyl or $C_1$-$C_4$-alkoxy, $R^3$ is hydrogen, optionally monosubstituted or identically or differently polysubstituted $C_1$-$C_4$-alkyl, $C_2$-$C_4$-alkenyl, $C_2$-$C_4$-alkynyl, $C_3$-$C_4$-cycloalkyl, aryl-$C_1$-$C_4$-alkyl, $C_1$-$C_4$-alkylcarbonyl, $C_1$-$C_4$-alkylsulphonyl, arylcarbonyl, hetarylcarbonyl, $C_1$-$C_4$-alkoxycarbonyl or aryloxycarbonyl, where the substituents are each independently halogen, cyano, nitro, hydroxyl, $C_1$-$C_6$-alkyl, $C_1$-$C_6$-alkoxy, $C_3$-$C_6$-cycloalkyl, $C_{1-6}$-haloalkoxy, $C_1$-$C_6$ -alkylthio, $C_1$-$C_4$-alkoxycarbonyl, aminocarbonyl, $C_1$-$C_4$-alkylaminocarbonyl or $C_1$-$C_4$-dialkylaminocarbonyl, V is $R^4$, where $R^4$ is hydrogen, halogeli or optionally monosubstituted or identically or differently polysubstituted $C_1$-$C_4$-alkyl, where the substituents are each independently halogen, $C_1$-$C_4$-alkyl or $C_1$-$C_4$-alkoxy, $R^5$ is hydrogen, halogen or optionally monosubstituted or identically or differently polysubstituted $C_1$-$C_4$-alkyl, where the substituents are each independently halogen, or $C_1$-$C_4$-alkyl, $R^6$ is hydrogen, halogen, nitro, cyano, amino, hydroxyl, optionally monosubstituted or identically or differently polysubstituted $C_1$-$C_4$-alkyl, $C_2$-$C_4$-alkenyl, $C_2$-$C_4$-alkynyl, $C_3$-$0_5$-cycloalkyl, $C_1$-$C_4$-alkoxy, ($C_1$-$C_4$-alkoxy)carbonyl, $C_1$-$C_4$-alkylamino, formyl, ($C_1$-$C_4$-alkyl)carbonyl, $C_1$-$C_4$-alkoxyimino-$C_1$-$C_4$-alkyl, $C_1$-$C_4$-dialkylamino, ($C_1$-$C_4$-alkylamino)carbonyl, ($C_1$-$C_4$-dialkylamino)carbonyl, $C_1$-$C_4$-alkylthio, $C_1$-$C_4$-alkylsulphinyl, $C_1$-$C_4$-alkylsulphonyl, $C_1$-$C_4$-alkylaminosulphonyl or $C_1$-$C_4$-alkylsulphonylamino, where the substituents are each independently halogen, cyano, nitro, hydroxyl, amino, $C_1$-$C_6$-alkyl, $C_1$-$C_6$-alkoxy, $C_3$-$C_6$-cycloalkyl, $C_1$-$C_6$-haloalkoxy or $C_1$-$C_6$-alkylthio, m is 0, 1, 2, or 3, X is unsubstituted $C_1$-$C_4$-haloalkyl, W is O, A-Y together are cyano or are optionally monosubstituted heterocyclyl selected from the group consisting of 1,2,4-triazolyl, 1,2,4-oxadiazolyl, and pyrazolyl, or A is a bivalent chemical moiety which is —$NR^{13}C(=O)$—, —$C(R^{11})(R^{12})NR^{13}C(=O)$—, —$C(=O)NR^{13}$—, —$C(=O)N(R^{13})$—O—, —$C(=O)NR^{13}CH_2$—, —$C(=O)$—O—, —$C(=O)NR^{13}CH_2C(=O)NR^{14}$—, —$C(=O)NR^{13}NR^{14}$—, —$C(R^{11})(R^{12})NR^{13}$—, —$S(=O)_2NR^{13}$—, or —$C(R^{11})(R^{12})NR^{13}S(=O)_2$—, where the first (left-hand) connection site in the bivalent chemical moieties in each case is connected to the ring at one of positions $Q^4$ to $Q^8$ and the second (right-hand) connection site in each case to Y, where $R^{11}$ and $R^{12}$ are each independently hydrogen or $C_1$-$C_4$-alkyl, and where $R^{13}$ and $R^{14}$ are each independently hydrogen, $C_1$-$C_4$-alkyl or $C_3$-$C_6$-cycloalkyl, $C_1$-$C_4$-alkylcarbonyl, or $C_1$-$C_4$-alkoxycarbonyl, Y is hydrogen or optionally monosubstituted or identically or differently polysubstituted $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkenyl, is an optionally monosubstituted phenyl, or Y is an optionally monosubstituted heterocycle selected from the group consisting of thienyl, thiazolyl, pyrazolyl, imidazolyl, pyridinyl, pyrimidinyl, pyridazinyl, pyrazinyl, tetrahydropyranyl, tetrahydrofuranyl, oxetanyl, thietanyl, oxidothietanyl, dioxidothietanyl, oxotetrahydrofaranyl, or oxopiperidinyl, $Q^1$ to $Q^3$ are each independently a carbon atom which is substituted by hydrogen or by $R^1$ $Q^4$ is a carbon atom which is substituted by hydrogen or $R^6$, and $Q^5$ to $Q^8$ are each independently a carbon atom which is substituted by hydrogen, $R^6$ or A-Y, where exactly one of $Q^5$, $Q^6$, $Q^7$, $Q^8$ is substituted by A-Y.

9. A compound of formula (I) or a diastereomer, enantiomer, E/Z isomer, or salt thereof according to claim 8, where the substituents on A-Y together are halogen, cyano, or $C_3$-$C_6$-cycloalkyl, and the substituents on Y are halogen, nitro, or cyano, or optionally monosubstituted or identically or differently polysubstituted $C_1$-$C_6$-alkyl, $C_3$-$C_6$-cycloalkyl, $C_1$-$C_6$-alkylcarbonyl, $C_1$-$C_6$-alkoxy, $C_1$-$C_6$-alkoxycarbonyl, $C_1$-$C_6$-alkylthio, aryl, or heterocyclyl, where the substituents are each independently halogen, $C_1$-$C_6$-alkyl, or cyano.

10. A compound of formula (I) or a diastereomer, enantiomer, E/Z isomer, or salt thereof according to claim 9, where aryl is phenyl and heterocyclyl is pyridinyl, pyrimidinyl, or thiazolyl.

11. A compound of formula (I) or a diastereomer, enantiomer, E/Z isomer, or salt thereof

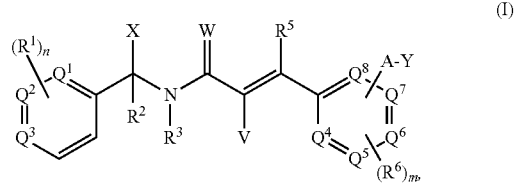

(I)

where $R^1$ is hydrogen, halogen, nitro, cyano, optionally monosubstituted or identically or differently polysubstituted $C_2$-$C_6$-alkenyl, $C_2$-$C_4$-alkynyl, $C_1$-$C_4$-alkoxy, $C_1$-$C_4$-alkylthio, $C_1$-$C_4$-alkylsulphinyl, $C_1$-$C_4$-alkylsulphonyl, $C_3$-$C_4$-cycloalkyl, $C_1$-$C_4$-alkylcarbonyl, $C_1$-$C_4$-alkoxycarbonyl, $C_1$-$C_4$-alkylaminocarbonyl, $C_1$-$C_4$-dialkylaminocarbonyl or $C_1$-$C_4$-alkylaminosulphonyl, where the substituents are each independently halogen, cyano, nitro, hydroxyl, $C_1$-$C_4$-alkyl, $C_1$-$C_4$-alkoxy, $C_3$-$C_4$-cycloalkyl, $C_1$-$C_4$-haloalkoxy or $C_1$-$C_4$-alkylthio, n is 1, 2 or 3, $R^2$ is hydrogen, cyano, hydroxyl, amino, optionally monosubstituted to identically or differently trisubstituted $C_1$-$C_4$-alkyl, $C_2$-$C_4$-alkenyl, $C_2$-$C_4$-alkynyl, $C_1$-$C_4$-alkoxy or $C_3$-$C_6$-cycloalkyl, where the substituents are each independently halogen, cyano, nitro, hydroxyl, amino, $C_1$-$C_4$-alkyl or $C_1$-$C_4$-alkoxy, $R^3$ is hydrogen, optionally monosubstituted or identically or differently polysubstituted $C_1$-$C_4$-alkyl, $C_2$-$C_4$-alkenyl, $C_2$-$C_4$-alkynyl, $C_3$-$C_4$-cycloalkyl, aryl-$C_1$-$C_4$-alkyl, $C_1$-$C_4$-alkylcarbonyl, $C_1$-$C_4$-alkylsulphonyl, arylcarbonyl, hetarylcarbonyl, $C_1$-$C_4$-alkoxycarbonyl or aryloxycarbonyl, where the substituents are each independently halogen, cyano, nitro, hydroxyl, $C_1$-$C_6$-alkyl, $C_1$-$C_6$-alkoxy, $C_3$-$C_6$-cycloalkyl, $C_1$-$C_6$-haloalkoxy, $C_1$-$C_6$-alkylthio, $C_1$-$C_4$-alkoxycarbonyl, aminocarbonyl, $C_1$-$C_4$-alkylaminocarbonyl or $C_1$-$C_4$-dialkylaminocarbonyl, V is $R^4$, where $R^4$ is hydrogen, halogen or optionally monosubstituted or identically or differently polysubstituted $C_1$-$C_4$-alkyl, where the substituents are each independently halogen, $C_1$-$C_4$-alkyl or $C_1$-$C_4$-alkoxy, $R^5$ is hydrogen, halogen or optionally monosubstituted or identically or differently polysubstituted $C_1$-$C_a$-alkyl, where the substituents are each independently halogen or $C_1$-$C_4$-alkyl, $R^6$ is hydrogen, halogen, nitro, cyano, amino, hydroxyl, optionally monosubstituted or identically or differently polysubstituted $C_1$-$C_4$-alkyl, $C_2$-$C_4$-alkenyl, $C_2$-$C_4$-alkynyl, $C_3$-$C_5$-cycloalkyl, $C_1$-$C_4$-alkoxy, ($C_1$-$C_4$-alkoxy)carbonyl, $C_1$-$C_4$-alkylamino, formyl, ($C_1$-$C_4$-alkyl)carbonyl, $C_1$-$C_4$-alkoxyimino-$C_1$-$C_4$-alkyl, $C_1$-$C_4$-dialkylamino, ($C_1$-$C_4$-alkylamino)carbonyl, ($C_1$-$C_4$-dialkylamino)carbonyl, $C_1$-$C_4$-alkylthio, $C_1$-$C_4$-alkylsulphinyl, $C_1$-$C_4$-alkylsulphonyl, $C_1$-$C_4$-alkylaminosulphonyl or $C_1$-$C_4$-alkylsulphonylamino, where the substituents are each independently halogen, cyano, nitro, hydroxyl, amino, $C_1$-$C_6$-alkyl, $C_1$-$C_6$- alkoxy, $C_3$-$C_6$-cycloalkyl, $C_1$-$C_6$-haloalkoxy or $C_1$-$C_6$-alkylthio, m is 0, 1, 2, or 3, X is unsubstituted $C_1$-$C_4$-haloalkyl, W is O A-Y together are cyano or optionally monosubstituted heterocyclyl from the group consisting of 1,2,4-triazolyl, 1,2,4-oxadiazolyl, and pyrazolyl, or A is a bivalent chemical moiety which is —$NR^{13}C(=O)$—, —$C(R^{11})(R^{12})NR^{13}C(=O)$—, —$C(=O)NR^{13}$—, —$C(=O)N(R^{13})$—O—, —$C(=O)NR^{13}CH_2$—, —$C(=O)$—O—, —$C(=O)NR^{13}CH_2C(=O)NR^{14}$—, —$C(=O)NR^{13}NR^{14}$—, —$C(R^{11})(R^{12})NR^{13}$—, —$S(=O)_2NR^{13}$—, or —$C(R^{11})(R^{12})NR^{13}S(=O)_2$—, where the first (left-hand) connection site in the bivalent chemical moieties in each case is connected to the ring at one of positions $Q^4$ to $Q^8$ and the second (right-hand) connection site in each case to Y, where $R^{11}$ and $R^{12}$ are each independently hydrogen or $C_1$-$C_4$-alkyl, and where $R^{13}$ and $R^{14}$ are each independently hydrogen, $C_1$-$C_4$-alkyl or $C_3$-$C_6$-cycloalkyl, $C_1$-$C_4$-alkylcarbonyl, or $C_1$-$C_4$-alkoxycarbonyl, Y is hydrogen or optionally monosubstituted $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkenyl, is an optionally monosubstituted phenyl, or Y is an optionally monosubstituted heterocycle from the group consisting of thienyl, thiazolyl, pyrazolyl, imidazolyl, pyridinyl, pyrimidinyl, pyridazinyl, pyrazinyl, tetrahydropyranyl, tetrahydrofuranyl, oxetanyl, thietanyl, oxidothietanyl, dioxidothietanyl, oxotetrahydrofuranyl, and oxopiperidinyl, $Q^1$ to $Q^3$ are each independently a carbon atom which is substituted by hydrogen or by $R^1$, $Q^4$ is a carbon atom which is substituted by hydrogen or $R^6$, and $Q^5$ to $Q^8$ are each independently a carbon atom which is substituted by hydrogen, $R^6$ or A-Y, where exactly one of $Q^5$, $Q^6$, $Q^7$, $Q^8$ is substituted by A-Y.

12. A compound of formula (I) or a diastereomer, enantiomer, E/Z isomer, or salt thereof according to claim 11, where the substituents on A-Y together are halogen, cyano, or $C_3$-$C_6$-cycloalkyl, and the substituents on Y are halogen, nitro, cyano, or optionally monosubstituted or identically or differently polysubstituted $C_1$-$C_6$-alkyl, $C_3$-$C_6$-cycloalkyl, $C_1$-$C_6$-alkylcarbonyl, $C_1$-$C_6$-alkoxy, $C_1$-$C_6$-alkoxycarbonyl, $C_1$-$C_6$-alkylthio, aryl, or heterocyclyl, where the substituents are each independently halogen, $C_1$-$C_6$-alkyl, or cyano.

13. A compound of formula (I) or a diastereomer, enantiomer, E/Z isomer, or salt thereof according to claim 12, where aryl is phenyl and heterocyclyl is pyridinyl, pyrimidinyl, or thiazolyl.

* * * * *